United States Patent
Kalns et al.

(10) Patent No.: US 9,316,651 B2
(45) Date of Patent: *Apr. 19, 2016

(54) METHODS AND COMPOSITIONS FOR BIOMARKERS OF FATIGUE

(71) Applicant: Hyperion Biotechnology, Inc., San Antonio, TX (US)

(72) Inventors: John E. Kalns, San Antonio, TX (US); Darren J. Michael, San Antonio, TX (US)

(73) Assignee: Hyperion Biotechnology, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/612,079

(22) Filed: Feb. 2, 2015

(65) Prior Publication Data

US 2015/0233939 A1 Aug. 20, 2015

Related U.S. Application Data

(63) Continuation of application No. 13/839,332, filed on Mar. 15, 2013, now Pat. No. 8,945,854, which is a continuation-in-part of application No. PCT/US2012/064798, filed on Nov. 13, 2012.

(60) Provisional application No. 61/559,632, filed on Nov. 14, 2011.

(51) Int. Cl.
| | |
|---|---|
| *G01N 33/53* | (2006.01) |
| *G01N 33/68* | (2006.01) |
| *G06F 19/00* | (2011.01) |

(52) U.S. Cl.
CPC ........ *G01N 33/6848* (2013.01); *G01N 33/6893* (2013.01); *G06F 19/34* (2013.01); *G01N 2800/306* (2013.01)

(58) Field of Classification Search
None
See application file for complete search history.

(56) References Cited

U.S. PATENT DOCUMENTS

| | | |
|---|---|---|
| 2002/0103429 A1 | 8/2002 | deCharms |
| 2009/0075387 A1 | 3/2009 | Kalns et al. |
| 2011/0077472 A1 | 3/2011 | Kalns et al. |

OTHER PUBLICATIONS

International Preliminary Report on Patentability corresponding to International Patent Application No. PCT/US2012/064798; mailed May 20, 2014.

International Search Report and the Written Opinion of the International Searching Authority corresponding to International Patent Application No. PCT/US2012/064798; mailed Feb. 25, 2013.

Michael et al. "Fatigue biomarker index: an objective salivary measure of fatigue level" *Accident Analysis & Prevention* 45(Suppl):68-73 (2012).

*Primary Examiner* — Jacob Cheu
(74) *Attorney, Agent, or Firm* — Myers Bigel & Sibley, P.A.

(57) ABSTRACT

The present invention provides methods and compositions for identifying fatigue, disease states associated with fatigue, recovery from fatigue and/or physical performance capability in a subject.

1 Claim, 6 Drawing Sheets

SEQUENCE LISTING

```
<160> NUMBER OF SEQ ID NOS: 1437

<210> SEQ ID NO 1
<211> LENGTH: 27
<212> TYPE: PRT
<213> ORGANISM: Homo sapiens

<400> SEQUENCE: 1

Pro Pro Gly Lys Pro Gln Gly Pro Pro Gln Gly Gly Asn Gln Pro
1               5                   10                  15

Gln Gly Pro Pro Pro Pro Gly Lys Pro Gln
            20                  25

<210> SEQ ID NO 2
<211> LENGTH: 25
<212> TYPE: PRT
<213> ORGANISM: Homo sapiens

<400> SEQUENCE: 2

Gly Asn Pro Gln Gly Pro Ser Pro Gln Gly Gly Asn Lys Pro Gln Gly
1               5                   10                  15

Pro Pro Pro Pro Pro Gly Lys Pro Gln
            20                  25

<210> SEQ ID NO 3
<211> LENGTH: 27
<212> TYPE: PRT
<213> ORGANISM: Homo sapiens

<400> SEQUENCE: 3

Ser Pro Pro Gly Lys Pro Gln Gly Pro Pro Gln Gln Glu Gly Asn Lys
1               5                   10                  15

Pro Gln Gly Pro Pro Pro Gly Lys Pro Gln
            20                  25

<210> SEQ ID NO 4
<211> LENGTH: 416
<212> TYPE: PRT
<213> ORGANISM: Homo sapiens

<400> SEQUENCE: 4

Met Leu Leu Ile Leu Leu Ser Val Ala Leu Leu Ala Leu Ser Ser Ala
1               5                   10                  15

Gln Asn Leu Asn Glu Asp Val Ser Gln Glu Glu Ser Pro Ser Leu Ile
            20                  25                  30

Ala Gly Asn Pro Gln Gly Ala Pro Gln Gly Gly Asn Lys Pro Gln
        35                  40                  45

Gly Pro Pro Ser Pro Pro Gly Lys Pro Gln Gly Pro Pro Gln Gly
    50                  55                  60

Gly Asn Gln Pro Gln Gly Pro Pro Pro Pro Gly Lys Pro Gly
```

```
                65                  70                  75                  80
        Pro Pro Pro Gln Gly Gly Asn Lys Pro Gln Gly Pro Pro Pro Gly
                        85                  90                  95
        Lys Pro Gln Gly Pro Pro Gln Gly Asp Lys Ser Arg Ser Pro Arg
                        100                 105                 110
        Ser Pro Gly Lys Pro Gln Gly Pro Pro Gln Gly Gly Asn Gln
                        115                 120                 125
        Pro Gln Gly Pro Pro Pro Gly Lys Pro Gln Gly Pro Pro
        130                 135                 140
        Gln Gly Gly Asn Lys Pro Gln Gly Pro Pro Pro Gly Lys Pro Gln
        145                 150                 155                 160
        Gly Pro Pro Pro Gln Gly Asp Asn Lys Ser Arg Ser Arg Ser Pro
                        165                 170                 175
        Pro Gly Lys Pro Gln Gly Pro Pro Gln Gly Gly Asn Gln Pro Gln
                        180                 185                 190
        Gly Pro Pro Pro Pro Gly Lys Pro Gln Gly Pro Pro Gln Gly
                    195                 200                 205
        Gly Asn Lys Pro Gln Gly Pro Pro Pro Gly Lys Pro Gln Gly Pro
            210                 215                 220
        Pro Pro Gln Gly Asp Asn Lys Ser Gln Ser Ala Arg Ser Pro Gly
        225                 230                 235                 240
        Lys Pro Gln Gly Pro Pro Gln Gly Gly Asn Gln Pro Gln Gly Pro
                        245                 250                 255
        Pro Pro Pro Gly Lys Pro Gln Gly Pro Pro Gln Gly Gly Asn
                        260                 265                 270
        Lys Ser Gln Gly Pro Pro Pro Gly Lys Pro Gln Gly Pro Pro Pro
            275                 280                 285
        Gln Gly Gly Ser Lys Ser Arg Ser Ser Arg Ser Pro Gly Lys Pro
                290                 295                 300
        Gln Gly Pro Pro Gln Gly Gly Asn Gln Pro Gln Gly Pro Pro Pro
        305                 310                 315                 320
        Pro Pro Gly Lys Pro Gln Gly Pro Pro Gln Gly Gly Asn Lys Pro
                        325                 330                 335
        Gln Gly Pro Pro Pro Gly Lys Pro Gln Gly Pro Pro Pro Gln Gly
                        340                 345                 350
        Gly Ser Lys Ser Arg Ser Ala Arg Ser Pro Gly Lys Pro Gln Gly
                        355                 360                 365
        Pro Pro Gln Gln Glu Gly Asn Asn Pro Gln Gly Pro Pro Pro Ala
                        370                 375                 380
        Gly Gly Asn Pro Gln Gln Pro Gln Ala Pro Ala Gly Gln Pro Gln
        385                 390                 395                 400
        Gly Pro Pro Arg Pro Pro Gln Gly Gly Arg Pro Ser Arg Pro Pro Gln
                        405                 410                 415

<210> SEQ ID NO 5
<211> LENGTH: 5
<212> TYPE: PRT
<213> ORGANISM: Homo sapiens

<400> SEQUENCE: 5

Met Leu Leu Ile Leu
1               5

<210> SEQ ID NO 6
<211> LENGTH: 5
```

```
<212> TYPE: PRT
<213> ORGANISM: Homo sapiens

<400> SEQUENCE: 6

Leu Leu Ile Leu Leu
1               5

<210> SEQ ID NO 7
<211> LENGTH: 5
<212> TYPE: PRT
<213> ORGANISM: Homo sapiens

<400> SEQUENCE: 7

Leu Ile Leu Leu Ser
1               5

<210> SEQ ID NO 8
<211> LENGTH: 5
<212> TYPE: PRT
<213> ORGANISM: Homo sapiens

<400> SEQUENCE: 8

Ile Leu Leu Ser Val
1               5

<210> SEQ ID NO 9
<211> LENGTH: 5
<212> TYPE: PRT
<213> ORGANISM: Homo sapiens

<400> SEQUENCE: 9

Leu Leu Ser Val Ala
1               5

<210> SEQ ID NO 10
<211> LENGTH: 5
<212> TYPE: PRT
<213> ORGANISM: Homo sapiens

<400> SEQUENCE: 10

Leu Ser Val Ala Leu
1               5

<210> SEQ ID NO 11
<211> LENGTH: 5
<212> TYPE: PRT
<213> ORGANISM: Homo sapiens

<400> SEQUENCE: 11

Ser Val Ala Leu Leu
1               5

<210> SEQ ID NO 12
<211> LENGTH: 5
<212> TYPE: PRT
<213> ORGANISM: Homo sapiens

<400> SEQUENCE: 12

Val Ala Leu Leu Ala
1               5

<210> SEQ ID NO 13
<211> LENGTH: 5
<212> TYPE: PRT
<213> ORGANISM: Homo sapiens
```

<400> SEQUENCE: 13

Ala Leu Leu Ala Leu
1               5

<210> SEQ ID NO 14
<211> LENGTH: 5
<212> TYPE: PRT
<213> ORGANISM: Homo sapiens

<400> SEQUENCE: 14

Leu Leu Ala Leu Ser
1               5

<210> SEQ ID NO 15
<211> LENGTH: 5
<212> TYPE: PRT
<213> ORGANISM: Homo sapiens

<400> SEQUENCE: 15

Leu Ala Leu Ser Ser
1               5

<210> SEQ ID NO 16
<211> LENGTH: 5
<212> TYPE: PRT
<213> ORGANISM: Homo sapiens

<400> SEQUENCE: 16

Ala Leu Ser Ser Ala
1               5

<210> SEQ ID NO 17
<211> LENGTH: 5
<212> TYPE: PRT
<213> ORGANISM: Homo sapiens

<400> SEQUENCE: 17

Leu Ser Ser Ala Gln
1               5

<210> SEQ ID NO 18
<211> LENGTH: 5
<212> TYPE: PRT
<213> ORGANISM: Homo sapiens

<400> SEQUENCE: 18

Ser Ser Ala Gln Asn
1               5

<210> SEQ ID NO 19
<211> LENGTH: 5
<212> TYPE: PRT
<213> ORGANISM: Homo sapiens

<400> SEQUENCE: 19

Ser Ala Gln Asn Leu
1               5

<210> SEQ ID NO 20
<211> LENGTH: 5
<212> TYPE: PRT
<213> ORGANISM: Homo sapiens

<400> SEQUENCE: 20

```
Ala Gln Asn Leu Asn
1               5

<210> SEQ ID NO 21
<211> LENGTH: 5
<212> TYPE: PRT
<213> ORGANISM: Homo sapiens

<400> SEQUENCE: 21

Gln Asn Leu Asn Glu
1               5

<210> SEQ ID NO 22
<211> LENGTH: 5
<212> TYPE: PRT
<213> ORGANISM: Homo sapiens

<400> SEQUENCE: 22

Asn Leu Asn Glu Asp
1               5

<210> SEQ ID NO 23
<211> LENGTH: 5
<212> TYPE: PRT
<213> ORGANISM: Homo sapiens

<400> SEQUENCE: 23

Leu Asn Glu Asp Val
1               5

<210> SEQ ID NO 24
<211> LENGTH: 5
<212> TYPE: PRT
<213> ORGANISM: Homo sapiens

<400> SEQUENCE: 24

Asn Glu Asp Val Ser
1               5

<210> SEQ ID NO 25
<211> LENGTH: 5
<212> TYPE: PRT
<213> ORGANISM: Homo sapiens

<400> SEQUENCE: 25

Glu Asp Val Ser Gln
1               5

<210> SEQ ID NO 26
<211> LENGTH: 5
<212> TYPE: PRT
<213> ORGANISM: Homo sapiens

<400> SEQUENCE: 26

Asp Val Ser Gln Glu
1               5

<210> SEQ ID NO 27
<211> LENGTH: 5
<212> TYPE: PRT
<213> ORGANISM: Homo sapiens

<400> SEQUENCE: 27

Val Ser Gln Glu Glu
```

```
-continued 1               5

<210> SEQ ID NO 28
<211> LENGTH: 5
<212> TYPE: PRT
<213> ORGANISM: Homo sapiens

<400> SEQUENCE: 28

Ser Gln Glu Glu Ser
1               5

<210> SEQ ID NO 29
<211> LENGTH: 5
<212> TYPE: PRT
<213> ORGANISM: Homo sapiens

<400> SEQUENCE: 29

Gln Glu Glu Ser Pro
1               5

<210> SEQ ID NO 30
<211> LENGTH: 5
<212> TYPE: PRT
<213> ORGANISM: Homo sapiens

<400> SEQUENCE: 30

Glu Glu Ser Pro Ser
1               5

<210> SEQ ID NO 31
<211> LENGTH: 5
<212> TYPE: PRT
<213> ORGANISM: Homo sapiens

<400> SEQUENCE: 31

Glu Ser Pro Ser Leu
1               5

<210> SEQ ID NO 32
<211> LENGTH: 5
<212> TYPE: PRT
<213> ORGANISM: Homo sapiens

<400> SEQUENCE: 32

Ser Pro Ser Leu Ile
1               5

<210> SEQ ID NO 33
<211> LENGTH: 5
<212> TYPE: PRT
<213> ORGANISM: Homo sapiens

<400> SEQUENCE: 33

Pro Ser Leu Ile Ala
1               5

<210> SEQ ID NO 34
<211> LENGTH: 5
<212> TYPE: PRT
<213> ORGANISM: Homo sapiens

<400> SEQUENCE: 34

Ser Leu Ile Ala Gly
1               5
```

```
<210> SEQ ID NO 35
<211> LENGTH: 5
<212> TYPE: PRT
<213> ORGANISM: Homo sapiens

<400> SEQUENCE: 35

Leu Ile Ala Gly Asn
1               5

<210> SEQ ID NO 36
<211> LENGTH: 5
<212> TYPE: PRT
<213> ORGANISM: Homo sapiens

<400> SEQUENCE: 36

Ile Ala Gly Asn Pro
1               5

<210> SEQ ID NO 37
<211> LENGTH: 5
<212> TYPE: PRT
<213> ORGANISM: Homo sapiens

<400> SEQUENCE: 37

Ala Gly Asn Pro Gln
1               5

<210> SEQ ID NO 38
<211> LENGTH: 5
<212> TYPE: PRT
<213> ORGANISM: Homo sapiens

<400> SEQUENCE: 38

Gly Asn Pro Gln Gly
1               5

<210> SEQ ID NO 39
<211> LENGTH: 5
<212> TYPE: PRT
<213> ORGANISM: Homo sapiens

<400> SEQUENCE: 39

Asn Pro Gln Gly Ala
1               5

<210> SEQ ID NO 40
<211> LENGTH: 5
<212> TYPE: PRT
<213> ORGANISM: Homo sapiens

<400> SEQUENCE: 40

Pro Gln Gly Ala Pro
1               5

<210> SEQ ID NO 41
<211> LENGTH: 5
<212> TYPE: PRT
<213> ORGANISM: Homo sapiens

<400> SEQUENCE: 41

Gln Gly Ala Pro Pro
1               5

<210> SEQ ID NO 42
```

```
<211> LENGTH: 5
<212> TYPE: PRT
<213> ORGANISM: Homo sapiens

<400> SEQUENCE: 42

Gly Ala Pro Pro Gln
1               5

<210> SEQ ID NO 43
<211> LENGTH: 5
<212> TYPE: PRT
<213> ORGANISM: Homo sapiens

<400> SEQUENCE: 43

Ala Pro Pro Gln Gly
1               5

<210> SEQ ID NO 44
<211> LENGTH: 5
<212> TYPE: PRT
<213> ORGANISM: Homo sapiens

<400> SEQUENCE: 44

Pro Pro Gln Gly Gly
1               5

<210> SEQ ID NO 45
<211> LENGTH: 5
<212> TYPE: PRT
<213> ORGANISM: Homo sapiens

<400> SEQUENCE: 45

Pro Gln Gly Gly Asn
1               5

<210> SEQ ID NO 46
<211> LENGTH: 5
<212> TYPE: PRT
<213> ORGANISM: Homo sapiens

<400> SEQUENCE: 46

Gln Gly Gly Asn Lys
1               5

<210> SEQ ID NO 47
<211> LENGTH: 5
<212> TYPE: PRT
<213> ORGANISM: Homo sapiens

<400> SEQUENCE: 47

Gly Gly Asn Lys Pro
1               5

<210> SEQ ID NO 48
<211> LENGTH: 5
<212> TYPE: PRT
<213> ORGANISM: Homo sapiens

<400> SEQUENCE: 48

Gly Asn Lys Pro Gln
1               5

<210> SEQ ID NO 49
<211> LENGTH: 5
<212> TYPE: PRT
```

<213> ORGANISM: Homo sapiens

<400> SEQUENCE: 49

Asn Lys Pro Gln Gly
1               5

<210> SEQ ID NO 50
<211> LENGTH: 5
<212> TYPE: PRT
<213> ORGANISM: Homo sapiens

<400> SEQUENCE: 50

Lys Pro Gln Gly Pro
1               5

<210> SEQ ID NO 51
<211> LENGTH: 5
<212> TYPE: PRT
<213> ORGANISM: Homo sapiens

<400> SEQUENCE: 51

Pro Gln Gly Pro Pro
1               5

<210> SEQ ID NO 52
<211> LENGTH: 5
<212> TYPE: PRT
<213> ORGANISM: Homo sapiens

<400> SEQUENCE: 52

Gln Gly Pro Pro Ser
1               5

<210> SEQ ID NO 53
<211> LENGTH: 5
<212> TYPE: PRT
<213> ORGANISM: Homo sapiens

<400> SEQUENCE: 53

Gly Pro Pro Ser Pro
1               5

<210> SEQ ID NO 54
<211> LENGTH: 5
<212> TYPE: PRT
<213> ORGANISM: Homo sapiens

<400> SEQUENCE: 54

Pro Pro Ser Pro Pro
1               5

<210> SEQ ID NO 55
<211> LENGTH: 5
<212> TYPE: PRT
<213> ORGANISM: Homo sapiens

<400> SEQUENCE: 55

Pro Ser Pro Pro Gly
1               5

<210> SEQ ID NO 56
<211> LENGTH: 5
<212> TYPE: PRT
<213> ORGANISM: Homo sapiens

```
<400> SEQUENCE: 56

Ser Pro Pro Gly Lys
1               5

<210> SEQ ID NO 57
<211> LENGTH: 5
<212> TYPE: PRT
<213> ORGANISM: Homo sapiens

<400> SEQUENCE: 57

Pro Pro Gly Lys Pro
1               5

<210> SEQ ID NO 58
<211> LENGTH: 5
<212> TYPE: PRT
<213> ORGANISM: Homo sapiens

<400> SEQUENCE: 58

Pro Gly Lys Pro Gln
1               5

<210> SEQ ID NO 59
<211> LENGTH: 5
<212> TYPE: PRT
<213> ORGANISM: Homo sapiens

<400> SEQUENCE: 59

Gly Lys Pro Gln Gly
1               5

<210> SEQ ID NO 60
<211> LENGTH: 5
<212> TYPE: PRT
<213> ORGANISM: Homo sapiens

<400> SEQUENCE: 60

Lys Pro Gln Gly Pro
1               5

<210> SEQ ID NO 61
<211> LENGTH: 5
<212> TYPE: PRT
<213> ORGANISM: Homo sapiens

<400> SEQUENCE: 61

Pro Gln Gly Pro Pro
1               5

<210> SEQ ID NO 62
<211> LENGTH: 5
<212> TYPE: PRT
<213> ORGANISM: Homo sapiens

<400> SEQUENCE: 62

Gln Gly Pro Pro Pro
1               5

<210> SEQ ID NO 63
<211> LENGTH: 5
<212> TYPE: PRT
<213> ORGANISM: Homo sapiens

<400> SEQUENCE: 63
```

```
Gly Pro Pro Pro Gln
1               5

<210> SEQ ID NO 64
<211> LENGTH: 5
<212> TYPE: PRT
<213> ORGANISM: Homo sapiens

<400> SEQUENCE: 64

Pro Pro Pro Gln Gly
1               5

<210> SEQ ID NO 65
<211> LENGTH: 5
<212> TYPE: PRT
<213> ORGANISM: Homo sapiens

<400> SEQUENCE: 65

Pro Pro Gln Gly Gly
1               5

<210> SEQ ID NO 66
<211> LENGTH: 5
<212> TYPE: PRT
<213> ORGANISM: Homo sapiens

<400> SEQUENCE: 66

Pro Gln Gly Gly Asn
1               5

<210> SEQ ID NO 67
<211> LENGTH: 5
<212> TYPE: PRT
<213> ORGANISM: Homo sapiens

<400> SEQUENCE: 67

Gln Gly Gly Asn Gln
1               5

<210> SEQ ID NO 68
<211> LENGTH: 5
<212> TYPE: PRT
<213> ORGANISM: Homo sapiens

<400> SEQUENCE: 68

Gly Gly Asn Gln Pro
1               5

<210> SEQ ID NO 69
<211> LENGTH: 5
<212> TYPE: PRT
<213> ORGANISM: Homo sapiens

<400> SEQUENCE: 69

Gly Asn Gln Pro Gln
1               5

<210> SEQ ID NO 70
<211> LENGTH: 5
<212> TYPE: PRT
<213> ORGANISM: Homo sapiens

<400> SEQUENCE: 70

Asn Gln Pro Gln Gly
1               5
```

<210> SEQ ID NO 71
<211> LENGTH: 5
<212> TYPE: PRT
<213> ORGANISM: Homo sapiens

<400> SEQUENCE: 71

Gln Pro Gln Gly Pro
1               5

<210> SEQ ID NO 72
<211> LENGTH: 5
<212> TYPE: PRT
<213> ORGANISM: Homo sapiens

<400> SEQUENCE: 72

Pro Gln Gly Pro Pro
1               5

<210> SEQ ID NO 73
<211> LENGTH: 5
<212> TYPE: PRT
<213> ORGANISM: Homo sapiens

<400> SEQUENCE: 73

Gln Gly Pro Pro Pro
1               5

<210> SEQ ID NO 74
<211> LENGTH: 5
<212> TYPE: PRT
<213> ORGANISM: Homo sapiens

<400> SEQUENCE: 74

Gly Pro Pro Pro Pro
1               5

<210> SEQ ID NO 75
<211> LENGTH: 5
<212> TYPE: PRT
<213> ORGANISM: Homo sapiens

<400> SEQUENCE: 75

Pro Pro Pro Pro Pro
1               5

<210> SEQ ID NO 76
<211> LENGTH: 5
<212> TYPE: PRT
<213> ORGANISM: Homo sapiens

<400> SEQUENCE: 76

Pro Pro Pro Pro Gly
1               5

<210> SEQ ID NO 77
<211> LENGTH: 5
<212> TYPE: PRT
<213> ORGANISM: Homo sapiens

<400> SEQUENCE: 77

Pro Pro Pro Gly Lys
1               5

```
<210> SEQ ID NO 78
<211> LENGTH: 5
<212> TYPE: PRT
<213> ORGANISM: Homo sapiens

<400> SEQUENCE: 78

Pro Pro Gly Lys Pro
1               5

<210> SEQ ID NO 79
<211> LENGTH: 5
<212> TYPE: PRT
<213> ORGANISM: Homo sapiens

<400> SEQUENCE: 79

Pro Gly Lys Pro Gln
1               5

<210> SEQ ID NO 80
<211> LENGTH: 5
<212> TYPE: PRT
<213> ORGANISM: Homo sapiens

<400> SEQUENCE: 80

Gly Lys Pro Gln Gly
1               5

<210> SEQ ID NO 81
<211> LENGTH: 5
<212> TYPE: PRT
<213> ORGANISM: Homo sapiens

<400> SEQUENCE: 81

Lys Pro Gln Gly Pro
1               5

<210> SEQ ID NO 82
<211> LENGTH: 5
<212> TYPE: PRT
<213> ORGANISM: Homo sapiens

<400> SEQUENCE: 82

Pro Gln Gly Pro Pro
1               5

<210> SEQ ID NO 83
<211> LENGTH: 5
<212> TYPE: PRT
<213> ORGANISM: Homo sapiens

<400> SEQUENCE: 83

Gln Gly Pro Pro Pro
1               5

<210> SEQ ID NO 84
<211> LENGTH: 5
<212> TYPE: PRT
<213> ORGANISM: Homo sapiens

<400> SEQUENCE: 84

Gly Pro Pro Pro Gln
1               5

<210> SEQ ID NO 85
<211> LENGTH: 5
```

```
<212> TYPE: PRT
<213> ORGANISM: Homo sapiens

<400> SEQUENCE: 85

Pro Pro Pro Gln Gly
1               5

<210> SEQ ID NO 86
<211> LENGTH: 5
<212> TYPE: PRT
<213> ORGANISM: Homo sapiens

<400> SEQUENCE: 86

Pro Pro Gln Gly Gly
1               5

<210> SEQ ID NO 87
<211> LENGTH: 5
<212> TYPE: PRT
<213> ORGANISM: Homo sapiens

<400> SEQUENCE: 87

Pro Gln Gly Gly Asn
1               5

<210> SEQ ID NO 88
<211> LENGTH: 5
<212> TYPE: PRT
<213> ORGANISM: Homo sapiens

<400> SEQUENCE: 88

Gln Gly Gly Asn Lys
1               5

<210> SEQ ID NO 89
<211> LENGTH: 5
<212> TYPE: PRT
<213> ORGANISM: Homo sapiens

<400> SEQUENCE: 89

Gly Gly Asn Lys Pro
1               5

<210> SEQ ID NO 90
<211> LENGTH: 5
<212> TYPE: PRT
<213> ORGANISM: Homo sapiens

<400> SEQUENCE: 90

Gly Asn Lys Pro Gln
1               5

<210> SEQ ID NO 91
<211> LENGTH: 5
<212> TYPE: PRT
<213> ORGANISM: Homo sapiens

<400> SEQUENCE: 91

Asn Lys Pro Gln Gly
1               5

<210> SEQ ID NO 92
<211> LENGTH: 5
<212> TYPE: PRT
<213> ORGANISM: Homo sapiens
```

<400> SEQUENCE: 92

Lys Pro Gln Gly Pro
1               5

<210> SEQ ID NO 93
<211> LENGTH: 5
<212> TYPE: PRT
<213> ORGANISM: Homo sapiens

<400> SEQUENCE: 93

Pro Gln Gly Pro Pro
1               5

<210> SEQ ID NO 94
<211> LENGTH: 5
<212> TYPE: PRT
<213> ORGANISM: Homo sapiens

<400> SEQUENCE: 94

Gln Gly Pro Pro Pro
1               5

<210> SEQ ID NO 95
<211> LENGTH: 5
<212> TYPE: PRT
<213> ORGANISM: Homo sapiens

<400> SEQUENCE: 95

Gly Pro Pro Pro Pro
1               5

<210> SEQ ID NO 96
<211> LENGTH: 5
<212> TYPE: PRT
<213> ORGANISM: Homo sapiens

<400> SEQUENCE: 96

Pro Pro Pro Pro Gly
1               5

<210> SEQ ID NO 97
<211> LENGTH: 5
<212> TYPE: PRT
<213> ORGANISM: Homo sapiens

<400> SEQUENCE: 97

Pro Pro Pro Gly Lys
1               5

<210> SEQ ID NO 98
<211> LENGTH: 5
<212> TYPE: PRT
<213> ORGANISM: Homo sapiens

<400> SEQUENCE: 98

Pro Pro Gly Lys Pro
1               5

<210> SEQ ID NO 99
<211> LENGTH: 5
<212> TYPE: PRT
<213> ORGANISM: Homo sapiens

<400> SEQUENCE: 99

```
Pro Gly Lys Pro Gln
1               5

<210> SEQ ID NO 100
<211> LENGTH: 5
<212> TYPE: PRT
<213> ORGANISM: Homo sapiens

<400> SEQUENCE: 100

Gly Lys Pro Gln Gly
1               5

<210> SEQ ID NO 101
<211> LENGTH: 5
<212> TYPE: PRT
<213> ORGANISM: Homo sapiens

<400> SEQUENCE: 101

Lys Pro Gln Gly Pro
1               5

<210> SEQ ID NO 102
<211> LENGTH: 5
<212> TYPE: PRT
<213> ORGANISM: Homo sapiens

<400> SEQUENCE: 102

Pro Gln Gly Pro Pro
1               5

<210> SEQ ID NO 103
<211> LENGTH: 5
<212> TYPE: PRT
<213> ORGANISM: Homo sapiens

<400> SEQUENCE: 103

Gln Gly Pro Pro Pro
1               5

<210> SEQ ID NO 104
<211> LENGTH: 5
<212> TYPE: PRT
<213> ORGANISM: Homo sapiens

<400> SEQUENCE: 104

Gly Pro Pro Pro Gln
1               5

<210> SEQ ID NO 105
<211> LENGTH: 5
<212> TYPE: PRT
<213> ORGANISM: Homo sapiens

<400> SEQUENCE: 105

Pro Pro Pro Gln Gly
1               5

<210> SEQ ID NO 106
<211> LENGTH: 5
<212> TYPE: PRT
<213> ORGANISM: Homo sapiens

<400> SEQUENCE: 106

Pro Pro Gln Gly Asp
```

```
1               5
```

<210> SEQ ID NO 107
<211> LENGTH: 5
<212> TYPE: PRT
<213> ORGANISM: Homo sapiens

<400> SEQUENCE: 107

```
Pro Gln Gly Asp Lys
1               5
```

<210> SEQ ID NO 108
<211> LENGTH: 5
<212> TYPE: PRT
<213> ORGANISM: Homo sapiens

<400> SEQUENCE: 108

```
Gln Gly Asp Lys Ser
1               5
```

<210> SEQ ID NO 109
<211> LENGTH: 5
<212> TYPE: PRT
<213> ORGANISM: Homo sapiens

<400> SEQUENCE: 109

```
Gly Asp Lys Ser Arg
1               5
```

<210> SEQ ID NO 110
<211> LENGTH: 5
<212> TYPE: PRT
<213> ORGANISM: Homo sapiens

<400> SEQUENCE: 110

```
Asp Lys Ser Arg Ser
1               5
```

<210> SEQ ID NO 111
<211> LENGTH: 5
<212> TYPE: PRT
<213> ORGANISM: Homo sapiens

<400> SEQUENCE: 111

```
Lys Ser Arg Ser Pro
1               5
```

<210> SEQ ID NO 112
<211> LENGTH: 5
<212> TYPE: PRT
<213> ORGANISM: Homo sapiens

<400> SEQUENCE: 112

```
Ser Arg Ser Pro Arg
1               5
```

<210> SEQ ID NO 113
<211> LENGTH: 5
<212> TYPE: PRT
<213> ORGANISM: Homo sapiens

<400> SEQUENCE: 113

```
Arg Ser Pro Arg Ser
1               5
```

```
<210> SEQ ID NO 114
<211> LENGTH: 5
<212> TYPE: PRT
<213> ORGANISM: Homo sapiens

<400> SEQUENCE: 114

Ser Pro Arg Ser Pro
1               5

<210> SEQ ID NO 115
<211> LENGTH: 5
<212> TYPE: PRT
<213> ORGANISM: Homo sapiens

<400> SEQUENCE: 115

Pro Arg Ser Pro Pro
1               5

<210> SEQ ID NO 116
<211> LENGTH: 5
<212> TYPE: PRT
<213> ORGANISM: Homo sapiens

<400> SEQUENCE: 116

Arg Ser Pro Pro Gly
1               5

<210> SEQ ID NO 117
<211> LENGTH: 5
<212> TYPE: PRT
<213> ORGANISM: Homo sapiens

<400> SEQUENCE: 117

Ser Pro Pro Gly Lys
1               5

<210> SEQ ID NO 118
<211> LENGTH: 5
<212> TYPE: PRT
<213> ORGANISM: Homo sapiens

<400> SEQUENCE: 118

Pro Pro Gly Lys Pro
1               5

<210> SEQ ID NO 119
<211> LENGTH: 5
<212> TYPE: PRT
<213> ORGANISM: Homo sapiens

<400> SEQUENCE: 119

Pro Gly Lys Pro Gln
1               5

<210> SEQ ID NO 120
<211> LENGTH: 5
<212> TYPE: PRT
<213> ORGANISM: Homo sapiens

<400> SEQUENCE: 120

Gly Lys Pro Gln Gly
1               5

<210> SEQ ID NO 121
```

```
<211> LENGTH: 5
<212> TYPE: PRT
<213> ORGANISM: Homo sapiens

<400> SEQUENCE: 121

Lys Pro Gln Gly Pro
1               5

<210> SEQ ID NO 122
<211> LENGTH: 5
<212> TYPE: PRT
<213> ORGANISM: Homo sapiens

<400> SEQUENCE: 122

Pro Gln Gly Pro Pro
1               5

<210> SEQ ID NO 123
<211> LENGTH: 5
<212> TYPE: PRT
<213> ORGANISM: Homo sapiens

<400> SEQUENCE: 123

Gln Gly Pro Pro Pro
1               5

<210> SEQ ID NO 124
<211> LENGTH: 5
<212> TYPE: PRT
<213> ORGANISM: Homo sapiens

<400> SEQUENCE: 124

Gly Pro Pro Pro Gln
1               5

<210> SEQ ID NO 125
<211> LENGTH: 5
<212> TYPE: PRT
<213> ORGANISM: Homo sapiens

<400> SEQUENCE: 125

Pro Pro Pro Gln Gly
1               5

<210> SEQ ID NO 126
<211> LENGTH: 5
<212> TYPE: PRT
<213> ORGANISM: Homo sapiens

<400> SEQUENCE: 126

Pro Pro Gln Gly Gly
1               5

<210> SEQ ID NO 127
<211> LENGTH: 5
<212> TYPE: PRT
<213> ORGANISM: Homo sapiens

<400> SEQUENCE: 127

Pro Gln Gly Gly Asn
1               5

<210> SEQ ID NO 128
<211> LENGTH: 5
<212> TYPE: PRT
```

```
<213> ORGANISM: Homo sapiens

<400> SEQUENCE: 128

Gln Gly Gly Asn Gln
1               5

<210> SEQ ID NO 129
<211> LENGTH: 5
<212> TYPE: PRT
<213> ORGANISM: Homo sapiens

<400> SEQUENCE: 129

Gly Gly Asn Gln Pro
1               5

<210> SEQ ID NO 130
<211> LENGTH: 5
<212> TYPE: PRT
<213> ORGANISM: Homo sapiens

<400> SEQUENCE: 130

Gly Asn Gln Pro Gln
1               5

<210> SEQ ID NO 131
<211> LENGTH: 5
<212> TYPE: PRT
<213> ORGANISM: Homo sapiens

<400> SEQUENCE: 131

Asn Gln Pro Gln Gly
1               5

<210> SEQ ID NO 132
<211> LENGTH: 5
<212> TYPE: PRT
<213> ORGANISM: Homo sapiens

<400> SEQUENCE: 132

Gln Pro Gln Gly Pro
1               5

<210> SEQ ID NO 133
<211> LENGTH: 5
<212> TYPE: PRT
<213> ORGANISM: Homo sapiens

<400> SEQUENCE: 133

Pro Gln Gly Pro Pro
1               5

<210> SEQ ID NO 134
<211> LENGTH: 5
<212> TYPE: PRT
<213> ORGANISM: Homo sapiens

<400> SEQUENCE: 134

Gln Gly Pro Pro Pro
1               5

<210> SEQ ID NO 135
<211> LENGTH: 5
<212> TYPE: PRT
<213> ORGANISM: Homo sapiens
```

```
<400> SEQUENCE: 135

Gly Pro Pro Pro Pro
1               5

<210> SEQ ID NO 136
<211> LENGTH: 5
<212> TYPE: PRT
<213> ORGANISM: Homo sapiens

<400> SEQUENCE: 136

Pro Pro Pro Pro Pro
1               5

<210> SEQ ID NO 137
<211> LENGTH: 5
<212> TYPE: PRT
<213> ORGANISM: Homo sapiens

<400> SEQUENCE: 137

Pro Pro Pro Pro Gly
1               5

<210> SEQ ID NO 138
<211> LENGTH: 5
<212> TYPE: PRT
<213> ORGANISM: Homo sapiens

<400> SEQUENCE: 138

Pro Pro Pro Gly Lys
1               5

<210> SEQ ID NO 139
<211> LENGTH: 5
<212> TYPE: PRT
<213> ORGANISM: Homo sapiens

<400> SEQUENCE: 139

Pro Pro Gly Lys Pro
1               5

<210> SEQ ID NO 140
<211> LENGTH: 5
<212> TYPE: PRT
<213> ORGANISM: Homo sapiens

<400> SEQUENCE: 140

Pro Gly Lys Pro Gln
1               5

<210> SEQ ID NO 141
<211> LENGTH: 5
<212> TYPE: PRT
<213> ORGANISM: Homo sapiens

<400> SEQUENCE: 141

Gly Lys Pro Gln Gly
1               5

<210> SEQ ID NO 142
<211> LENGTH: 5
<212> TYPE: PRT
<213> ORGANISM: Homo sapiens

<400> SEQUENCE: 142
```

Lys Pro Gln Gly Pro
1               5

<210> SEQ ID NO 143
<211> LENGTH: 5
<212> TYPE: PRT
<213> ORGANISM: Homo sapiens

<400> SEQUENCE: 143

Pro Gln Gly Pro Pro
1               5

<210> SEQ ID NO 144
<211> LENGTH: 5
<212> TYPE: PRT
<213> ORGANISM: Homo sapiens

<400> SEQUENCE: 144

Gln Gly Pro Pro Pro
1               5

<210> SEQ ID NO 145
<211> LENGTH: 5
<212> TYPE: PRT
<213> ORGANISM: Homo sapiens

<400> SEQUENCE: 145

Gly Pro Pro Pro Gln
1               5

<210> SEQ ID NO 146
<211> LENGTH: 5
<212> TYPE: PRT
<213> ORGANISM: Homo sapiens

<400> SEQUENCE: 146

Pro Pro Pro Gln Gly
1               5

<210> SEQ ID NO 147
<211> LENGTH: 5
<212> TYPE: PRT
<213> ORGANISM: Homo sapiens

<400> SEQUENCE: 147

Pro Pro Gln Gly Gly
1               5

<210> SEQ ID NO 148
<211> LENGTH: 5
<212> TYPE: PRT
<213> ORGANISM: Homo sapiens

<400> SEQUENCE: 148

Pro Gln Gly Gly Asn
1               5

<210> SEQ ID NO 149
<211> LENGTH: 5
<212> TYPE: PRT
<213> ORGANISM: Homo sapiens

<400> SEQUENCE: 149

Gln Gly Gly Asn Lys
1               5

```
<210> SEQ ID NO 150
<211> LENGTH: 5
<212> TYPE: PRT
<213> ORGANISM: Homo sapiens

<400> SEQUENCE: 150

Gly Gly Asn Lys Pro
1               5

<210> SEQ ID NO 151
<211> LENGTH: 5
<212> TYPE: PRT
<213> ORGANISM: Homo sapiens

<400> SEQUENCE: 151

Gly Asn Lys Pro Gln
1               5

<210> SEQ ID NO 152
<211> LENGTH: 5
<212> TYPE: PRT
<213> ORGANISM: Homo sapiens

<400> SEQUENCE: 152

Asn Lys Pro Gln Gly
1               5

<210> SEQ ID NO 153
<211> LENGTH: 5
<212> TYPE: PRT
<213> ORGANISM: Homo sapiens

<400> SEQUENCE: 153

Lys Pro Gln Gly Pro
1               5

<210> SEQ ID NO 154
<211> LENGTH: 5
<212> TYPE: PRT
<213> ORGANISM: Homo sapiens

<400> SEQUENCE: 154

Pro Gln Gly Pro Pro
1               5

<210> SEQ ID NO 155
<211> LENGTH: 5
<212> TYPE: PRT
<213> ORGANISM: Homo sapiens

<400> SEQUENCE: 155

Gln Gly Pro Pro Pro
1               5

<210> SEQ ID NO 156
<211> LENGTH: 5
<212> TYPE: PRT
<213> ORGANISM: Homo sapiens

<400> SEQUENCE: 156

Gly Pro Pro Pro Pro
1               5
```

```
<210> SEQ ID NO 157
<211> LENGTH: 5
<212> TYPE: PRT
<213> ORGANISM: Homo sapiens

<400> SEQUENCE: 157

Pro Pro Pro Pro Gly
1               5

<210> SEQ ID NO 158
<211> LENGTH: 5
<212> TYPE: PRT
<213> ORGANISM: Homo sapiens

<400> SEQUENCE: 158

Pro Pro Pro Gly Lys
1               5

<210> SEQ ID NO 159
<211> LENGTH: 5
<212> TYPE: PRT
<213> ORGANISM: Homo sapiens

<400> SEQUENCE: 159

Pro Pro Gly Lys Pro
1               5

<210> SEQ ID NO 160
<211> LENGTH: 5
<212> TYPE: PRT
<213> ORGANISM: Homo sapiens

<400> SEQUENCE: 160

Pro Gly Lys Pro Gln
1               5

<210> SEQ ID NO 161
<211> LENGTH: 5
<212> TYPE: PRT
<213> ORGANISM: Homo sapiens

<400> SEQUENCE: 161

Gly Lys Pro Gln Gly
1               5

<210> SEQ ID NO 162
<211> LENGTH: 5
<212> TYPE: PRT
<213> ORGANISM: Homo sapiens

<400> SEQUENCE: 162

Lys Pro Gln Gly Pro
1               5

<210> SEQ ID NO 163
<211> LENGTH: 5
<212> TYPE: PRT
<213> ORGANISM: Homo sapiens

<400> SEQUENCE: 163

Pro Gln Gly Pro Pro
1               5

<210> SEQ ID NO 164
<211> LENGTH: 5
```

```
<212> TYPE: PRT
<213> ORGANISM: Homo sapiens

<400> SEQUENCE: 164

Gln Gly Pro Pro Pro
1               5

<210> SEQ ID NO 165
<211> LENGTH: 5
<212> TYPE: PRT
<213> ORGANISM: Homo sapiens

<400> SEQUENCE: 165

Gly Pro Pro Pro Gln
1               5

<210> SEQ ID NO 166
<211> LENGTH: 5
<212> TYPE: PRT
<213> ORGANISM: Homo sapiens

<400> SEQUENCE: 166

Pro Pro Pro Gln Gly
1               5

<210> SEQ ID NO 167
<211> LENGTH: 5
<212> TYPE: PRT
<213> ORGANISM: Homo sapiens

<400> SEQUENCE: 167

Pro Pro Gln Gly Asp
1               5

<210> SEQ ID NO 168
<211> LENGTH: 5
<212> TYPE: PRT
<213> ORGANISM: Homo sapiens

<400> SEQUENCE: 168

Pro Gln Gly Asp Asn
1               5

<210> SEQ ID NO 169
<211> LENGTH: 5
<212> TYPE: PRT
<213> ORGANISM: Homo sapiens

<400> SEQUENCE: 169

Gln Gly Asp Asn Lys
1               5

<210> SEQ ID NO 170
<211> LENGTH: 5
<212> TYPE: PRT
<213> ORGANISM: Homo sapiens

<400> SEQUENCE: 170

Gly Asp Asn Lys Ser
1               5

<210> SEQ ID NO 171
<211> LENGTH: 5
<212> TYPE: PRT
<213> ORGANISM: Homo sapiens
```

```
<400> SEQUENCE: 171

Asp Asn Lys Ser Arg
1               5

<210> SEQ ID NO 172
<211> LENGTH: 5
<212> TYPE: PRT
<213> ORGANISM: Homo sapiens

<400> SEQUENCE: 172

Asn Lys Ser Arg Ser
1               5

<210> SEQ ID NO 173
<211> LENGTH: 5
<212> TYPE: PRT
<213> ORGANISM: Homo sapiens

<400> SEQUENCE: 173

Lys Ser Arg Ser Ser
1               5

<210> SEQ ID NO 174
<211> LENGTH: 5
<212> TYPE: PRT
<213> ORGANISM: Homo sapiens

<400> SEQUENCE: 174

Ser Arg Ser Ser Arg
1               5

<210> SEQ ID NO 175
<211> LENGTH: 5
<212> TYPE: PRT
<213> ORGANISM: Homo sapiens

<400> SEQUENCE: 175

Arg Ser Ser Arg Ser
1               5

<210> SEQ ID NO 176
<211> LENGTH: 5
<212> TYPE: PRT
<213> ORGANISM: Homo sapiens

<400> SEQUENCE: 176

Ser Ser Arg Ser Pro
1               5

<210> SEQ ID NO 177
<211> LENGTH: 5
<212> TYPE: PRT
<213> ORGANISM: Homo sapiens

<400> SEQUENCE: 177

Ser Arg Ser Pro Pro
1               5

<210> SEQ ID NO 178
<211> LENGTH: 5
<212> TYPE: PRT
<213> ORGANISM: Homo sapiens

<400> SEQUENCE: 178
```

```
Arg Ser Pro Pro Gly
1               5

<210> SEQ ID NO 179
<211> LENGTH: 5
<212> TYPE: PRT
<213> ORGANISM: Homo sapiens

<400> SEQUENCE: 179

Ser Pro Pro Gly Lys
1               5

<210> SEQ ID NO 180
<211> LENGTH: 5
<212> TYPE: PRT
<213> ORGANISM: Homo sapiens

<400> SEQUENCE: 180

Pro Pro Gly Lys Pro
1               5

<210> SEQ ID NO 181
<211> LENGTH: 5
<212> TYPE: PRT
<213> ORGANISM: Homo sapiens

<400> SEQUENCE: 181

Pro Gly Lys Pro Gln
1               5

<210> SEQ ID NO 182
<211> LENGTH: 5
<212> TYPE: PRT
<213> ORGANISM: Homo sapiens

<400> SEQUENCE: 182

Gly Lys Pro Gln Gly
1               5

<210> SEQ ID NO 183
<211> LENGTH: 5
<212> TYPE: PRT
<213> ORGANISM: Homo sapiens

<400> SEQUENCE: 183

Lys Pro Gln Gly Pro
1               5

<210> SEQ ID NO 184
<211> LENGTH: 5
<212> TYPE: PRT
<213> ORGANISM: Homo sapiens

<400> SEQUENCE: 184

Pro Gln Gly Pro Pro
1               5

<210> SEQ ID NO 185
<211> LENGTH: 5
<212> TYPE: PRT
<213> ORGANISM: Homo sapiens

<400> SEQUENCE: 185

Gln Gly Pro Pro Pro
```

```
1               5

<210> SEQ ID NO 186
<211> LENGTH: 5
<212> TYPE: PRT
<213> ORGANISM: Homo sapiens

<400> SEQUENCE: 186

Gly Pro Pro Pro Gln
1               5

<210> SEQ ID NO 187
<211> LENGTH: 5
<212> TYPE: PRT
<213> ORGANISM: Homo sapiens

<400> SEQUENCE: 187

Pro Pro Pro Gln Gly
1               5

<210> SEQ ID NO 188
<211> LENGTH: 5
<212> TYPE: PRT
<213> ORGANISM: Homo sapiens

<400> SEQUENCE: 188

Pro Pro Gln Gly Gly
1               5

<210> SEQ ID NO 189
<211> LENGTH: 5
<212> TYPE: PRT
<213> ORGANISM: Homo sapiens

<400> SEQUENCE: 189

Pro Gln Gly Gly Asn
1               5

<210> SEQ ID NO 190
<211> LENGTH: 5
<212> TYPE: PRT
<213> ORGANISM: Homo sapiens

<400> SEQUENCE: 190

Gln Gly Gly Asn Gln
1               5

<210> SEQ ID NO 191
<211> LENGTH: 5
<212> TYPE: PRT
<213> ORGANISM: Homo sapiens

<400> SEQUENCE: 191

Gly Gly Asn Gln Pro
1               5

<210> SEQ ID NO 192
<211> LENGTH: 5
<212> TYPE: PRT
<213> ORGANISM: Homo sapiens

<400> SEQUENCE: 192

Gly Asn Gln Pro Gln
1               5
```

<210> SEQ ID NO 193
<211> LENGTH: 5
<212> TYPE: PRT
<213> ORGANISM: Homo sapiens

<400> SEQUENCE: 193

Asn Gln Pro Gln Gly
1               5

<210> SEQ ID NO 194
<211> LENGTH: 5
<212> TYPE: PRT
<213> ORGANISM: Homo sapiens

<400> SEQUENCE: 194

Gln Pro Gln Gly Pro
1               5

<210> SEQ ID NO 195
<211> LENGTH: 5
<212> TYPE: PRT
<213> ORGANISM: Homo sapiens

<400> SEQUENCE: 195

Pro Gln Gly Pro Pro
1               5

<210> SEQ ID NO 196
<211> LENGTH: 5
<212> TYPE: PRT
<213> ORGANISM: Homo sapiens

<400> SEQUENCE: 196

Gln Gly Pro Pro Pro
1               5

<210> SEQ ID NO 197
<211> LENGTH: 5
<212> TYPE: PRT
<213> ORGANISM: Homo sapiens

<400> SEQUENCE: 197

Gly Pro Pro Pro Pro
1               5

<210> SEQ ID NO 198
<211> LENGTH: 5
<212> TYPE: PRT
<213> ORGANISM: Homo sapiens

<400> SEQUENCE: 198

Pro Pro Pro Pro Pro
1               5

<210> SEQ ID NO 199
<211> LENGTH: 5
<212> TYPE: PRT
<213> ORGANISM: Homo sapiens

<400> SEQUENCE: 199

Pro Pro Pro Pro Gly
1               5

<210> SEQ ID NO 200

```
<211> LENGTH: 5
<212> TYPE: PRT
<213> ORGANISM: Homo sapiens

<400> SEQUENCE: 200

Pro Pro Pro Gly Lys
1               5

<210> SEQ ID NO 201
<211> LENGTH: 5
<212> TYPE: PRT
<213> ORGANISM: Homo sapiens

<400> SEQUENCE: 201

Pro Pro Gly Lys Pro
1               5

<210> SEQ ID NO 202
<211> LENGTH: 5
<212> TYPE: PRT
<213> ORGANISM: Homo sapiens

<400> SEQUENCE: 202

Pro Gly Lys Pro Gln
1               5

<210> SEQ ID NO 203
<211> LENGTH: 5
<212> TYPE: PRT
<213> ORGANISM: Homo sapiens

<400> SEQUENCE: 203

Gly Lys Pro Gln Gly
1               5

<210> SEQ ID NO 204
<211> LENGTH: 5
<212> TYPE: PRT
<213> ORGANISM: Homo sapiens

<400> SEQUENCE: 204

Lys Pro Gln Gly Pro
1               5

<210> SEQ ID NO 205
<211> LENGTH: 5
<212> TYPE: PRT
<213> ORGANISM: Homo sapiens

<400> SEQUENCE: 205

Pro Gln Gly Pro Pro
1               5

<210> SEQ ID NO 206
<211> LENGTH: 5
<212> TYPE: PRT
<213> ORGANISM: Homo sapiens

<400> SEQUENCE: 206

Gln Gly Pro Pro Pro
1               5

<210> SEQ ID NO 207
<211> LENGTH: 5
<212> TYPE: PRT
```

```
<213> ORGANISM: Homo sapiens

<400> SEQUENCE: 207

Gly Pro Pro Pro Gln
1               5

<210> SEQ ID NO 208
<211> LENGTH: 5
<212> TYPE: PRT
<213> ORGANISM: Homo sapiens

<400> SEQUENCE: 208

Pro Pro Pro Gln Gly
1               5

<210> SEQ ID NO 209
<211> LENGTH: 5
<212> TYPE: PRT
<213> ORGANISM: Homo sapiens

<400> SEQUENCE: 209

Pro Pro Gln Gly Gly
1               5

<210> SEQ ID NO 210
<211> LENGTH: 5
<212> TYPE: PRT
<213> ORGANISM: Homo sapiens

<400> SEQUENCE: 210

Pro Gln Gly Gly Asn
1               5

<210> SEQ ID NO 211
<211> LENGTH: 5
<212> TYPE: PRT
<213> ORGANISM: Homo sapiens

<400> SEQUENCE: 211

Gln Gly Gly Asn Lys
1               5

<210> SEQ ID NO 212
<211> LENGTH: 5
<212> TYPE: PRT
<213> ORGANISM: Homo sapiens

<400> SEQUENCE: 212

Gly Gly Asn Lys Pro
1               5

<210> SEQ ID NO 213
<211> LENGTH: 5
<212> TYPE: PRT
<213> ORGANISM: Homo sapiens

<400> SEQUENCE: 213

Gly Asn Lys Pro Gln
1               5

<210> SEQ ID NO 214
<211> LENGTH: 5
<212> TYPE: PRT
<213> ORGANISM: Homo sapiens
```

```
<400> SEQUENCE: 214

Asn Lys Pro Gln Gly
1               5

<210> SEQ ID NO 215
<211> LENGTH: 5
<212> TYPE: PRT
<213> ORGANISM: Homo sapiens

<400> SEQUENCE: 215

Lys Pro Gln Gly Pro
1               5

<210> SEQ ID NO 216
<211> LENGTH: 5
<212> TYPE: PRT
<213> ORGANISM: Homo sapiens

<400> SEQUENCE: 216

Pro Gln Gly Pro Pro
1               5

<210> SEQ ID NO 217
<211> LENGTH: 5
<212> TYPE: PRT
<213> ORGANISM: Homo sapiens

<400> SEQUENCE: 217

Gln Gly Pro Pro Pro
1               5

<210> SEQ ID NO 218
<211> LENGTH: 5
<212> TYPE: PRT
<213> ORGANISM: Homo sapiens

<400> SEQUENCE: 218

Gly Pro Pro Pro Pro
1               5

<210> SEQ ID NO 219
<211> LENGTH: 5
<212> TYPE: PRT
<213> ORGANISM: Homo sapiens

<400> SEQUENCE: 219

Pro Pro Pro Pro Gly
1               5

<210> SEQ ID NO 220
<211> LENGTH: 5
<212> TYPE: PRT
<213> ORGANISM: Homo sapiens

<400> SEQUENCE: 220

Pro Pro Pro Gly Lys
1               5

<210> SEQ ID NO 221
<211> LENGTH: 5
<212> TYPE: PRT
<213> ORGANISM: Homo sapiens

<400> SEQUENCE: 221
```

Pro Pro Gly Lys Pro
1               5

<210> SEQ ID NO 222
<211> LENGTH: 5
<212> TYPE: PRT
<213> ORGANISM: Homo sapiens

<400> SEQUENCE: 222

Pro Gly Lys Pro Gln
1               5

<210> SEQ ID NO 223
<211> LENGTH: 5
<212> TYPE: PRT
<213> ORGANISM: Homo sapiens

<400> SEQUENCE: 223

Gly Lys Pro Gln Gly
1               5

<210> SEQ ID NO 224
<211> LENGTH: 5
<212> TYPE: PRT
<213> ORGANISM: Homo sapiens

<400> SEQUENCE: 224

Lys Pro Gln Gly Pro
1               5

<210> SEQ ID NO 225
<211> LENGTH: 5
<212> TYPE: PRT
<213> ORGANISM: Homo sapiens

<400> SEQUENCE: 225

Pro Gln Gly Pro Pro
1               5

<210> SEQ ID NO 226
<211> LENGTH: 5
<212> TYPE: PRT
<213> ORGANISM: Homo sapiens

<400> SEQUENCE: 226

Gln Gly Pro Pro Pro
1               5

<210> SEQ ID NO 227
<211> LENGTH: 5
<212> TYPE: PRT
<213> ORGANISM: Homo sapiens

<400> SEQUENCE: 227

Gly Pro Pro Pro Gln
1               5

<210> SEQ ID NO 228
<211> LENGTH: 5
<212> TYPE: PRT
<213> ORGANISM: Homo sapiens

<400> SEQUENCE: 228

Pro Pro Pro Gln Gly
1               5

<210> SEQ ID NO 229
<211> LENGTH: 5
<212> TYPE: PRT
<213> ORGANISM: Homo sapiens

<400> SEQUENCE: 229

Pro Pro Gln Gly Asp
1               5

<210> SEQ ID NO 230
<211> LENGTH: 5
<212> TYPE: PRT
<213> ORGANISM: Homo sapiens

<400> SEQUENCE: 230

Pro Gln Gly Asp Asn
1               5

<210> SEQ ID NO 231
<211> LENGTH: 5
<212> TYPE: PRT
<213> ORGANISM: Homo sapiens

<400> SEQUENCE: 231

Gln Gly Asp Asn Lys
1               5

<210> SEQ ID NO 232
<211> LENGTH: 5
<212> TYPE: PRT
<213> ORGANISM: Homo sapiens

<400> SEQUENCE: 232

Gly Asp Asn Lys Ser
1               5

<210> SEQ ID NO 233
<211> LENGTH: 5
<212> TYPE: PRT
<213> ORGANISM: Homo sapiens

<400> SEQUENCE: 233

Asp Asn Lys Ser Gln
1               5

<210> SEQ ID NO 234
<211> LENGTH: 5
<212> TYPE: PRT
<213> ORGANISM: Homo sapiens

<400> SEQUENCE: 234

Asn Lys Ser Gln Ser
1               5

<210> SEQ ID NO 235
<211> LENGTH: 5
<212> TYPE: PRT
<213> ORGANISM: Homo sapiens

<400> SEQUENCE: 235

Lys Ser Gln Ser Ala
1               5

```
<210> SEQ ID NO 236
<211> LENGTH: 5
<212> TYPE: PRT
<213> ORGANISM: Homo sapiens

<400> SEQUENCE: 236

Ser Gln Ser Ala Arg
1               5

<210> SEQ ID NO 237
<211> LENGTH: 5
<212> TYPE: PRT
<213> ORGANISM: Homo sapiens

<400> SEQUENCE: 237

Gln Ser Ala Arg Ser
1               5

<210> SEQ ID NO 238
<211> LENGTH: 5
<212> TYPE: PRT
<213> ORGANISM: Homo sapiens

<400> SEQUENCE: 238

Ser Ala Arg Ser Pro
1               5

<210> SEQ ID NO 239
<211> LENGTH: 5
<212> TYPE: PRT
<213> ORGANISM: Homo sapiens

<400> SEQUENCE: 239

Ala Arg Ser Pro Pro
1               5

<210> SEQ ID NO 240
<211> LENGTH: 5
<212> TYPE: PRT
<213> ORGANISM: Homo sapiens

<400> SEQUENCE: 240

Arg Ser Pro Pro Gly
1               5

<210> SEQ ID NO 241
<211> LENGTH: 5
<212> TYPE: PRT
<213> ORGANISM: Homo sapiens

<400> SEQUENCE: 241

Ser Pro Pro Gly Lys
1               5

<210> SEQ ID NO 242
<211> LENGTH: 5
<212> TYPE: PRT
<213> ORGANISM: Homo sapiens

<400> SEQUENCE: 242

Pro Pro Gly Lys Pro
1               5

<210> SEQ ID NO 243
<211> LENGTH: 5
```

```
<212> TYPE: PRT
<213> ORGANISM: Homo sapiens

<400> SEQUENCE: 243

Pro Gly Lys Pro Gln
1               5

<210> SEQ ID NO 244
<211> LENGTH: 5
<212> TYPE: PRT
<213> ORGANISM: Homo sapiens

<400> SEQUENCE: 244

Gly Lys Pro Gln Gly
1               5

<210> SEQ ID NO 245
<211> LENGTH: 5
<212> TYPE: PRT
<213> ORGANISM: Homo sapiens

<400> SEQUENCE: 245

Lys Pro Gln Gly Pro
1               5

<210> SEQ ID NO 246
<211> LENGTH: 5
<212> TYPE: PRT
<213> ORGANISM: Homo sapiens

<400> SEQUENCE: 246

Pro Gln Gly Pro Pro
1               5

<210> SEQ ID NO 247
<211> LENGTH: 5
<212> TYPE: PRT
<213> ORGANISM: Homo sapiens

<400> SEQUENCE: 247

Gln Gly Pro Pro Pro
1               5

<210> SEQ ID NO 248
<211> LENGTH: 5
<212> TYPE: PRT
<213> ORGANISM: Homo sapiens

<400> SEQUENCE: 248

Gly Pro Pro Pro Gln
1               5

<210> SEQ ID NO 249
<211> LENGTH: 5
<212> TYPE: PRT
<213> ORGANISM: Homo sapiens

<400> SEQUENCE: 249

Pro Pro Pro Gln Gly
1               5

<210> SEQ ID NO 250
<211> LENGTH: 5
<212> TYPE: PRT
<213> ORGANISM: Homo sapiens
```

<400> SEQUENCE: 250

Pro Pro Gln Gly Gly
1               5

<210> SEQ ID NO 251
<211> LENGTH: 5
<212> TYPE: PRT
<213> ORGANISM: Homo sapiens

<400> SEQUENCE: 251

Pro Gln Gly Gly Asn
1               5

<210> SEQ ID NO 252
<211> LENGTH: 5
<212> TYPE: PRT
<213> ORGANISM: Homo sapiens

<400> SEQUENCE: 252

Gln Gly Gly Asn Gln
1               5

<210> SEQ ID NO 253
<211> LENGTH: 5
<212> TYPE: PRT
<213> ORGANISM: Homo sapiens

<400> SEQUENCE: 253

Gly Gly Asn Gln Pro
1               5

<210> SEQ ID NO 254
<211> LENGTH: 5
<212> TYPE: PRT
<213> ORGANISM: Homo sapiens

<400> SEQUENCE: 254

Gly Asn Gln Pro Gln
1               5

<210> SEQ ID NO 255
<211> LENGTH: 5
<212> TYPE: PRT
<213> ORGANISM: Homo sapiens

<400> SEQUENCE: 255

Asn Gln Pro Gln Gly
1               5

<210> SEQ ID NO 256
<211> LENGTH: 5
<212> TYPE: PRT
<213> ORGANISM: Homo sapiens

<400> SEQUENCE: 256

Gln Pro Gln Gly Pro
1               5

<210> SEQ ID NO 257
<211> LENGTH: 5
<212> TYPE: PRT
<213> ORGANISM: Homo sapiens

<400> SEQUENCE: 257

```
Pro Gln Gly Pro Pro
1               5

<210> SEQ ID NO 258
<211> LENGTH: 5
<212> TYPE: PRT
<213> ORGANISM: Homo sapiens

<400> SEQUENCE: 258

Gln Gly Pro Pro Pro
1               5

<210> SEQ ID NO 259
<211> LENGTH: 5
<212> TYPE: PRT
<213> ORGANISM: Homo sapiens

<400> SEQUENCE: 259

Gly Pro Pro Pro Pro
1               5

<210> SEQ ID NO 260
<211> LENGTH: 5
<212> TYPE: PRT
<213> ORGANISM: Homo sapiens

<400> SEQUENCE: 260

Pro Pro Pro Pro Pro
1               5

<210> SEQ ID NO 261
<211> LENGTH: 5
<212> TYPE: PRT
<213> ORGANISM: Homo sapiens

<400> SEQUENCE: 261

Pro Pro Pro Pro Gly
1               5

<210> SEQ ID NO 262
<211> LENGTH: 5
<212> TYPE: PRT
<213> ORGANISM: Homo sapiens

<400> SEQUENCE: 262

Pro Pro Pro Gly Lys
1               5

<210> SEQ ID NO 263
<211> LENGTH: 5
<212> TYPE: PRT
<213> ORGANISM: Homo sapiens

<400> SEQUENCE: 263

Pro Pro Gly Lys Pro
1               5

<210> SEQ ID NO 264
<211> LENGTH: 5
<212> TYPE: PRT
<213> ORGANISM: Homo sapiens

<400> SEQUENCE: 264

Pro Gly Lys Pro Gln
```

```
1               5

<210> SEQ ID NO 265
<211> LENGTH: 5
<212> TYPE: PRT
<213> ORGANISM: Homo sapiens

<400> SEQUENCE: 265

Gly Lys Pro Gln Gly
1               5

<210> SEQ ID NO 266
<211> LENGTH: 5
<212> TYPE: PRT
<213> ORGANISM: Homo sapiens

<400> SEQUENCE: 266

Lys Pro Gln Gly Pro
1               5

<210> SEQ ID NO 267
<211> LENGTH: 5
<212> TYPE: PRT
<213> ORGANISM: Homo sapiens

<400> SEQUENCE: 267

Pro Gln Gly Pro Pro
1               5

<210> SEQ ID NO 268
<211> LENGTH: 5
<212> TYPE: PRT
<213> ORGANISM: Homo sapiens

<400> SEQUENCE: 268

Gln Gly Pro Pro Pro
1               5

<210> SEQ ID NO 269
<211> LENGTH: 5
<212> TYPE: PRT
<213> ORGANISM: Homo sapiens

<400> SEQUENCE: 269

Gly Pro Pro Pro Gln
1               5

<210> SEQ ID NO 270
<211> LENGTH: 5
<212> TYPE: PRT
<213> ORGANISM: Homo sapiens

<400> SEQUENCE: 270

Pro Pro Pro Gln Gly
1               5

<210> SEQ ID NO 271
<211> LENGTH: 5
<212> TYPE: PRT
<213> ORGANISM: Homo sapiens

<400> SEQUENCE: 271

Pro Pro Gln Gly Gly
1               5
```

```
<210> SEQ ID NO 272
<211> LENGTH: 5
<212> TYPE: PRT
<213> ORGANISM: Homo sapiens

<400> SEQUENCE: 272

Pro Gln Gly Gly Asn
1               5

<210> SEQ ID NO 273
<211> LENGTH: 5
<212> TYPE: PRT
<213> ORGANISM: Homo sapiens

<400> SEQUENCE: 273

Gln Gly Gly Asn Lys
1               5

<210> SEQ ID NO 274
<211> LENGTH: 5
<212> TYPE: PRT
<213> ORGANISM: Homo sapiens

<400> SEQUENCE: 274

Gly Gly Asn Lys Ser
1               5

<210> SEQ ID NO 275
<211> LENGTH: 5
<212> TYPE: PRT
<213> ORGANISM: Homo sapiens

<400> SEQUENCE: 275

Gly Asn Lys Ser Gln
1               5

<210> SEQ ID NO 276
<211> LENGTH: 5
<212> TYPE: PRT
<213> ORGANISM: Homo sapiens

<400> SEQUENCE: 276

Asn Lys Ser Gln Gly
1               5

<210> SEQ ID NO 277
<211> LENGTH: 5
<212> TYPE: PRT
<213> ORGANISM: Homo sapiens

<400> SEQUENCE: 277

Lys Ser Gln Gly Pro
1               5

<210> SEQ ID NO 278
<211> LENGTH: 5
<212> TYPE: PRT
<213> ORGANISM: Homo sapiens

<400> SEQUENCE: 278

Ser Gln Gly Pro Pro
1               5

<210> SEQ ID NO 279
```

```
<211> LENGTH: 5
<212> TYPE: PRT
<213> ORGANISM: Homo sapiens

<400> SEQUENCE: 279

Gln Gly Pro Pro Pro
1               5

<210> SEQ ID NO 280
<211> LENGTH: 5
<212> TYPE: PRT
<213> ORGANISM: Homo sapiens

<400> SEQUENCE: 280

Gly Pro Pro Pro Pro
1               5

<210> SEQ ID NO 281
<211> LENGTH: 5
<212> TYPE: PRT
<213> ORGANISM: Homo sapiens

<400> SEQUENCE: 281

Pro Pro Pro Pro Gly
1               5

<210> SEQ ID NO 282
<211> LENGTH: 5
<212> TYPE: PRT
<213> ORGANISM: Homo sapiens

<400> SEQUENCE: 282

Pro Pro Pro Gly Lys
1               5

<210> SEQ ID NO 283
<211> LENGTH: 5
<212> TYPE: PRT
<213> ORGANISM: Homo sapiens

<400> SEQUENCE: 283

Pro Pro Gly Lys Pro
1               5

<210> SEQ ID NO 284
<211> LENGTH: 5
<212> TYPE: PRT
<213> ORGANISM: Homo sapiens

<400> SEQUENCE: 284

Pro Gly Lys Pro Gln
1               5

<210> SEQ ID NO 285
<211> LENGTH: 5
<212> TYPE: PRT
<213> ORGANISM: Homo sapiens

<400> SEQUENCE: 285

Gly Lys Pro Gln Gly
1               5

<210> SEQ ID NO 286
<211> LENGTH: 5
<212> TYPE: PRT
```

```
<213> ORGANISM: Homo sapiens

<400> SEQUENCE: 286

Lys Pro Gln Gly Pro
1               5

<210> SEQ ID NO 287
<211> LENGTH: 5
<212> TYPE: PRT
<213> ORGANISM: Homo sapiens

<400> SEQUENCE: 287

Pro Gln Gly Pro Pro
1               5

<210> SEQ ID NO 288
<211> LENGTH: 5
<212> TYPE: PRT
<213> ORGANISM: Homo sapiens

<400> SEQUENCE: 288

Gln Gly Pro Pro Pro
1               5

<210> SEQ ID NO 289
<211> LENGTH: 5
<212> TYPE: PRT
<213> ORGANISM: Homo sapiens

<400> SEQUENCE: 289

Gly Pro Pro Pro Gln
1               5

<210> SEQ ID NO 290
<211> LENGTH: 5
<212> TYPE: PRT
<213> ORGANISM: Homo sapiens

<400> SEQUENCE: 290

Pro Pro Pro Gln Gly
1               5

<210> SEQ ID NO 291
<211> LENGTH: 5
<212> TYPE: PRT
<213> ORGANISM: Homo sapiens

<400> SEQUENCE: 291

Pro Pro Gln Gly Gly
1               5

<210> SEQ ID NO 292
<211> LENGTH: 5
<212> TYPE: PRT
<213> ORGANISM: Homo sapiens

<400> SEQUENCE: 292

Pro Gln Gly Gly Ser
1               5

<210> SEQ ID NO 293
<211> LENGTH: 5
<212> TYPE: PRT
<213> ORGANISM: Homo sapiens
```

```
<400> SEQUENCE: 293

Gln Gly Gly Ser Lys
1               5

<210> SEQ ID NO 294
<211> LENGTH: 5
<212> TYPE: PRT
<213> ORGANISM: Homo sapiens

<400> SEQUENCE: 294

Gly Gly Ser Lys Ser
1               5

<210> SEQ ID NO 295
<211> LENGTH: 5
<212> TYPE: PRT
<213> ORGANISM: Homo sapiens

<400> SEQUENCE: 295

Gly Ser Lys Ser Arg
1               5

<210> SEQ ID NO 296
<211> LENGTH: 5
<212> TYPE: PRT
<213> ORGANISM: Homo sapiens

<400> SEQUENCE: 296

Ser Lys Ser Arg Ser
1               5

<210> SEQ ID NO 297
<211> LENGTH: 5
<212> TYPE: PRT
<213> ORGANISM: Homo sapiens

<400> SEQUENCE: 297

Lys Ser Arg Ser Ser
1               5

<210> SEQ ID NO 298
<211> LENGTH: 5
<212> TYPE: PRT
<213> ORGANISM: Homo sapiens

<400> SEQUENCE: 298

Ser Arg Ser Ser Arg
1               5

<210> SEQ ID NO 299
<211> LENGTH: 5
<212> TYPE: PRT
<213> ORGANISM: Homo sapiens

<400> SEQUENCE: 299

Arg Ser Ser Arg Ser
1               5

<210> SEQ ID NO 300
<211> LENGTH: 5
<212> TYPE: PRT
<213> ORGANISM: Homo sapiens

<400> SEQUENCE: 300
```

Ser Ser Arg Ser Pro
1               5

<210> SEQ ID NO 301
<211> LENGTH: 5
<212> TYPE: PRT
<213> ORGANISM: Homo sapiens

<400> SEQUENCE: 301

Ser Arg Ser Pro Pro
1               5

<210> SEQ ID NO 302
<211> LENGTH: 5
<212> TYPE: PRT
<213> ORGANISM: Homo sapiens

<400> SEQUENCE: 302

Arg Ser Pro Pro Gly
1               5

<210> SEQ ID NO 303
<211> LENGTH: 5
<212> TYPE: PRT
<213> ORGANISM: Homo sapiens

<400> SEQUENCE: 303

Ser Pro Pro Gly Lys
1               5

<210> SEQ ID NO 304
<211> LENGTH: 5
<212> TYPE: PRT
<213> ORGANISM: Homo sapiens

<400> SEQUENCE: 304

Pro Pro Gly Lys Pro
1               5

<210> SEQ ID NO 305
<211> LENGTH: 5
<212> TYPE: PRT
<213> ORGANISM: Homo sapiens

<400> SEQUENCE: 305

Pro Gly Lys Pro Gln
1               5

<210> SEQ ID NO 306
<211> LENGTH: 5
<212> TYPE: PRT
<213> ORGANISM: Homo sapiens

<400> SEQUENCE: 306

Gly Lys Pro Gln Gly
1               5

<210> SEQ ID NO 307
<211> LENGTH: 5
<212> TYPE: PRT
<213> ORGANISM: Homo sapiens

<400> SEQUENCE: 307

Lys Pro Gln Gly Pro
1               5

```
<210> SEQ ID NO 308
<211> LENGTH: 5
<212> TYPE: PRT
<213> ORGANISM: Homo sapiens

<400> SEQUENCE: 308

Pro Gln Gly Pro Pro
1               5

<210> SEQ ID NO 309
<211> LENGTH: 5
<212> TYPE: PRT
<213> ORGANISM: Homo sapiens

<400> SEQUENCE: 309

Gln Gly Pro Pro Pro
1               5

<210> SEQ ID NO 310
<211> LENGTH: 5
<212> TYPE: PRT
<213> ORGANISM: Homo sapiens

<400> SEQUENCE: 310

Gly Pro Pro Pro Gln
1               5

<210> SEQ ID NO 311
<211> LENGTH: 5
<212> TYPE: PRT
<213> ORGANISM: Homo sapiens

<400> SEQUENCE: 311

Pro Pro Pro Gln Gly
1               5

<210> SEQ ID NO 312
<211> LENGTH: 5
<212> TYPE: PRT
<213> ORGANISM: Homo sapiens

<400> SEQUENCE: 312

Pro Pro Gln Gly Gly
1               5

<210> SEQ ID NO 313
<211> LENGTH: 5
<212> TYPE: PRT
<213> ORGANISM: Homo sapiens

<400> SEQUENCE: 313

Pro Gln Gly Gly Asn
1               5

<210> SEQ ID NO 314
<211> LENGTH: 5
<212> TYPE: PRT
<213> ORGANISM: Homo sapiens

<400> SEQUENCE: 314

Gln Gly Gly Asn Gln
1               5
```

```
<210> SEQ ID NO 315
<211> LENGTH: 5
<212> TYPE: PRT
<213> ORGANISM: Homo sapiens

<400> SEQUENCE: 315

Gly Gly Asn Gln Pro
1               5

<210> SEQ ID NO 316
<211> LENGTH: 5
<212> TYPE: PRT
<213> ORGANISM: Homo sapiens

<400> SEQUENCE: 316

Gly Asn Gln Pro Gln
1               5

<210> SEQ ID NO 317
<211> LENGTH: 5
<212> TYPE: PRT
<213> ORGANISM: Homo sapiens

<400> SEQUENCE: 317

Asn Gln Pro Gln Gly
1               5

<210> SEQ ID NO 318
<211> LENGTH: 5
<212> TYPE: PRT
<213> ORGANISM: Homo sapiens

<400> SEQUENCE: 318

Gln Pro Gln Gly Pro
1               5

<210> SEQ ID NO 319
<211> LENGTH: 5
<212> TYPE: PRT
<213> ORGANISM: Homo sapiens

<400> SEQUENCE: 319

Pro Gln Gly Pro Pro
1               5

<210> SEQ ID NO 320
<211> LENGTH: 5
<212> TYPE: PRT
<213> ORGANISM: Homo sapiens

<400> SEQUENCE: 320

Gln Gly Pro Pro Pro
1               5

<210> SEQ ID NO 321
<211> LENGTH: 5
<212> TYPE: PRT
<213> ORGANISM: Homo sapiens

<400> SEQUENCE: 321

Gly Pro Pro Pro Pro
1               5

<210> SEQ ID NO 322
<211> LENGTH: 5
```

<212> TYPE: PRT
<213> ORGANISM: Homo sapiens

<400> SEQUENCE: 322

Pro Pro Pro Pro Pro
1               5

<210> SEQ ID NO 323
<211> LENGTH: 5
<212> TYPE: PRT
<213> ORGANISM: Homo sapiens

<400> SEQUENCE: 323

Pro Pro Pro Pro Gly
1               5

<210> SEQ ID NO 324
<211> LENGTH: 5
<212> TYPE: PRT
<213> ORGANISM: Homo sapiens

<400> SEQUENCE: 324

Pro Pro Pro Gly Lys
1               5

<210> SEQ ID NO 325
<211> LENGTH: 5
<212> TYPE: PRT
<213> ORGANISM: Homo sapiens

<400> SEQUENCE: 325

Pro Pro Gly Lys Pro
1               5

<210> SEQ ID NO 326
<211> LENGTH: 5
<212> TYPE: PRT
<213> ORGANISM: Homo sapiens

<400> SEQUENCE: 326

Pro Gly Lys Pro Gln
1               5

<210> SEQ ID NO 327
<211> LENGTH: 5
<212> TYPE: PRT
<213> ORGANISM: Homo sapiens

<400> SEQUENCE: 327

Gly Lys Pro Gln Gly
1               5

<210> SEQ ID NO 328
<211> LENGTH: 5
<212> TYPE: PRT
<213> ORGANISM: Homo sapiens

<400> SEQUENCE: 328

Lys Pro Gln Gly Pro
1               5

<210> SEQ ID NO 329
<211> LENGTH: 5
<212> TYPE: PRT
<213> ORGANISM: Homo sapiens

<400> SEQUENCE: 329

Pro Gln Gly Pro Pro
1               5

<210> SEQ ID NO 330
<211> LENGTH: 5
<212> TYPE: PRT
<213> ORGANISM: Homo sapiens

<400> SEQUENCE: 330

Gln Gly Pro Pro Pro
1               5

<210> SEQ ID NO 331
<211> LENGTH: 5
<212> TYPE: PRT
<213> ORGANISM: Homo sapiens

<400> SEQUENCE: 331

Gly Pro Pro Pro Gln
1               5

<210> SEQ ID NO 332
<211> LENGTH: 5
<212> TYPE: PRT
<213> ORGANISM: Homo sapiens

<400> SEQUENCE: 332

Pro Pro Pro Gln Gly
1               5

<210> SEQ ID NO 333
<211> LENGTH: 5
<212> TYPE: PRT
<213> ORGANISM: Homo sapiens

<400> SEQUENCE: 333

Pro Pro Gln Gly Gly
1               5

<210> SEQ ID NO 334
<211> LENGTH: 5
<212> TYPE: PRT
<213> ORGANISM: Homo sapiens

<400> SEQUENCE: 334

Pro Gln Gly Gly Asn
1               5

<210> SEQ ID NO 335
<211> LENGTH: 5
<212> TYPE: PRT
<213> ORGANISM: Homo sapiens

<400> SEQUENCE: 335

Gln Gly Gly Asn Lys
1               5

<210> SEQ ID NO 336
<211> LENGTH: 5
<212> TYPE: PRT
<213> ORGANISM: Homo sapiens

<400> SEQUENCE: 336

Gly Gly Asn Lys Pro
1               5

<210> SEQ ID NO 337
<211> LENGTH: 5
<212> TYPE: PRT
<213> ORGANISM: Homo sapiens

<400> SEQUENCE: 337

Gly Asn Lys Pro Gln
1               5

<210> SEQ ID NO 338
<211> LENGTH: 5
<212> TYPE: PRT
<213> ORGANISM: Homo sapiens

<400> SEQUENCE: 338

Asn Lys Pro Gln Gly
1               5

<210> SEQ ID NO 339
<211> LENGTH: 5
<212> TYPE: PRT
<213> ORGANISM: Homo sapiens

<400> SEQUENCE: 339

Lys Pro Gln Gly Pro
1               5

<210> SEQ ID NO 340
<211> LENGTH: 5
<212> TYPE: PRT
<213> ORGANISM: Homo sapiens

<400> SEQUENCE: 340

Pro Gln Gly Pro Pro
1               5

<210> SEQ ID NO 341
<211> LENGTH: 5
<212> TYPE: PRT
<213> ORGANISM: Homo sapiens

<400> SEQUENCE: 341

Gln Gly Pro Pro Pro
1               5

<210> SEQ ID NO 342
<211> LENGTH: 5
<212> TYPE: PRT
<213> ORGANISM: Homo sapiens

<400> SEQUENCE: 342

Gly Pro Pro Pro Pro
1               5

<210> SEQ ID NO 343
<211> LENGTH: 5
<212> TYPE: PRT
<213> ORGANISM: Homo sapiens

<400> SEQUENCE: 343

Pro Pro Pro Pro Gly

```
1               5

<210> SEQ ID NO 344
<211> LENGTH: 5
<212> TYPE: PRT
<213> ORGANISM: Homo sapiens

<400> SEQUENCE: 344

Pro Pro Pro Gly Lys
1               5

<210> SEQ ID NO 345
<211> LENGTH: 5
<212> TYPE: PRT
<213> ORGANISM: Homo sapiens

<400> SEQUENCE: 345

Pro Pro Gly Lys Pro
1               5

<210> SEQ ID NO 346
<211> LENGTH: 5
<212> TYPE: PRT
<213> ORGANISM: Homo sapiens

<400> SEQUENCE: 346

Pro Gly Lys Pro Gln
1               5

<210> SEQ ID NO 347
<211> LENGTH: 5
<212> TYPE: PRT
<213> ORGANISM: Homo sapiens

<400> SEQUENCE: 347

Gly Lys Pro Gln Gly
1               5

<210> SEQ ID NO 348
<211> LENGTH: 5
<212> TYPE: PRT
<213> ORGANISM: Homo sapiens

<400> SEQUENCE: 348

Lys Pro Gln Gly Pro
1               5

<210> SEQ ID NO 349
<211> LENGTH: 5
<212> TYPE: PRT
<213> ORGANISM: Homo sapiens

<400> SEQUENCE: 349

Pro Gln Gly Pro Pro
1               5

<210> SEQ ID NO 350
<211> LENGTH: 5
<212> TYPE: PRT
<213> ORGANISM: Homo sapiens

<400> SEQUENCE: 350

Gln Gly Pro Pro Pro
1               5
```

```
<210> SEQ ID NO 351
<211> LENGTH: 5
<212> TYPE: PRT
<213> ORGANISM: Homo sapiens

<400> SEQUENCE: 351

Gly Pro Pro Pro Gln
1               5

<210> SEQ ID NO 352
<211> LENGTH: 5
<212> TYPE: PRT
<213> ORGANISM: Homo sapiens

<400> SEQUENCE: 352

Pro Pro Pro Gln Gly
1               5

<210> SEQ ID NO 353
<211> LENGTH: 5
<212> TYPE: PRT
<213> ORGANISM: Homo sapiens

<400> SEQUENCE: 353

Pro Pro Gln Gly Gly
1               5

<210> SEQ ID NO 354
<211> LENGTH: 5
<212> TYPE: PRT
<213> ORGANISM: Homo sapiens

<400> SEQUENCE: 354

Pro Gln Gly Gly Ser
1               5

<210> SEQ ID NO 355
<211> LENGTH: 5
<212> TYPE: PRT
<213> ORGANISM: Homo sapiens

<400> SEQUENCE: 355

Gln Gly Gly Ser Lys
1               5

<210> SEQ ID NO 356
<211> LENGTH: 5
<212> TYPE: PRT
<213> ORGANISM: Homo sapiens

<400> SEQUENCE: 356

Gly Gly Ser Lys Ser
1               5

<210> SEQ ID NO 357
<211> LENGTH: 5
<212> TYPE: PRT
<213> ORGANISM: Homo sapiens

<400> SEQUENCE: 357

Gly Ser Lys Ser Arg
1               5

<210> SEQ ID NO 358
```

```
<211> LENGTH: 5
<212> TYPE: PRT
<213> ORGANISM: Homo sapiens

<400> SEQUENCE: 358

Ser Lys Ser Arg Ser
1               5

<210> SEQ ID NO 359
<211> LENGTH: 5
<212> TYPE: PRT
<213> ORGANISM: Homo sapiens

<400> SEQUENCE: 359

Lys Ser Arg Ser Ala
1               5

<210> SEQ ID NO 360
<211> LENGTH: 5
<212> TYPE: PRT
<213> ORGANISM: Homo sapiens

<400> SEQUENCE: 360

Ser Arg Ser Ala Arg
1               5

<210> SEQ ID NO 361
<211> LENGTH: 5
<212> TYPE: PRT
<213> ORGANISM: Homo sapiens

<400> SEQUENCE: 361

Arg Ser Ala Arg Ser
1               5

<210> SEQ ID NO 362
<211> LENGTH: 5
<212> TYPE: PRT
<213> ORGANISM: Homo sapiens

<400> SEQUENCE: 362

Ser Ala Arg Ser Pro
1               5

<210> SEQ ID NO 363
<211> LENGTH: 5
<212> TYPE: PRT
<213> ORGANISM: Homo sapiens

<400> SEQUENCE: 363

Ala Arg Ser Pro Pro
1               5

<210> SEQ ID NO 364
<211> LENGTH: 5
<212> TYPE: PRT
<213> ORGANISM: Homo sapiens

<400> SEQUENCE: 364

Arg Ser Pro Pro Gly
1               5

<210> SEQ ID NO 365
<211> LENGTH: 5
<212> TYPE: PRT
```

<213> ORGANISM: Homo sapiens

<400> SEQUENCE: 365

Ser Pro Pro Gly Lys
1               5

<210> SEQ ID NO 366
<211> LENGTH: 5
<212> TYPE: PRT
<213> ORGANISM: Homo sapiens

<400> SEQUENCE: 366

Pro Pro Gly Lys Pro
1               5

<210> SEQ ID NO 367
<211> LENGTH: 5
<212> TYPE: PRT
<213> ORGANISM: Homo sapiens

<400> SEQUENCE: 367

Pro Gly Lys Pro Gln
1               5

<210> SEQ ID NO 368
<211> LENGTH: 5
<212> TYPE: PRT
<213> ORGANISM: Homo sapiens

<400> SEQUENCE: 368

Gly Lys Pro Gln Gly
1               5

<210> SEQ ID NO 369
<211> LENGTH: 5
<212> TYPE: PRT
<213> ORGANISM: Homo sapiens

<400> SEQUENCE: 369

Lys Pro Gln Gly Pro
1               5

<210> SEQ ID NO 370
<211> LENGTH: 5
<212> TYPE: PRT
<213> ORGANISM: Homo sapiens

<400> SEQUENCE: 370

Pro Gln Gly Pro Pro
1               5

<210> SEQ ID NO 371
<211> LENGTH: 5
<212> TYPE: PRT
<213> ORGANISM: Homo sapiens

<400> SEQUENCE: 371

Gln Gly Pro Pro Gln
1               5

<210> SEQ ID NO 372
<211> LENGTH: 5
<212> TYPE: PRT
<213> ORGANISM: Homo sapiens

```
<400> SEQUENCE: 372

Gly Pro Pro Gln Gln
1               5

<210> SEQ ID NO 373
<211> LENGTH: 5
<212> TYPE: PRT
<213> ORGANISM: Homo sapiens

<400> SEQUENCE: 373

Pro Pro Gln Gln Glu
1               5

<210> SEQ ID NO 374
<211> LENGTH: 5
<212> TYPE: PRT
<213> ORGANISM: Homo sapiens

<400> SEQUENCE: 374

Pro Gln Gln Glu Gly
1               5

<210> SEQ ID NO 375
<211> LENGTH: 5
<212> TYPE: PRT
<213> ORGANISM: Homo sapiens

<400> SEQUENCE: 375

Gln Gln Glu Gly Asn
1               5

<210> SEQ ID NO 376
<211> LENGTH: 5
<212> TYPE: PRT
<213> ORGANISM: Homo sapiens

<400> SEQUENCE: 376

Gln Glu Gly Asn Asn
1               5

<210> SEQ ID NO 377
<211> LENGTH: 5
<212> TYPE: PRT
<213> ORGANISM: Homo sapiens

<400> SEQUENCE: 377

Glu Gly Asn Asn Pro
1               5

<210> SEQ ID NO 378
<211> LENGTH: 5
<212> TYPE: PRT
<213> ORGANISM: Homo sapiens

<400> SEQUENCE: 378

Gly Asn Asn Pro Gln
1               5

<210> SEQ ID NO 379
<211> LENGTH: 5
<212> TYPE: PRT
<213> ORGANISM: Homo sapiens

<400> SEQUENCE: 379
```

```
Asn Asn Pro Gln Gly
1               5

<210> SEQ ID NO 380
<211> LENGTH: 5
<212> TYPE: PRT
<213> ORGANISM: Homo sapiens

<400> SEQUENCE: 380

Asn Pro Gln Gly Pro
1               5

<210> SEQ ID NO 381
<211> LENGTH: 5
<212> TYPE: PRT
<213> ORGANISM: Homo sapiens

<400> SEQUENCE: 381

Pro Gln Gly Pro Pro
1               5

<210> SEQ ID NO 382
<211> LENGTH: 5
<212> TYPE: PRT
<213> ORGANISM: Homo sapiens

<400> SEQUENCE: 382

Gln Gly Pro Pro Pro
1               5

<210> SEQ ID NO 383
<211> LENGTH: 5
<212> TYPE: PRT
<213> ORGANISM: Homo sapiens

<400> SEQUENCE: 383

Gly Pro Pro Pro Pro
1               5

<210> SEQ ID NO 384
<211> LENGTH: 5
<212> TYPE: PRT
<213> ORGANISM: Homo sapiens

<400> SEQUENCE: 384

Pro Pro Pro Pro Ala
1               5

<210> SEQ ID NO 385
<211> LENGTH: 5
<212> TYPE: PRT
<213> ORGANISM: Homo sapiens

<400> SEQUENCE: 385

Pro Pro Pro Ala Gly
1               5

<210> SEQ ID NO 386
<211> LENGTH: 5
<212> TYPE: PRT
<213> ORGANISM: Homo sapiens

<400> SEQUENCE: 386

Pro Pro Ala Gly Gly
1               5
```

<210> SEQ ID NO 387
<211> LENGTH: 5
<212> TYPE: PRT
<213> ORGANISM: Homo sapiens

<400> SEQUENCE: 387

Pro Ala Gly Gly Asn
1               5

<210> SEQ ID NO 388
<211> LENGTH: 5
<212> TYPE: PRT
<213> ORGANISM: Homo sapiens

<400> SEQUENCE: 388

Ala Gly Gly Asn Pro
1               5

<210> SEQ ID NO 389
<211> LENGTH: 5
<212> TYPE: PRT
<213> ORGANISM: Homo sapiens

<400> SEQUENCE: 389

Gly Gly Asn Pro Gln
1               5

<210> SEQ ID NO 390
<211> LENGTH: 5
<212> TYPE: PRT
<213> ORGANISM: Homo sapiens

<400> SEQUENCE: 390

Gly Asn Pro Gln Gln
1               5

<210> SEQ ID NO 391
<211> LENGTH: 5
<212> TYPE: PRT
<213> ORGANISM: Homo sapiens

<400> SEQUENCE: 391

Asn Pro Gln Gln Pro
1               5

<210> SEQ ID NO 392
<211> LENGTH: 5
<212> TYPE: PRT
<213> ORGANISM: Homo sapiens

<400> SEQUENCE: 392

Pro Gln Gln Pro Gln
1               5

<210> SEQ ID NO 393
<211> LENGTH: 5
<212> TYPE: PRT
<213> ORGANISM: Homo sapiens

<400> SEQUENCE: 393

Gln Gln Pro Gln Ala
1               5

```
<210> SEQ ID NO 394
<211> LENGTH: 5
<212> TYPE: PRT
<213> ORGANISM: Homo sapiens

<400> SEQUENCE: 394

Gln Pro Gln Ala Pro
1               5

<210> SEQ ID NO 395
<211> LENGTH: 5
<212> TYPE: PRT
<213> ORGANISM: Homo sapiens

<400> SEQUENCE: 395

Pro Gln Ala Pro Pro
1               5

<210> SEQ ID NO 396
<211> LENGTH: 5
<212> TYPE: PRT
<213> ORGANISM: Homo sapiens

<400> SEQUENCE: 396

Gln Ala Pro Pro Ala
1               5

<210> SEQ ID NO 397
<211> LENGTH: 5
<212> TYPE: PRT
<213> ORGANISM: Homo sapiens

<400> SEQUENCE: 397

Ala Pro Pro Ala Gly
1               5

<210> SEQ ID NO 398
<211> LENGTH: 5
<212> TYPE: PRT
<213> ORGANISM: Homo sapiens

<400> SEQUENCE: 398

Pro Pro Ala Gly Gln
1               5

<210> SEQ ID NO 399
<211> LENGTH: 5
<212> TYPE: PRT
<213> ORGANISM: Homo sapiens

<400> SEQUENCE: 399

Pro Ala Gly Gln Pro
1               5

<210> SEQ ID NO 400
<211> LENGTH: 5
<212> TYPE: PRT
<213> ORGANISM: Homo sapiens

<400> SEQUENCE: 400

Ala Gly Gln Pro Gln
1               5

<210> SEQ ID NO 401
<211> LENGTH: 5
```

<212> TYPE: PRT
<213> ORGANISM: Homo sapiens

<400> SEQUENCE: 401

Gly Gln Pro Gln Gly
1               5

<210> SEQ ID NO 402
<211> LENGTH: 5
<212> TYPE: PRT
<213> ORGANISM: Homo sapiens

<400> SEQUENCE: 402

Gln Pro Gln Gly Pro
1               5

<210> SEQ ID NO 403
<211> LENGTH: 5
<212> TYPE: PRT
<213> ORGANISM: Homo sapiens

<400> SEQUENCE: 403

Pro Gln Gly Pro Pro
1               5

<210> SEQ ID NO 404
<211> LENGTH: 5
<212> TYPE: PRT
<213> ORGANISM: Homo sapiens

<400> SEQUENCE: 404

Gln Gly Pro Pro Arg
1               5

<210> SEQ ID NO 405
<211> LENGTH: 5
<212> TYPE: PRT
<213> ORGANISM: Homo sapiens

<400> SEQUENCE: 405

Gly Pro Pro Arg Pro
1               5

<210> SEQ ID NO 406
<211> LENGTH: 5
<212> TYPE: PRT
<213> ORGANISM: Homo sapiens

<400> SEQUENCE: 406

Pro Pro Arg Pro Pro
1               5

<210> SEQ ID NO 407
<211> LENGTH: 5
<212> TYPE: PRT
<213> ORGANISM: Homo sapiens

<400> SEQUENCE: 407

Pro Arg Pro Pro Gln
1               5

<210> SEQ ID NO 408
<211> LENGTH: 5
<212> TYPE: PRT
<213> ORGANISM: Homo sapiens

<400> SEQUENCE: 408

Arg Pro Pro Gln Gly
1               5

<210> SEQ ID NO 409
<211> LENGTH: 5
<212> TYPE: PRT
<213> ORGANISM: Homo sapiens

<400> SEQUENCE: 409

Pro Pro Gln Gly Gly
1               5

<210> SEQ ID NO 410
<211> LENGTH: 5
<212> TYPE: PRT
<213> ORGANISM: Homo sapiens

<400> SEQUENCE: 410

Pro Gln Gly Gly Arg
1               5

<210> SEQ ID NO 411
<211> LENGTH: 5
<212> TYPE: PRT
<213> ORGANISM: Homo sapiens

<400> SEQUENCE: 411

Gln Gly Gly Arg Pro
1               5

<210> SEQ ID NO 412
<211> LENGTH: 5
<212> TYPE: PRT
<213> ORGANISM: Homo sapiens

<400> SEQUENCE: 412

Gly Gly Arg Pro Ser
1               5

<210> SEQ ID NO 413
<211> LENGTH: 5
<212> TYPE: PRT
<213> ORGANISM: Homo sapiens

<400> SEQUENCE: 413

Gly Arg Pro Ser Arg
1               5

<210> SEQ ID NO 414
<211> LENGTH: 5
<212> TYPE: PRT
<213> ORGANISM: Homo sapiens

<400> SEQUENCE: 414

Arg Pro Ser Arg Pro
1               5

<210> SEQ ID NO 415
<211> LENGTH: 5
<212> TYPE: PRT
<213> ORGANISM: Homo sapiens

<400> SEQUENCE: 415

```
Pro Ser Arg Pro Pro
1               5

<210> SEQ ID NO 416
<211> LENGTH: 5
<212> TYPE: PRT
<213> ORGANISM: Homo sapiens

<400> SEQUENCE: 416

Ser Arg Pro Pro Gln
1               5

<210> SEQ ID NO 417
<211> LENGTH: 309
<212> TYPE: PRT
<213> ORGANISM: Homo sapiens

<400> SEQUENCE: 417

Met Leu Leu Ile Leu Leu Ser Val Ala Leu Leu Ala Leu Ser Ser Ala
1               5                   10                  15

Gln Ser Leu Asn Glu Asp Val Ser Gln Glu Ser Pro Ser Val Ile
            20                  25                  30

Ser Gly Lys Pro Glu Gly Arg Arg Pro Gln Gly Gly Asn Gln Pro Gln
        35                  40                  45

Arg Thr Pro Pro Pro Gly Lys Pro Glu Gly Arg Pro Pro Gln Gly
    50                  55                  60

Gly Asn Gln Ser Gln Gly Pro Pro Arg Pro Gly Lys Pro Glu Gly
65                  70                  75                  80

Pro Pro Pro Gln Gly Gly Asn Gln Ser Gln Gly Pro Pro Arg Pro
                85                  90                  95

Gly Lys Pro Glu Gly Gln Pro Pro Gln Gly Gly Asn Gln Ser Gln Gly
            100                 105                 110

Pro Pro Pro Arg Pro Gly Lys Pro Glu Gly Pro Pro Gln Gly Gly
        115                 120                 125

Asn Gln Ser Gln Gly Pro Pro Arg Pro Gly Lys Pro Glu Gly Pro
    130                 135                 140

Pro Pro Gln Gly Gly Asn Gln Ser Gln Gly Pro Pro His Pro Gly
145                 150                 155                 160

Lys Pro Glu Gly Pro Pro Gln Gly Gly Asn Gln Ser Gln Gly Pro
                165                 170                 175

Pro Pro Arg Pro Gly Lys Pro Glu Gly Pro Pro Gln Gly Gly Asn
            180                 185                 190

Gln Ser Gln Gly Pro Pro Pro Arg Pro Gly Lys Pro Glu Gly Pro Pro
        195                 200                 205

Pro Gln Gly Gly Asn Gln Ser Gln Gly Pro Pro Arg Pro Gly Lys
    210                 215                 220

Pro Glu Gly Ser Pro Ser Gln Gly Gly Asn Lys Pro Gln Gly Pro Pro
225                 230                 235                 240

Pro His Pro Gly Lys Pro Gln Gly Pro Pro Gln Glu Gly Asn Lys
                245                 250                 255

Pro Gln Arg Pro Pro Pro Gly Arg Pro Gln Gly Pro Pro Pro
            260                 265                 270

Gly Gly Asn Pro Gln Gln Pro Leu Pro Pro Ala Gly Lys Pro Gln
        275                 280                 285

Gly Pro Pro Pro Pro Gln Gly Gly Arg Pro His Arg Pro Pro Gln
    290                 295                 300
```

Gly Gln Pro Pro Gln
305

<210> SEQ ID NO 418
<211> LENGTH: 5
<212> TYPE: PRT
<213> ORGANISM: Homo sapiens

<400> SEQUENCE: 418

Met Leu Leu Ile Leu
1               5

<210> SEQ ID NO 419
<211> LENGTH: 5
<212> TYPE: PRT
<213> ORGANISM: Homo sapiens

<400> SEQUENCE: 419

Leu Leu Ile Leu Leu
1               5

<210> SEQ ID NO 420
<211> LENGTH: 5
<212> TYPE: PRT
<213> ORGANISM: Homo sapiens

<400> SEQUENCE: 420

Leu Ile Leu Leu Ser
1               5

<210> SEQ ID NO 421
<211> LENGTH: 5
<212> TYPE: PRT
<213> ORGANISM: Homo sapiens

<400> SEQUENCE: 421

Ile Leu Leu Ser Val
1               5

<210> SEQ ID NO 422
<211> LENGTH: 5
<212> TYPE: PRT
<213> ORGANISM: Homo sapiens

<400> SEQUENCE: 422

Leu Leu Ser Val Ala
1               5

<210> SEQ ID NO 423
<211> LENGTH: 5
<212> TYPE: PRT
<213> ORGANISM: Homo sapiens

<400> SEQUENCE: 423

Leu Ser Val Ala Leu
1               5

<210> SEQ ID NO 424
<211> LENGTH: 5
<212> TYPE: PRT
<213> ORGANISM: Homo sapiens

<400> SEQUENCE: 424

Ser Val Ala Leu Leu

```
1               5

<210> SEQ ID NO 425
<211> LENGTH: 5
<212> TYPE: PRT
<213> ORGANISM: Homo sapiens

<400> SEQUENCE: 425

Val Ala Leu Leu Ala
1               5

<210> SEQ ID NO 426
<211> LENGTH: 5
<212> TYPE: PRT
<213> ORGANISM: Homo sapiens

<400> SEQUENCE: 426

Ala Leu Leu Ala Leu
1               5

<210> SEQ ID NO 427
<211> LENGTH: 5
<212> TYPE: PRT
<213> ORGANISM: Homo sapiens

<400> SEQUENCE: 427

Leu Leu Ala Leu Ser
1               5

<210> SEQ ID NO 428
<211> LENGTH: 5
<212> TYPE: PRT
<213> ORGANISM: Homo sapiens

<400> SEQUENCE: 428

Leu Ala Leu Ser Ser
1               5

<210> SEQ ID NO 429
<211> LENGTH: 5
<212> TYPE: PRT
<213> ORGANISM: Homo sapiens

<400> SEQUENCE: 429

Ala Leu Ser Ser Ala
1               5

<210> SEQ ID NO 430
<211> LENGTH: 5
<212> TYPE: PRT
<213> ORGANISM: Homo sapiens

<400> SEQUENCE: 430

Leu Ser Ser Ala Gln
1               5

<210> SEQ ID NO 431
<211> LENGTH: 5
<212> TYPE: PRT
<213> ORGANISM: Homo sapiens

<400> SEQUENCE: 431

Ser Ser Ala Gln Ser
1               5
```

```
<210> SEQ ID NO 432
<211> LENGTH: 5
<212> TYPE: PRT
<213> ORGANISM: Homo sapiens

<400> SEQUENCE: 432

Ser Ala Gln Ser Leu
1               5

<210> SEQ ID NO 433
<211> LENGTH: 5
<212> TYPE: PRT
<213> ORGANISM: Homo sapiens

<400> SEQUENCE: 433

Ala Gln Ser Leu Asn
1               5

<210> SEQ ID NO 434
<211> LENGTH: 5
<212> TYPE: PRT
<213> ORGANISM: Homo sapiens

<400> SEQUENCE: 434

Gln Ser Leu Asn Glu
1               5

<210> SEQ ID NO 435
<211> LENGTH: 5
<212> TYPE: PRT
<213> ORGANISM: Homo sapiens

<400> SEQUENCE: 435

Ser Leu Asn Glu Asp
1               5

<210> SEQ ID NO 436
<211> LENGTH: 5
<212> TYPE: PRT
<213> ORGANISM: Homo sapiens

<400> SEQUENCE: 436

Leu Asn Glu Asp Val
1               5

<210> SEQ ID NO 437
<211> LENGTH: 5
<212> TYPE: PRT
<213> ORGANISM: Homo sapiens

<400> SEQUENCE: 437

Asn Glu Asp Val Ser
1               5

<210> SEQ ID NO 438
<211> LENGTH: 5
<212> TYPE: PRT
<213> ORGANISM: Homo sapiens

<400> SEQUENCE: 438

Glu Asp Val Ser Gln
1               5

<210> SEQ ID NO 439
```

```
<211> LENGTH: 5
<212> TYPE: PRT
<213> ORGANISM: Homo sapiens

<400> SEQUENCE: 439

Asp Val Ser Gln Glu
1               5

<210> SEQ ID NO 440
<211> LENGTH: 5
<212> TYPE: PRT
<213> ORGANISM: Homo sapiens

<400> SEQUENCE: 440

Val Ser Gln Glu Glu
1               5

<210> SEQ ID NO 441
<211> LENGTH: 5
<212> TYPE: PRT
<213> ORGANISM: Homo sapiens

<400> SEQUENCE: 441

Ser Gln Glu Glu Ser
1               5

<210> SEQ ID NO 442
<211> LENGTH: 5
<212> TYPE: PRT
<213> ORGANISM: Homo sapiens

<400> SEQUENCE: 442

Gln Glu Glu Ser Pro
1               5

<210> SEQ ID NO 443
<211> LENGTH: 5
<212> TYPE: PRT
<213> ORGANISM: Homo sapiens

<400> SEQUENCE: 443

Glu Glu Ser Pro Ser
1               5

<210> SEQ ID NO 444
<211> LENGTH: 5
<212> TYPE: PRT
<213> ORGANISM: Homo sapiens

<400> SEQUENCE: 444

Glu Ser Pro Ser Val
1               5

<210> SEQ ID NO 445
<211> LENGTH: 5
<212> TYPE: PRT
<213> ORGANISM: Homo sapiens

<400> SEQUENCE: 445

Ser Pro Ser Val Ile
1               5

<210> SEQ ID NO 446
<211> LENGTH: 5
<212> TYPE: PRT
```

<213> ORGANISM: Homo sapiens

<400> SEQUENCE: 446

Pro Ser Val Ile Ser
1               5

<210> SEQ ID NO 447
<211> LENGTH: 5
<212> TYPE: PRT
<213> ORGANISM: Homo sapiens

<400> SEQUENCE: 447

Ser Val Ile Ser Gly
1               5

<210> SEQ ID NO 448
<211> LENGTH: 5
<212> TYPE: PRT
<213> ORGANISM: Homo sapiens

<400> SEQUENCE: 448

Val Ile Ser Gly Lys
1               5

<210> SEQ ID NO 449
<211> LENGTH: 5
<212> TYPE: PRT
<213> ORGANISM: Homo sapiens

<400> SEQUENCE: 449

Ile Ser Gly Lys Pro
1               5

<210> SEQ ID NO 450
<211> LENGTH: 5
<212> TYPE: PRT
<213> ORGANISM: Homo sapiens

<400> SEQUENCE: 450

Ser Gly Lys Pro Glu
1               5

<210> SEQ ID NO 451
<211> LENGTH: 5
<212> TYPE: PRT
<213> ORGANISM: Homo sapiens

<400> SEQUENCE: 451

Gly Lys Pro Glu Gly
1               5

<210> SEQ ID NO 452
<211> LENGTH: 5
<212> TYPE: PRT
<213> ORGANISM: Homo sapiens

<400> SEQUENCE: 452

Lys Pro Glu Gly Arg
1               5

<210> SEQ ID NO 453
<211> LENGTH: 5
<212> TYPE: PRT
<213> ORGANISM: Homo sapiens

```
<400> SEQUENCE: 453

Pro Glu Gly Arg Arg
1               5

<210> SEQ ID NO 454
<211> LENGTH: 5
<212> TYPE: PRT
<213> ORGANISM: Homo sapiens

<400> SEQUENCE: 454

Glu Gly Arg Arg Pro
1               5

<210> SEQ ID NO 455
<211> LENGTH: 5
<212> TYPE: PRT
<213> ORGANISM: Homo sapiens

<400> SEQUENCE: 455

Gly Arg Arg Pro Gln
1               5

<210> SEQ ID NO 456
<211> LENGTH: 5
<212> TYPE: PRT
<213> ORGANISM: Homo sapiens

<400> SEQUENCE: 456

Arg Arg Pro Gln Gly
1               5

<210> SEQ ID NO 457
<211> LENGTH: 5
<212> TYPE: PRT
<213> ORGANISM: Homo sapiens

<400> SEQUENCE: 457

Arg Pro Gln Gly Gly
1               5

<210> SEQ ID NO 458
<211> LENGTH: 5
<212> TYPE: PRT
<213> ORGANISM: Homo sapiens

<400> SEQUENCE: 458

Pro Gln Gly Gly Asn
1               5

<210> SEQ ID NO 459
<211> LENGTH: 5
<212> TYPE: PRT
<213> ORGANISM: Homo sapiens

<400> SEQUENCE: 459

Gln Gly Gly Asn Gln
1               5

<210> SEQ ID NO 460
<211> LENGTH: 5
<212> TYPE: PRT
<213> ORGANISM: Homo sapiens

<400> SEQUENCE: 460
```

Gly Gly Asn Gln Pro
1               5

<210> SEQ ID NO 461
<211> LENGTH: 5
<212> TYPE: PRT
<213> ORGANISM: Homo sapiens

<400> SEQUENCE: 461

Gly Asn Gln Pro Gln
1               5

<210> SEQ ID NO 462
<211> LENGTH: 5
<212> TYPE: PRT
<213> ORGANISM: Homo sapiens

<400> SEQUENCE: 462

Asn Gln Pro Gln Arg
1               5

<210> SEQ ID NO 463
<211> LENGTH: 5
<212> TYPE: PRT
<213> ORGANISM: Homo sapiens

<400> SEQUENCE: 463

Gln Pro Gln Arg Thr
1               5

<210> SEQ ID NO 464
<211> LENGTH: 5
<212> TYPE: PRT
<213> ORGANISM: Homo sapiens

<400> SEQUENCE: 464

Pro Gln Arg Thr Pro
1               5

<210> SEQ ID NO 465
<211> LENGTH: 5
<212> TYPE: PRT
<213> ORGANISM: Homo sapiens

<400> SEQUENCE: 465

Gln Arg Thr Pro Pro
1               5

<210> SEQ ID NO 466
<211> LENGTH: 5
<212> TYPE: PRT
<213> ORGANISM: Homo sapiens

<400> SEQUENCE: 466

Arg Thr Pro Pro Pro
1               5

<210> SEQ ID NO 467
<211> LENGTH: 5
<212> TYPE: PRT
<213> ORGANISM: Homo sapiens

<400> SEQUENCE: 467

Thr Pro Pro Pro Pro
1               5

<210> SEQ ID NO 468
<211> LENGTH: 5
<212> TYPE: PRT
<213> ORGANISM: Homo sapiens

<400> SEQUENCE: 468

Pro Pro Pro Pro Gly
1               5

<210> SEQ ID NO 469
<211> LENGTH: 5
<212> TYPE: PRT
<213> ORGANISM: Homo sapiens

<400> SEQUENCE: 469

Pro Pro Pro Gly Lys
1               5

<210> SEQ ID NO 470
<211> LENGTH: 5
<212> TYPE: PRT
<213> ORGANISM: Homo sapiens

<400> SEQUENCE: 470

Pro Pro Gly Lys Pro
1               5

<210> SEQ ID NO 471
<211> LENGTH: 5
<212> TYPE: PRT
<213> ORGANISM: Homo sapiens

<400> SEQUENCE: 471

Pro Gly Lys Pro Glu
1               5

<210> SEQ ID NO 472
<211> LENGTH: 5
<212> TYPE: PRT
<213> ORGANISM: Homo sapiens

<400> SEQUENCE: 472

Gly Lys Pro Glu Gly
1               5

<210> SEQ ID NO 473
<211> LENGTH: 5
<212> TYPE: PRT
<213> ORGANISM: Homo sapiens

<400> SEQUENCE: 473

Lys Pro Glu Gly Arg
1               5

<210> SEQ ID NO 474
<211> LENGTH: 5
<212> TYPE: PRT
<213> ORGANISM: Homo sapiens

<400> SEQUENCE: 474

Pro Glu Gly Arg Pro
1               5

```
<210> SEQ ID NO 475
<211> LENGTH: 5
<212> TYPE: PRT
<213> ORGANISM: Homo sapiens

<400> SEQUENCE: 475

Glu Gly Arg Pro Pro
1               5

<210> SEQ ID NO 476
<211> LENGTH: 5
<212> TYPE: PRT
<213> ORGANISM: Homo sapiens

<400> SEQUENCE: 476

Gly Arg Pro Pro Gln
1               5

<210> SEQ ID NO 477
<211> LENGTH: 5
<212> TYPE: PRT
<213> ORGANISM: Homo sapiens

<400> SEQUENCE: 477

Arg Pro Pro Gln Gly
1               5

<210> SEQ ID NO 478
<211> LENGTH: 5
<212> TYPE: PRT
<213> ORGANISM: Homo sapiens

<400> SEQUENCE: 478

Pro Pro Gln Gly Gly
1               5

<210> SEQ ID NO 479
<211> LENGTH: 5
<212> TYPE: PRT
<213> ORGANISM: Homo sapiens

<400> SEQUENCE: 479

Pro Gln Gly Gly Asn
1               5

<210> SEQ ID NO 480
<211> LENGTH: 5
<212> TYPE: PRT
<213> ORGANISM: Homo sapiens

<400> SEQUENCE: 480

Gln Gly Gly Asn Gln
1               5

<210> SEQ ID NO 481
<211> LENGTH: 5
<212> TYPE: PRT
<213> ORGANISM: Homo sapiens

<400> SEQUENCE: 481

Gly Gly Asn Gln Ser
1               5

<210> SEQ ID NO 482
<211> LENGTH: 5
```

```
<212> TYPE: PRT
<213> ORGANISM: Homo sapiens

<400> SEQUENCE: 482

Gly Asn Gln Ser Gln
1               5

<210> SEQ ID NO 483
<211> LENGTH: 5
<212> TYPE: PRT
<213> ORGANISM: Homo sapiens

<400> SEQUENCE: 483

Asn Gln Ser Gln Gly
1               5

<210> SEQ ID NO 484
<211> LENGTH: 5
<212> TYPE: PRT
<213> ORGANISM: Homo sapiens

<400> SEQUENCE: 484

Gln Ser Gln Gly Pro
1               5

<210> SEQ ID NO 485
<211> LENGTH: 5
<212> TYPE: PRT
<213> ORGANISM: Homo sapiens

<400> SEQUENCE: 485

Ser Gln Gly Pro Pro
1               5

<210> SEQ ID NO 486
<211> LENGTH: 5
<212> TYPE: PRT
<213> ORGANISM: Homo sapiens

<400> SEQUENCE: 486

Gln Gly Pro Pro Pro
1               5

<210> SEQ ID NO 487
<211> LENGTH: 5
<212> TYPE: PRT
<213> ORGANISM: Homo sapiens

<400> SEQUENCE: 487

Gly Pro Pro Pro Arg
1               5

<210> SEQ ID NO 488
<211> LENGTH: 5
<212> TYPE: PRT
<213> ORGANISM: Homo sapiens

<400> SEQUENCE: 488

Pro Pro Pro Arg Pro
1               5

<210> SEQ ID NO 489
<211> LENGTH: 5
<212> TYPE: PRT
<213> ORGANISM: Homo sapiens
```

```
<400> SEQUENCE: 489

Pro Pro Arg Pro Gly
1               5

<210> SEQ ID NO 490
<211> LENGTH: 5
<212> TYPE: PRT
<213> ORGANISM: Homo sapiens

<400> SEQUENCE: 490

Pro Arg Pro Gly Lys
1               5

<210> SEQ ID NO 491
<211> LENGTH: 5
<212> TYPE: PRT
<213> ORGANISM: Homo sapiens

<400> SEQUENCE: 491

Arg Pro Gly Lys Pro
1               5

<210> SEQ ID NO 492
<211> LENGTH: 5
<212> TYPE: PRT
<213> ORGANISM: Homo sapiens

<400> SEQUENCE: 492

Pro Gly Lys Pro Glu
1               5

<210> SEQ ID NO 493
<211> LENGTH: 5
<212> TYPE: PRT
<213> ORGANISM: Homo sapiens

<400> SEQUENCE: 493

Gly Lys Pro Glu Gly
1               5

<210> SEQ ID NO 494
<211> LENGTH: 5
<212> TYPE: PRT
<213> ORGANISM: Homo sapiens

<400> SEQUENCE: 494

Lys Pro Glu Gly Pro
1               5

<210> SEQ ID NO 495
<211> LENGTH: 5
<212> TYPE: PRT
<213> ORGANISM: Homo sapiens

<400> SEQUENCE: 495

Pro Glu Gly Pro Pro
1               5

<210> SEQ ID NO 496
<211> LENGTH: 5
<212> TYPE: PRT
<213> ORGANISM: Homo sapiens

<400> SEQUENCE: 496
```

Glu Gly Pro Pro Pro
1               5

<210> SEQ ID NO 497
<211> LENGTH: 5
<212> TYPE: PRT
<213> ORGANISM: Homo sapiens

<400> SEQUENCE: 497

Gly Pro Pro Pro Gln
1               5

<210> SEQ ID NO 498
<211> LENGTH: 5
<212> TYPE: PRT
<213> ORGANISM: Homo sapiens

<400> SEQUENCE: 498

Pro Pro Pro Gln Gly
1               5

<210> SEQ ID NO 499
<211> LENGTH: 5
<212> TYPE: PRT
<213> ORGANISM: Homo sapiens

<400> SEQUENCE: 499

Pro Pro Gln Gly Gly
1               5

<210> SEQ ID NO 500
<211> LENGTH: 5
<212> TYPE: PRT
<213> ORGANISM: Homo sapiens

<400> SEQUENCE: 500

Pro Gln Gly Gly Asn
1               5

<210> SEQ ID NO 501
<211> LENGTH: 5
<212> TYPE: PRT
<213> ORGANISM: Homo sapiens

<400> SEQUENCE: 501

Gln Gly Gly Asn Gln
1               5

<210> SEQ ID NO 502
<211> LENGTH: 5
<212> TYPE: PRT
<213> ORGANISM: Homo sapiens

<400> SEQUENCE: 502

Gly Gly Asn Gln Ser
1               5

<210> SEQ ID NO 503
<211> LENGTH: 5
<212> TYPE: PRT
<213> ORGANISM: Homo sapiens

<400> SEQUENCE: 503

Gly Asn Gln Ser Gln

```
1               5

<210> SEQ ID NO 504
<211> LENGTH: 5
<212> TYPE: PRT
<213> ORGANISM: Homo sapiens

<400> SEQUENCE: 504

Asn Gln Ser Gln Gly
1               5

<210> SEQ ID NO 505
<211> LENGTH: 5
<212> TYPE: PRT
<213> ORGANISM: Homo sapiens

<400> SEQUENCE: 505

Gln Ser Gln Gly Pro
1               5

<210> SEQ ID NO 506
<211> LENGTH: 5
<212> TYPE: PRT
<213> ORGANISM: Homo sapiens

<400> SEQUENCE: 506

Ser Gln Gly Pro Pro
1               5

<210> SEQ ID NO 507
<211> LENGTH: 5
<212> TYPE: PRT
<213> ORGANISM: Homo sapiens

<400> SEQUENCE: 507

Gln Gly Pro Pro Pro
1               5

<210> SEQ ID NO 508
<211> LENGTH: 5
<212> TYPE: PRT
<213> ORGANISM: Homo sapiens

<400> SEQUENCE: 508

Gly Pro Pro Pro Arg
1               5

<210> SEQ ID NO 509
<211> LENGTH: 5
<212> TYPE: PRT
<213> ORGANISM: Homo sapiens

<400> SEQUENCE: 509

Pro Pro Pro Arg Pro
1               5

<210> SEQ ID NO 510
<211> LENGTH: 5
<212> TYPE: PRT
<213> ORGANISM: Homo sapiens

<400> SEQUENCE: 510

Pro Pro Arg Pro Gly
1               5
```

<210> SEQ ID NO 511
<211> LENGTH: 5
<212> TYPE: PRT
<213> ORGANISM: Homo sapiens

<400> SEQUENCE: 511

Pro Arg Pro Gly Lys
1               5

<210> SEQ ID NO 512
<211> LENGTH: 5
<212> TYPE: PRT
<213> ORGANISM: Homo sapiens

<400> SEQUENCE: 512

Arg Pro Gly Lys Pro
1               5

<210> SEQ ID NO 513
<211> LENGTH: 5
<212> TYPE: PRT
<213> ORGANISM: Homo sapiens

<400> SEQUENCE: 513

Pro Gly Lys Pro Glu
1               5

<210> SEQ ID NO 514
<211> LENGTH: 5
<212> TYPE: PRT
<213> ORGANISM: Homo sapiens

<400> SEQUENCE: 514

Gly Lys Pro Glu Gly
1               5

<210> SEQ ID NO 515
<211> LENGTH: 5
<212> TYPE: PRT
<213> ORGANISM: Homo sapiens

<400> SEQUENCE: 515

Lys Pro Glu Gly Gln
1               5

<210> SEQ ID NO 516
<211> LENGTH: 5
<212> TYPE: PRT
<213> ORGANISM: Homo sapiens

<400> SEQUENCE: 516

Pro Glu Gly Gln Pro
1               5

<210> SEQ ID NO 517
<211> LENGTH: 5
<212> TYPE: PRT
<213> ORGANISM: Homo sapiens

<400> SEQUENCE: 517

Glu Gly Gln Pro Pro
1               5

<210> SEQ ID NO 518

```
<211> LENGTH: 5
<212> TYPE: PRT
<213> ORGANISM: Homo sapiens

<400> SEQUENCE: 518

Gly Gln Pro Pro Gln
1               5

<210> SEQ ID NO 519
<211> LENGTH: 5
<212> TYPE: PRT
<213> ORGANISM: Homo sapiens

<400> SEQUENCE: 519

Gln Pro Pro Gln Gly
1               5

<210> SEQ ID NO 520
<211> LENGTH: 5
<212> TYPE: PRT
<213> ORGANISM: Homo sapiens

<400> SEQUENCE: 520

Pro Pro Gln Gly Gly
1               5

<210> SEQ ID NO 521
<211> LENGTH: 5
<212> TYPE: PRT
<213> ORGANISM: Homo sapiens

<400> SEQUENCE: 521

Pro Gln Gly Gly Asn
1               5

<210> SEQ ID NO 522
<211> LENGTH: 5
<212> TYPE: PRT
<213> ORGANISM: Homo sapiens

<400> SEQUENCE: 522

Gln Gly Gly Asn Gln
1               5

<210> SEQ ID NO 523
<211> LENGTH: 5
<212> TYPE: PRT
<213> ORGANISM: Homo sapiens

<400> SEQUENCE: 523

Gly Gly Asn Gln Ser
1               5

<210> SEQ ID NO 524
<211> LENGTH: 5
<212> TYPE: PRT
<213> ORGANISM: Homo sapiens

<400> SEQUENCE: 524

Gly Asn Gln Ser Gln
1               5

<210> SEQ ID NO 525
<211> LENGTH: 5
<212> TYPE: PRT
```

```
<213> ORGANISM: Homo sapiens

<400> SEQUENCE: 525

Asn Gln Ser Gln Gly
1               5

<210> SEQ ID NO 526
<211> LENGTH: 5
<212> TYPE: PRT
<213> ORGANISM: Homo sapiens

<400> SEQUENCE: 526

Gln Ser Gln Gly Pro
1               5

<210> SEQ ID NO 527
<211> LENGTH: 5
<212> TYPE: PRT
<213> ORGANISM: Homo sapiens

<400> SEQUENCE: 527

Ser Gln Gly Pro Pro
1               5

<210> SEQ ID NO 528
<211> LENGTH: 5
<212> TYPE: PRT
<213> ORGANISM: Homo sapiens

<400> SEQUENCE: 528

Gln Gly Pro Pro Pro
1               5

<210> SEQ ID NO 529
<211> LENGTH: 5
<212> TYPE: PRT
<213> ORGANISM: Homo sapiens

<400> SEQUENCE: 529

Gly Pro Pro Pro Arg
1               5

<210> SEQ ID NO 530
<211> LENGTH: 5
<212> TYPE: PRT
<213> ORGANISM: Homo sapiens

<400> SEQUENCE: 530

Pro Pro Pro Arg Pro
1               5

<210> SEQ ID NO 531
<211> LENGTH: 5
<212> TYPE: PRT
<213> ORGANISM: Homo sapiens

<400> SEQUENCE: 531

Pro Pro Arg Pro Gly
1               5

<210> SEQ ID NO 532
<211> LENGTH: 5
<212> TYPE: PRT
<213> ORGANISM: Homo sapiens
```

```
<400> SEQUENCE: 532

Pro Arg Pro Gly Lys
1               5

<210> SEQ ID NO 533
<211> LENGTH: 5
<212> TYPE: PRT
<213> ORGANISM: Homo sapiens

<400> SEQUENCE: 533

Arg Pro Gly Lys Pro
1               5

<210> SEQ ID NO 534
<211> LENGTH: 5
<212> TYPE: PRT
<213> ORGANISM: Homo sapiens

<400> SEQUENCE: 534

Pro Gly Lys Pro Glu
1               5

<210> SEQ ID NO 535
<211> LENGTH: 5
<212> TYPE: PRT
<213> ORGANISM: Homo sapiens

<400> SEQUENCE: 535

Gly Lys Pro Glu Gly
1               5

<210> SEQ ID NO 536
<211> LENGTH: 5
<212> TYPE: PRT
<213> ORGANISM: Homo sapiens

<400> SEQUENCE: 536

Lys Pro Glu Gly Pro
1               5

<210> SEQ ID NO 537
<211> LENGTH: 5
<212> TYPE: PRT
<213> ORGANISM: Homo sapiens

<400> SEQUENCE: 537

Pro Glu Gly Pro Pro
1               5

<210> SEQ ID NO 538
<211> LENGTH: 5
<212> TYPE: PRT
<213> ORGANISM: Homo sapiens

<400> SEQUENCE: 538

Glu Gly Pro Pro Pro
1               5

<210> SEQ ID NO 539
<211> LENGTH: 5
<212> TYPE: PRT
<213> ORGANISM: Homo sapiens

<400> SEQUENCE: 539
```

Gly Pro Pro Pro Gln
1               5

<210> SEQ ID NO 540
<211> LENGTH: 5
<212> TYPE: PRT
<213> ORGANISM: Homo sapiens

<400> SEQUENCE: 540

Pro Pro Pro Gln Gly
1               5

<210> SEQ ID NO 541
<211> LENGTH: 5
<212> TYPE: PRT
<213> ORGANISM: Homo sapiens

<400> SEQUENCE: 541

Pro Pro Gln Gly Gly
1               5

<210> SEQ ID NO 542
<211> LENGTH: 5
<212> TYPE: PRT
<213> ORGANISM: Homo sapiens

<400> SEQUENCE: 542

Pro Gln Gly Gly Asn
1               5

<210> SEQ ID NO 543
<211> LENGTH: 5
<212> TYPE: PRT
<213> ORGANISM: Homo sapiens

<400> SEQUENCE: 543

Gln Gly Gly Asn Gln
1               5

<210> SEQ ID NO 544
<211> LENGTH: 5
<212> TYPE: PRT
<213> ORGANISM: Homo sapiens

<400> SEQUENCE: 544

Gly Gly Asn Gln Ser
1               5

<210> SEQ ID NO 545
<211> LENGTH: 5
<212> TYPE: PRT
<213> ORGANISM: Homo sapiens

<400> SEQUENCE: 545

Gly Asn Gln Ser Gln
1               5

<210> SEQ ID NO 546
<211> LENGTH: 5
<212> TYPE: PRT
<213> ORGANISM: Homo sapiens

<400> SEQUENCE: 546

Asn Gln Ser Gln Gly
1               5

<210> SEQ ID NO 547
<211> LENGTH: 5
<212> TYPE: PRT
<213> ORGANISM: Homo sapiens

<400> SEQUENCE: 547

Gln Ser Gln Gly Pro
1               5

<210> SEQ ID NO 548
<211> LENGTH: 5
<212> TYPE: PRT
<213> ORGANISM: Homo sapiens

<400> SEQUENCE: 548

Ser Gln Gly Pro Pro
1               5

<210> SEQ ID NO 549
<211> LENGTH: 5
<212> TYPE: PRT
<213> ORGANISM: Homo sapiens

<400> SEQUENCE: 549

Gln Gly Pro Pro Pro
1               5

<210> SEQ ID NO 550
<211> LENGTH: 5
<212> TYPE: PRT
<213> ORGANISM: Homo sapiens

<400> SEQUENCE: 550

Gly Pro Pro Pro Arg
1               5

<210> SEQ ID NO 551
<211> LENGTH: 5
<212> TYPE: PRT
<213> ORGANISM: Homo sapiens

<400> SEQUENCE: 551

Pro Pro Pro Arg Pro
1               5

<210> SEQ ID NO 552
<211> LENGTH: 5
<212> TYPE: PRT
<213> ORGANISM: Homo sapiens

<400> SEQUENCE: 552

Pro Pro Arg Pro Gly
1               5

<210> SEQ ID NO 553
<211> LENGTH: 5
<212> TYPE: PRT
<213> ORGANISM: Homo sapiens

<400> SEQUENCE: 553

Pro Arg Pro Gly Lys
1               5

```
<210> SEQ ID NO 554
<211> LENGTH: 5
<212> TYPE: PRT
<213> ORGANISM: Homo sapiens

<400> SEQUENCE: 554

Arg Pro Gly Lys Pro
1               5

<210> SEQ ID NO 555
<211> LENGTH: 5
<212> TYPE: PRT
<213> ORGANISM: Homo sapiens

<400> SEQUENCE: 555

Pro Gly Lys Pro Glu
1               5

<210> SEQ ID NO 556
<211> LENGTH: 5
<212> TYPE: PRT
<213> ORGANISM: Homo sapiens

<400> SEQUENCE: 556

Gly Lys Pro Glu Gly
1               5

<210> SEQ ID NO 557
<211> LENGTH: 5
<212> TYPE: PRT
<213> ORGANISM: Homo sapiens

<400> SEQUENCE: 557

Lys Pro Glu Gly Pro
1               5

<210> SEQ ID NO 558
<211> LENGTH: 5
<212> TYPE: PRT
<213> ORGANISM: Homo sapiens

<400> SEQUENCE: 558

Pro Glu Gly Pro Pro
1               5

<210> SEQ ID NO 559
<211> LENGTH: 5
<212> TYPE: PRT
<213> ORGANISM: Homo sapiens

<400> SEQUENCE: 559

Glu Gly Pro Pro Pro
1               5

<210> SEQ ID NO 560
<211> LENGTH: 5
<212> TYPE: PRT
<213> ORGANISM: Homo sapiens

<400> SEQUENCE: 560

Gly Pro Pro Pro Gln
1               5

<210> SEQ ID NO 561
<211> LENGTH: 5
```

```
<212> TYPE: PRT
<213> ORGANISM: Homo sapiens

<400> SEQUENCE: 561

Pro Pro Pro Gln Gly
1               5

<210> SEQ ID NO 562
<211> LENGTH: 5
<212> TYPE: PRT
<213> ORGANISM: Homo sapiens

<400> SEQUENCE: 562

Pro Pro Gln Gly Gly
1               5

<210> SEQ ID NO 563
<211> LENGTH: 5
<212> TYPE: PRT
<213> ORGANISM: Homo sapiens

<400> SEQUENCE: 563

Pro Gln Gly Gly Asn
1               5

<210> SEQ ID NO 564
<211> LENGTH: 5
<212> TYPE: PRT
<213> ORGANISM: Homo sapiens

<400> SEQUENCE: 564

Gln Gly Gly Asn Gln
1               5

<210> SEQ ID NO 565
<211> LENGTH: 5
<212> TYPE: PRT
<213> ORGANISM: Homo sapiens

<400> SEQUENCE: 565

Gly Gly Asn Gln Ser
1               5

<210> SEQ ID NO 566
<211> LENGTH: 5
<212> TYPE: PRT
<213> ORGANISM: Homo sapiens

<400> SEQUENCE: 566

Gly Asn Gln Ser Gln
1               5

<210> SEQ ID NO 567
<211> LENGTH: 5
<212> TYPE: PRT
<213> ORGANISM: Homo sapiens

<400> SEQUENCE: 567

Asn Gln Ser Gln Gly
1               5

<210> SEQ ID NO 568
<211> LENGTH: 5
<212> TYPE: PRT
<213> ORGANISM: Homo sapiens
```

<400> SEQUENCE: 568

Gln Ser Gln Gly Pro
1               5

<210> SEQ ID NO 569
<211> LENGTH: 5
<212> TYPE: PRT
<213> ORGANISM: Homo sapiens

<400> SEQUENCE: 569

Ser Gln Gly Pro Pro
1               5

<210> SEQ ID NO 570
<211> LENGTH: 5
<212> TYPE: PRT
<213> ORGANISM: Homo sapiens

<400> SEQUENCE: 570

Gln Gly Pro Pro Pro
1               5

<210> SEQ ID NO 571
<211> LENGTH: 5
<212> TYPE: PRT
<213> ORGANISM: Homo sapiens

<400> SEQUENCE: 571

Gly Pro Pro Pro His
1               5

<210> SEQ ID NO 572
<211> LENGTH: 5
<212> TYPE: PRT
<213> ORGANISM: Homo sapiens

<400> SEQUENCE: 572

Pro Pro Pro His Pro
1               5

<210> SEQ ID NO 573
<211> LENGTH: 5
<212> TYPE: PRT
<213> ORGANISM: Homo sapiens

<400> SEQUENCE: 573

Pro Pro His Pro Gly
1               5

<210> SEQ ID NO 574
<211> LENGTH: 5
<212> TYPE: PRT
<213> ORGANISM: Homo sapiens

<400> SEQUENCE: 574

Pro His Pro Gly Lys
1               5

<210> SEQ ID NO 575
<211> LENGTH: 5
<212> TYPE: PRT
<213> ORGANISM: Homo sapiens

<400> SEQUENCE: 575

His Pro Gly Lys Pro
1               5

<210> SEQ ID NO 576
<211> LENGTH: 5
<212> TYPE: PRT
<213> ORGANISM: Homo sapiens

<400> SEQUENCE: 576

Pro Gly Lys Pro Glu
1               5

<210> SEQ ID NO 577
<211> LENGTH: 5
<212> TYPE: PRT
<213> ORGANISM: Homo sapiens

<400> SEQUENCE: 577

Gly Lys Pro Glu Gly
1               5

<210> SEQ ID NO 578
<211> LENGTH: 5
<212> TYPE: PRT
<213> ORGANISM: Homo sapiens

<400> SEQUENCE: 578

Lys Pro Glu Gly Pro
1               5

<210> SEQ ID NO 579
<211> LENGTH: 5
<212> TYPE: PRT
<213> ORGANISM: Homo sapiens

<400> SEQUENCE: 579

Pro Glu Gly Pro Pro
1               5

<210> SEQ ID NO 580
<211> LENGTH: 5
<212> TYPE: PRT
<213> ORGANISM: Homo sapiens

<400> SEQUENCE: 580

Glu Gly Pro Pro Pro
1               5

<210> SEQ ID NO 581
<211> LENGTH: 5
<212> TYPE: PRT
<213> ORGANISM: Homo sapiens

<400> SEQUENCE: 581

Gly Pro Pro Pro Gln
1               5

<210> SEQ ID NO 582
<211> LENGTH: 5
<212> TYPE: PRT
<213> ORGANISM: Homo sapiens

<400> SEQUENCE: 582

Pro Pro Pro Gln Gly

```
1               5

<210> SEQ ID NO 583
<211> LENGTH: 5
<212> TYPE: PRT
<213> ORGANISM: Homo sapiens

<400> SEQUENCE: 583

Pro Pro Gln Gly Gly
1               5

<210> SEQ ID NO 584
<211> LENGTH: 5
<212> TYPE: PRT
<213> ORGANISM: Homo sapiens

<400> SEQUENCE: 584

Pro Gln Gly Gly Asn
1               5

<210> SEQ ID NO 585
<211> LENGTH: 5
<212> TYPE: PRT
<213> ORGANISM: Homo sapiens

<400> SEQUENCE: 585

Gln Gly Gly Asn Gln
1               5

<210> SEQ ID NO 586
<211> LENGTH: 5
<212> TYPE: PRT
<213> ORGANISM: Homo sapiens

<400> SEQUENCE: 586

Gly Gly Asn Gln Ser
1               5

<210> SEQ ID NO 587
<211> LENGTH: 5
<212> TYPE: PRT
<213> ORGANISM: Homo sapiens

<400> SEQUENCE: 587

Gly Asn Gln Ser Gln
1               5

<210> SEQ ID NO 588
<211> LENGTH: 5
<212> TYPE: PRT
<213> ORGANISM: Homo sapiens

<400> SEQUENCE: 588

Asn Gln Ser Gln Gly
1               5

<210> SEQ ID NO 589
<211> LENGTH: 5
<212> TYPE: PRT
<213> ORGANISM: Homo sapiens

<400> SEQUENCE: 589

Gln Ser Gln Gly Pro
1               5
```

```
<210> SEQ ID NO 590
<211> LENGTH: 5
<212> TYPE: PRT
<213> ORGANISM: Homo sapiens

<400> SEQUENCE: 590

Ser Gln Gly Pro Pro
1               5

<210> SEQ ID NO 591
<211> LENGTH: 5
<212> TYPE: PRT
<213> ORGANISM: Homo sapiens

<400> SEQUENCE: 591

Gln Gly Pro Pro Pro
1               5

<210> SEQ ID NO 592
<211> LENGTH: 5
<212> TYPE: PRT
<213> ORGANISM: Homo sapiens

<400> SEQUENCE: 592

Gly Pro Pro Pro Arg
1               5

<210> SEQ ID NO 593
<211> LENGTH: 5
<212> TYPE: PRT
<213> ORGANISM: Homo sapiens

<400> SEQUENCE: 593

Pro Pro Pro Arg Pro
1               5

<210> SEQ ID NO 594
<211> LENGTH: 5
<212> TYPE: PRT
<213> ORGANISM: Homo sapiens

<400> SEQUENCE: 594

Pro Pro Arg Pro Gly
1               5

<210> SEQ ID NO 595
<211> LENGTH: 5
<212> TYPE: PRT
<213> ORGANISM: Homo sapiens

<400> SEQUENCE: 595

Pro Arg Pro Gly Lys
1               5

<210> SEQ ID NO 596
<211> LENGTH: 5
<212> TYPE: PRT
<213> ORGANISM: Homo sapiens

<400> SEQUENCE: 596

Arg Pro Gly Lys Pro
1               5

<210> SEQ ID NO 597
```

```
<211> LENGTH: 5
<212> TYPE: PRT
<213> ORGANISM: Homo sapiens

<400> SEQUENCE: 597

Pro Gly Lys Pro Glu
1               5

<210> SEQ ID NO 598
<211> LENGTH: 5
<212> TYPE: PRT
<213> ORGANISM: Homo sapiens

<400> SEQUENCE: 598

Gly Lys Pro Glu Gly
1               5

<210> SEQ ID NO 599
<211> LENGTH: 5
<212> TYPE: PRT
<213> ORGANISM: Homo sapiens

<400> SEQUENCE: 599

Lys Pro Glu Gly Pro
1               5

<210> SEQ ID NO 600
<211> LENGTH: 5
<212> TYPE: PRT
<213> ORGANISM: Homo sapiens

<400> SEQUENCE: 600

Pro Glu Gly Pro Pro
1               5

<210> SEQ ID NO 601
<211> LENGTH: 5
<212> TYPE: PRT
<213> ORGANISM: Homo sapiens

<400> SEQUENCE: 601

Glu Gly Pro Pro Pro
1               5

<210> SEQ ID NO 602
<211> LENGTH: 5
<212> TYPE: PRT
<213> ORGANISM: Homo sapiens

<400> SEQUENCE: 602

Gly Pro Pro Pro Gln
1               5

<210> SEQ ID NO 603
<211> LENGTH: 5
<212> TYPE: PRT
<213> ORGANISM: Homo sapiens

<400> SEQUENCE: 603

Pro Pro Pro Gln Gly
1               5

<210> SEQ ID NO 604
<211> LENGTH: 5
<212> TYPE: PRT
```

```
<213> ORGANISM: Homo sapiens

<400> SEQUENCE: 604

Pro Pro Gln Gly Gly
1               5

<210> SEQ ID NO 605
<211> LENGTH: 5
<212> TYPE: PRT
<213> ORGANISM: Homo sapiens

<400> SEQUENCE: 605

Pro Gln Gly Gly Asn
1               5

<210> SEQ ID NO 606
<211> LENGTH: 5
<212> TYPE: PRT
<213> ORGANISM: Homo sapiens

<400> SEQUENCE: 606

Gln Gly Gly Asn Gln
1               5

<210> SEQ ID NO 607
<211> LENGTH: 5
<212> TYPE: PRT
<213> ORGANISM: Homo sapiens

<400> SEQUENCE: 607

Gly Gly Asn Gln Ser
1               5

<210> SEQ ID NO 608
<211> LENGTH: 5
<212> TYPE: PRT
<213> ORGANISM: Homo sapiens

<400> SEQUENCE: 608

Gly Asn Gln Ser Gln
1               5

<210> SEQ ID NO 609
<211> LENGTH: 5
<212> TYPE: PRT
<213> ORGANISM: Homo sapiens

<400> SEQUENCE: 609

Asn Gln Ser Gln Gly
1               5

<210> SEQ ID NO 610
<211> LENGTH: 5
<212> TYPE: PRT
<213> ORGANISM: Homo sapiens

<400> SEQUENCE: 610

Gln Ser Gln Gly Pro
1               5

<210> SEQ ID NO 611
<211> LENGTH: 5
<212> TYPE: PRT
<213> ORGANISM: Homo sapiens
```

```
<400> SEQUENCE: 611

Ser Gln Gly Pro Pro
1               5

<210> SEQ ID NO 612
<211> LENGTH: 5
<212> TYPE: PRT
<213> ORGANISM: Homo sapiens

<400> SEQUENCE: 612

Gln Gly Pro Pro Pro
1               5

<210> SEQ ID NO 613
<211> LENGTH: 5
<212> TYPE: PRT
<213> ORGANISM: Homo sapiens

<400> SEQUENCE: 613

Gly Pro Pro Pro Arg
1               5

<210> SEQ ID NO 614
<211> LENGTH: 5
<212> TYPE: PRT
<213> ORGANISM: Homo sapiens

<400> SEQUENCE: 614

Pro Pro Pro Arg Pro
1               5

<210> SEQ ID NO 615
<211> LENGTH: 5
<212> TYPE: PRT
<213> ORGANISM: Homo sapiens

<400> SEQUENCE: 615

Pro Pro Arg Pro Gly
1               5

<210> SEQ ID NO 616
<211> LENGTH: 5
<212> TYPE: PRT
<213> ORGANISM: Homo sapiens

<400> SEQUENCE: 616

Pro Arg Pro Gly Lys
1               5

<210> SEQ ID NO 617
<211> LENGTH: 5
<212> TYPE: PRT
<213> ORGANISM: Homo sapiens

<400> SEQUENCE: 617

Arg Pro Gly Lys Pro
1               5

<210> SEQ ID NO 618
<211> LENGTH: 5
<212> TYPE: PRT
<213> ORGANISM: Homo sapiens

<400> SEQUENCE: 618
```

Pro Gly Lys Pro Glu
1               5

<210> SEQ ID NO 619
<211> LENGTH: 5
<212> TYPE: PRT
<213> ORGANISM: Homo sapiens

<400> SEQUENCE: 619

Gly Lys Pro Glu Gly
1               5

<210> SEQ ID NO 620
<211> LENGTH: 5
<212> TYPE: PRT
<213> ORGANISM: Homo sapiens

<400> SEQUENCE: 620

Lys Pro Glu Gly Pro
1               5

<210> SEQ ID NO 621
<211> LENGTH: 5
<212> TYPE: PRT
<213> ORGANISM: Homo sapiens

<400> SEQUENCE: 621

Pro Glu Gly Pro Pro
1               5

<210> SEQ ID NO 622
<211> LENGTH: 5
<212> TYPE: PRT
<213> ORGANISM: Homo sapiens

<400> SEQUENCE: 622

Glu Gly Pro Pro Pro
1               5

<210> SEQ ID NO 623
<211> LENGTH: 5
<212> TYPE: PRT
<213> ORGANISM: Homo sapiens

<400> SEQUENCE: 623

Gly Pro Pro Pro Gln
1               5

<210> SEQ ID NO 624
<211> LENGTH: 5
<212> TYPE: PRT
<213> ORGANISM: Homo sapiens

<400> SEQUENCE: 624

Pro Pro Pro Gln Gly
1               5

<210> SEQ ID NO 625
<211> LENGTH: 5
<212> TYPE: PRT
<213> ORGANISM: Homo sapiens

<400> SEQUENCE: 625

Pro Pro Gln Gly Gly
1               5

<210> SEQ ID NO 626
<211> LENGTH: 5
<212> TYPE: PRT
<213> ORGANISM: Homo sapiens

<400> SEQUENCE: 626

Pro Gln Gly Gly Asn
1               5

<210> SEQ ID NO 627
<211> LENGTH: 5
<212> TYPE: PRT
<213> ORGANISM: Homo sapiens

<400> SEQUENCE: 627

Gln Gly Gly Asn Gln
1               5

<210> SEQ ID NO 628
<211> LENGTH: 5
<212> TYPE: PRT
<213> ORGANISM: Homo sapiens

<400> SEQUENCE: 628

Gly Gly Asn Gln Ser
1               5

<210> SEQ ID NO 629
<211> LENGTH: 5
<212> TYPE: PRT
<213> ORGANISM: Homo sapiens

<400> SEQUENCE: 629

Gly Asn Gln Ser Gln
1               5

<210> SEQ ID NO 630
<211> LENGTH: 5
<212> TYPE: PRT
<213> ORGANISM: Homo sapiens

<400> SEQUENCE: 630

Asn Gln Ser Gln Gly
1               5

<210> SEQ ID NO 631
<211> LENGTH: 5
<212> TYPE: PRT
<213> ORGANISM: Homo sapiens

<400> SEQUENCE: 631

Gln Ser Gln Gly Pro
1               5

<210> SEQ ID NO 632
<211> LENGTH: 5
<212> TYPE: PRT
<213> ORGANISM: Homo sapiens

<400> SEQUENCE: 632

Ser Gln Gly Pro Pro
1               5

```
<210> SEQ ID NO 633
<211> LENGTH: 5
<212> TYPE: PRT
<213> ORGANISM: Homo sapiens

<400> SEQUENCE: 633

Gln Gly Pro Pro Pro
1               5

<210> SEQ ID NO 634
<211> LENGTH: 5
<212> TYPE: PRT
<213> ORGANISM: Homo sapiens

<400> SEQUENCE: 634

Gly Pro Pro Pro Arg
1               5

<210> SEQ ID NO 635
<211> LENGTH: 5
<212> TYPE: PRT
<213> ORGANISM: Homo sapiens

<400> SEQUENCE: 635

Pro Pro Pro Arg Pro
1               5

<210> SEQ ID NO 636
<211> LENGTH: 5
<212> TYPE: PRT
<213> ORGANISM: Homo sapiens

<400> SEQUENCE: 636

Pro Pro Arg Pro Gly
1               5

<210> SEQ ID NO 637
<211> LENGTH: 5
<212> TYPE: PRT
<213> ORGANISM: Homo sapiens

<400> SEQUENCE: 637

Pro Arg Pro Gly Lys
1               5

<210> SEQ ID NO 638
<211> LENGTH: 5
<212> TYPE: PRT
<213> ORGANISM: Homo sapiens

<400> SEQUENCE: 638

Arg Pro Gly Lys Pro
1               5

<210> SEQ ID NO 639
<211> LENGTH: 5
<212> TYPE: PRT
<213> ORGANISM: Homo sapiens

<400> SEQUENCE: 639

Pro Gly Lys Pro Glu
1               5

<210> SEQ ID NO 640
<211> LENGTH: 5
```

```
<212> TYPE: PRT
<213> ORGANISM: Homo sapiens

<400> SEQUENCE: 640

Gly Lys Pro Glu Gly
1               5

<210> SEQ ID NO 641
<211> LENGTH: 5
<212> TYPE: PRT
<213> ORGANISM: Homo sapiens

<400> SEQUENCE: 641

Lys Pro Glu Gly Ser
1               5

<210> SEQ ID NO 642
<211> LENGTH: 5
<212> TYPE: PRT
<213> ORGANISM: Homo sapiens

<400> SEQUENCE: 642

Pro Glu Gly Ser Pro
1               5

<210> SEQ ID NO 643
<211> LENGTH: 5
<212> TYPE: PRT
<213> ORGANISM: Homo sapiens

<400> SEQUENCE: 643

Glu Gly Ser Pro Ser
1               5

<210> SEQ ID NO 644
<211> LENGTH: 5
<212> TYPE: PRT
<213> ORGANISM: Homo sapiens

<400> SEQUENCE: 644

Gly Ser Pro Ser Gln
1               5

<210> SEQ ID NO 645
<211> LENGTH: 5
<212> TYPE: PRT
<213> ORGANISM: Homo sapiens

<400> SEQUENCE: 645

Ser Pro Ser Gln Gly
1               5

<210> SEQ ID NO 646
<211> LENGTH: 5
<212> TYPE: PRT
<213> ORGANISM: Homo sapiens

<400> SEQUENCE: 646

Pro Ser Gln Gly Gly
1               5

<210> SEQ ID NO 647
<211> LENGTH: 5
<212> TYPE: PRT
<213> ORGANISM: Homo sapiens
```

<400> SEQUENCE: 647

Ser Gln Gly Gly Asn
1               5

<210> SEQ ID NO 648
<211> LENGTH: 5
<212> TYPE: PRT
<213> ORGANISM: Homo sapiens

<400> SEQUENCE: 648

Gln Gly Gly Asn Lys
1               5

<210> SEQ ID NO 649
<211> LENGTH: 5
<212> TYPE: PRT
<213> ORGANISM: Homo sapiens

<400> SEQUENCE: 649

Gly Gly Asn Lys Pro
1               5

<210> SEQ ID NO 650
<211> LENGTH: 5
<212> TYPE: PRT
<213> ORGANISM: Homo sapiens

<400> SEQUENCE: 650

Gly Asn Lys Pro Gln
1               5

<210> SEQ ID NO 651
<211> LENGTH: 5
<212> TYPE: PRT
<213> ORGANISM: Homo sapiens

<400> SEQUENCE: 651

Asn Lys Pro Gln Gly
1               5

<210> SEQ ID NO 652
<211> LENGTH: 5
<212> TYPE: PRT
<213> ORGANISM: Homo sapiens

<400> SEQUENCE: 652

Lys Pro Gln Gly Pro
1               5

<210> SEQ ID NO 653
<211> LENGTH: 5
<212> TYPE: PRT
<213> ORGANISM: Homo sapiens

<400> SEQUENCE: 653

Pro Gln Gly Pro Pro
1               5

<210> SEQ ID NO 654
<211> LENGTH: 5
<212> TYPE: PRT
<213> ORGANISM: Homo sapiens

<400> SEQUENCE: 654

Gln Gly Pro Pro Pro
1               5

<210> SEQ ID NO 655
<211> LENGTH: 5
<212> TYPE: PRT
<213> ORGANISM: Homo sapiens

<400> SEQUENCE: 655

Gly Pro Pro Pro His
1               5

<210> SEQ ID NO 656
<211> LENGTH: 5
<212> TYPE: PRT
<213> ORGANISM: Homo sapiens

<400> SEQUENCE: 656

Pro Pro Pro His Pro
1               5

<210> SEQ ID NO 657
<211> LENGTH: 5
<212> TYPE: PRT
<213> ORGANISM: Homo sapiens

<400> SEQUENCE: 657

Pro Pro His Pro Gly
1               5

<210> SEQ ID NO 658
<211> LENGTH: 5
<212> TYPE: PRT
<213> ORGANISM: Homo sapiens

<400> SEQUENCE: 658

Pro His Pro Gly Lys
1               5

<210> SEQ ID NO 659
<211> LENGTH: 5
<212> TYPE: PRT
<213> ORGANISM: Homo sapiens

<400> SEQUENCE: 659

His Pro Gly Lys Pro
1               5

<210> SEQ ID NO 660
<211> LENGTH: 5
<212> TYPE: PRT
<213> ORGANISM: Homo sapiens

<400> SEQUENCE: 660

Pro Gly Lys Pro Gln
1               5

<210> SEQ ID NO 661
<211> LENGTH: 5
<212> TYPE: PRT
<213> ORGANISM: Homo sapiens

<400> SEQUENCE: 661

Gly Lys Pro Gln Gly

```
1               5

<210> SEQ ID NO 662
<211> LENGTH: 5
<212> TYPE: PRT
<213> ORGANISM: Homo sapiens

<400> SEQUENCE: 662

Lys Pro Gln Gly Pro
1               5

<210> SEQ ID NO 663
<211> LENGTH: 5
<212> TYPE: PRT
<213> ORGANISM: Homo sapiens

<400> SEQUENCE: 663

Pro Gln Gly Pro Pro
1               5

<210> SEQ ID NO 664
<211> LENGTH: 5
<212> TYPE: PRT
<213> ORGANISM: Homo sapiens

<400> SEQUENCE: 664

Gln Gly Pro Pro Pro
1               5

<210> SEQ ID NO 665
<211> LENGTH: 5
<212> TYPE: PRT
<213> ORGANISM: Homo sapiens

<400> SEQUENCE: 665

Gly Pro Pro Pro Gln
1               5

<210> SEQ ID NO 666
<211> LENGTH: 5
<212> TYPE: PRT
<213> ORGANISM: Homo sapiens

<400> SEQUENCE: 666

Pro Pro Pro Gln Glu
1               5

<210> SEQ ID NO 667
<211> LENGTH: 5
<212> TYPE: PRT
<213> ORGANISM: Homo sapiens

<400> SEQUENCE: 667

Pro Pro Gln Glu Gly
1               5

<210> SEQ ID NO 668
<211> LENGTH: 5
<212> TYPE: PRT
<213> ORGANISM: Homo sapiens

<400> SEQUENCE: 668

Pro Gln Glu Gly Asn
1               5
```

<210> SEQ ID NO 669
<211> LENGTH: 5
<212> TYPE: PRT
<213> ORGANISM: Homo sapiens

<400> SEQUENCE: 669

Gln Glu Gly Asn Lys
1               5

<210> SEQ ID NO 670
<211> LENGTH: 5
<212> TYPE: PRT
<213> ORGANISM: Homo sapiens

<400> SEQUENCE: 670

Glu Gly Asn Lys Pro
1               5

<210> SEQ ID NO 671
<211> LENGTH: 5
<212> TYPE: PRT
<213> ORGANISM: Homo sapiens

<400> SEQUENCE: 671

Gly Asn Lys Pro Gln
1               5

<210> SEQ ID NO 672
<211> LENGTH: 5
<212> TYPE: PRT
<213> ORGANISM: Homo sapiens

<400> SEQUENCE: 672

Asn Lys Pro Gln Arg
1               5

<210> SEQ ID NO 673
<211> LENGTH: 5
<212> TYPE: PRT
<213> ORGANISM: Homo sapiens

<400> SEQUENCE: 673

Lys Pro Gln Arg Pro
1               5

<210> SEQ ID NO 674
<211> LENGTH: 5
<212> TYPE: PRT
<213> ORGANISM: Homo sapiens

<400> SEQUENCE: 674

Pro Gln Arg Pro Pro
1               5

<210> SEQ ID NO 675
<211> LENGTH: 5
<212> TYPE: PRT
<213> ORGANISM: Homo sapiens

<400> SEQUENCE: 675

Gln Arg Pro Pro Pro
1               5

<210> SEQ ID NO 676

```
<211> LENGTH: 5
<212> TYPE: PRT
<213> ORGANISM: Homo sapiens

<400> SEQUENCE: 676

Arg Pro Pro Pro Pro
1               5

<210> SEQ ID NO 677
<211> LENGTH: 5
<212> TYPE: PRT
<213> ORGANISM: Homo sapiens

<400> SEQUENCE: 677

Pro Pro Pro Pro Gly
1               5

<210> SEQ ID NO 678
<211> LENGTH: 5
<212> TYPE: PRT
<213> ORGANISM: Homo sapiens

<400> SEQUENCE: 678

Pro Pro Pro Gly Arg
1               5

<210> SEQ ID NO 679
<211> LENGTH: 5
<212> TYPE: PRT
<213> ORGANISM: Homo sapiens

<400> SEQUENCE: 679

Pro Pro Gly Arg Pro
1               5

<210> SEQ ID NO 680
<211> LENGTH: 5
<212> TYPE: PRT
<213> ORGANISM: Homo sapiens

<400> SEQUENCE: 680

Pro Gly Arg Pro Gln
1               5

<210> SEQ ID NO 681
<211> LENGTH: 5
<212> TYPE: PRT
<213> ORGANISM: Homo sapiens

<400> SEQUENCE: 681

Gly Arg Pro Gln Gly
1               5

<210> SEQ ID NO 682
<211> LENGTH: 5
<212> TYPE: PRT
<213> ORGANISM: Homo sapiens

<400> SEQUENCE: 682

Arg Pro Gln Gly Pro
1               5

<210> SEQ ID NO 683
<211> LENGTH: 5
<212> TYPE: PRT
```

```
<213> ORGANISM: Homo sapiens

<400> SEQUENCE: 683

Pro Gln Gly Pro Pro
1               5

<210> SEQ ID NO 684
<211> LENGTH: 5
<212> TYPE: PRT
<213> ORGANISM: Homo sapiens

<400> SEQUENCE: 684

Gln Gly Pro Pro Pro
1               5

<210> SEQ ID NO 685
<211> LENGTH: 5
<212> TYPE: PRT
<213> ORGANISM: Homo sapiens

<400> SEQUENCE: 685

Gly Pro Pro Pro Pro
1               5

<210> SEQ ID NO 686
<211> LENGTH: 5
<212> TYPE: PRT
<213> ORGANISM: Homo sapiens

<400> SEQUENCE: 686

Pro Pro Pro Pro Gly
1               5

<210> SEQ ID NO 687
<211> LENGTH: 5
<212> TYPE: PRT
<213> ORGANISM: Homo sapiens

<400> SEQUENCE: 687

Pro Pro Pro Gly Gly
1               5

<210> SEQ ID NO 688
<211> LENGTH: 5
<212> TYPE: PRT
<213> ORGANISM: Homo sapiens

<400> SEQUENCE: 688

Pro Pro Gly Gly Asn
1               5

<210> SEQ ID NO 689
<211> LENGTH: 5
<212> TYPE: PRT
<213> ORGANISM: Homo sapiens

<400> SEQUENCE: 689

Pro Gly Gly Asn Pro
1               5

<210> SEQ ID NO 690
<211> LENGTH: 5
<212> TYPE: PRT
<213> ORGANISM: Homo sapiens
```

```
<400> SEQUENCE: 690

Gly Gly Asn Pro Gln
1               5

<210> SEQ ID NO 691
<211> LENGTH: 5
<212> TYPE: PRT
<213> ORGANISM: Homo sapiens

<400> SEQUENCE: 691

Gly Asn Pro Gln Gln
1               5

<210> SEQ ID NO 692
<211> LENGTH: 5
<212> TYPE: PRT
<213> ORGANISM: Homo sapiens

<400> SEQUENCE: 692

Asn Pro Gln Gln Pro
1               5

<210> SEQ ID NO 693
<211> LENGTH: 5
<212> TYPE: PRT
<213> ORGANISM: Homo sapiens

<400> SEQUENCE: 693

Pro Gln Gln Pro Leu
1               5

<210> SEQ ID NO 694
<211> LENGTH: 5
<212> TYPE: PRT
<213> ORGANISM: Homo sapiens

<400> SEQUENCE: 694

Gln Gln Pro Leu Pro
1               5

<210> SEQ ID NO 695
<211> LENGTH: 5
<212> TYPE: PRT
<213> ORGANISM: Homo sapiens

<400> SEQUENCE: 695

Gln Pro Leu Pro Pro
1               5

<210> SEQ ID NO 696
<211> LENGTH: 5
<212> TYPE: PRT
<213> ORGANISM: Homo sapiens

<400> SEQUENCE: 696

Pro Leu Pro Pro Pro
1               5

<210> SEQ ID NO 697
<211> LENGTH: 5
<212> TYPE: PRT
<213> ORGANISM: Homo sapiens

<400> SEQUENCE: 697
```

Leu Pro Pro Pro Ala
1               5

<210> SEQ ID NO 698
<211> LENGTH: 5
<212> TYPE: PRT
<213> ORGANISM: Homo sapiens

<400> SEQUENCE: 698

Pro Pro Pro Ala Gly
1               5

<210> SEQ ID NO 699
<211> LENGTH: 5
<212> TYPE: PRT
<213> ORGANISM: Homo sapiens

<400> SEQUENCE: 699

Pro Pro Ala Gly Lys
1               5

<210> SEQ ID NO 700
<211> LENGTH: 5
<212> TYPE: PRT
<213> ORGANISM: Homo sapiens

<400> SEQUENCE: 700

Pro Ala Gly Lys Pro
1               5

<210> SEQ ID NO 701
<211> LENGTH: 5
<212> TYPE: PRT
<213> ORGANISM: Homo sapiens

<400> SEQUENCE: 701

Ala Gly Lys Pro Gln
1               5

<210> SEQ ID NO 702
<211> LENGTH: 5
<212> TYPE: PRT
<213> ORGANISM: Homo sapiens

<400> SEQUENCE: 702

Gly Lys Pro Gln Gly
1               5

<210> SEQ ID NO 703
<211> LENGTH: 5
<212> TYPE: PRT
<213> ORGANISM: Homo sapiens

<400> SEQUENCE: 703

Lys Pro Gln Gly Pro
1               5

<210> SEQ ID NO 704
<211> LENGTH: 5
<212> TYPE: PRT
<213> ORGANISM: Homo sapiens

<400> SEQUENCE: 704

Pro Gln Gly Pro Pro
1               5

```
<210> SEQ ID NO 705
<211> LENGTH: 5
<212> TYPE: PRT
<213> ORGANISM: Homo sapiens

<400> SEQUENCE: 705

Gln Gly Pro Pro Pro
1               5

<210> SEQ ID NO 706
<211> LENGTH: 5
<212> TYPE: PRT
<213> ORGANISM: Homo sapiens

<400> SEQUENCE: 706

Gly Pro Pro Pro Pro
1               5

<210> SEQ ID NO 707
<211> LENGTH: 5
<212> TYPE: PRT
<213> ORGANISM: Homo sapiens

<400> SEQUENCE: 707

Pro Pro Pro Pro Pro
1               5

<210> SEQ ID NO 708
<211> LENGTH: 5
<212> TYPE: PRT
<213> ORGANISM: Homo sapiens

<400> SEQUENCE: 708

Pro Pro Pro Pro Gln
1               5

<210> SEQ ID NO 709
<211> LENGTH: 5
<212> TYPE: PRT
<213> ORGANISM: Homo sapiens

<400> SEQUENCE: 709

Pro Pro Pro Gln Gly
1               5

<210> SEQ ID NO 710
<211> LENGTH: 5
<212> TYPE: PRT
<213> ORGANISM: Homo sapiens

<400> SEQUENCE: 710

Pro Pro Gln Gly Gly
1               5

<210> SEQ ID NO 711
<211> LENGTH: 5
<212> TYPE: PRT
<213> ORGANISM: Homo sapiens

<400> SEQUENCE: 711

Pro Gln Gly Gly Arg
1               5
```

```
<210> SEQ ID NO 712
<211> LENGTH: 5
<212> TYPE: PRT
<213> ORGANISM: Homo sapiens

<400> SEQUENCE: 712

Gln Gly Gly Arg Pro
1               5

<210> SEQ ID NO 713
<211> LENGTH: 5
<212> TYPE: PRT
<213> ORGANISM: Homo sapiens

<400> SEQUENCE: 713

Gly Gly Arg Pro His
1               5

<210> SEQ ID NO 714
<211> LENGTH: 5
<212> TYPE: PRT
<213> ORGANISM: Homo sapiens

<400> SEQUENCE: 714

Gly Arg Pro His Arg
1               5

<210> SEQ ID NO 715
<211> LENGTH: 5
<212> TYPE: PRT
<213> ORGANISM: Homo sapiens

<400> SEQUENCE: 715

Arg Pro His Arg Pro
1               5

<210> SEQ ID NO 716
<211> LENGTH: 5
<212> TYPE: PRT
<213> ORGANISM: Homo sapiens

<400> SEQUENCE: 716

Pro His Arg Pro Pro
1               5

<210> SEQ ID NO 717
<211> LENGTH: 5
<212> TYPE: PRT
<213> ORGANISM: Homo sapiens

<400> SEQUENCE: 717

His Arg Pro Pro Gln
1               5

<210> SEQ ID NO 718
<211> LENGTH: 5
<212> TYPE: PRT
<213> ORGANISM: Homo sapiens

<400> SEQUENCE: 718

Arg Pro Pro Gln Gly
1               5

<210> SEQ ID NO 719
<211> LENGTH: 5
```

-continued

<212> TYPE: PRT
<213> ORGANISM: Homo sapiens

<400> SEQUENCE: 719

Pro Pro Gln Gly Gln
1               5

<210> SEQ ID NO 720
<211> LENGTH: 5
<212> TYPE: PRT
<213> ORGANISM: Homo sapiens

<400> SEQUENCE: 720

Pro Gln Gly Gln Pro
1               5

<210> SEQ ID NO 721
<211> LENGTH: 5
<212> TYPE: PRT
<213> ORGANISM: Homo sapiens

<400> SEQUENCE: 721

Gln Gly Gln Pro Pro
1               5

<210> SEQ ID NO 722
<211> LENGTH: 5
<212> TYPE: PRT
<213> ORGANISM: Homo sapiens

<400> SEQUENCE: 722

Gly Gln Pro Pro Gln
1               5

<210> SEQ ID NO 723
<211> LENGTH: 247
<212> TYPE: PRT
<213> ORGANISM: Homo sapiens

<400> SEQUENCE: 723

Met Leu Leu Ile Leu Leu Ser Val Ala Leu Ala Leu Ser Ser Ala
1               5                   10                  15

Glu Ser Ser Ser Glu Asp Val Ser Gln Glu Glu Ser Leu Phe Leu Ile
                20                  25                  30

Ser Gly Lys Pro Glu Gly Arg Arg Pro Gln Gly Gly Asn Gln Pro Gln
            35                  40                  45

Arg Pro Pro Pro Pro Gly Lys Pro Gln Gly Pro Pro Gln Gly
    50                  55                  60

Gly Asn Gln Ser Gln Gly Pro Pro Pro Gly Lys Pro Glu Gly
65                  70                  75                  80

Arg Pro Pro Gln Gly Gly Asn Gln Ser Gln Gly Pro Pro His Pro
                85                  90                  95

Gly Lys Pro Glu Arg Pro Pro Gln Gly Gly Asn Gln Ser Gln Gly
            100                 105                 110

Thr Pro Pro Pro Gly Lys Pro Glu Arg Pro Pro Gln Gly Gly
        115                 120                 125

Asn Gln Ser His Arg Pro Pro Pro Pro Gly Lys Pro Glu Arg Pro
            130                 135                 140

Pro Pro Gln Gly Gly Asn Gln Ser Gln Gly Pro Pro His Pro Gly
145                 150                 155                 160

-continued

```
Lys Pro Glu Gly Pro Pro Gln Glu Gly Asn Lys Ser Arg Ser Ala
                165                 170                 175
Arg Ser Pro Pro Gly Lys Pro Gln Gly Pro Gln Gln Glu Gly Asn
            180                 185                 190
Lys Pro Gln Gly Pro Pro Pro Gly Lys Pro Gln Gly Pro Pro Pro
        195                 200                 205
Ala Gly Gly Asn Pro Gln Gln Pro Gln Ala Pro Pro Ala Gly Lys Pro
    210                 215                 220
Gln Gly Pro Pro Pro Pro Gln Gly Gly Arg Pro Pro Arg Pro Ala
225                 230                 235                 240
Gln Gly Gln Gln Pro Pro Gln
                245

<210> SEQ ID NO 724
<211> LENGTH: 5
<212> TYPE: PRT
<213> ORGANISM: Homo sapiens

<400> SEQUENCE: 724

Met Leu Leu Ile Leu
1               5

<210> SEQ ID NO 725
<211> LENGTH: 5
<212> TYPE: PRT
<213> ORGANISM: Homo sapiens

<400> SEQUENCE: 725

Leu Leu Ile Leu Leu
1               5

<210> SEQ ID NO 726
<211> LENGTH: 5
<212> TYPE: PRT
<213> ORGANISM: Homo sapiens

<400> SEQUENCE: 726

Leu Ile Leu Leu Ser
1               5

<210> SEQ ID NO 727
<211> LENGTH: 5
<212> TYPE: PRT
<213> ORGANISM: Homo sapiens

<400> SEQUENCE: 727

Ile Leu Leu Ser Val
1               5

<210> SEQ ID NO 728
<211> LENGTH: 5
<212> TYPE: PRT
<213> ORGANISM: Homo sapiens

<400> SEQUENCE: 728

Leu Leu Ser Val Ala
1               5

<210> SEQ ID NO 729
<211> LENGTH: 5
<212> TYPE: PRT
<213> ORGANISM: Homo sapiens
```

<400> SEQUENCE: 729

Leu Ser Val Ala Leu
1               5

<210> SEQ ID NO 730
<211> LENGTH: 5
<212> TYPE: PRT
<213> ORGANISM: Homo sapiens

<400> SEQUENCE: 730

Ser Val Ala Leu Leu
1               5

<210> SEQ ID NO 731
<211> LENGTH: 5
<212> TYPE: PRT
<213> ORGANISM: Homo sapiens

<400> SEQUENCE: 731

Val Ala Leu Leu Ala
1               5

<210> SEQ ID NO 732
<211> LENGTH: 5
<212> TYPE: PRT
<213> ORGANISM: Homo sapiens

<400> SEQUENCE: 732

Ala Leu Leu Ala Leu
1               5

<210> SEQ ID NO 733
<211> LENGTH: 5
<212> TYPE: PRT
<213> ORGANISM: Homo sapiens

<400> SEQUENCE: 733

Leu Leu Ala Leu Ser
1               5

<210> SEQ ID NO 734
<211> LENGTH: 5
<212> TYPE: PRT
<213> ORGANISM: Homo sapiens

<400> SEQUENCE: 734

Leu Ala Leu Ser Ser
1               5

<210> SEQ ID NO 735
<211> LENGTH: 5
<212> TYPE: PRT
<213> ORGANISM: Homo sapiens

<400> SEQUENCE: 735

Ala Leu Ser Ser Ala
1               5

<210> SEQ ID NO 736
<211> LENGTH: 5
<212> TYPE: PRT
<213> ORGANISM: Homo sapiens

<400> SEQUENCE: 736

```
Leu Ser Ser Ala Glu
1               5

<210> SEQ ID NO 737
<211> LENGTH: 5
<212> TYPE: PRT
<213> ORGANISM: Homo sapiens

<400> SEQUENCE: 737

Ser Ser Ala Glu Ser
1               5

<210> SEQ ID NO 738
<211> LENGTH: 5
<212> TYPE: PRT
<213> ORGANISM: Homo sapiens

<400> SEQUENCE: 738

Ser Ala Glu Ser Ser
1               5

<210> SEQ ID NO 739
<211> LENGTH: 5
<212> TYPE: PRT
<213> ORGANISM: Homo sapiens

<400> SEQUENCE: 739

Ala Glu Ser Ser Ser
1               5

<210> SEQ ID NO 740
<211> LENGTH: 5
<212> TYPE: PRT
<213> ORGANISM: Homo sapiens

<400> SEQUENCE: 740

Glu Ser Ser Ser Glu
1               5

<210> SEQ ID NO 741
<211> LENGTH: 5
<212> TYPE: PRT
<213> ORGANISM: Homo sapiens

<400> SEQUENCE: 741

Ser Ser Ser Glu Asp
1               5

<210> SEQ ID NO 742
<211> LENGTH: 5
<212> TYPE: PRT
<213> ORGANISM: Homo sapiens

<400> SEQUENCE: 742

Ser Ser Glu Asp Val
1               5

<210> SEQ ID NO 743
<211> LENGTH: 5
<212> TYPE: PRT
<213> ORGANISM: Homo sapiens

<400> SEQUENCE: 743

Ser Glu Asp Val Ser
1               5
```

```
<210> SEQ ID NO 744
<211> LENGTH: 5
<212> TYPE: PRT
<213> ORGANISM: Homo sapiens

<400> SEQUENCE: 744

Glu Asp Val Ser Gln
1               5

<210> SEQ ID NO 745
<211> LENGTH: 5
<212> TYPE: PRT
<213> ORGANISM: Homo sapiens

<400> SEQUENCE: 745

Asp Val Ser Gln Glu
1               5

<210> SEQ ID NO 746
<211> LENGTH: 5
<212> TYPE: PRT
<213> ORGANISM: Homo sapiens

<400> SEQUENCE: 746

Val Ser Gln Glu Glu
1               5

<210> SEQ ID NO 747
<211> LENGTH: 5
<212> TYPE: PRT
<213> ORGANISM: Homo sapiens

<400> SEQUENCE: 747

Ser Gln Glu Glu Ser
1               5

<210> SEQ ID NO 748
<211> LENGTH: 5
<212> TYPE: PRT
<213> ORGANISM: Homo sapiens

<400> SEQUENCE: 748

Gln Glu Glu Ser Leu
1               5

<210> SEQ ID NO 749
<211> LENGTH: 5
<212> TYPE: PRT
<213> ORGANISM: Homo sapiens

<400> SEQUENCE: 749

Glu Glu Ser Leu Phe
1               5

<210> SEQ ID NO 750
<211> LENGTH: 5
<212> TYPE: PRT
<213> ORGANISM: Homo sapiens

<400> SEQUENCE: 750

Glu Ser Leu Phe Leu
1               5
```

```
<210> SEQ ID NO 751
<211> LENGTH: 5
<212> TYPE: PRT
<213> ORGANISM: Homo sapiens

<400> SEQUENCE: 751

Ser Leu Phe Leu Ile
1               5

<210> SEQ ID NO 752
<211> LENGTH: 5
<212> TYPE: PRT
<213> ORGANISM: Homo sapiens

<400> SEQUENCE: 752

Leu Phe Leu Ile Ser
1               5

<210> SEQ ID NO 753
<211> LENGTH: 5
<212> TYPE: PRT
<213> ORGANISM: Homo sapiens

<400> SEQUENCE: 753

Phe Leu Ile Ser Gly
1               5

<210> SEQ ID NO 754
<211> LENGTH: 5
<212> TYPE: PRT
<213> ORGANISM: Homo sapiens

<400> SEQUENCE: 754

Leu Ile Ser Gly Lys
1               5

<210> SEQ ID NO 755
<211> LENGTH: 5
<212> TYPE: PRT
<213> ORGANISM: Homo sapiens

<400> SEQUENCE: 755

Ile Ser Gly Lys Pro
1               5

<210> SEQ ID NO 756
<211> LENGTH: 5
<212> TYPE: PRT
<213> ORGANISM: Homo sapiens

<400> SEQUENCE: 756

Ser Gly Lys Pro Glu
1               5

<210> SEQ ID NO 757
<211> LENGTH: 5
<212> TYPE: PRT
<213> ORGANISM: Homo sapiens

<400> SEQUENCE: 757

Gly Lys Pro Glu Gly
1               5

<210> SEQ ID NO 758
<211> LENGTH: 5
```

```
<212> TYPE: PRT
<213> ORGANISM: Homo sapiens

<400> SEQUENCE: 758

Lys Pro Glu Gly Arg
1               5

<210> SEQ ID NO 759
<211> LENGTH: 5
<212> TYPE: PRT
<213> ORGANISM: Homo sapiens

<400> SEQUENCE: 759

Pro Glu Gly Arg Arg
1               5

<210> SEQ ID NO 760
<211> LENGTH: 5
<212> TYPE: PRT
<213> ORGANISM: Homo sapiens

<400> SEQUENCE: 760

Glu Gly Arg Arg Pro
1               5

<210> SEQ ID NO 761
<211> LENGTH: 5
<212> TYPE: PRT
<213> ORGANISM: Homo sapiens

<400> SEQUENCE: 761

Gly Arg Arg Pro Gln
1               5

<210> SEQ ID NO 762
<211> LENGTH: 5
<212> TYPE: PRT
<213> ORGANISM: Homo sapiens

<400> SEQUENCE: 762

Arg Arg Pro Gln Gly
1               5

<210> SEQ ID NO 763
<211> LENGTH: 5
<212> TYPE: PRT
<213> ORGANISM: Homo sapiens

<400> SEQUENCE: 763

Arg Pro Gln Gly Gly
1               5

<210> SEQ ID NO 764
<211> LENGTH: 5
<212> TYPE: PRT
<213> ORGANISM: Homo sapiens

<400> SEQUENCE: 764

Pro Gln Gly Gly Asn
1               5

<210> SEQ ID NO 765
<211> LENGTH: 5
<212> TYPE: PRT
<213> ORGANISM: Homo sapiens
```

```
<400> SEQUENCE: 765

Gln Gly Gly Asn Gln
1               5

<210> SEQ ID NO 766
<211> LENGTH: 5
<212> TYPE: PRT
<213> ORGANISM: Homo sapiens

<400> SEQUENCE: 766

Gly Gly Asn Gln Pro
1               5

<210> SEQ ID NO 767
<211> LENGTH: 5
<212> TYPE: PRT
<213> ORGANISM: Homo sapiens

<400> SEQUENCE: 767

Gly Asn Gln Pro Gln
1               5

<210> SEQ ID NO 768
<211> LENGTH: 5
<212> TYPE: PRT
<213> ORGANISM: Homo sapiens

<400> SEQUENCE: 768

Asn Gln Pro Gln Arg
1               5

<210> SEQ ID NO 769
<211> LENGTH: 5
<212> TYPE: PRT
<213> ORGANISM: Homo sapiens

<400> SEQUENCE: 769

Gln Pro Gln Arg Pro
1               5

<210> SEQ ID NO 770
<211> LENGTH: 5
<212> TYPE: PRT
<213> ORGANISM: Homo sapiens

<400> SEQUENCE: 770

Pro Gln Arg Pro Pro
1               5

<210> SEQ ID NO 771
<211> LENGTH: 5
<212> TYPE: PRT
<213> ORGANISM: Homo sapiens

<400> SEQUENCE: 771

Gln Arg Pro Pro Pro
1               5

<210> SEQ ID NO 772
<211> LENGTH: 5
<212> TYPE: PRT
<213> ORGANISM: Homo sapiens

<400> SEQUENCE: 772
```

```
Arg Pro Pro Pro Pro
1               5

<210> SEQ ID NO 773
<211> LENGTH: 5
<212> TYPE: PRT
<213> ORGANISM: Homo sapiens

<400> SEQUENCE: 773

Pro Pro Pro Pro Pro
1               5

<210> SEQ ID NO 774
<211> LENGTH: 5
<212> TYPE: PRT
<213> ORGANISM: Homo sapiens

<400> SEQUENCE: 774

Pro Pro Pro Pro Gly
1               5

<210> SEQ ID NO 775
<211> LENGTH: 5
<212> TYPE: PRT
<213> ORGANISM: Homo sapiens

<400> SEQUENCE: 775

Pro Pro Pro Gly Lys
1               5

<210> SEQ ID NO 776
<211> LENGTH: 5
<212> TYPE: PRT
<213> ORGANISM: Homo sapiens

<400> SEQUENCE: 776

Pro Pro Gly Lys Pro
1               5

<210> SEQ ID NO 777
<211> LENGTH: 5
<212> TYPE: PRT
<213> ORGANISM: Homo sapiens

<400> SEQUENCE: 777

Pro Gly Lys Pro Gln
1               5

<210> SEQ ID NO 778
<211> LENGTH: 5
<212> TYPE: PRT
<213> ORGANISM: Homo sapiens

<400> SEQUENCE: 778

Gly Lys Pro Gln Gly
1               5

<210> SEQ ID NO 779
<211> LENGTH: 5
<212> TYPE: PRT
<213> ORGANISM: Homo sapiens

<400> SEQUENCE: 779

Lys Pro Gln Gly Pro
```

```
1               5
```

<210> SEQ ID NO 780
<211> LENGTH: 5
<212> TYPE: PRT
<213> ORGANISM: Homo sapiens

<400> SEQUENCE: 780

```
Pro Gln Gly Pro Pro
1               5
```

<210> SEQ ID NO 781
<211> LENGTH: 5
<212> TYPE: PRT
<213> ORGANISM: Homo sapiens

<400> SEQUENCE: 781

```
Gln Gly Pro Pro Pro
1               5
```

<210> SEQ ID NO 782
<211> LENGTH: 5
<212> TYPE: PRT
<213> ORGANISM: Homo sapiens

<400> SEQUENCE: 782

```
Gly Pro Pro Pro Gln
1               5
```

<210> SEQ ID NO 783
<211> LENGTH: 5
<212> TYPE: PRT
<213> ORGANISM: Homo sapiens

<400> SEQUENCE: 783

```
Pro Pro Pro Gln Gly
1               5
```

<210> SEQ ID NO 784
<211> LENGTH: 5
<212> TYPE: PRT
<213> ORGANISM: Homo sapiens

<400> SEQUENCE: 784

```
Pro Pro Gln Gly Gly
1               5
```

<210> SEQ ID NO 785
<211> LENGTH: 5
<212> TYPE: PRT
<213> ORGANISM: Homo sapiens

<400> SEQUENCE: 785

```
Pro Gln Gly Gly Asn
1               5
```

<210> SEQ ID NO 786
<211> LENGTH: 5
<212> TYPE: PRT
<213> ORGANISM: Homo sapiens

<400> SEQUENCE: 786

```
Gln Gly Gly Asn Gln
1               5
```

<210> SEQ ID NO 787
<211> LENGTH: 5
<212> TYPE: PRT
<213> ORGANISM: Homo sapiens

<400> SEQUENCE: 787

Gly Gly Asn Gln Ser
1               5

<210> SEQ ID NO 788
<211> LENGTH: 5
<212> TYPE: PRT
<213> ORGANISM: Homo sapiens

<400> SEQUENCE: 788

Gly Asn Gln Ser Gln
1               5

<210> SEQ ID NO 789
<211> LENGTH: 5
<212> TYPE: PRT
<213> ORGANISM: Homo sapiens

<400> SEQUENCE: 789

Asn Gln Ser Gln Gly
1               5

<210> SEQ ID NO 790
<211> LENGTH: 5
<212> TYPE: PRT
<213> ORGANISM: Homo sapiens

<400> SEQUENCE: 790

Gln Ser Gln Gly Pro
1               5

<210> SEQ ID NO 791
<211> LENGTH: 5
<212> TYPE: PRT
<213> ORGANISM: Homo sapiens

<400> SEQUENCE: 791

Ser Gln Gly Pro Pro
1               5

<210> SEQ ID NO 792
<211> LENGTH: 5
<212> TYPE: PRT
<213> ORGANISM: Homo sapiens

<400> SEQUENCE: 792

Gln Gly Pro Pro Pro
1               5

<210> SEQ ID NO 793
<211> LENGTH: 5
<212> TYPE: PRT
<213> ORGANISM: Homo sapiens

<400> SEQUENCE: 793

Gly Pro Pro Pro Pro
1               5

<210> SEQ ID NO 794

```
<211> LENGTH: 5
<212> TYPE: PRT
<213> ORGANISM: Homo sapiens

<400> SEQUENCE: 794

Pro Pro Pro Pro Pro
1               5

<210> SEQ ID NO 795
<211> LENGTH: 5
<212> TYPE: PRT
<213> ORGANISM: Homo sapiens

<400> SEQUENCE: 795

Pro Pro Pro Pro Gly
1               5

<210> SEQ ID NO 796
<211> LENGTH: 5
<212> TYPE: PRT
<213> ORGANISM: Homo sapiens

<400> SEQUENCE: 796

Pro Pro Pro Gly Lys
1               5

<210> SEQ ID NO 797
<211> LENGTH: 5
<212> TYPE: PRT
<213> ORGANISM: Homo sapiens

<400> SEQUENCE: 797

Pro Pro Gly Lys Pro
1               5

<210> SEQ ID NO 798
<211> LENGTH: 5
<212> TYPE: PRT
<213> ORGANISM: Homo sapiens

<400> SEQUENCE: 798

Pro Gly Lys Pro Glu
1               5

<210> SEQ ID NO 799
<211> LENGTH: 5
<212> TYPE: PRT
<213> ORGANISM: Homo sapiens

<400> SEQUENCE: 799

Gly Lys Pro Glu Gly
1               5

<210> SEQ ID NO 800
<211> LENGTH: 5
<212> TYPE: PRT
<213> ORGANISM: Homo sapiens

<400> SEQUENCE: 800

Lys Pro Glu Gly Arg
1               5

<210> SEQ ID NO 801
<211> LENGTH: 5
<212> TYPE: PRT
```

<213> ORGANISM: Homo sapiens

<400> SEQUENCE: 801

Pro Glu Gly Arg Pro
1               5

<210> SEQ ID NO 802
<211> LENGTH: 5
<212> TYPE: PRT
<213> ORGANISM: Homo sapiens

<400> SEQUENCE: 802

Glu Gly Arg Pro Pro
1               5

<210> SEQ ID NO 803
<211> LENGTH: 5
<212> TYPE: PRT
<213> ORGANISM: Homo sapiens

<400> SEQUENCE: 803

Gly Arg Pro Pro Gln
1               5

<210> SEQ ID NO 804
<211> LENGTH: 5
<212> TYPE: PRT
<213> ORGANISM: Homo sapiens

<400> SEQUENCE: 804

Arg Pro Pro Gln Gly
1               5

<210> SEQ ID NO 805
<211> LENGTH: 5
<212> TYPE: PRT
<213> ORGANISM: Homo sapiens

<400> SEQUENCE: 805

Pro Pro Gln Gly Gly
1               5

<210> SEQ ID NO 806
<211> LENGTH: 5
<212> TYPE: PRT
<213> ORGANISM: Homo sapiens

<400> SEQUENCE: 806

Pro Gln Gly Gly Asn
1               5

<210> SEQ ID NO 807
<211> LENGTH: 5
<212> TYPE: PRT
<213> ORGANISM: Homo sapiens

<400> SEQUENCE: 807

Gln Gly Gly Asn Gln
1               5

<210> SEQ ID NO 808
<211> LENGTH: 5
<212> TYPE: PRT
<213> ORGANISM: Homo sapiens

```
<400> SEQUENCE: 808

Gly Gly Asn Gln Ser
1               5

<210> SEQ ID NO 809
<211> LENGTH: 5
<212> TYPE: PRT
<213> ORGANISM: Homo sapiens

<400> SEQUENCE: 809

Gly Asn Gln Ser Gln
1               5

<210> SEQ ID NO 810
<211> LENGTH: 5
<212> TYPE: PRT
<213> ORGANISM: Homo sapiens

<400> SEQUENCE: 810

Asn Gln Ser Gln Gly
1               5

<210> SEQ ID NO 811
<211> LENGTH: 5
<212> TYPE: PRT
<213> ORGANISM: Homo sapiens

<400> SEQUENCE: 811

Gln Ser Gln Gly Pro
1               5

<210> SEQ ID NO 812
<211> LENGTH: 5
<212> TYPE: PRT
<213> ORGANISM: Homo sapiens

<400> SEQUENCE: 812

Ser Gln Gly Pro Pro
1               5

<210> SEQ ID NO 813
<211> LENGTH: 5
<212> TYPE: PRT
<213> ORGANISM: Homo sapiens

<400> SEQUENCE: 813

Gln Gly Pro Pro Pro
1               5

<210> SEQ ID NO 814
<211> LENGTH: 5
<212> TYPE: PRT
<213> ORGANISM: Homo sapiens

<400> SEQUENCE: 814

Gly Pro Pro Pro His
1               5

<210> SEQ ID NO 815
<211> LENGTH: 5
<212> TYPE: PRT
<213> ORGANISM: Homo sapiens

<400> SEQUENCE: 815
```

```
Pro Pro Pro His Pro
1               5

<210> SEQ ID NO 816
<211> LENGTH: 5
<212> TYPE: PRT
<213> ORGANISM: Homo sapiens

<400> SEQUENCE: 816

Pro Pro His Pro Gly
1               5

<210> SEQ ID NO 817
<211> LENGTH: 5
<212> TYPE: PRT
<213> ORGANISM: Homo sapiens

<400> SEQUENCE: 817

Pro His Pro Gly Lys
1               5

<210> SEQ ID NO 818
<211> LENGTH: 5
<212> TYPE: PRT
<213> ORGANISM: Homo sapiens

<400> SEQUENCE: 818

His Pro Gly Lys Pro
1               5

<210> SEQ ID NO 819
<211> LENGTH: 5
<212> TYPE: PRT
<213> ORGANISM: Homo sapiens

<400> SEQUENCE: 819

Pro Gly Lys Pro Glu
1               5

<210> SEQ ID NO 820
<211> LENGTH: 5
<212> TYPE: PRT
<213> ORGANISM: Homo sapiens

<400> SEQUENCE: 820

Gly Lys Pro Glu Arg
1               5

<210> SEQ ID NO 821
<211> LENGTH: 5
<212> TYPE: PRT
<213> ORGANISM: Homo sapiens

<400> SEQUENCE: 821

Lys Pro Glu Arg Pro
1               5

<210> SEQ ID NO 822
<211> LENGTH: 5
<212> TYPE: PRT
<213> ORGANISM: Homo sapiens

<400> SEQUENCE: 822

Pro Glu Arg Pro Pro
1               5
```

```
<210> SEQ ID NO 823
<211> LENGTH: 5
<212> TYPE: PRT
<213> ORGANISM: Homo sapiens

<400> SEQUENCE: 823

Glu Arg Pro Pro Pro
1               5

<210> SEQ ID NO 824
<211> LENGTH: 5
<212> TYPE: PRT
<213> ORGANISM: Homo sapiens

<400> SEQUENCE: 824

Arg Pro Pro Pro Gln
1               5

<210> SEQ ID NO 825
<211> LENGTH: 5
<212> TYPE: PRT
<213> ORGANISM: Homo sapiens

<400> SEQUENCE: 825

Pro Pro Pro Gln Gly
1               5

<210> SEQ ID NO 826
<211> LENGTH: 5
<212> TYPE: PRT
<213> ORGANISM: Homo sapiens

<400> SEQUENCE: 826

Pro Pro Gln Gly Gly
1               5

<210> SEQ ID NO 827
<211> LENGTH: 5
<212> TYPE: PRT
<213> ORGANISM: Homo sapiens

<400> SEQUENCE: 827

Pro Gln Gly Gly Asn
1               5

<210> SEQ ID NO 828
<211> LENGTH: 5
<212> TYPE: PRT
<213> ORGANISM: Homo sapiens

<400> SEQUENCE: 828

Gln Gly Gly Asn Gln
1               5

<210> SEQ ID NO 829
<211> LENGTH: 5
<212> TYPE: PRT
<213> ORGANISM: Homo sapiens

<400> SEQUENCE: 829

Gly Gly Asn Gln Ser
1               5
```

```
<210> SEQ ID NO 830
<211> LENGTH: 5
<212> TYPE: PRT
<213> ORGANISM: Homo sapiens

<400> SEQUENCE: 830

Gly Asn Gln Ser Gln
1               5

<210> SEQ ID NO 831
<211> LENGTH: 5
<212> TYPE: PRT
<213> ORGANISM: Homo sapiens

<400> SEQUENCE: 831

Asn Gln Ser Gln Gly
1               5

<210> SEQ ID NO 832
<211> LENGTH: 5
<212> TYPE: PRT
<213> ORGANISM: Homo sapiens

<400> SEQUENCE: 832

Gln Ser Gln Gly Thr
1               5

<210> SEQ ID NO 833
<211> LENGTH: 5
<212> TYPE: PRT
<213> ORGANISM: Homo sapiens

<400> SEQUENCE: 833

Ser Gln Gly Thr Pro
1               5

<210> SEQ ID NO 834
<211> LENGTH: 5
<212> TYPE: PRT
<213> ORGANISM: Homo sapiens

<400> SEQUENCE: 834

Gln Gly Thr Pro Pro
1               5

<210> SEQ ID NO 835
<211> LENGTH: 5
<212> TYPE: PRT
<213> ORGANISM: Homo sapiens

<400> SEQUENCE: 835

Gly Thr Pro Pro Pro
1               5

<210> SEQ ID NO 836
<211> LENGTH: 5
<212> TYPE: PRT
<213> ORGANISM: Homo sapiens

<400> SEQUENCE: 836

Thr Pro Pro Pro Pro
1               5

<210> SEQ ID NO 837
<211> LENGTH: 5
```

```
<212> TYPE: PRT
<213> ORGANISM: Homo sapiens

<400> SEQUENCE: 837

Pro Pro Pro Pro Gly
1               5

<210> SEQ ID NO 838
<211> LENGTH: 5
<212> TYPE: PRT
<213> ORGANISM: Homo sapiens

<400> SEQUENCE: 838

Pro Pro Pro Gly Lys
1               5

<210> SEQ ID NO 839
<211> LENGTH: 5
<212> TYPE: PRT
<213> ORGANISM: Homo sapiens

<400> SEQUENCE: 839

Pro Pro Gly Lys Pro
1               5

<210> SEQ ID NO 840
<211> LENGTH: 5
<212> TYPE: PRT
<213> ORGANISM: Homo sapiens

<400> SEQUENCE: 840

Pro Gly Lys Pro Glu
1               5

<210> SEQ ID NO 841
<211> LENGTH: 5
<212> TYPE: PRT
<213> ORGANISM: Homo sapiens

<400> SEQUENCE: 841

Gly Lys Pro Glu Arg
1               5

<210> SEQ ID NO 842
<211> LENGTH: 5
<212> TYPE: PRT
<213> ORGANISM: Homo sapiens

<400> SEQUENCE: 842

Lys Pro Glu Arg Pro
1               5

<210> SEQ ID NO 843
<211> LENGTH: 5
<212> TYPE: PRT
<213> ORGANISM: Homo sapiens

<400> SEQUENCE: 843

Pro Glu Arg Pro Pro
1               5

<210> SEQ ID NO 844
<211> LENGTH: 5
<212> TYPE: PRT
<213> ORGANISM: Homo sapiens
```

<400> SEQUENCE: 844

Glu Arg Pro Pro Pro
1               5

<210> SEQ ID NO 845
<211> LENGTH: 5
<212> TYPE: PRT
<213> ORGANISM: Homo sapiens

<400> SEQUENCE: 845

Arg Pro Pro Pro Gln
1               5

<210> SEQ ID NO 846
<211> LENGTH: 5
<212> TYPE: PRT
<213> ORGANISM: Homo sapiens

<400> SEQUENCE: 846

Pro Pro Pro Gln Gly
1               5

<210> SEQ ID NO 847
<211> LENGTH: 5
<212> TYPE: PRT
<213> ORGANISM: Homo sapiens

<400> SEQUENCE: 847

Pro Pro Gln Gly Gly
1               5

<210> SEQ ID NO 848
<211> LENGTH: 5
<212> TYPE: PRT
<213> ORGANISM: Homo sapiens

<400> SEQUENCE: 848

Pro Gln Gly Gly Asn
1               5

<210> SEQ ID NO 849
<211> LENGTH: 5
<212> TYPE: PRT
<213> ORGANISM: Homo sapiens

<400> SEQUENCE: 849

Gln Gly Gly Asn Gln
1               5

<210> SEQ ID NO 850
<211> LENGTH: 5
<212> TYPE: PRT
<213> ORGANISM: Homo sapiens

<400> SEQUENCE: 850

Gly Gly Asn Gln Ser
1               5

<210> SEQ ID NO 851
<211> LENGTH: 5
<212> TYPE: PRT
<213> ORGANISM: Homo sapiens

<400> SEQUENCE: 851

Gly Asn Gln Ser His
1               5

<210> SEQ ID NO 852
<211> LENGTH: 5
<212> TYPE: PRT
<213> ORGANISM: Homo sapiens

<400> SEQUENCE: 852

Asn Gln Ser His Arg
1               5

<210> SEQ ID NO 853
<211> LENGTH: 5
<212> TYPE: PRT
<213> ORGANISM: Homo sapiens

<400> SEQUENCE: 853

Gln Ser His Arg Pro
1               5

<210> SEQ ID NO 854
<211> LENGTH: 5
<212> TYPE: PRT
<213> ORGANISM: Homo sapiens

<400> SEQUENCE: 854

Ser His Arg Pro Pro
1               5

<210> SEQ ID NO 855
<211> LENGTH: 5
<212> TYPE: PRT
<213> ORGANISM: Homo sapiens

<400> SEQUENCE: 855

His Arg Pro Pro Pro
1               5

<210> SEQ ID NO 856
<211> LENGTH: 5
<212> TYPE: PRT
<213> ORGANISM: Homo sapiens

<400> SEQUENCE: 856

Arg Pro Pro Pro Pro
1               5

<210> SEQ ID NO 857
<211> LENGTH: 5
<212> TYPE: PRT
<213> ORGANISM: Homo sapiens

<400> SEQUENCE: 857

Pro Pro Pro Pro Pro
1               5

<210> SEQ ID NO 858
<211> LENGTH: 5
<212> TYPE: PRT
<213> ORGANISM: Homo sapiens

<400> SEQUENCE: 858

Pro Pro Pro Pro Gly

```
1               5

<210> SEQ ID NO 859
<211> LENGTH: 5
<212> TYPE: PRT
<213> ORGANISM: Homo sapiens

<400> SEQUENCE: 859

Pro Pro Pro Gly Lys
1               5

<210> SEQ ID NO 860
<211> LENGTH: 5
<212> TYPE: PRT
<213> ORGANISM: Homo sapiens

<400> SEQUENCE: 860

Pro Pro Gly Lys Pro
1               5

<210> SEQ ID NO 861
<211> LENGTH: 5
<212> TYPE: PRT
<213> ORGANISM: Homo sapiens

<400> SEQUENCE: 861

Pro Gly Lys Pro Glu
1               5

<210> SEQ ID NO 862
<211> LENGTH: 5
<212> TYPE: PRT
<213> ORGANISM: Homo sapiens

<400> SEQUENCE: 862

Gly Lys Pro Glu Arg
1               5

<210> SEQ ID NO 863
<211> LENGTH: 5
<212> TYPE: PRT
<213> ORGANISM: Homo sapiens

<400> SEQUENCE: 863

Lys Pro Glu Arg Pro
1               5

<210> SEQ ID NO 864
<211> LENGTH: 5
<212> TYPE: PRT
<213> ORGANISM: Homo sapiens

<400> SEQUENCE: 864

Pro Glu Arg Pro Pro
1               5

<210> SEQ ID NO 865
<211> LENGTH: 5
<212> TYPE: PRT
<213> ORGANISM: Homo sapiens

<400> SEQUENCE: 865

Glu Arg Pro Pro Pro
1               5
```

<210> SEQ ID NO 866
<211> LENGTH: 5
<212> TYPE: PRT
<213> ORGANISM: Homo sapiens

<400> SEQUENCE: 866

Arg Pro Pro Pro Gln
1               5

<210> SEQ ID NO 867
<211> LENGTH: 5
<212> TYPE: PRT
<213> ORGANISM: Homo sapiens

<400> SEQUENCE: 867

Pro Pro Pro Gln Gly
1               5

<210> SEQ ID NO 868
<211> LENGTH: 5
<212> TYPE: PRT
<213> ORGANISM: Homo sapiens

<400> SEQUENCE: 868

Pro Pro Gln Gly Gly
1               5

<210> SEQ ID NO 869
<211> LENGTH: 5
<212> TYPE: PRT
<213> ORGANISM: Homo sapiens

<400> SEQUENCE: 869

Pro Gln Gly Gly Asn
1               5

<210> SEQ ID NO 870
<211> LENGTH: 5
<212> TYPE: PRT
<213> ORGANISM: Homo sapiens

<400> SEQUENCE: 870

Gln Gly Gly Asn Gln
1               5

<210> SEQ ID NO 871
<211> LENGTH: 5
<212> TYPE: PRT
<213> ORGANISM: Homo sapiens

<400> SEQUENCE: 871

Gly Gly Asn Gln Ser
1               5

<210> SEQ ID NO 872
<211> LENGTH: 5
<212> TYPE: PRT
<213> ORGANISM: Homo sapiens

<400> SEQUENCE: 872

Gly Asn Gln Ser Gln
1               5

<210> SEQ ID NO 873

```
<211> LENGTH: 5
<212> TYPE: PRT
<213> ORGANISM: Homo sapiens

<400> SEQUENCE: 873

Asn Gln Ser Gln Gly
1               5

<210> SEQ ID NO 874
<211> LENGTH: 5
<212> TYPE: PRT
<213> ORGANISM: Homo sapiens

<400> SEQUENCE: 874

Gln Ser Gln Gly Pro
1               5

<210> SEQ ID NO 875
<211> LENGTH: 5
<212> TYPE: PRT
<213> ORGANISM: Homo sapiens

<400> SEQUENCE: 875

Ser Gln Gly Pro Pro
1               5

<210> SEQ ID NO 876
<211> LENGTH: 5
<212> TYPE: PRT
<213> ORGANISM: Homo sapiens

<400> SEQUENCE: 876

Gln Gly Pro Pro Pro
1               5

<210> SEQ ID NO 877
<211> LENGTH: 5
<212> TYPE: PRT
<213> ORGANISM: Homo sapiens

<400> SEQUENCE: 877

Gly Pro Pro Pro His
1               5

<210> SEQ ID NO 878
<211> LENGTH: 5
<212> TYPE: PRT
<213> ORGANISM: Homo sapiens

<400> SEQUENCE: 878

Pro Pro Pro His Pro
1               5

<210> SEQ ID NO 879
<211> LENGTH: 5
<212> TYPE: PRT
<213> ORGANISM: Homo sapiens

<400> SEQUENCE: 879

Pro Pro His Pro Gly
1               5

<210> SEQ ID NO 880
<211> LENGTH: 5
<212> TYPE: PRT
```

<400> SEQUENCE: 880

Pro His Pro Gly Lys
1               5

<210> SEQ ID NO 881
<211> LENGTH: 5
<212> TYPE: PRT
<213> ORGANISM: Homo sapiens

<400> SEQUENCE: 881

His Pro Gly Lys Pro
1               5

<210> SEQ ID NO 882
<211> LENGTH: 5
<212> TYPE: PRT
<213> ORGANISM: Homo sapiens

<400> SEQUENCE: 882

Pro Gly Lys Pro Glu
1               5

<210> SEQ ID NO 883
<211> LENGTH: 5
<212> TYPE: PRT
<213> ORGANISM: Homo sapiens

<400> SEQUENCE: 883

Gly Lys Pro Glu Gly
1               5

<210> SEQ ID NO 884
<211> LENGTH: 5
<212> TYPE: PRT
<213> ORGANISM: Homo sapiens

<400> SEQUENCE: 884

Lys Pro Glu Gly Pro
1               5

<210> SEQ ID NO 885
<211> LENGTH: 5
<212> TYPE: PRT
<213> ORGANISM: Homo sapiens

<400> SEQUENCE: 885

Pro Glu Gly Pro Pro
1               5

<210> SEQ ID NO 886
<211> LENGTH: 5
<212> TYPE: PRT
<213> ORGANISM: Homo sapiens

<400> SEQUENCE: 886

Glu Gly Pro Pro Pro
1               5

<210> SEQ ID NO 887
<211> LENGTH: 5
<212> TYPE: PRT
<213> ORGANISM: Homo sapiens

```
<400> SEQUENCE: 887

Gly Pro Pro Pro Gln
1               5

<210> SEQ ID NO 888
<211> LENGTH: 5
<212> TYPE: PRT
<213> ORGANISM: Homo sapiens

<400> SEQUENCE: 888

Pro Pro Pro Gln Glu
1               5

<210> SEQ ID NO 889
<211> LENGTH: 5
<212> TYPE: PRT
<213> ORGANISM: Homo sapiens

<400> SEQUENCE: 889

Pro Pro Gln Glu Gly
1               5

<210> SEQ ID NO 890
<211> LENGTH: 5
<212> TYPE: PRT
<213> ORGANISM: Homo sapiens

<400> SEQUENCE: 890

Pro Gln Glu Gly Asn
1               5

<210> SEQ ID NO 891
<211> LENGTH: 5
<212> TYPE: PRT
<213> ORGANISM: Homo sapiens

<400> SEQUENCE: 891

Gln Glu Gly Asn Lys
1               5

<210> SEQ ID NO 892
<211> LENGTH: 5
<212> TYPE: PRT
<213> ORGANISM: Homo sapiens

<400> SEQUENCE: 892

Glu Gly Asn Lys Ser
1               5

<210> SEQ ID NO 893
<211> LENGTH: 5
<212> TYPE: PRT
<213> ORGANISM: Homo sapiens

<400> SEQUENCE: 893

Gly Asn Lys Ser Arg
1               5

<210> SEQ ID NO 894
<211> LENGTH: 5
<212> TYPE: PRT
<213> ORGANISM: Homo sapiens

<400> SEQUENCE: 894
```

Asn Lys Ser Arg Ser
1               5

<210> SEQ ID NO 895
<211> LENGTH: 5
<212> TYPE: PRT
<213> ORGANISM: Homo sapiens

<400> SEQUENCE: 895

Lys Ser Arg Ser Ala
1               5

<210> SEQ ID NO 896
<211> LENGTH: 5
<212> TYPE: PRT
<213> ORGANISM: Homo sapiens

<400> SEQUENCE: 896

Ser Arg Ser Ala Arg
1               5

<210> SEQ ID NO 897
<211> LENGTH: 5
<212> TYPE: PRT
<213> ORGANISM: Homo sapiens

<400> SEQUENCE: 897

Arg Ser Ala Arg Ser
1               5

<210> SEQ ID NO 898
<211> LENGTH: 5
<212> TYPE: PRT
<213> ORGANISM: Homo sapiens

<400> SEQUENCE: 898

Ser Ala Arg Ser Pro
1               5

<210> SEQ ID NO 899
<211> LENGTH: 5
<212> TYPE: PRT
<213> ORGANISM: Homo sapiens

<400> SEQUENCE: 899

Ala Arg Ser Pro Pro
1               5

<210> SEQ ID NO 900
<211> LENGTH: 5
<212> TYPE: PRT
<213> ORGANISM: Homo sapiens

<400> SEQUENCE: 900

Arg Ser Pro Pro Gly
1               5

<210> SEQ ID NO 901
<211> LENGTH: 5
<212> TYPE: PRT
<213> ORGANISM: Homo sapiens

<400> SEQUENCE: 901

Ser Pro Pro Gly Lys
1               5

<210> SEQ ID NO 902
<211> LENGTH: 5
<212> TYPE: PRT
<213> ORGANISM: Homo sapiens

<400> SEQUENCE: 902

Pro Pro Gly Lys Pro
1               5

<210> SEQ ID NO 903
<211> LENGTH: 5
<212> TYPE: PRT
<213> ORGANISM: Homo sapiens

<400> SEQUENCE: 903

Pro Gly Lys Pro Gln
1               5

<210> SEQ ID NO 904
<211> LENGTH: 5
<212> TYPE: PRT
<213> ORGANISM: Homo sapiens

<400> SEQUENCE: 904

Gly Lys Pro Gln Gly
1               5

<210> SEQ ID NO 905
<211> LENGTH: 5
<212> TYPE: PRT
<213> ORGANISM: Homo sapiens

<400> SEQUENCE: 905

Lys Pro Gln Gly Pro
1               5

<210> SEQ ID NO 906
<211> LENGTH: 5
<212> TYPE: PRT
<213> ORGANISM: Homo sapiens

<400> SEQUENCE: 906

Pro Gln Gly Pro Pro
1               5

<210> SEQ ID NO 907
<211> LENGTH: 5
<212> TYPE: PRT
<213> ORGANISM: Homo sapiens

<400> SEQUENCE: 907

Gln Gly Pro Pro Gln
1               5

<210> SEQ ID NO 908
<211> LENGTH: 5
<212> TYPE: PRT
<213> ORGANISM: Homo sapiens

<400> SEQUENCE: 908

Gly Pro Pro Gln Gln
1               5

```
<210> SEQ ID NO 909
<211> LENGTH: 5
<212> TYPE: PRT
<213> ORGANISM: Homo sapiens

<400> SEQUENCE: 909

Pro Pro Gln Gln Glu
1               5

<210> SEQ ID NO 910
<211> LENGTH: 5
<212> TYPE: PRT
<213> ORGANISM: Homo sapiens

<400> SEQUENCE: 910

Pro Gln Gln Glu Gly
1               5

<210> SEQ ID NO 911
<211> LENGTH: 5
<212> TYPE: PRT
<213> ORGANISM: Homo sapiens

<400> SEQUENCE: 911

Gln Gln Glu Gly Asn
1               5

<210> SEQ ID NO 912
<211> LENGTH: 5
<212> TYPE: PRT
<213> ORGANISM: Homo sapiens

<400> SEQUENCE: 912

Gln Glu Gly Asn Lys
1               5

<210> SEQ ID NO 913
<211> LENGTH: 5
<212> TYPE: PRT
<213> ORGANISM: Homo sapiens

<400> SEQUENCE: 913

Glu Gly Asn Lys Pro
1               5

<210> SEQ ID NO 914
<211> LENGTH: 5
<212> TYPE: PRT
<213> ORGANISM: Homo sapiens

<400> SEQUENCE: 914

Gly Asn Lys Pro Gln
1               5

<210> SEQ ID NO 915
<211> LENGTH: 5
<212> TYPE: PRT
<213> ORGANISM: Homo sapiens

<400> SEQUENCE: 915

Asn Lys Pro Gln Gly
1               5

<210> SEQ ID NO 916
<211> LENGTH: 5
```

```
<212> TYPE: PRT
<213> ORGANISM: Homo sapiens

<400> SEQUENCE: 916

Lys Pro Gln Gly Pro
1               5

<210> SEQ ID NO 917
<211> LENGTH: 5
<212> TYPE: PRT
<213> ORGANISM: Homo sapiens

<400> SEQUENCE: 917

Pro Gln Gly Pro Pro
1               5

<210> SEQ ID NO 918
<211> LENGTH: 5
<212> TYPE: PRT
<213> ORGANISM: Homo sapiens

<400> SEQUENCE: 918

Gln Gly Pro Pro Pro
1               5

<210> SEQ ID NO 919
<211> LENGTH: 5
<212> TYPE: PRT
<213> ORGANISM: Homo sapiens

<400> SEQUENCE: 919

Gly Pro Pro Pro Pro
1               5

<210> SEQ ID NO 920
<211> LENGTH: 5
<212> TYPE: PRT
<213> ORGANISM: Homo sapiens

<400> SEQUENCE: 920

Pro Pro Pro Pro Gly
1               5

<210> SEQ ID NO 921
<211> LENGTH: 5
<212> TYPE: PRT
<213> ORGANISM: Homo sapiens

<400> SEQUENCE: 921

Pro Pro Pro Gly Lys
1               5

<210> SEQ ID NO 922
<211> LENGTH: 5
<212> TYPE: PRT
<213> ORGANISM: Homo sapiens

<400> SEQUENCE: 922

Pro Pro Gly Lys Pro
1               5

<210> SEQ ID NO 923
<211> LENGTH: 5
<212> TYPE: PRT
<213> ORGANISM: Homo sapiens
```

<400> SEQUENCE: 923

Pro Gly Lys Pro Gln
1               5

<210> SEQ ID NO 924
<211> LENGTH: 5
<212> TYPE: PRT
<213> ORGANISM: Homo sapiens

<400> SEQUENCE: 924

Gly Lys Pro Gln Gly
1               5

<210> SEQ ID NO 925
<211> LENGTH: 5
<212> TYPE: PRT
<213> ORGANISM: Homo sapiens

<400> SEQUENCE: 925

Lys Pro Gln Gly Pro
1               5

<210> SEQ ID NO 926
<211> LENGTH: 5
<212> TYPE: PRT
<213> ORGANISM: Homo sapiens

<400> SEQUENCE: 926

Pro Gln Gly Pro Pro
1               5

<210> SEQ ID NO 927
<211> LENGTH: 5
<212> TYPE: PRT
<213> ORGANISM: Homo sapiens

<400> SEQUENCE: 927

Gln Gly Pro Pro Pro
1               5

<210> SEQ ID NO 928
<211> LENGTH: 5
<212> TYPE: PRT
<213> ORGANISM: Homo sapiens

<400> SEQUENCE: 928

Gly Pro Pro Pro Ala
1               5

<210> SEQ ID NO 929
<211> LENGTH: 5
<212> TYPE: PRT
<213> ORGANISM: Homo sapiens

<400> SEQUENCE: 929

Pro Pro Pro Ala Gly
1               5

<210> SEQ ID NO 930
<211> LENGTH: 5
<212> TYPE: PRT
<213> ORGANISM: Homo sapiens

<400> SEQUENCE: 930

```
Pro Pro Ala Gly Gly
1               5

<210> SEQ ID NO 931
<211> LENGTH: 5
<212> TYPE: PRT
<213> ORGANISM: Homo sapiens

<400> SEQUENCE: 931

Pro Ala Gly Gly Asn
1               5

<210> SEQ ID NO 932
<211> LENGTH: 5
<212> TYPE: PRT
<213> ORGANISM: Homo sapiens

<400> SEQUENCE: 932

Ala Gly Gly Asn Pro
1               5

<210> SEQ ID NO 933
<211> LENGTH: 5
<212> TYPE: PRT
<213> ORGANISM: Homo sapiens

<400> SEQUENCE: 933

Gly Gly Asn Pro Gln
1               5

<210> SEQ ID NO 934
<211> LENGTH: 5
<212> TYPE: PRT
<213> ORGANISM: Homo sapiens

<400> SEQUENCE: 934

Gly Asn Pro Gln Gln
1               5

<210> SEQ ID NO 935
<211> LENGTH: 5
<212> TYPE: PRT
<213> ORGANISM: Homo sapiens

<400> SEQUENCE: 935

Asn Pro Gln Gln Pro
1               5

<210> SEQ ID NO 936
<211> LENGTH: 5
<212> TYPE: PRT
<213> ORGANISM: Homo sapiens

<400> SEQUENCE: 936

Pro Gln Gln Pro Gln
1               5

<210> SEQ ID NO 937
<211> LENGTH: 5
<212> TYPE: PRT
<213> ORGANISM: Homo sapiens

<400> SEQUENCE: 937

Gln Gln Pro Gln Ala
```

```
1               5

<210> SEQ ID NO 938
<211> LENGTH: 5
<212> TYPE: PRT
<213> ORGANISM: Homo sapiens

<400> SEQUENCE: 938

Gln Pro Gln Ala Pro
1               5

<210> SEQ ID NO 939
<211> LENGTH: 5
<212> TYPE: PRT
<213> ORGANISM: Homo sapiens

<400> SEQUENCE: 939

Pro Gln Ala Pro Pro
1               5

<210> SEQ ID NO 940
<211> LENGTH: 5
<212> TYPE: PRT
<213> ORGANISM: Homo sapiens

<400> SEQUENCE: 940

Gln Ala Pro Pro Ala
1               5

<210> SEQ ID NO 941
<211> LENGTH: 5
<212> TYPE: PRT
<213> ORGANISM: Homo sapiens

<400> SEQUENCE: 941

Ala Pro Pro Ala Gly
1               5

<210> SEQ ID NO 942
<211> LENGTH: 5
<212> TYPE: PRT
<213> ORGANISM: Homo sapiens

<400> SEQUENCE: 942

Pro Pro Ala Gly Lys
1               5

<210> SEQ ID NO 943
<211> LENGTH: 5
<212> TYPE: PRT
<213> ORGANISM: Homo sapiens

<400> SEQUENCE: 943

Pro Ala Gly Lys Pro
1               5

<210> SEQ ID NO 944
<211> LENGTH: 5
<212> TYPE: PRT
<213> ORGANISM: Homo sapiens

<400> SEQUENCE: 944

Ala Gly Lys Pro Gln
1               5
```

<210> SEQ ID NO 945
<211> LENGTH: 5
<212> TYPE: PRT
<213> ORGANISM: Homo sapiens

<400> SEQUENCE: 945

Gly Lys Pro Gln Gly
1               5

<210> SEQ ID NO 946
<211> LENGTH: 5
<212> TYPE: PRT
<213> ORGANISM: Homo sapiens

<400> SEQUENCE: 946

Lys Pro Gln Gly Pro
1               5

<210> SEQ ID NO 947
<211> LENGTH: 5
<212> TYPE: PRT
<213> ORGANISM: Homo sapiens

<400> SEQUENCE: 947

Pro Gln Gly Pro Pro
1               5

<210> SEQ ID NO 948
<211> LENGTH: 5
<212> TYPE: PRT
<213> ORGANISM: Homo sapiens

<400> SEQUENCE: 948

Gln Gly Pro Pro Pro
1               5

<210> SEQ ID NO 949
<211> LENGTH: 5
<212> TYPE: PRT
<213> ORGANISM: Homo sapiens

<400> SEQUENCE: 949

Gly Pro Pro Pro Pro
1               5

<210> SEQ ID NO 950
<211> LENGTH: 5
<212> TYPE: PRT
<213> ORGANISM: Homo sapiens

<400> SEQUENCE: 950

Pro Pro Pro Pro Pro
1               5

<210> SEQ ID NO 951
<211> LENGTH: 5
<212> TYPE: PRT
<213> ORGANISM: Homo sapiens

<400> SEQUENCE: 951

Pro Pro Pro Pro Gln
1               5

<210> SEQ ID NO 952

```
<211> LENGTH: 5
<212> TYPE: PRT
<213> ORGANISM: Homo sapiens

<400> SEQUENCE: 952

Pro Pro Pro Gln Gly
1               5

<210> SEQ ID NO 953
<211> LENGTH: 5
<212> TYPE: PRT
<213> ORGANISM: Homo sapiens

<400> SEQUENCE: 953

Pro Pro Gln Gly Gly
1               5

<210> SEQ ID NO 954
<211> LENGTH: 5
<212> TYPE: PRT
<213> ORGANISM: Homo sapiens

<400> SEQUENCE: 954

Pro Gln Gly Gly Arg
1               5

<210> SEQ ID NO 955
<211> LENGTH: 5
<212> TYPE: PRT
<213> ORGANISM: Homo sapiens

<400> SEQUENCE: 955

Gln Gly Gly Arg Pro
1               5

<210> SEQ ID NO 956
<211> LENGTH: 5
<212> TYPE: PRT
<213> ORGANISM: Homo sapiens

<400> SEQUENCE: 956

Gly Gly Arg Pro Pro
1               5

<210> SEQ ID NO 957
<211> LENGTH: 5
<212> TYPE: PRT
<213> ORGANISM: Homo sapiens

<400> SEQUENCE: 957

Gly Arg Pro Pro Arg
1               5

<210> SEQ ID NO 958
<211> LENGTH: 5
<212> TYPE: PRT
<213> ORGANISM: Homo sapiens

<400> SEQUENCE: 958

Arg Pro Pro Arg Pro
1               5

<210> SEQ ID NO 959
<211> LENGTH: 5
<212> TYPE: PRT
```

<213> ORGANISM: Homo sapiens

<400> SEQUENCE: 959

Pro Pro Arg Pro Ala
1               5

<210> SEQ ID NO 960
<211> LENGTH: 5
<212> TYPE: PRT
<213> ORGANISM: Homo sapiens

<400> SEQUENCE: 960

Pro Arg Pro Ala Gln
1               5

<210> SEQ ID NO 961
<211> LENGTH: 5
<212> TYPE: PRT
<213> ORGANISM: Homo sapiens

<400> SEQUENCE: 961

Arg Pro Ala Gln Gly
1               5

<210> SEQ ID NO 962
<211> LENGTH: 5
<212> TYPE: PRT
<213> ORGANISM: Homo sapiens

<400> SEQUENCE: 962

Pro Ala Gln Gly Gln
1               5

<210> SEQ ID NO 963
<211> LENGTH: 5
<212> TYPE: PRT
<213> ORGANISM: Homo sapiens

<400> SEQUENCE: 963

Ala Gln Gly Gln Gln
1               5

<210> SEQ ID NO 964
<211> LENGTH: 5
<212> TYPE: PRT
<213> ORGANISM: Homo sapiens

<400> SEQUENCE: 964

Gln Gly Gln Gln Pro
1               5

<210> SEQ ID NO 965
<211> LENGTH: 5
<212> TYPE: PRT
<213> ORGANISM: Homo sapiens

<400> SEQUENCE: 965

Gly Gln Gln Pro Pro
1               5

<210> SEQ ID NO 966
<211> LENGTH: 5
<212> TYPE: PRT
<213> ORGANISM: Homo sapiens

```
<400> SEQUENCE: 966

Gln Gln Pro Pro Gln
1               5

<210> SEQ ID NO 967
<211> LENGTH: 310
<212> TYPE: PRT
<213> ORGANISM: Homo sapiens

<400> SEQUENCE: 967

Met Leu Leu Ile Leu Leu Ser Val Ala Leu Ala Leu Ser Ser Ala
1               5                   10                  15

Glu Ser Ser Ser Glu Asp Val Ser Gln Glu Ser Leu Phe Leu Ile
                20                  25                  30

Ser Gly Lys Pro Glu Gly Arg Arg Pro Gln Gly Gly Asn Gln Pro
                35                  40                  45

Arg Pro Pro Pro Pro Gly Lys Pro Gln Gly Pro Pro Gln Gly
50                  55                  60

Gly Asn Gln Ser Gln Gly Pro Pro Pro Pro Gly Lys Pro Glu Gly
65                  70                  75                  80

Arg Pro Pro Gln Gly Gly Asn Gln Ser Gln Gly Pro Pro His Pro
                85                  90                  95

Gly Lys Pro Glu Arg Pro Pro Gln Gly Gly Asn Gln Ser Gln Gly
                100                 105                 110

Pro Pro His Pro Gly Lys Pro Glu Ser Arg Pro Pro Gln Gly Gly
                115                 120                 125

His Gln Ser Gln Gly Pro Pro Thr Pro Gly Lys Pro Glu Gly Pro
130                 135                 140

Pro Pro Gln Gly Gly Asn Gln Ser Gln Gly Thr Pro Pro Pro Gly
145                 150                 155                 160

Lys Pro Glu Gly Arg Pro Pro Gln Gly Gly Asn Gln Ser Gln Gly Pro
                165                 170                 175

Pro Pro His Pro Gly Lys Pro Glu Arg Pro Pro Gln Gly Gly Asn
                180                 185                 190

Gln Ser His Arg Pro Pro Pro Pro Gly Lys Pro Glu Arg Pro Pro
                195                 200                 205

Pro Gln Gly Gly Asn Gln Ser Gln Gly Pro Pro His Pro Gly Lys
                210                 215                 220

Pro Glu Gly Pro Pro Gln Glu Gly Asn Lys Ser Arg Ser Ala Arg
225                 230                 235                 240

Ser Pro Pro Gly Lys Pro Gln Gly Pro Pro Gln Glu Gly Asn Lys
                245                 250                 255

Pro Gln Gly Pro Pro Pro Gly Lys Pro Gln Gly Pro Pro Pro Pro
                260                 265                 270

Gly Gly Asn Pro Gln Gln Pro Gln Ala Pro Ala Gly Lys Pro Gln
                275                 280                 285

Gly Pro Pro Pro Pro Gln Gly Gly Arg Pro Pro Arg Pro Ala Gln
                290                 295                 300

Gly Gln Gln Pro Pro Gln
305                 310

<210> SEQ ID NO 968
<211> LENGTH: 5
<212> TYPE: PRT
<213> ORGANISM: Homo sapiens
```

```
<400> SEQUENCE: 968

Met Leu Leu Ile Leu
1               5

<210> SEQ ID NO 969
<211> LENGTH: 5
<212> TYPE: PRT
<213> ORGANISM: Homo sapiens

<400> SEQUENCE: 969

Leu Leu Ile Leu Leu
1               5

<210> SEQ ID NO 970
<211> LENGTH: 5
<212> TYPE: PRT
<213> ORGANISM: Homo sapiens

<400> SEQUENCE: 970

Leu Ile Leu Leu Ser
1               5

<210> SEQ ID NO 971
<211> LENGTH: 5
<212> TYPE: PRT
<213> ORGANISM: Homo sapiens

<400> SEQUENCE: 971

Ile Leu Leu Ser Val
1               5

<210> SEQ ID NO 972
<211> LENGTH: 5
<212> TYPE: PRT
<213> ORGANISM: Homo sapiens

<400> SEQUENCE: 972

Leu Leu Ser Val Ala
1               5

<210> SEQ ID NO 973
<211> LENGTH: 5
<212> TYPE: PRT
<213> ORGANISM: Homo sapiens

<400> SEQUENCE: 973

Leu Ser Val Ala Leu
1               5

<210> SEQ ID NO 974
<211> LENGTH: 5
<212> TYPE: PRT
<213> ORGANISM: Homo sapiens

<400> SEQUENCE: 974

Ser Val Ala Leu Leu
1               5

<210> SEQ ID NO 975
<211> LENGTH: 5
<212> TYPE: PRT
<213> ORGANISM: Homo sapiens

<400> SEQUENCE: 975
```

Val Ala Leu Leu Ala
1               5

<210> SEQ ID NO 976
<211> LENGTH: 5
<212> TYPE: PRT
<213> ORGANISM: Homo sapiens

<400> SEQUENCE: 976

Ala Leu Leu Ala Leu
1               5

<210> SEQ ID NO 977
<211> LENGTH: 5
<212> TYPE: PRT
<213> ORGANISM: Homo sapiens

<400> SEQUENCE: 977

Leu Leu Ala Leu Ser
1               5

<210> SEQ ID NO 978
<211> LENGTH: 5
<212> TYPE: PRT
<213> ORGANISM: Homo sapiens

<400> SEQUENCE: 978

Leu Ala Leu Ser Ser
1               5

<210> SEQ ID NO 979
<211> LENGTH: 5
<212> TYPE: PRT
<213> ORGANISM: Homo sapiens

<400> SEQUENCE: 979

Ala Leu Ser Ser Ala
1               5

<210> SEQ ID NO 980
<211> LENGTH: 5
<212> TYPE: PRT
<213> ORGANISM: Homo sapiens

<400> SEQUENCE: 980

Leu Ser Ser Ala Glu
1               5

<210> SEQ ID NO 981
<211> LENGTH: 5
<212> TYPE: PRT
<213> ORGANISM: Homo sapiens

<400> SEQUENCE: 981

Ser Ser Ala Glu Ser
1               5

<210> SEQ ID NO 982
<211> LENGTH: 5
<212> TYPE: PRT
<213> ORGANISM: Homo sapiens

<400> SEQUENCE: 982

Ser Ala Glu Ser Ser
1               5

<210> SEQ ID NO 983
<211> LENGTH: 5
<212> TYPE: PRT
<213> ORGANISM: Homo sapiens

<400> SEQUENCE: 983

Ala Glu Ser Ser Ser
1               5

<210> SEQ ID NO 984
<211> LENGTH: 5
<212> TYPE: PRT
<213> ORGANISM: Homo sapiens

<400> SEQUENCE: 984

Glu Ser Ser Ser Glu
1               5

<210> SEQ ID NO 985
<211> LENGTH: 5
<212> TYPE: PRT
<213> ORGANISM: Homo sapiens

<400> SEQUENCE: 985

Ser Ser Ser Glu Asp
1               5

<210> SEQ ID NO 986
<211> LENGTH: 5
<212> TYPE: PRT
<213> ORGANISM: Homo sapiens

<400> SEQUENCE: 986

Ser Ser Glu Asp Val
1               5

<210> SEQ ID NO 987
<211> LENGTH: 5
<212> TYPE: PRT
<213> ORGANISM: Homo sapiens

<400> SEQUENCE: 987

Ser Glu Asp Val Ser
1               5

<210> SEQ ID NO 988
<211> LENGTH: 5
<212> TYPE: PRT
<213> ORGANISM: Homo sapiens

<400> SEQUENCE: 988

Glu Asp Val Ser Gln
1               5

<210> SEQ ID NO 989
<211> LENGTH: 5
<212> TYPE: PRT
<213> ORGANISM: Homo sapiens

<400> SEQUENCE: 989

Asp Val Ser Gln Glu
1               5

```
<210> SEQ ID NO 990
<211> LENGTH: 5
<212> TYPE: PRT
<213> ORGANISM: Homo sapiens

<400> SEQUENCE: 990

Val Ser Gln Glu Glu
1               5

<210> SEQ ID NO 991
<211> LENGTH: 5
<212> TYPE: PRT
<213> ORGANISM: Homo sapiens

<400> SEQUENCE: 991

Ser Gln Glu Glu Ser
1               5

<210> SEQ ID NO 992
<211> LENGTH: 5
<212> TYPE: PRT
<213> ORGANISM: Homo sapiens

<400> SEQUENCE: 992

Gln Glu Glu Ser Leu
1               5

<210> SEQ ID NO 993
<211> LENGTH: 5
<212> TYPE: PRT
<213> ORGANISM: Homo sapiens

<400> SEQUENCE: 993

Glu Glu Ser Leu Phe
1               5

<210> SEQ ID NO 994
<211> LENGTH: 5
<212> TYPE: PRT
<213> ORGANISM: Homo sapiens

<400> SEQUENCE: 994

Glu Ser Leu Phe Leu
1               5

<210> SEQ ID NO 995
<211> LENGTH: 5
<212> TYPE: PRT
<213> ORGANISM: Homo sapiens

<400> SEQUENCE: 995

Ser Leu Phe Leu Ile
1               5

<210> SEQ ID NO 996
<211> LENGTH: 5
<212> TYPE: PRT
<213> ORGANISM: Homo sapiens

<400> SEQUENCE: 996

Leu Phe Leu Ile Ser
1               5

<210> SEQ ID NO 997
<211> LENGTH: 5
```

```
<212> TYPE: PRT
<213> ORGANISM: Homo sapiens

<400> SEQUENCE: 997

Phe Leu Ile Ser Gly
1               5

<210> SEQ ID NO 998
<211> LENGTH: 5
<212> TYPE: PRT
<213> ORGANISM: Homo sapiens

<400> SEQUENCE: 998

Leu Ile Ser Gly Lys
1               5

<210> SEQ ID NO 999
<211> LENGTH: 5
<212> TYPE: PRT
<213> ORGANISM: Homo sapiens

<400> SEQUENCE: 999

Ile Ser Gly Lys Pro
1               5

<210> SEQ ID NO 1000
<211> LENGTH: 5
<212> TYPE: PRT
<213> ORGANISM: Homo sapiens

<400> SEQUENCE: 1000

Ser Gly Lys Pro Glu
1               5

<210> SEQ ID NO 1001
<211> LENGTH: 5
<212> TYPE: PRT
<213> ORGANISM: Homo sapiens

<400> SEQUENCE: 1001

Gly Lys Pro Glu Gly
1               5

<210> SEQ ID NO 1002
<211> LENGTH: 5
<212> TYPE: PRT
<213> ORGANISM: Homo sapiens

<400> SEQUENCE: 1002

Lys Pro Glu Gly Arg
1               5

<210> SEQ ID NO 1003
<211> LENGTH: 5
<212> TYPE: PRT
<213> ORGANISM: Homo sapiens

<400> SEQUENCE: 1003

Pro Glu Gly Arg Arg
1               5

<210> SEQ ID NO 1004
<211> LENGTH: 5
<212> TYPE: PRT
<213> ORGANISM: Homo sapiens
```

<400> SEQUENCE: 1004

Glu Gly Arg Arg Pro
1               5

<210> SEQ ID NO 1005
<211> LENGTH: 5
<212> TYPE: PRT
<213> ORGANISM: Homo sapiens

<400> SEQUENCE: 1005

Gly Arg Arg Pro Gln
1               5

<210> SEQ ID NO 1006
<211> LENGTH: 5
<212> TYPE: PRT
<213> ORGANISM: Homo sapiens

<400> SEQUENCE: 1006

Arg Arg Pro Gln Gly
1               5

<210> SEQ ID NO 1007
<211> LENGTH: 5
<212> TYPE: PRT
<213> ORGANISM: Homo sapiens

<400> SEQUENCE: 1007

Arg Pro Gln Gly Gly
1               5

<210> SEQ ID NO 1008
<211> LENGTH: 5
<212> TYPE: PRT
<213> ORGANISM: Homo sapiens

<400> SEQUENCE: 1008

Pro Gln Gly Gly Asn
1               5

<210> SEQ ID NO 1009
<211> LENGTH: 5
<212> TYPE: PRT
<213> ORGANISM: Homo sapiens

<400> SEQUENCE: 1009

Gln Gly Gly Asn Gln
1               5

<210> SEQ ID NO 1010
<211> LENGTH: 5
<212> TYPE: PRT
<213> ORGANISM: Homo sapiens

<400> SEQUENCE: 1010

Gly Gly Asn Gln Pro
1               5

<210> SEQ ID NO 1011
<211> LENGTH: 5
<212> TYPE: PRT
<213> ORGANISM: Homo sapiens

<400> SEQUENCE: 1011

```
Gly Asn Gln Pro Gln
1               5

<210> SEQ ID NO 1012
<211> LENGTH: 5
<212> TYPE: PRT
<213> ORGANISM: Homo sapiens

<400> SEQUENCE: 1012

Asn Gln Pro Gln Arg
1               5

<210> SEQ ID NO 1013
<211> LENGTH: 5
<212> TYPE: PRT
<213> ORGANISM: Homo sapiens

<400> SEQUENCE: 1013

Gln Pro Gln Arg Pro
1               5

<210> SEQ ID NO 1014
<211> LENGTH: 5
<212> TYPE: PRT
<213> ORGANISM: Homo sapiens

<400> SEQUENCE: 1014

Pro Gln Arg Pro Pro
1               5

<210> SEQ ID NO 1015
<211> LENGTH: 5
<212> TYPE: PRT
<213> ORGANISM: Homo sapiens

<400> SEQUENCE: 1015

Gln Arg Pro Pro Pro
1               5

<210> SEQ ID NO 1016
<211> LENGTH: 5
<212> TYPE: PRT
<213> ORGANISM: Homo sapiens

<400> SEQUENCE: 1016

Arg Pro Pro Pro Pro
1               5

<210> SEQ ID NO 1017
<211> LENGTH: 5
<212> TYPE: PRT
<213> ORGANISM: Homo sapiens

<400> SEQUENCE: 1017

Pro Pro Pro Pro Pro
1               5

<210> SEQ ID NO 1018
<211> LENGTH: 5
<212> TYPE: PRT
<213> ORGANISM: Homo sapiens

<400> SEQUENCE: 1018

Pro Pro Pro Pro Gly
```

```
<210> SEQ ID NO 1019
<211> LENGTH: 5
<212> TYPE: PRT
<213> ORGANISM: Homo sapiens

<400> SEQUENCE: 1019

Pro Pro Pro Gly Lys
1               5

<210> SEQ ID NO 1020
<211> LENGTH: 5
<212> TYPE: PRT
<213> ORGANISM: Homo sapiens

<400> SEQUENCE: 1020

Pro Pro Gly Lys Pro
1               5

<210> SEQ ID NO 1021
<211> LENGTH: 5
<212> TYPE: PRT
<213> ORGANISM: Homo sapiens

<400> SEQUENCE: 1021

Pro Gly Lys Pro Gln
1               5

<210> SEQ ID NO 1022
<211> LENGTH: 5
<212> TYPE: PRT
<213> ORGANISM: Homo sapiens

<400> SEQUENCE: 1022

Gly Lys Pro Gln Gly
1               5

<210> SEQ ID NO 1023
<211> LENGTH: 5
<212> TYPE: PRT
<213> ORGANISM: Homo sapiens

<400> SEQUENCE: 1023

Lys Pro Gln Gly Pro
1               5

<210> SEQ ID NO 1024
<211> LENGTH: 5
<212> TYPE: PRT
<213> ORGANISM: Homo sapiens

<400> SEQUENCE: 1024

Pro Gln Gly Pro Pro
1               5

<210> SEQ ID NO 1025
<211> LENGTH: 5
<212> TYPE: PRT
<213> ORGANISM: Homo sapiens

<400> SEQUENCE: 1025

Gln Gly Pro Pro Pro
1               5
```

<210> SEQ ID NO 1026
<211> LENGTH: 5
<212> TYPE: PRT
<213> ORGANISM: Homo sapiens

<400> SEQUENCE: 1026

Gly Pro Pro Pro Gln
1               5

<210> SEQ ID NO 1027
<211> LENGTH: 5
<212> TYPE: PRT
<213> ORGANISM: Homo sapiens

<400> SEQUENCE: 1027

Pro Pro Pro Gln Gly
1               5

<210> SEQ ID NO 1028
<211> LENGTH: 5
<212> TYPE: PRT
<213> ORGANISM: Homo sapiens

<400> SEQUENCE: 1028

Pro Pro Gln Gly Gly
1               5

<210> SEQ ID NO 1029
<211> LENGTH: 5
<212> TYPE: PRT
<213> ORGANISM: Homo sapiens

<400> SEQUENCE: 1029

Pro Gln Gly Gly Asn
1               5

<210> SEQ ID NO 1030
<211> LENGTH: 5
<212> TYPE: PRT
<213> ORGANISM: Homo sapiens

<400> SEQUENCE: 1030

Gln Gly Gly Asn Gln
1               5

<210> SEQ ID NO 1031
<211> LENGTH: 5
<212> TYPE: PRT
<213> ORGANISM: Homo sapiens

<400> SEQUENCE: 1031

Gly Gly Asn Gln Ser
1               5

<210> SEQ ID NO 1032
<211> LENGTH: 5
<212> TYPE: PRT
<213> ORGANISM: Homo sapiens

<400> SEQUENCE: 1032

Gly Asn Gln Ser Gln
1               5

<210> SEQ ID NO 1033

```
<211> LENGTH: 5
<212> TYPE: PRT
<213> ORGANISM: Homo sapiens

<400> SEQUENCE: 1033

Asn Gln Ser Gln Gly
1               5

<210> SEQ ID NO 1034
<211> LENGTH: 5
<212> TYPE: PRT
<213> ORGANISM: Homo sapiens

<400> SEQUENCE: 1034

Gln Ser Gln Gly Pro
1               5

<210> SEQ ID NO 1035
<211> LENGTH: 5
<212> TYPE: PRT
<213> ORGANISM: Homo sapiens

<400> SEQUENCE: 1035

Ser Gln Gly Pro Pro
1               5

<210> SEQ ID NO 1036
<211> LENGTH: 5
<212> TYPE: PRT
<213> ORGANISM: Homo sapiens

<400> SEQUENCE: 1036

Gln Gly Pro Pro Pro
1               5

<210> SEQ ID NO 1037
<211> LENGTH: 5
<212> TYPE: PRT
<213> ORGANISM: Homo sapiens

<400> SEQUENCE: 1037

Gly Pro Pro Pro Pro
1               5

<210> SEQ ID NO 1038
<211> LENGTH: 5
<212> TYPE: PRT
<213> ORGANISM: Homo sapiens

<400> SEQUENCE: 1038

Pro Pro Pro Pro Pro
1               5

<210> SEQ ID NO 1039
<211> LENGTH: 5
<212> TYPE: PRT
<213> ORGANISM: Homo sapiens

<400> SEQUENCE: 1039

Pro Pro Pro Pro Gly
1               5

<210> SEQ ID NO 1040
<211> LENGTH: 5
<212> TYPE: PRT
```

<213> ORGANISM: Homo sapiens

<400> SEQUENCE: 1040

Pro Pro Pro Gly Lys
1               5

<210> SEQ ID NO 1041
<211> LENGTH: 5
<212> TYPE: PRT
<213> ORGANISM: Homo sapiens

<400> SEQUENCE: 1041

Pro Pro Gly Lys Pro
1               5

<210> SEQ ID NO 1042
<211> LENGTH: 5
<212> TYPE: PRT
<213> ORGANISM: Homo sapiens

<400> SEQUENCE: 1042

Pro Gly Lys Pro Glu
1               5

<210> SEQ ID NO 1043
<211> LENGTH: 5
<212> TYPE: PRT
<213> ORGANISM: Homo sapiens

<400> SEQUENCE: 1043

Gly Lys Pro Glu Gly
1               5

<210> SEQ ID NO 1044
<211> LENGTH: 5
<212> TYPE: PRT
<213> ORGANISM: Homo sapiens

<400> SEQUENCE: 1044

Lys Pro Glu Gly Arg
1               5

<210> SEQ ID NO 1045
<211> LENGTH: 5
<212> TYPE: PRT
<213> ORGANISM: Homo sapiens

<400> SEQUENCE: 1045

Pro Glu Gly Arg Pro
1               5

<210> SEQ ID NO 1046
<211> LENGTH: 5
<212> TYPE: PRT
<213> ORGANISM: Homo sapiens

<400> SEQUENCE: 1046

Glu Gly Arg Pro Pro
1               5

<210> SEQ ID NO 1047
<211> LENGTH: 5
<212> TYPE: PRT
<213> ORGANISM: Homo sapiens

```
<400> SEQUENCE: 1047

Gly Arg Pro Pro Gln
1               5

<210> SEQ ID NO 1048
<211> LENGTH: 5
<212> TYPE: PRT
<213> ORGANISM: Homo sapiens

<400> SEQUENCE: 1048

Arg Pro Pro Gln Gly
1               5

<210> SEQ ID NO 1049
<211> LENGTH: 5
<212> TYPE: PRT
<213> ORGANISM: Homo sapiens

<400> SEQUENCE: 1049

Pro Pro Gln Gly Gly
1               5

<210> SEQ ID NO 1050
<211> LENGTH: 5
<212> TYPE: PRT
<213> ORGANISM: Homo sapiens

<400> SEQUENCE: 1050

Pro Gln Gly Gly Asn
1               5

<210> SEQ ID NO 1051
<211> LENGTH: 5
<212> TYPE: PRT
<213> ORGANISM: Homo sapiens

<400> SEQUENCE: 1051

Gln Gly Gly Asn Gln
1               5

<210> SEQ ID NO 1052
<211> LENGTH: 5
<212> TYPE: PRT
<213> ORGANISM: Homo sapiens

<400> SEQUENCE: 1052

Gly Gly Asn Gln Ser
1               5

<210> SEQ ID NO 1053
<211> LENGTH: 5
<212> TYPE: PRT
<213> ORGANISM: Homo sapiens

<400> SEQUENCE: 1053

Gly Asn Gln Ser Gln
1               5

<210> SEQ ID NO 1054
<211> LENGTH: 5
<212> TYPE: PRT
<213> ORGANISM: Homo sapiens

<400> SEQUENCE: 1054
```

Asn Gln Ser Gln Gly
1               5

<210> SEQ ID NO 1055
<211> LENGTH: 5
<212> TYPE: PRT
<213> ORGANISM: Homo sapiens

<400> SEQUENCE: 1055

Gln Ser Gln Gly Pro
1               5

<210> SEQ ID NO 1056
<211> LENGTH: 5
<212> TYPE: PRT
<213> ORGANISM: Homo sapiens

<400> SEQUENCE: 1056

Ser Gln Gly Pro Pro
1               5

<210> SEQ ID NO 1057
<211> LENGTH: 5
<212> TYPE: PRT
<213> ORGANISM: Homo sapiens

<400> SEQUENCE: 1057

Gln Gly Pro Pro Pro
1               5

<210> SEQ ID NO 1058
<211> LENGTH: 5
<212> TYPE: PRT
<213> ORGANISM: Homo sapiens

<400> SEQUENCE: 1058

Gly Pro Pro Pro His
1               5

<210> SEQ ID NO 1059
<211> LENGTH: 5
<212> TYPE: PRT
<213> ORGANISM: Homo sapiens

<400> SEQUENCE: 1059

Pro Pro Pro His Pro
1               5

<210> SEQ ID NO 1060
<211> LENGTH: 5
<212> TYPE: PRT
<213> ORGANISM: Homo sapiens

<400> SEQUENCE: 1060

Pro Pro His Pro Gly
1               5

<210> SEQ ID NO 1061
<211> LENGTH: 5
<212> TYPE: PRT
<213> ORGANISM: Homo sapiens

<400> SEQUENCE: 1061

Pro His Pro Gly Lys
1               5

<210> SEQ ID NO 1062
<211> LENGTH: 5
<212> TYPE: PRT
<213> ORGANISM: Homo sapiens

<400> SEQUENCE: 1062

His Pro Gly Lys Pro
1               5

<210> SEQ ID NO 1063
<211> LENGTH: 5
<212> TYPE: PRT
<213> ORGANISM: Homo sapiens

<400> SEQUENCE: 1063

Pro Gly Lys Pro Glu
1               5

<210> SEQ ID NO 1064
<211> LENGTH: 5
<212> TYPE: PRT
<213> ORGANISM: Homo sapiens

<400> SEQUENCE: 1064

Gly Lys Pro Glu Arg
1               5

<210> SEQ ID NO 1065
<211> LENGTH: 5
<212> TYPE: PRT
<213> ORGANISM: Homo sapiens

<400> SEQUENCE: 1065

Lys Pro Glu Arg Pro
1               5

<210> SEQ ID NO 1066
<211> LENGTH: 5
<212> TYPE: PRT
<213> ORGANISM: Homo sapiens

<400> SEQUENCE: 1066

Pro Glu Arg Pro Pro
1               5

<210> SEQ ID NO 1067
<211> LENGTH: 5
<212> TYPE: PRT
<213> ORGANISM: Homo sapiens

<400> SEQUENCE: 1067

Glu Arg Pro Pro Pro
1               5

<210> SEQ ID NO 1068
<211> LENGTH: 5
<212> TYPE: PRT
<213> ORGANISM: Homo sapiens

<400> SEQUENCE: 1068

Arg Pro Pro Pro Gln
1               5

<210> SEQ ID NO 1069
<211> LENGTH: 5
<212> TYPE: PRT
<213> ORGANISM: Homo sapiens

<400> SEQUENCE: 1069

Pro Pro Pro Gln Gly
1               5

<210> SEQ ID NO 1070
<211> LENGTH: 5
<212> TYPE: PRT
<213> ORGANISM: Homo sapiens

<400> SEQUENCE: 1070

Pro Pro Gln Gly Gly
1               5

<210> SEQ ID NO 1071
<211> LENGTH: 5
<212> TYPE: PRT
<213> ORGANISM: Homo sapiens

<400> SEQUENCE: 1071

Pro Gln Gly Gly Asn
1               5

<210> SEQ ID NO 1072
<211> LENGTH: 5
<212> TYPE: PRT
<213> ORGANISM: Homo sapiens

<400> SEQUENCE: 1072

Gln Gly Gly Asn Gln
1               5

<210> SEQ ID NO 1073
<211> LENGTH: 5
<212> TYPE: PRT
<213> ORGANISM: Homo sapiens

<400> SEQUENCE: 1073

Gly Gly Asn Gln Ser
1               5

<210> SEQ ID NO 1074
<211> LENGTH: 5
<212> TYPE: PRT
<213> ORGANISM: Homo sapiens

<400> SEQUENCE: 1074

Gly Asn Gln Ser Gln
1               5

<210> SEQ ID NO 1075
<211> LENGTH: 5
<212> TYPE: PRT
<213> ORGANISM: Homo sapiens

<400> SEQUENCE: 1075

Asn Gln Ser Gln Gly
1               5

<210> SEQ ID NO 1076
<211> LENGTH: 5

```
<212> TYPE: PRT
<213> ORGANISM: Homo sapiens

<400> SEQUENCE: 1076

Gln Ser Gln Gly Pro
1               5

<210> SEQ ID NO 1077
<211> LENGTH: 5
<212> TYPE: PRT
<213> ORGANISM: Homo sapiens

<400> SEQUENCE: 1077

Ser Gln Gly Pro Pro
1               5

<210> SEQ ID NO 1078
<211> LENGTH: 5
<212> TYPE: PRT
<213> ORGANISM: Homo sapiens

<400> SEQUENCE: 1078

Gln Gly Pro Pro Pro
1               5

<210> SEQ ID NO 1079
<211> LENGTH: 5
<212> TYPE: PRT
<213> ORGANISM: Homo sapiens

<400> SEQUENCE: 1079

Gly Pro Pro Pro His
1               5

<210> SEQ ID NO 1080
<211> LENGTH: 5
<212> TYPE: PRT
<213> ORGANISM: Homo sapiens

<400> SEQUENCE: 1080

Pro Pro Pro His Pro
1               5

<210> SEQ ID NO 1081
<211> LENGTH: 5
<212> TYPE: PRT
<213> ORGANISM: Homo sapiens

<400> SEQUENCE: 1081

Pro Pro His Pro Gly
1               5

<210> SEQ ID NO 1082
<211> LENGTH: 5
<212> TYPE: PRT
<213> ORGANISM: Homo sapiens

<400> SEQUENCE: 1082

Pro His Pro Gly Lys
1               5

<210> SEQ ID NO 1083
<211> LENGTH: 5
<212> TYPE: PRT
<213> ORGANISM: Homo sapiens
```

<400> SEQUENCE: 1083

His Pro Gly Lys Pro
1               5

<210> SEQ ID NO 1084
<211> LENGTH: 5
<212> TYPE: PRT
<213> ORGANISM: Homo sapiens

<400> SEQUENCE: 1084

Pro Gly Lys Pro Glu
1               5

<210> SEQ ID NO 1085
<211> LENGTH: 5
<212> TYPE: PRT
<213> ORGANISM: Homo sapiens

<400> SEQUENCE: 1085

Gly Lys Pro Glu Ser
1               5

<210> SEQ ID NO 1086
<211> LENGTH: 5
<212> TYPE: PRT
<213> ORGANISM: Homo sapiens

<400> SEQUENCE: 1086

Lys Pro Glu Ser Arg
1               5

<210> SEQ ID NO 1087
<211> LENGTH: 5
<212> TYPE: PRT
<213> ORGANISM: Homo sapiens

<400> SEQUENCE: 1087

Pro Glu Ser Arg Pro
1               5

<210> SEQ ID NO 1088
<211> LENGTH: 5
<212> TYPE: PRT
<213> ORGANISM: Homo sapiens

<400> SEQUENCE: 1088

Glu Ser Arg Pro Pro
1               5

<210> SEQ ID NO 1089
<211> LENGTH: 5
<212> TYPE: PRT
<213> ORGANISM: Homo sapiens

<400> SEQUENCE: 1089

Ser Arg Pro Pro Gln
1               5

<210> SEQ ID NO 1090
<211> LENGTH: 5
<212> TYPE: PRT
<213> ORGANISM: Homo sapiens

<400> SEQUENCE: 1090

Arg Pro Pro Gln Gly
1               5

<210> SEQ ID NO 1091
<211> LENGTH: 5
<212> TYPE: PRT
<213> ORGANISM: Homo sapiens

<400> SEQUENCE: 1091

Pro Pro Gln Gly Gly
1               5

<210> SEQ ID NO 1092
<211> LENGTH: 5
<212> TYPE: PRT
<213> ORGANISM: Homo sapiens

<400> SEQUENCE: 1092

Pro Gln Gly Gly His
1               5

<210> SEQ ID NO 1093
<211> LENGTH: 5
<212> TYPE: PRT
<213> ORGANISM: Homo sapiens

<400> SEQUENCE: 1093

Gln Gly Gly His Gln
1               5

<210> SEQ ID NO 1094
<211> LENGTH: 5
<212> TYPE: PRT
<213> ORGANISM: Homo sapiens

<400> SEQUENCE: 1094

Gly Gly His Gln Ser
1               5

<210> SEQ ID NO 1095
<211> LENGTH: 5
<212> TYPE: PRT
<213> ORGANISM: Homo sapiens

<400> SEQUENCE: 1095

Gly His Gln Ser Gln
1               5

<210> SEQ ID NO 1096
<211> LENGTH: 5
<212> TYPE: PRT
<213> ORGANISM: Homo sapiens

<400> SEQUENCE: 1096

His Gln Ser Gln Gly
1               5

<210> SEQ ID NO 1097
<211> LENGTH: 5
<212> TYPE: PRT
<213> ORGANISM: Homo sapiens

<400> SEQUENCE: 1097

Gln Ser Gln Gly Pro

```
1               5

<210> SEQ ID NO 1098
<211> LENGTH: 5
<212> TYPE: PRT
<213> ORGANISM: Homo sapiens

<400> SEQUENCE: 1098

Ser Gln Gly Pro Pro
1               5

<210> SEQ ID NO 1099
<211> LENGTH: 5
<212> TYPE: PRT
<213> ORGANISM: Homo sapiens

<400> SEQUENCE: 1099

Gln Gly Pro Pro Pro
1               5

<210> SEQ ID NO 1100
<211> LENGTH: 5
<212> TYPE: PRT
<213> ORGANISM: Homo sapiens

<400> SEQUENCE: 1100

Gly Pro Pro Pro Thr
1               5

<210> SEQ ID NO 1101
<211> LENGTH: 5
<212> TYPE: PRT
<213> ORGANISM: Homo sapiens

<400> SEQUENCE: 1101

Pro Pro Pro Thr Pro
1               5

<210> SEQ ID NO 1102
<211> LENGTH: 5
<212> TYPE: PRT
<213> ORGANISM: Homo sapiens

<400> SEQUENCE: 1102

Pro Pro Thr Pro Gly
1               5

<210> SEQ ID NO 1103
<211> LENGTH: 5
<212> TYPE: PRT
<213> ORGANISM: Homo sapiens

<400> SEQUENCE: 1103

Pro Thr Pro Gly Lys
1               5

<210> SEQ ID NO 1104
<211> LENGTH: 5
<212> TYPE: PRT
<213> ORGANISM: Homo sapiens

<400> SEQUENCE: 1104

Thr Pro Gly Lys Pro
1               5
```

<210> SEQ ID NO 1105
<211> LENGTH: 5
<212> TYPE: PRT
<213> ORGANISM: Homo sapiens

<400> SEQUENCE: 1105

Pro Gly Lys Pro Glu
1               5

<210> SEQ ID NO 1106
<211> LENGTH: 5
<212> TYPE: PRT
<213> ORGANISM: Homo sapiens

<400> SEQUENCE: 1106

Gly Lys Pro Glu Gly
1               5

<210> SEQ ID NO 1107
<211> LENGTH: 5
<212> TYPE: PRT
<213> ORGANISM: Homo sapiens

<400> SEQUENCE: 1107

Lys Pro Glu Gly Pro
1               5

<210> SEQ ID NO 1108
<211> LENGTH: 5
<212> TYPE: PRT
<213> ORGANISM: Homo sapiens

<400> SEQUENCE: 1108

Pro Glu Gly Pro Pro
1               5

<210> SEQ ID NO 1109
<211> LENGTH: 5
<212> TYPE: PRT
<213> ORGANISM: Homo sapiens

<400> SEQUENCE: 1109

Glu Gly Pro Pro Pro
1               5

<210> SEQ ID NO 1110
<211> LENGTH: 5
<212> TYPE: PRT
<213> ORGANISM: Homo sapiens

<400> SEQUENCE: 1110

Gly Pro Pro Pro Gln
1               5

<210> SEQ ID NO 1111
<211> LENGTH: 5
<212> TYPE: PRT
<213> ORGANISM: Homo sapiens

<400> SEQUENCE: 1111

Pro Pro Pro Gln Gly
1               5

<210> SEQ ID NO 1112

```
<211> LENGTH: 5
<212> TYPE: PRT
<213> ORGANISM: Homo sapiens

<400> SEQUENCE: 1112

Pro Pro Gln Gly Gly
1               5

<210> SEQ ID NO 1113
<211> LENGTH: 5
<212> TYPE: PRT
<213> ORGANISM: Homo sapiens

<400> SEQUENCE: 1113

Pro Gln Gly Gly Asn
1               5

<210> SEQ ID NO 1114
<211> LENGTH: 5
<212> TYPE: PRT
<213> ORGANISM: Homo sapiens

<400> SEQUENCE: 1114

Gln Gly Gly Asn Gln
1               5

<210> SEQ ID NO 1115
<211> LENGTH: 5
<212> TYPE: PRT
<213> ORGANISM: Homo sapiens

<400> SEQUENCE: 1115

Gly Gly Asn Gln Ser
1               5

<210> SEQ ID NO 1116
<211> LENGTH: 5
<212> TYPE: PRT
<213> ORGANISM: Homo sapiens

<400> SEQUENCE: 1116

Gly Asn Gln Ser Gln
1               5

<210> SEQ ID NO 1117
<211> LENGTH: 5
<212> TYPE: PRT
<213> ORGANISM: Homo sapiens

<400> SEQUENCE: 1117

Asn Gln Ser Gln Gly
1               5

<210> SEQ ID NO 1118
<211> LENGTH: 5
<212> TYPE: PRT
<213> ORGANISM: Homo sapiens

<400> SEQUENCE: 1118

Gln Ser Gln Gly Thr
1               5

<210> SEQ ID NO 1119
<211> LENGTH: 5
<212> TYPE: PRT
```

<213> ORGANISM: Homo sapiens

<400> SEQUENCE: 1119

Ser Gln Gly Thr Pro
1               5

<210> SEQ ID NO 1120
<211> LENGTH: 5
<212> TYPE: PRT
<213> ORGANISM: Homo sapiens

<400> SEQUENCE: 1120

Gln Gly Thr Pro Pro
1               5

<210> SEQ ID NO 1121
<211> LENGTH: 5
<212> TYPE: PRT
<213> ORGANISM: Homo sapiens

<400> SEQUENCE: 1121

Gly Thr Pro Pro Pro
1               5

<210> SEQ ID NO 1122
<211> LENGTH: 5
<212> TYPE: PRT
<213> ORGANISM: Homo sapiens

<400> SEQUENCE: 1122

Thr Pro Pro Pro Pro
1               5

<210> SEQ ID NO 1123
<211> LENGTH: 5
<212> TYPE: PRT
<213> ORGANISM: Homo sapiens

<400> SEQUENCE: 1123

Pro Pro Pro Pro Gly
1               5

<210> SEQ ID NO 1124
<211> LENGTH: 5
<212> TYPE: PRT
<213> ORGANISM: Homo sapiens

<400> SEQUENCE: 1124

Pro Pro Pro Gly Lys
1               5

<210> SEQ ID NO 1125
<211> LENGTH: 5
<212> TYPE: PRT
<213> ORGANISM: Homo sapiens

<400> SEQUENCE: 1125

Pro Pro Gly Lys Pro
1               5

<210> SEQ ID NO 1126
<211> LENGTH: 5
<212> TYPE: PRT
<213> ORGANISM: Homo sapiens

```
<400> SEQUENCE: 1126

Pro Gly Lys Pro Glu
1               5

<210> SEQ ID NO 1127
<211> LENGTH: 5
<212> TYPE: PRT
<213> ORGANISM: Homo sapiens

<400> SEQUENCE: 1127

Gly Lys Pro Glu Gly
1               5

<210> SEQ ID NO 1128
<211> LENGTH: 5
<212> TYPE: PRT
<213> ORGANISM: Homo sapiens

<400> SEQUENCE: 1128

Lys Pro Glu Gly Arg
1               5

<210> SEQ ID NO 1129
<211> LENGTH: 5
<212> TYPE: PRT
<213> ORGANISM: Homo sapiens

<400> SEQUENCE: 1129

Pro Glu Gly Arg Pro
1               5

<210> SEQ ID NO 1130
<211> LENGTH: 5
<212> TYPE: PRT
<213> ORGANISM: Homo sapiens

<400> SEQUENCE: 1130

Glu Gly Arg Pro Pro
1               5

<210> SEQ ID NO 1131
<211> LENGTH: 5
<212> TYPE: PRT
<213> ORGANISM: Homo sapiens

<400> SEQUENCE: 1131

Gly Arg Pro Pro Gln
1               5

<210> SEQ ID NO 1132
<211> LENGTH: 5
<212> TYPE: PRT
<213> ORGANISM: Homo sapiens

<400> SEQUENCE: 1132

Arg Pro Pro Gln Gly
1               5

<210> SEQ ID NO 1133
<211> LENGTH: 5
<212> TYPE: PRT
<213> ORGANISM: Homo sapiens

<400> SEQUENCE: 1133
```

Pro Pro Gln Gly Gly
1               5

<210> SEQ ID NO 1134
<211> LENGTH: 5
<212> TYPE: PRT
<213> ORGANISM: Homo sapiens

<400> SEQUENCE: 1134

Pro Gln Gly Gly Asn
1               5

<210> SEQ ID NO 1135
<211> LENGTH: 5
<212> TYPE: PRT
<213> ORGANISM: Homo sapiens

<400> SEQUENCE: 1135

Gln Gly Gly Asn Gln
1               5

<210> SEQ ID NO 1136
<211> LENGTH: 5
<212> TYPE: PRT
<213> ORGANISM: Homo sapiens

<400> SEQUENCE: 1136

Gly Gly Asn Gln Ser
1               5

<210> SEQ ID NO 1137
<211> LENGTH: 5
<212> TYPE: PRT
<213> ORGANISM: Homo sapiens

<400> SEQUENCE: 1137

Gly Asn Gln Ser Gln
1               5

<210> SEQ ID NO 1138
<211> LENGTH: 5
<212> TYPE: PRT
<213> ORGANISM: Homo sapiens

<400> SEQUENCE: 1138

Asn Gln Ser Gln Gly
1               5

<210> SEQ ID NO 1139
<211> LENGTH: 5
<212> TYPE: PRT
<213> ORGANISM: Homo sapiens

<400> SEQUENCE: 1139

Gln Ser Gln Gly Pro
1               5

<210> SEQ ID NO 1140
<211> LENGTH: 5
<212> TYPE: PRT
<213> ORGANISM: Homo sapiens

<400> SEQUENCE: 1140

Ser Gln Gly Pro Pro
1               5

```
<210> SEQ ID NO 1141
<211> LENGTH: 5
<212> TYPE: PRT
<213> ORGANISM: Homo sapiens

<400> SEQUENCE: 1141

Gln Gly Pro Pro Pro
1               5

<210> SEQ ID NO 1142
<211> LENGTH: 5
<212> TYPE: PRT
<213> ORGANISM: Homo sapiens

<400> SEQUENCE: 1142

Gly Pro Pro Pro His
1               5

<210> SEQ ID NO 1143
<211> LENGTH: 5
<212> TYPE: PRT
<213> ORGANISM: Homo sapiens

<400> SEQUENCE: 1143

Pro Pro Pro His Pro
1               5

<210> SEQ ID NO 1144
<211> LENGTH: 5
<212> TYPE: PRT
<213> ORGANISM: Homo sapiens

<400> SEQUENCE: 1144

Pro Pro His Pro Gly
1               5

<210> SEQ ID NO 1145
<211> LENGTH: 5
<212> TYPE: PRT
<213> ORGANISM: Homo sapiens

<400> SEQUENCE: 1145

Pro His Pro Gly Lys
1               5

<210> SEQ ID NO 1146
<211> LENGTH: 5
<212> TYPE: PRT
<213> ORGANISM: Homo sapiens

<400> SEQUENCE: 1146

His Pro Gly Lys Pro
1               5

<210> SEQ ID NO 1147
<211> LENGTH: 5
<212> TYPE: PRT
<213> ORGANISM: Homo sapiens

<400> SEQUENCE: 1147

Pro Gly Lys Pro Glu
1               5
```

```
<210> SEQ ID NO 1148
<211> LENGTH: 5
<212> TYPE: PRT
<213> ORGANISM: Homo sapiens

<400> SEQUENCE: 1148

Gly Lys Pro Glu Arg
1               5

<210> SEQ ID NO 1149
<211> LENGTH: 5
<212> TYPE: PRT
<213> ORGANISM: Homo sapiens

<400> SEQUENCE: 1149

Lys Pro Glu Arg Pro
1               5

<210> SEQ ID NO 1150
<211> LENGTH: 5
<212> TYPE: PRT
<213> ORGANISM: Homo sapiens

<400> SEQUENCE: 1150

Pro Glu Arg Pro Pro
1               5

<210> SEQ ID NO 1151
<211> LENGTH: 5
<212> TYPE: PRT
<213> ORGANISM: Homo sapiens

<400> SEQUENCE: 1151

Glu Arg Pro Pro Pro
1               5

<210> SEQ ID NO 1152
<211> LENGTH: 5
<212> TYPE: PRT
<213> ORGANISM: Homo sapiens

<400> SEQUENCE: 1152

Arg Pro Pro Pro Gln
1               5

<210> SEQ ID NO 1153
<211> LENGTH: 5
<212> TYPE: PRT
<213> ORGANISM: Homo sapiens

<400> SEQUENCE: 1153

Pro Pro Pro Gln Gly
1               5

<210> SEQ ID NO 1154
<211> LENGTH: 5
<212> TYPE: PRT
<213> ORGANISM: Homo sapiens

<400> SEQUENCE: 1154

Pro Pro Gln Gly Gly
1               5

<210> SEQ ID NO 1155
<211> LENGTH: 5
```

```
<212> TYPE: PRT
<213> ORGANISM: Homo sapiens

<400> SEQUENCE: 1155

Pro Gln Gly Gly Asn
1               5

<210> SEQ ID NO 1156
<211> LENGTH: 5
<212> TYPE: PRT
<213> ORGANISM: Homo sapiens

<400> SEQUENCE: 1156

Gln Gly Gly Asn Gln
1               5

<210> SEQ ID NO 1157
<211> LENGTH: 5
<212> TYPE: PRT
<213> ORGANISM: Homo sapiens

<400> SEQUENCE: 1157

Gly Gly Asn Gln Ser
1               5

<210> SEQ ID NO 1158
<211> LENGTH: 5
<212> TYPE: PRT
<213> ORGANISM: Homo sapiens

<400> SEQUENCE: 1158

Gly Asn Gln Ser His
1               5

<210> SEQ ID NO 1159
<211> LENGTH: 5
<212> TYPE: PRT
<213> ORGANISM: Homo sapiens

<400> SEQUENCE: 1159

Asn Gln Ser His Arg
1               5

<210> SEQ ID NO 1160
<211> LENGTH: 5
<212> TYPE: PRT
<213> ORGANISM: Homo sapiens

<400> SEQUENCE: 1160

Gln Ser His Arg Pro
1               5

<210> SEQ ID NO 1161
<211> LENGTH: 5
<212> TYPE: PRT
<213> ORGANISM: Homo sapiens

<400> SEQUENCE: 1161

Ser His Arg Pro Pro
1               5

<210> SEQ ID NO 1162
<211> LENGTH: 5
<212> TYPE: PRT
<213> ORGANISM: Homo sapiens
```

<400> SEQUENCE: 1162

His Arg Pro Pro Pro
1               5

<210> SEQ ID NO 1163
<211> LENGTH: 5
<212> TYPE: PRT
<213> ORGANISM: Homo sapiens

<400> SEQUENCE: 1163

Arg Pro Pro Pro Pro
1               5

<210> SEQ ID NO 1164
<211> LENGTH: 5
<212> TYPE: PRT
<213> ORGANISM: Homo sapiens

<400> SEQUENCE: 1164

Pro Pro Pro Pro Pro
1               5

<210> SEQ ID NO 1165
<211> LENGTH: 5
<212> TYPE: PRT
<213> ORGANISM: Homo sapiens

<400> SEQUENCE: 1165

Pro Pro Pro Pro Gly
1               5

<210> SEQ ID NO 1166
<211> LENGTH: 5
<212> TYPE: PRT
<213> ORGANISM: Homo sapiens

<400> SEQUENCE: 1166

Pro Pro Pro Gly Lys
1               5

<210> SEQ ID NO 1167
<211> LENGTH: 5
<212> TYPE: PRT
<213> ORGANISM: Homo sapiens

<400> SEQUENCE: 1167

Pro Pro Gly Lys Pro
1               5

<210> SEQ ID NO 1168
<211> LENGTH: 5
<212> TYPE: PRT
<213> ORGANISM: Homo sapiens

<400> SEQUENCE: 1168

Pro Gly Lys Pro Glu
1               5

<210> SEQ ID NO 1169
<211> LENGTH: 5
<212> TYPE: PRT
<213> ORGANISM: Homo sapiens

<400> SEQUENCE: 1169

Gly Lys Pro Glu Arg
1               5

<210> SEQ ID NO 1170
<211> LENGTH: 5
<212> TYPE: PRT
<213> ORGANISM: Homo sapiens

<400> SEQUENCE: 1170

Lys Pro Glu Arg Pro
1               5

<210> SEQ ID NO 1171
<211> LENGTH: 5
<212> TYPE: PRT
<213> ORGANISM: Homo sapiens

<400> SEQUENCE: 1171

Pro Glu Arg Pro Pro
1               5

<210> SEQ ID NO 1172
<211> LENGTH: 5
<212> TYPE: PRT
<213> ORGANISM: Homo sapiens

<400> SEQUENCE: 1172

Glu Arg Pro Pro Pro
1               5

<210> SEQ ID NO 1173
<211> LENGTH: 5
<212> TYPE: PRT
<213> ORGANISM: Homo sapiens

<400> SEQUENCE: 1173

Arg Pro Pro Pro Gln
1               5

<210> SEQ ID NO 1174
<211> LENGTH: 5
<212> TYPE: PRT
<213> ORGANISM: Homo sapiens

<400> SEQUENCE: 1174

Pro Pro Pro Gln Gly
1               5

<210> SEQ ID NO 1175
<211> LENGTH: 5
<212> TYPE: PRT
<213> ORGANISM: Homo sapiens

<400> SEQUENCE: 1175

Pro Pro Gln Gly Gly
1               5

<210> SEQ ID NO 1176
<211> LENGTH: 5
<212> TYPE: PRT
<213> ORGANISM: Homo sapiens

<400> SEQUENCE: 1176

Pro Gln Gly Gly Asn

```
1               5

<210> SEQ ID NO 1177
<211> LENGTH: 5
<212> TYPE: PRT
<213> ORGANISM: Homo sapiens

<400> SEQUENCE: 1177

Gln Gly Gly Asn Gln
1               5

<210> SEQ ID NO 1178
<211> LENGTH: 5
<212> TYPE: PRT
<213> ORGANISM: Homo sapiens

<400> SEQUENCE: 1178

Gly Gly Asn Gln Ser
1               5

<210> SEQ ID NO 1179
<211> LENGTH: 5
<212> TYPE: PRT
<213> ORGANISM: Homo sapiens

<400> SEQUENCE: 1179

Gly Asn Gln Ser Gln
1               5

<210> SEQ ID NO 1180
<211> LENGTH: 5
<212> TYPE: PRT
<213> ORGANISM: Homo sapiens

<400> SEQUENCE: 1180

Asn Gln Ser Gln Gly
1               5

<210> SEQ ID NO 1181
<211> LENGTH: 5
<212> TYPE: PRT
<213> ORGANISM: Homo sapiens

<400> SEQUENCE: 1181

Gln Ser Gln Gly Pro
1               5

<210> SEQ ID NO 1182
<211> LENGTH: 5
<212> TYPE: PRT
<213> ORGANISM: Homo sapiens

<400> SEQUENCE: 1182

Ser Gln Gly Pro Pro
1               5

<210> SEQ ID NO 1183
<211> LENGTH: 5
<212> TYPE: PRT
<213> ORGANISM: Homo sapiens

<400> SEQUENCE: 1183

Gln Gly Pro Pro Pro
1               5
```

<210> SEQ ID NO 1184
<211> LENGTH: 5
<212> TYPE: PRT
<213> ORGANISM: Homo sapiens

<400> SEQUENCE: 1184

Gly Pro Pro Pro His
1               5

<210> SEQ ID NO 1185
<211> LENGTH: 5
<212> TYPE: PRT
<213> ORGANISM: Homo sapiens

<400> SEQUENCE: 1185

Pro Pro Pro His Pro
1               5

<210> SEQ ID NO 1186
<211> LENGTH: 5
<212> TYPE: PRT
<213> ORGANISM: Homo sapiens

<400> SEQUENCE: 1186

Pro Pro His Pro Gly
1               5

<210> SEQ ID NO 1187
<211> LENGTH: 5
<212> TYPE: PRT
<213> ORGANISM: Homo sapiens

<400> SEQUENCE: 1187

Pro His Pro Gly Lys
1               5

<210> SEQ ID NO 1188
<211> LENGTH: 5
<212> TYPE: PRT
<213> ORGANISM: Homo sapiens

<400> SEQUENCE: 1188

His Pro Gly Lys Pro
1               5

<210> SEQ ID NO 1189
<211> LENGTH: 5
<212> TYPE: PRT
<213> ORGANISM: Homo sapiens

<400> SEQUENCE: 1189

Pro Gly Lys Pro Glu
1               5

<210> SEQ ID NO 1190
<211> LENGTH: 5
<212> TYPE: PRT
<213> ORGANISM: Homo sapiens

<400> SEQUENCE: 1190

Gly Lys Pro Glu Gly
1               5

<210> SEQ ID NO 1191

```
<211> LENGTH: 5
<212> TYPE: PRT
<213> ORGANISM: Homo sapiens

<400> SEQUENCE: 1191

Lys Pro Glu Gly Pro
1               5

<210> SEQ ID NO 1192
<211> LENGTH: 5
<212> TYPE: PRT
<213> ORGANISM: Homo sapiens

<400> SEQUENCE: 1192

Pro Glu Gly Pro Pro
1               5

<210> SEQ ID NO 1193
<211> LENGTH: 5
<212> TYPE: PRT
<213> ORGANISM: Homo sapiens

<400> SEQUENCE: 1193

Glu Gly Pro Pro Pro
1               5

<210> SEQ ID NO 1194
<211> LENGTH: 5
<212> TYPE: PRT
<213> ORGANISM: Homo sapiens

<400> SEQUENCE: 1194

Gly Pro Pro Pro Gln
1               5

<210> SEQ ID NO 1195
<211> LENGTH: 5
<212> TYPE: PRT
<213> ORGANISM: Homo sapiens

<400> SEQUENCE: 1195

Pro Pro Pro Gln Glu
1               5

<210> SEQ ID NO 1196
<211> LENGTH: 5
<212> TYPE: PRT
<213> ORGANISM: Homo sapiens

<400> SEQUENCE: 1196

Pro Pro Gln Glu Gly
1               5

<210> SEQ ID NO 1197
<211> LENGTH: 5
<212> TYPE: PRT
<213> ORGANISM: Homo sapiens

<400> SEQUENCE: 1197

Pro Gln Glu Gly Asn
1               5

<210> SEQ ID NO 1198
<211> LENGTH: 5
<212> TYPE: PRT
```

<213> ORGANISM: Homo sapiens

<400> SEQUENCE: 1198

Gln Glu Gly Asn Lys
1               5

<210> SEQ ID NO 1199
<211> LENGTH: 5
<212> TYPE: PRT
<213> ORGANISM: Homo sapiens

<400> SEQUENCE: 1199

Glu Gly Asn Lys Ser
1               5

<210> SEQ ID NO 1200
<211> LENGTH: 5
<212> TYPE: PRT
<213> ORGANISM: Homo sapiens

<400> SEQUENCE: 1200

Gly Asn Lys Ser Arg
1               5

<210> SEQ ID NO 1201
<211> LENGTH: 5
<212> TYPE: PRT
<213> ORGANISM: Homo sapiens

<400> SEQUENCE: 1201

Asn Lys Ser Arg Ser
1               5

<210> SEQ ID NO 1202
<211> LENGTH: 5
<212> TYPE: PRT
<213> ORGANISM: Homo sapiens

<400> SEQUENCE: 1202

Lys Ser Arg Ser Ala
1               5

<210> SEQ ID NO 1203
<211> LENGTH: 5
<212> TYPE: PRT
<213> ORGANISM: Homo sapiens

<400> SEQUENCE: 1203

Ser Arg Ser Ala Arg
1               5

<210> SEQ ID NO 1204
<211> LENGTH: 5
<212> TYPE: PRT
<213> ORGANISM: Homo sapiens

<400> SEQUENCE: 1204

Arg Ser Ala Arg Ser
1               5

<210> SEQ ID NO 1205
<211> LENGTH: 5
<212> TYPE: PRT
<213> ORGANISM: Homo sapiens

```
<400> SEQUENCE: 1205

Ser Ala Arg Ser Pro
1               5

<210> SEQ ID NO 1206
<211> LENGTH: 5
<212> TYPE: PRT
<213> ORGANISM: Homo sapiens

<400> SEQUENCE: 1206

Ala Arg Ser Pro Pro
1               5

<210> SEQ ID NO 1207
<211> LENGTH: 5
<212> TYPE: PRT
<213> ORGANISM: Homo sapiens

<400> SEQUENCE: 1207

Arg Ser Pro Pro Gly
1               5

<210> SEQ ID NO 1208
<211> LENGTH: 5
<212> TYPE: PRT
<213> ORGANISM: Homo sapiens

<400> SEQUENCE: 1208

Ser Pro Pro Gly Lys
1               5

<210> SEQ ID NO 1209
<211> LENGTH: 5
<212> TYPE: PRT
<213> ORGANISM: Homo sapiens

<400> SEQUENCE: 1209

Pro Pro Gly Lys Pro
1               5

<210> SEQ ID NO 1210
<211> LENGTH: 5
<212> TYPE: PRT
<213> ORGANISM: Homo sapiens

<400> SEQUENCE: 1210

Pro Gly Lys Pro Gln
1               5

<210> SEQ ID NO 1211
<211> LENGTH: 5
<212> TYPE: PRT
<213> ORGANISM: Homo sapiens

<400> SEQUENCE: 1211

Gly Lys Pro Gln Gly
1               5

<210> SEQ ID NO 1212
<211> LENGTH: 5
<212> TYPE: PRT
<213> ORGANISM: Homo sapiens

<400> SEQUENCE: 1212
```

```
Lys Pro Gln Gly Pro
1               5

<210> SEQ ID NO 1213
<211> LENGTH: 5
<212> TYPE: PRT
<213> ORGANISM: Homo sapiens

<400> SEQUENCE: 1213

Pro Gln Gly Pro Pro
1               5

<210> SEQ ID NO 1214
<211> LENGTH: 5
<212> TYPE: PRT
<213> ORGANISM: Homo sapiens

<400> SEQUENCE: 1214

Gln Gly Pro Pro Gln
1               5

<210> SEQ ID NO 1215
<211> LENGTH: 5
<212> TYPE: PRT
<213> ORGANISM: Homo sapiens

<400> SEQUENCE: 1215

Gly Pro Pro Gln Gln
1               5

<210> SEQ ID NO 1216
<211> LENGTH: 5
<212> TYPE: PRT
<213> ORGANISM: Homo sapiens

<400> SEQUENCE: 1216

Pro Pro Gln Gln Glu
1               5

<210> SEQ ID NO 1217
<211> LENGTH: 5
<212> TYPE: PRT
<213> ORGANISM: Homo sapiens

<400> SEQUENCE: 1217

Pro Gln Gln Glu Gly
1               5

<210> SEQ ID NO 1218
<211> LENGTH: 5
<212> TYPE: PRT
<213> ORGANISM: Homo sapiens

<400> SEQUENCE: 1218

Gln Gln Glu Gly Asn
1               5

<210> SEQ ID NO 1219
<211> LENGTH: 5
<212> TYPE: PRT
<213> ORGANISM: Homo sapiens

<400> SEQUENCE: 1219

Gln Glu Gly Asn Lys
1               5
```

```
<210> SEQ ID NO 1220
<211> LENGTH: 5
<212> TYPE: PRT
<213> ORGANISM: Homo sapiens

<400> SEQUENCE: 1220

Glu Gly Asn Lys Pro
1               5

<210> SEQ ID NO 1221
<211> LENGTH: 5
<212> TYPE: PRT
<213> ORGANISM: Homo sapiens

<400> SEQUENCE: 1221

Gly Asn Lys Pro Gln
1               5

<210> SEQ ID NO 1222
<211> LENGTH: 5
<212> TYPE: PRT
<213> ORGANISM: Homo sapiens

<400> SEQUENCE: 1222

Asn Lys Pro Gln Gly
1               5

<210> SEQ ID NO 1223
<211> LENGTH: 5
<212> TYPE: PRT
<213> ORGANISM: Homo sapiens

<400> SEQUENCE: 1223

Lys Pro Gln Gly Pro
1               5

<210> SEQ ID NO 1224
<211> LENGTH: 5
<212> TYPE: PRT
<213> ORGANISM: Homo sapiens

<400> SEQUENCE: 1224

Pro Gln Gly Pro Pro
1               5

<210> SEQ ID NO 1225
<211> LENGTH: 5
<212> TYPE: PRT
<213> ORGANISM: Homo sapiens

<400> SEQUENCE: 1225

Gln Gly Pro Pro Pro
1               5

<210> SEQ ID NO 1226
<211> LENGTH: 5
<212> TYPE: PRT
<213> ORGANISM: Homo sapiens

<400> SEQUENCE: 1226

Gly Pro Pro Pro Pro
1               5
```

<210> SEQ ID NO 1227
<211> LENGTH: 5
<212> TYPE: PRT
<213> ORGANISM: Homo sapiens

<400> SEQUENCE: 1227

Pro Pro Pro Pro Gly
1               5

<210> SEQ ID NO 1228
<211> LENGTH: 5
<212> TYPE: PRT
<213> ORGANISM: Homo sapiens

<400> SEQUENCE: 1228

Pro Pro Pro Gly Lys
1               5

<210> SEQ ID NO 1229
<211> LENGTH: 5
<212> TYPE: PRT
<213> ORGANISM: Homo sapiens

<400> SEQUENCE: 1229

Pro Pro Gly Lys Pro
1               5

<210> SEQ ID NO 1230
<211> LENGTH: 5
<212> TYPE: PRT
<213> ORGANISM: Homo sapiens

<400> SEQUENCE: 1230

Pro Gly Lys Pro Gln
1               5

<210> SEQ ID NO 1231
<211> LENGTH: 5
<212> TYPE: PRT
<213> ORGANISM: Homo sapiens

<400> SEQUENCE: 1231

Gly Lys Pro Gln Gly
1               5

<210> SEQ ID NO 1232
<211> LENGTH: 5
<212> TYPE: PRT
<213> ORGANISM: Homo sapiens

<400> SEQUENCE: 1232

Lys Pro Gln Gly Pro
1               5

<210> SEQ ID NO 1233
<211> LENGTH: 5
<212> TYPE: PRT
<213> ORGANISM: Homo sapiens

<400> SEQUENCE: 1233

Pro Gln Gly Pro Pro
1               5

<210> SEQ ID NO 1234
<211> LENGTH: 5

```
<212> TYPE: PRT
<213> ORGANISM: Homo sapiens

<400> SEQUENCE: 1234

Gln Gly Pro Pro Pro
1               5

<210> SEQ ID NO 1235
<211> LENGTH: 5
<212> TYPE: PRT
<213> ORGANISM: Homo sapiens

<400> SEQUENCE: 1235

Gly Pro Pro Pro Pro
1               5

<210> SEQ ID NO 1236
<211> LENGTH: 5
<212> TYPE: PRT
<213> ORGANISM: Homo sapiens

<400> SEQUENCE: 1236

Pro Pro Pro Pro Gly
1               5

<210> SEQ ID NO 1237
<211> LENGTH: 5
<212> TYPE: PRT
<213> ORGANISM: Homo sapiens

<400> SEQUENCE: 1237

Pro Pro Pro Gly Gly
1               5

<210> SEQ ID NO 1238
<211> LENGTH: 5
<212> TYPE: PRT
<213> ORGANISM: Homo sapiens

<400> SEQUENCE: 1238

Pro Pro Gly Gly Asn
1               5

<210> SEQ ID NO 1239
<211> LENGTH: 5
<212> TYPE: PRT
<213> ORGANISM: Homo sapiens

<400> SEQUENCE: 1239

Pro Gly Gly Asn Pro
1               5

<210> SEQ ID NO 1240
<211> LENGTH: 5
<212> TYPE: PRT
<213> ORGANISM: Homo sapiens

<400> SEQUENCE: 1240

Gly Gly Asn Pro Gln
1               5

<210> SEQ ID NO 1241
<211> LENGTH: 5
<212> TYPE: PRT
<213> ORGANISM: Homo sapiens
```

<400> SEQUENCE: 1241

Gly Asn Pro Gln Gln
1               5

<210> SEQ ID NO 1242
<211> LENGTH: 5
<212> TYPE: PRT
<213> ORGANISM: Homo sapiens

<400> SEQUENCE: 1242

Asn Pro Gln Gln Pro
1               5

<210> SEQ ID NO 1243
<211> LENGTH: 5
<212> TYPE: PRT
<213> ORGANISM: Homo sapiens

<400> SEQUENCE: 1243

Pro Gln Gln Pro Gln
1               5

<210> SEQ ID NO 1244
<211> LENGTH: 5
<212> TYPE: PRT
<213> ORGANISM: Homo sapiens

<400> SEQUENCE: 1244

Gln Gln Pro Gln Ala
1               5

<210> SEQ ID NO 1245
<211> LENGTH: 5
<212> TYPE: PRT
<213> ORGANISM: Homo sapiens

<400> SEQUENCE: 1245

Gln Pro Gln Ala Pro
1               5

<210> SEQ ID NO 1246
<211> LENGTH: 5
<212> TYPE: PRT
<213> ORGANISM: Homo sapiens

<400> SEQUENCE: 1246

Pro Gln Ala Pro Pro
1               5

<210> SEQ ID NO 1247
<211> LENGTH: 5
<212> TYPE: PRT
<213> ORGANISM: Homo sapiens

<400> SEQUENCE: 1247

Gln Ala Pro Pro Ala
1               5

<210> SEQ ID NO 1248
<211> LENGTH: 5
<212> TYPE: PRT
<213> ORGANISM: Homo sapiens

<400> SEQUENCE: 1248

Ala Pro Pro Ala Gly
1               5

<210> SEQ ID NO 1249
<211> LENGTH: 5
<212> TYPE: PRT
<213> ORGANISM: Homo sapiens

<400> SEQUENCE: 1249

Pro Pro Ala Gly Lys
1               5

<210> SEQ ID NO 1250
<211> LENGTH: 5
<212> TYPE: PRT
<213> ORGANISM: Homo sapiens

<400> SEQUENCE: 1250

Pro Ala Gly Lys Pro
1               5

<210> SEQ ID NO 1251
<211> LENGTH: 5
<212> TYPE: PRT
<213> ORGANISM: Homo sapiens

<400> SEQUENCE: 1251

Ala Gly Lys Pro Gln
1               5

<210> SEQ ID NO 1252
<211> LENGTH: 5
<212> TYPE: PRT
<213> ORGANISM: Homo sapiens

<400> SEQUENCE: 1252

Gly Lys Pro Gln Gly
1               5

<210> SEQ ID NO 1253
<211> LENGTH: 5
<212> TYPE: PRT
<213> ORGANISM: Homo sapiens

<400> SEQUENCE: 1253

Lys Pro Gln Gly Pro
1               5

<210> SEQ ID NO 1254
<211> LENGTH: 5
<212> TYPE: PRT
<213> ORGANISM: Homo sapiens

<400> SEQUENCE: 1254

Pro Gln Gly Pro Pro
1               5

<210> SEQ ID NO 1255
<211> LENGTH: 5
<212> TYPE: PRT
<213> ORGANISM: Homo sapiens

<400> SEQUENCE: 1255

Gln Gly Pro Pro Pro 1               5

<210> SEQ ID NO 1256
<211> LENGTH: 5
<212> TYPE: PRT
<213> ORGANISM: Homo sapiens

<400> SEQUENCE: 1256

Gly Pro Pro Pro Pro
1               5

<210> SEQ ID NO 1257
<211> LENGTH: 5
<212> TYPE: PRT
<213> ORGANISM: Homo sapiens

<400> SEQUENCE: 1257

Pro Pro Pro Pro Pro
1               5

<210> SEQ ID NO 1258
<211> LENGTH: 5
<212> TYPE: PRT
<213> ORGANISM: Homo sapiens

<400> SEQUENCE: 1258

Pro Pro Pro Pro Gln
1               5

<210> SEQ ID NO 1259
<211> LENGTH: 5
<212> TYPE: PRT
<213> ORGANISM: Homo sapiens

<400> SEQUENCE: 1259

Pro Pro Pro Gln Gly
1               5

<210> SEQ ID NO 1260
<211> LENGTH: 5
<212> TYPE: PRT
<213> ORGANISM: Homo sapiens

<400> SEQUENCE: 1260

Pro Pro Gln Gly Gly
1               5

<210> SEQ ID NO 1261
<211> LENGTH: 5
<212> TYPE: PRT
<213> ORGANISM: Homo sapiens

<400> SEQUENCE: 1261

Pro Gln Gly Gly Arg
1               5

<210> SEQ ID NO 1262
<211> LENGTH: 5
<212> TYPE: PRT
<213> ORGANISM: Homo sapiens

<400> SEQUENCE: 1262

Gln Gly Gly Arg Pro
1               5

<210> SEQ ID NO 1263
<211> LENGTH: 5
<212> TYPE: PRT
<213> ORGANISM: Homo sapiens

<400> SEQUENCE: 1263

Gly Gly Arg Pro Pro
1               5

<210> SEQ ID NO 1264
<211> LENGTH: 5
<212> TYPE: PRT
<213> ORGANISM: Homo sapiens

<400> SEQUENCE: 1264

Gly Arg Pro Pro Arg
1               5

<210> SEQ ID NO 1265
<211> LENGTH: 5
<212> TYPE: PRT
<213> ORGANISM: Homo sapiens

<400> SEQUENCE: 1265

Arg Pro Pro Arg Pro
1               5

<210> SEQ ID NO 1266
<211> LENGTH: 5
<212> TYPE: PRT
<213> ORGANISM: Homo sapiens

<400> SEQUENCE: 1266

Pro Pro Arg Pro Ala
1               5

<210> SEQ ID NO 1267
<211> LENGTH: 5
<212> TYPE: PRT
<213> ORGANISM: Homo sapiens

<400> SEQUENCE: 1267

Pro Arg Pro Ala Gln
1               5

<210> SEQ ID NO 1268
<211> LENGTH: 5
<212> TYPE: PRT
<213> ORGANISM: Homo sapiens

<400> SEQUENCE: 1268

Arg Pro Ala Gln Gly
1               5

<210> SEQ ID NO 1269
<211> LENGTH: 5
<212> TYPE: PRT
<213> ORGANISM: Homo sapiens

<400> SEQUENCE: 1269

Pro Ala Gln Gly Gln
1               5

<210> SEQ ID NO 1270

```
<211> LENGTH: 5
<212> TYPE: PRT
<213> ORGANISM: Homo sapiens

<400> SEQUENCE: 1270

Ala Gln Gly Gln Gln
1               5

<210> SEQ ID NO 1271
<211> LENGTH: 5
<212> TYPE: PRT
<213> ORGANISM: Homo sapiens

<400> SEQUENCE: 1271

Gln Gly Gln Gln Pro
1               5

<210> SEQ ID NO 1272
<211> LENGTH: 5
<212> TYPE: PRT
<213> ORGANISM: Homo sapiens

<400> SEQUENCE: 1272

Gly Gln Gln Pro Pro
1               5

<210> SEQ ID NO 1273
<211> LENGTH: 5
<212> TYPE: PRT
<213> ORGANISM: Homo sapiens

<400> SEQUENCE: 1273

Gln Gln Pro Pro Gln
1               5

<210> SEQ ID NO 1274
<211> LENGTH: 166
<212> TYPE: PRT
<213> ORGANISM: Homo sapiens

<400> SEQUENCE: 1274

Met Leu Leu Ile Leu Leu Ser Val Ala Leu Leu Ala Phe Ser Ser Ala
1               5                   10                  15

Gln Asp Leu Asp Glu Asp Val Ser Gln Glu Asp Val Pro Leu Val Ile
                20                  25                  30

Ser Asp Gly Gly Asp Ser Glu Gln Phe Ile Asp Glu Glu Arg Gln Gly
            35                  40                  45

Pro Pro Leu Gly Gly Gln Gln Ser Gln Pro Ser Ala Gly Asp Gly Asn
        50                  55                  60

Gln Asp Asp Gly Pro Gln Gln Gly Pro Pro Gln Gly Gly Gln Gln
65                  70                  75                  80

Gln Gln Gly Pro Pro Pro Gln Gly Lys Pro Gln Gly Pro Pro Gln
                85                  90                  95

Gln Gly Gly His Pro Pro Pro Gln Gly Arg Pro Gln Gly Pro Pro
            100                 105                 110

Gln Gln Gly Gly His Pro Arg Pro Pro Arg Gly Arg Pro Gln Gly Pro
        115                 120                 125

Pro Gln Gln Gly Gly His Gln Gln Gly Pro Pro Pro Pro Gly
        130                 135                 140

Lys Pro Gln Gly Pro Pro Gln Gly Gly Arg Pro Gln Gly Pro Pro
145                 150                 155                 160
```

Gln Gly Gln Ser Pro Gln
            165

<210> SEQ ID NO 1275
<211> LENGTH: 5
<212> TYPE: PRT
<213> ORGANISM: Homo sapiens

<400> SEQUENCE: 1275

Met Leu Leu Ile Leu
1               5

<210> SEQ ID NO 1276
<211> LENGTH: 5
<212> TYPE: PRT
<213> ORGANISM: Homo sapiens

<400> SEQUENCE: 1276

Leu Leu Ile Leu Leu
1               5

<210> SEQ ID NO 1277
<211> LENGTH: 5
<212> TYPE: PRT
<213> ORGANISM: Homo sapiens

<400> SEQUENCE: 1277

Leu Ile Leu Leu Ser
1               5

<210> SEQ ID NO 1278
<211> LENGTH: 5
<212> TYPE: PRT
<213> ORGANISM: Homo sapiens

<400> SEQUENCE: 1278

Ile Leu Leu Ser Val
1               5

<210> SEQ ID NO 1279
<211> LENGTH: 5
<212> TYPE: PRT
<213> ORGANISM: Homo sapiens

<400> SEQUENCE: 1279

Leu Leu Ser Val Ala
1               5

<210> SEQ ID NO 1280
<211> LENGTH: 5
<212> TYPE: PRT
<213> ORGANISM: Homo sapiens

<400> SEQUENCE: 1280

Leu Ser Val Ala Leu
1               5

<210> SEQ ID NO 1281
<211> LENGTH: 5
<212> TYPE: PRT
<213> ORGANISM: Homo sapiens

<400> SEQUENCE: 1281

Ser Val Ala Leu Leu

```
1               5

<210> SEQ ID NO 1282
<211> LENGTH: 5
<212> TYPE: PRT
<213> ORGANISM: Homo sapiens

<400> SEQUENCE: 1282

Val Ala Leu Leu Ala
1               5

<210> SEQ ID NO 1283
<211> LENGTH: 5
<212> TYPE: PRT
<213> ORGANISM: Homo sapiens

<400> SEQUENCE: 1283

Ala Leu Leu Ala Phe
1               5

<210> SEQ ID NO 1284
<211> LENGTH: 5
<212> TYPE: PRT
<213> ORGANISM: Homo sapiens

<400> SEQUENCE: 1284

Leu Leu Ala Phe Ser
1               5

<210> SEQ ID NO 1285
<211> LENGTH: 5
<212> TYPE: PRT
<213> ORGANISM: Homo sapiens

<400> SEQUENCE: 1285

Leu Ala Phe Ser Ser
1               5

<210> SEQ ID NO 1286
<211> LENGTH: 5
<212> TYPE: PRT
<213> ORGANISM: Homo sapiens

<400> SEQUENCE: 1286

Ala Phe Ser Ser Ala
1               5

<210> SEQ ID NO 1287
<211> LENGTH: 5
<212> TYPE: PRT
<213> ORGANISM: Homo sapiens

<400> SEQUENCE: 1287

Phe Ser Ser Ala Gln
1               5

<210> SEQ ID NO 1288
<211> LENGTH: 5
<212> TYPE: PRT
<213> ORGANISM: Homo sapiens

<400> SEQUENCE: 1288

Ser Ser Ala Gln Asp
1               5
```

<210> SEQ ID NO 1289
<211> LENGTH: 5
<212> TYPE: PRT
<213> ORGANISM: Homo sapiens

<400> SEQUENCE: 1289

Ser Ala Gln Asp Leu
1               5

<210> SEQ ID NO 1290
<211> LENGTH: 5
<212> TYPE: PRT
<213> ORGANISM: Homo sapiens

<400> SEQUENCE: 1290

Ala Gln Asp Leu Asp
1               5

<210> SEQ ID NO 1291
<211> LENGTH: 5
<212> TYPE: PRT
<213> ORGANISM: Homo sapiens

<400> SEQUENCE: 1291

Gln Asp Leu Asp Glu
1               5

<210> SEQ ID NO 1292
<211> LENGTH: 5
<212> TYPE: PRT
<213> ORGANISM: Homo sapiens

<400> SEQUENCE: 1292

Asp Leu Asp Glu Asp
1               5

<210> SEQ ID NO 1293
<211> LENGTH: 5
<212> TYPE: PRT
<213> ORGANISM: Homo sapiens

<400> SEQUENCE: 1293

Leu Asp Glu Asp Val
1               5

<210> SEQ ID NO 1294
<211> LENGTH: 5
<212> TYPE: PRT
<213> ORGANISM: Homo sapiens

<400> SEQUENCE: 1294

Asp Glu Asp Val Ser
1               5

<210> SEQ ID NO 1295
<211> LENGTH: 5
<212> TYPE: PRT
<213> ORGANISM: Homo sapiens

<400> SEQUENCE: 1295

Glu Asp Val Ser Gln
1               5

<210> SEQ ID NO 1296

```
<211> LENGTH: 5
<212> TYPE: PRT
<213> ORGANISM: Homo sapiens

<400> SEQUENCE: 1296

Asp Val Ser Gln Glu
1               5

<210> SEQ ID NO 1297
<211> LENGTH: 5
<212> TYPE: PRT
<213> ORGANISM: Homo sapiens

<400> SEQUENCE: 1297

Val Ser Gln Glu Asp
1               5

<210> SEQ ID NO 1298
<211> LENGTH: 5
<212> TYPE: PRT
<213> ORGANISM: Homo sapiens

<400> SEQUENCE: 1298

Ser Gln Glu Asp Val
1               5

<210> SEQ ID NO 1299
<211> LENGTH: 5
<212> TYPE: PRT
<213> ORGANISM: Homo sapiens

<400> SEQUENCE: 1299

Gln Glu Asp Val Pro
1               5

<210> SEQ ID NO 1300
<211> LENGTH: 5
<212> TYPE: PRT
<213> ORGANISM: Homo sapiens

<400> SEQUENCE: 1300

Glu Asp Val Pro Leu
1               5

<210> SEQ ID NO 1301
<211> LENGTH: 5
<212> TYPE: PRT
<213> ORGANISM: Homo sapiens

<400> SEQUENCE: 1301

Asp Val Pro Leu Val
1               5

<210> SEQ ID NO 1302
<211> LENGTH: 5
<212> TYPE: PRT
<213> ORGANISM: Homo sapiens

<400> SEQUENCE: 1302

Val Pro Leu Val Ile
1               5

<210> SEQ ID NO 1303
<211> LENGTH: 5
<212> TYPE: PRT
```

<213> ORGANISM: Homo sapiens

<400> SEQUENCE: 1303

Pro Leu Val Ile Ser
1               5

<210> SEQ ID NO 1304
<211> LENGTH: 5
<212> TYPE: PRT
<213> ORGANISM: Homo sapiens

<400> SEQUENCE: 1304

Leu Val Ile Ser Asp
1               5

<210> SEQ ID NO 1305
<211> LENGTH: 5
<212> TYPE: PRT
<213> ORGANISM: Homo sapiens

<400> SEQUENCE: 1305

Val Ile Ser Asp Gly
1               5

<210> SEQ ID NO 1306
<211> LENGTH: 5
<212> TYPE: PRT
<213> ORGANISM: Homo sapiens

<400> SEQUENCE: 1306

Ile Ser Asp Gly Gly
1               5

<210> SEQ ID NO 1307
<211> LENGTH: 5
<212> TYPE: PRT
<213> ORGANISM: Homo sapiens

<400> SEQUENCE: 1307

Ser Asp Gly Gly Asp
1               5

<210> SEQ ID NO 1308
<211> LENGTH: 5
<212> TYPE: PRT
<213> ORGANISM: Homo sapiens

<400> SEQUENCE: 1308

Asp Gly Gly Asp Ser
1               5

<210> SEQ ID NO 1309
<211> LENGTH: 5
<212> TYPE: PRT
<213> ORGANISM: Homo sapiens

<400> SEQUENCE: 1309

Gly Gly Asp Ser Glu
1               5

<210> SEQ ID NO 1310
<211> LENGTH: 5
<212> TYPE: PRT
<213> ORGANISM: Homo sapiens

```
<400> SEQUENCE: 1310

Gly Asp Ser Glu Gln
1               5

<210> SEQ ID NO 1311
<211> LENGTH: 5
<212> TYPE: PRT
<213> ORGANISM: Homo sapiens

<400> SEQUENCE: 1311

Asp Ser Glu Gln Phe
1               5

<210> SEQ ID NO 1312
<211> LENGTH: 5
<212> TYPE: PRT
<213> ORGANISM: Homo sapiens

<400> SEQUENCE: 1312

Ser Glu Gln Phe Ile
1               5

<210> SEQ ID NO 1313
<211> LENGTH: 5
<212> TYPE: PRT
<213> ORGANISM: Homo sapiens

<400> SEQUENCE: 1313

Glu Gln Phe Ile Asp
1               5

<210> SEQ ID NO 1314
<211> LENGTH: 5
<212> TYPE: PRT
<213> ORGANISM: Homo sapiens

<400> SEQUENCE: 1314

Gln Phe Ile Asp Glu
1               5

<210> SEQ ID NO 1315
<211> LENGTH: 5
<212> TYPE: PRT
<213> ORGANISM: Homo sapiens

<400> SEQUENCE: 1315

Phe Ile Asp Glu Glu
1               5

<210> SEQ ID NO 1316
<211> LENGTH: 5
<212> TYPE: PRT
<213> ORGANISM: Homo sapiens

<400> SEQUENCE: 1316

Ile Asp Glu Glu Arg
1               5

<210> SEQ ID NO 1317
<211> LENGTH: 5
<212> TYPE: PRT
<213> ORGANISM: Homo sapiens

<400> SEQUENCE: 1317
```

Asp Glu Glu Arg Gln
1               5

<210> SEQ ID NO 1318
<211> LENGTH: 5
<212> TYPE: PRT
<213> ORGANISM: Homo sapiens

<400> SEQUENCE: 1318

Glu Glu Arg Gln Gly
1               5

<210> SEQ ID NO 1319
<211> LENGTH: 5
<212> TYPE: PRT
<213> ORGANISM: Homo sapiens

<400> SEQUENCE: 1319

Glu Arg Gln Gly Pro
1               5

<210> SEQ ID NO 1320
<211> LENGTH: 5
<212> TYPE: PRT
<213> ORGANISM: Homo sapiens

<400> SEQUENCE: 1320

Arg Gln Gly Pro Pro
1               5

<210> SEQ ID NO 1321
<211> LENGTH: 5
<212> TYPE: PRT
<213> ORGANISM: Homo sapiens

<400> SEQUENCE: 1321

Gln Gly Pro Pro Leu
1               5

<210> SEQ ID NO 1322
<211> LENGTH: 5
<212> TYPE: PRT
<213> ORGANISM: Homo sapiens

<400> SEQUENCE: 1322

Gly Pro Pro Leu Gly
1               5

<210> SEQ ID NO 1323
<211> LENGTH: 5
<212> TYPE: PRT
<213> ORGANISM: Homo sapiens

<400> SEQUENCE: 1323

Pro Pro Leu Gly Gly
1               5

<210> SEQ ID NO 1324
<211> LENGTH: 5
<212> TYPE: PRT
<213> ORGANISM: Homo sapiens

<400> SEQUENCE: 1324

Pro Leu Gly Gly Gln
1               5

<210> SEQ ID NO 1325
<211> LENGTH: 5
<212> TYPE: PRT
<213> ORGANISM: Homo sapiens

<400> SEQUENCE: 1325

Leu Gly Gly Gln Gln
1               5

<210> SEQ ID NO 1326
<211> LENGTH: 5
<212> TYPE: PRT
<213> ORGANISM: Homo sapiens

<400> SEQUENCE: 1326

Gly Gly Gln Gln Ser
1               5

<210> SEQ ID NO 1327
<211> LENGTH: 5
<212> TYPE: PRT
<213> ORGANISM: Homo sapiens

<400> SEQUENCE: 1327

Gly Gln Gln Ser Gln
1               5

<210> SEQ ID NO 1328
<211> LENGTH: 5
<212> TYPE: PRT
<213> ORGANISM: Homo sapiens

<400> SEQUENCE: 1328

Gln Gln Ser Gln Pro
1               5

<210> SEQ ID NO 1329
<211> LENGTH: 5
<212> TYPE: PRT
<213> ORGANISM: Homo sapiens

<400> SEQUENCE: 1329

Gln Ser Gln Pro Ser
1               5

<210> SEQ ID NO 1330
<211> LENGTH: 5
<212> TYPE: PRT
<213> ORGANISM: Homo sapiens

<400> SEQUENCE: 1330

Ser Gln Pro Ser Ala
1               5

<210> SEQ ID NO 1331
<211> LENGTH: 5
<212> TYPE: PRT
<213> ORGANISM: Homo sapiens

<400> SEQUENCE: 1331

Gln Pro Ser Ala Gly
1               5

```
<210> SEQ ID NO 1332
<211> LENGTH: 5
<212> TYPE: PRT
<213> ORGANISM: Homo sapiens

<400> SEQUENCE: 1332

Pro Ser Ala Gly Asp
1               5

<210> SEQ ID NO 1333
<211> LENGTH: 5
<212> TYPE: PRT
<213> ORGANISM: Homo sapiens

<400> SEQUENCE: 1333

Ser Ala Gly Asp Gly
1               5

<210> SEQ ID NO 1334
<211> LENGTH: 5
<212> TYPE: PRT
<213> ORGANISM: Homo sapiens

<400> SEQUENCE: 1334

Ala Gly Asp Gly Asn
1               5

<210> SEQ ID NO 1335
<211> LENGTH: 5
<212> TYPE: PRT
<213> ORGANISM: Homo sapiens

<400> SEQUENCE: 1335

Gly Asp Gly Asn Gln
1               5

<210> SEQ ID NO 1336
<211> LENGTH: 5
<212> TYPE: PRT
<213> ORGANISM: Homo sapiens

<400> SEQUENCE: 1336

Asp Gly Asn Gln Asp
1               5

<210> SEQ ID NO 1337
<211> LENGTH: 5
<212> TYPE: PRT
<213> ORGANISM: Homo sapiens

<400> SEQUENCE: 1337

Gly Asn Gln Asp Asp
1               5

<210> SEQ ID NO 1338
<211> LENGTH: 5
<212> TYPE: PRT
<213> ORGANISM: Homo sapiens

<400> SEQUENCE: 1338

Asn Gln Asp Asp Gly
1               5

<210> SEQ ID NO 1339
<211> LENGTH: 5
```

<212> TYPE: PRT
<213> ORGANISM: Homo sapiens

<400> SEQUENCE: 1339

Gln Asp Asp Gly Pro
1               5

<210> SEQ ID NO 1340
<211> LENGTH: 5
<212> TYPE: PRT
<213> ORGANISM: Homo sapiens

<400> SEQUENCE: 1340

Asp Asp Gly Pro Gln
1               5

<210> SEQ ID NO 1341
<211> LENGTH: 5
<212> TYPE: PRT
<213> ORGANISM: Homo sapiens

<400> SEQUENCE: 1341

Asp Gly Pro Gln Gln
1               5

<210> SEQ ID NO 1342
<211> LENGTH: 5
<212> TYPE: PRT
<213> ORGANISM: Homo sapiens

<400> SEQUENCE: 1342

Gly Pro Gln Gln Gly
1               5

<210> SEQ ID NO 1343
<211> LENGTH: 5
<212> TYPE: PRT
<213> ORGANISM: Homo sapiens

<400> SEQUENCE: 1343

Pro Gln Gln Gly Pro
1               5

<210> SEQ ID NO 1344
<211> LENGTH: 5
<212> TYPE: PRT
<213> ORGANISM: Homo sapiens

<400> SEQUENCE: 1344

Gln Gln Gly Pro Pro
1               5

<210> SEQ ID NO 1345
<211> LENGTH: 5
<212> TYPE: PRT
<213> ORGANISM: Homo sapiens

<400> SEQUENCE: 1345

Gln Gly Pro Pro Gln
1               5

<210> SEQ ID NO 1346
<211> LENGTH: 5
<212> TYPE: PRT
<213> ORGANISM: Homo sapiens

```
<400> SEQUENCE: 1346

Gly Pro Pro Gln Gln
1               5

<210> SEQ ID NO 1347
<211> LENGTH: 5
<212> TYPE: PRT
<213> ORGANISM: Homo sapiens

<400> SEQUENCE: 1347

Pro Pro Gln Gln Gly
1               5

<210> SEQ ID NO 1348
<211> LENGTH: 5
<212> TYPE: PRT
<213> ORGANISM: Homo sapiens

<400> SEQUENCE: 1348

Pro Gln Gln Gly Gly
1               5

<210> SEQ ID NO 1349
<211> LENGTH: 5
<212> TYPE: PRT
<213> ORGANISM: Homo sapiens

<400> SEQUENCE: 1349

Gln Gln Gly Gly Gln
1               5

<210> SEQ ID NO 1350
<211> LENGTH: 5
<212> TYPE: PRT
<213> ORGANISM: Homo sapiens

<400> SEQUENCE: 1350

Gln Gly Gly Gln Gln
1               5

<210> SEQ ID NO 1351
<211> LENGTH: 5
<212> TYPE: PRT
<213> ORGANISM: Homo sapiens

<400> SEQUENCE: 1351

Gly Gly Gln Gln Gln
1               5

<210> SEQ ID NO 1352
<211> LENGTH: 5
<212> TYPE: PRT
<213> ORGANISM: Homo sapiens

<400> SEQUENCE: 1352

Gly Gln Gln Gln Gln
1               5

<210> SEQ ID NO 1353
<211> LENGTH: 5
<212> TYPE: PRT
<213> ORGANISM: Homo sapiens

<400> SEQUENCE: 1353
```

```
Gln Gln Gln Gln Gly
1               5

<210> SEQ ID NO 1354
<211> LENGTH: 5
<212> TYPE: PRT
<213> ORGANISM: Homo sapiens

<400> SEQUENCE: 1354

Gln Gln Gln Gly Pro
1               5

<210> SEQ ID NO 1355
<211> LENGTH: 5
<212> TYPE: PRT
<213> ORGANISM: Homo sapiens

<400> SEQUENCE: 1355

Gln Gln Gly Pro Pro
1               5

<210> SEQ ID NO 1356
<211> LENGTH: 5
<212> TYPE: PRT
<213> ORGANISM: Homo sapiens

<400> SEQUENCE: 1356

Gln Gly Pro Pro Pro
1               5

<210> SEQ ID NO 1357
<211> LENGTH: 5
<212> TYPE: PRT
<213> ORGANISM: Homo sapiens

<400> SEQUENCE: 1357

Gly Pro Pro Pro Pro
1               5

<210> SEQ ID NO 1358
<211> LENGTH: 5
<212> TYPE: PRT
<213> ORGANISM: Homo sapiens

<400> SEQUENCE: 1358

Pro Pro Pro Pro Gln
1               5

<210> SEQ ID NO 1359
<211> LENGTH: 5
<212> TYPE: PRT
<213> ORGANISM: Homo sapiens

<400> SEQUENCE: 1359

Pro Pro Pro Gln Gly
1               5

<210> SEQ ID NO 1360
<211> LENGTH: 5
<212> TYPE: PRT
<213> ORGANISM: Homo sapiens

<400> SEQUENCE: 1360

Pro Pro Gln Gly Lys
```

```
1               5
```

<210> SEQ ID NO 1361
<211> LENGTH: 5
<212> TYPE: PRT
<213> ORGANISM: Homo sapiens

<400> SEQUENCE: 1361

```
Pro Gln Gly Lys Pro
1               5
```

<210> SEQ ID NO 1362
<211> LENGTH: 5
<212> TYPE: PRT
<213> ORGANISM: Homo sapiens

<400> SEQUENCE: 1362

```
Gln Gly Lys Pro Gln
1               5
```

<210> SEQ ID NO 1363
<211> LENGTH: 5
<212> TYPE: PRT
<213> ORGANISM: Homo sapiens

<400> SEQUENCE: 1363

```
Gly Lys Pro Gln Gly
1               5
```

<210> SEQ ID NO 1364
<211> LENGTH: 5
<212> TYPE: PRT
<213> ORGANISM: Homo sapiens

<400> SEQUENCE: 1364

```
Lys Pro Gln Gly Pro
1               5
```

<210> SEQ ID NO 1365
<211> LENGTH: 5
<212> TYPE: PRT
<213> ORGANISM: Homo sapiens

<400> SEQUENCE: 1365

```
Pro Gln Gly Pro Pro
1               5
```

<210> SEQ ID NO 1366
<211> LENGTH: 5
<212> TYPE: PRT
<213> ORGANISM: Homo sapiens

<400> SEQUENCE: 1366

```
Gln Gly Pro Pro Gln
1               5
```

<210> SEQ ID NO 1367
<211> LENGTH: 5
<212> TYPE: PRT
<213> ORGANISM: Homo sapiens

<400> SEQUENCE: 1367

```
Gly Pro Pro Gln Gln
1               5
```

<210> SEQ ID NO 1368
<211> LENGTH: 5
<212> TYPE: PRT
<213> ORGANISM: Homo sapiens

<400> SEQUENCE: 1368

Pro Pro Gln Gln Gly
1               5

<210> SEQ ID NO 1369
<211> LENGTH: 5
<212> TYPE: PRT
<213> ORGANISM: Homo sapiens

<400> SEQUENCE: 1369

Pro Gln Gln Gly Gly
1               5

<210> SEQ ID NO 1370
<211> LENGTH: 5
<212> TYPE: PRT
<213> ORGANISM: Homo sapiens

<400> SEQUENCE: 1370

Gln Gln Gly Gly His
1               5

<210> SEQ ID NO 1371
<211> LENGTH: 5
<212> TYPE: PRT
<213> ORGANISM: Homo sapiens

<400> SEQUENCE: 1371

Gln Gly Gly His Pro
1               5

<210> SEQ ID NO 1372
<211> LENGTH: 5
<212> TYPE: PRT
<213> ORGANISM: Homo sapiens

<400> SEQUENCE: 1372

Gly Gly His Pro Pro
1               5

<210> SEQ ID NO 1373
<211> LENGTH: 5
<212> TYPE: PRT
<213> ORGANISM: Homo sapiens

<400> SEQUENCE: 1373

Gly His Pro Pro Pro
1               5

<210> SEQ ID NO 1374
<211> LENGTH: 5
<212> TYPE: PRT
<213> ORGANISM: Homo sapiens

<400> SEQUENCE: 1374

His Pro Pro Pro Pro
1               5

<210> SEQ ID NO 1375

```
<211> LENGTH: 5
<212> TYPE: PRT
<213> ORGANISM: Homo sapiens

<400> SEQUENCE: 1375

Pro Pro Pro Pro Gln
1               5

<210> SEQ ID NO 1376
<211> LENGTH: 5
<212> TYPE: PRT
<213> ORGANISM: Homo sapiens

<400> SEQUENCE: 1376

Pro Pro Pro Gln Gly
1               5

<210> SEQ ID NO 1377
<211> LENGTH: 5
<212> TYPE: PRT
<213> ORGANISM: Homo sapiens

<400> SEQUENCE: 1377

Pro Pro Gln Gly Arg
1               5

<210> SEQ ID NO 1378
<211> LENGTH: 5
<212> TYPE: PRT
<213> ORGANISM: Homo sapiens

<400> SEQUENCE: 1378

Pro Gln Gly Arg Pro
1               5

<210> SEQ ID NO 1379
<211> LENGTH: 5
<212> TYPE: PRT
<213> ORGANISM: Homo sapiens

<400> SEQUENCE: 1379

Gln Gly Arg Pro Gln
1               5

<210> SEQ ID NO 1380
<211> LENGTH: 5
<212> TYPE: PRT
<213> ORGANISM: Homo sapiens

<400> SEQUENCE: 1380

Gly Arg Pro Gln Gly
1               5

<210> SEQ ID NO 1381
<211> LENGTH: 5
<212> TYPE: PRT
<213> ORGANISM: Homo sapiens

<400> SEQUENCE: 1381

Arg Pro Gln Gly Pro
1               5

<210> SEQ ID NO 1382
<211> LENGTH: 5
<212> TYPE: PRT
```

<213> ORGANISM: Homo sapiens

<400> SEQUENCE: 1382

Pro Gln Gly Pro Pro
1               5

<210> SEQ ID NO 1383
<211> LENGTH: 5
<212> TYPE: PRT
<213> ORGANISM: Homo sapiens

<400> SEQUENCE: 1383

Gln Gly Pro Pro Gln
1               5

<210> SEQ ID NO 1384
<211> LENGTH: 5
<212> TYPE: PRT
<213> ORGANISM: Homo sapiens

<400> SEQUENCE: 1384

Gly Pro Pro Gln Gln
1               5

<210> SEQ ID NO 1385
<211> LENGTH: 5
<212> TYPE: PRT
<213> ORGANISM: Homo sapiens

<400> SEQUENCE: 1385

Pro Pro Gln Gln Gly
1               5

<210> SEQ ID NO 1386
<211> LENGTH: 5
<212> TYPE: PRT
<213> ORGANISM: Homo sapiens

<400> SEQUENCE: 1386

Pro Gln Gln Gly Gly
1               5

<210> SEQ ID NO 1387
<211> LENGTH: 5
<212> TYPE: PRT
<213> ORGANISM: Homo sapiens

<400> SEQUENCE: 1387

Gln Gln Gly Gly His
1               5

<210> SEQ ID NO 1388
<211> LENGTH: 5
<212> TYPE: PRT
<213> ORGANISM: Homo sapiens

<400> SEQUENCE: 1388

Gln Gly Gly His Pro
1               5

<210> SEQ ID NO 1389
<211> LENGTH: 5
<212> TYPE: PRT
<213> ORGANISM: Homo sapiens

<400> SEQUENCE: 1389

Gly Gly His Pro Arg
1               5

<210> SEQ ID NO 1390
<211> LENGTH: 5
<212> TYPE: PRT
<213> ORGANISM: Homo sapiens

<400> SEQUENCE: 1390

Gly His Pro Arg Pro
1               5

<210> SEQ ID NO 1391
<211> LENGTH: 5
<212> TYPE: PRT
<213> ORGANISM: Homo sapiens

<400> SEQUENCE: 1391

His Pro Arg Pro Pro
1               5

<210> SEQ ID NO 1392
<211> LENGTH: 5
<212> TYPE: PRT
<213> ORGANISM: Homo sapiens

<400> SEQUENCE: 1392

Pro Arg Pro Pro Arg
1               5

<210> SEQ ID NO 1393
<211> LENGTH: 5
<212> TYPE: PRT
<213> ORGANISM: Homo sapiens

<400> SEQUENCE: 1393

Arg Pro Pro Arg Gly
1               5

<210> SEQ ID NO 1394
<211> LENGTH: 5
<212> TYPE: PRT
<213> ORGANISM: Homo sapiens

<400> SEQUENCE: 1394

Pro Pro Arg Gly Arg
1               5

<210> SEQ ID NO 1395
<211> LENGTH: 5
<212> TYPE: PRT
<213> ORGANISM: Homo sapiens

<400> SEQUENCE: 1395

Pro Arg Gly Arg Pro
1               5

<210> SEQ ID NO 1396
<211> LENGTH: 5
<212> TYPE: PRT
<213> ORGANISM: Homo sapiens

<400> SEQUENCE: 1396

```
Arg Gly Arg Pro Gln
1               5

<210> SEQ ID NO 1397
<211> LENGTH: 5
<212> TYPE: PRT
<213> ORGANISM: Homo sapiens

<400> SEQUENCE: 1397

Gly Arg Pro Gln Gly
1               5

<210> SEQ ID NO 1398
<211> LENGTH: 5
<212> TYPE: PRT
<213> ORGANISM: Homo sapiens

<400> SEQUENCE: 1398

Arg Pro Gln Gly Pro
1               5

<210> SEQ ID NO 1399
<211> LENGTH: 5
<212> TYPE: PRT
<213> ORGANISM: Homo sapiens

<400> SEQUENCE: 1399

Pro Gln Gly Pro Pro
1               5

<210> SEQ ID NO 1400
<211> LENGTH: 5
<212> TYPE: PRT
<213> ORGANISM: Homo sapiens

<400> SEQUENCE: 1400

Gln Gly Pro Pro Gln
1               5

<210> SEQ ID NO 1401
<211> LENGTH: 5
<212> TYPE: PRT
<213> ORGANISM: Homo sapiens

<400> SEQUENCE: 1401

Gly Pro Pro Gln Gln
1               5

<210> SEQ ID NO 1402
<211> LENGTH: 5
<212> TYPE: PRT
<213> ORGANISM: Homo sapiens

<400> SEQUENCE: 1402

Pro Pro Gln Gln Gly
1               5

<210> SEQ ID NO 1403
<211> LENGTH: 5
<212> TYPE: PRT
<213> ORGANISM: Homo sapiens

<400> SEQUENCE: 1403

Pro Gln Gln Gly Gly
1               5
```

-continued

```
<210> SEQ ID NO 1404
<211> LENGTH: 5
<212> TYPE: PRT
<213> ORGANISM: Homo sapiens

<400> SEQUENCE: 1404

Gln Gln Gly Gly His
1               5

<210> SEQ ID NO 1405
<211> LENGTH: 5
<212> TYPE: PRT
<213> ORGANISM: Homo sapiens

<400> SEQUENCE: 1405

Gln Gly Gly His Gln
1               5

<210> SEQ ID NO 1406
<211> LENGTH: 5
<212> TYPE: PRT
<213> ORGANISM: Homo sapiens

<400> SEQUENCE: 1406

Gly Gly His Gln Gln
1               5

<210> SEQ ID NO 1407
<211> LENGTH: 5
<212> TYPE: PRT
<213> ORGANISM: Homo sapiens

<400> SEQUENCE: 1407

Gly His Gln Gln Gly
1               5

<210> SEQ ID NO 1408
<211> LENGTH: 5
<212> TYPE: PRT
<213> ORGANISM: Homo sapiens

<400> SEQUENCE: 1408

His Gln Gln Gly Pro
1               5

<210> SEQ ID NO 1409
<211> LENGTH: 5
<212> TYPE: PRT
<213> ORGANISM: Homo sapiens

<400> SEQUENCE: 1409

Gln Gln Gly Pro Pro
1               5

<210> SEQ ID NO 1410
<211> LENGTH: 5
<212> TYPE: PRT
<213> ORGANISM: Homo sapiens

<400> SEQUENCE: 1410

Gln Gly Pro Pro Pro
1               5
```

```
<210> SEQ ID NO 1411
<211> LENGTH: 5
<212> TYPE: PRT
<213> ORGANISM: Homo sapiens

<400> SEQUENCE: 1411

Gly Pro Pro Pro Pro
1               5

<210> SEQ ID NO 1412
<211> LENGTH: 5
<212> TYPE: PRT
<213> ORGANISM: Homo sapiens

<400> SEQUENCE: 1412

Pro Pro Pro Pro Pro
1               5

<210> SEQ ID NO 1413
<211> LENGTH: 5
<212> TYPE: PRT
<213> ORGANISM: Homo sapiens

<400> SEQUENCE: 1413

Pro Pro Pro Pro Pro
1               5

<210> SEQ ID NO 1414
<211> LENGTH: 5
<212> TYPE: PRT
<213> ORGANISM: Homo sapiens

<400> SEQUENCE: 1414

Pro Pro Pro Pro Gly
1               5

<210> SEQ ID NO 1415
<211> LENGTH: 5
<212> TYPE: PRT
<213> ORGANISM: Homo sapiens

<400> SEQUENCE: 1415

Pro Pro Pro Gly Lys
1               5

<210> SEQ ID NO 1416
<211> LENGTH: 5
<212> TYPE: PRT
<213> ORGANISM: Homo sapiens

<400> SEQUENCE: 1416

Pro Pro Gly Lys Pro
1               5

<210> SEQ ID NO 1417
<211> LENGTH: 5
<212> TYPE: PRT
<213> ORGANISM: Homo sapiens

<400> SEQUENCE: 1417

Pro Gly Lys Pro Gln
1               5

<210> SEQ ID NO 1418
<211> LENGTH: 5
```

```
<212> TYPE: PRT
<213> ORGANISM: Homo sapiens

<400> SEQUENCE: 1418

Gly Lys Pro Gln Gly
1               5

<210> SEQ ID NO 1419
<211> LENGTH: 5
<212> TYPE: PRT
<213> ORGANISM: Homo sapiens

<400> SEQUENCE: 1419

Lys Pro Gln Gly Pro
1               5

<210> SEQ ID NO 1420
<211> LENGTH: 5
<212> TYPE: PRT
<213> ORGANISM: Homo sapiens

<400> SEQUENCE: 1420

Pro Gln Gly Pro Pro
1               5

<210> SEQ ID NO 1421
<211> LENGTH: 5
<212> TYPE: PRT
<213> ORGANISM: Homo sapiens

<400> SEQUENCE: 1421

Gln Gly Pro Pro Pro
1               5

<210> SEQ ID NO 1422
<211> LENGTH: 5
<212> TYPE: PRT
<213> ORGANISM: Homo sapiens

<400> SEQUENCE: 1422

Gly Pro Pro Pro Gln
1               5

<210> SEQ ID NO 1423
<211> LENGTH: 5
<212> TYPE: PRT
<213> ORGANISM: Homo sapiens

<400> SEQUENCE: 1423

Pro Pro Pro Gln Gly
1               5

<210> SEQ ID NO 1424
<211> LENGTH: 5
<212> TYPE: PRT
<213> ORGANISM: Homo sapiens

<400> SEQUENCE: 1424

Pro Pro Gln Gly Gly
1               5

<210> SEQ ID NO 1425
<211> LENGTH: 5
<212> TYPE: PRT
<213> ORGANISM: Homo sapiens
```

<400> SEQUENCE: 1425

Pro Gln Gly Gly Arg
1               5

<210> SEQ ID NO 1426
<211> LENGTH: 5
<212> TYPE: PRT
<213> ORGANISM: Homo sapiens

<400> SEQUENCE: 1426

Gln Gly Gly Arg Pro
1               5

<210> SEQ ID NO 1427
<211> LENGTH: 5
<212> TYPE: PRT
<213> ORGANISM: Homo sapiens

<400> SEQUENCE: 1427

Gly Gly Arg Pro Gln
1               5

<210> SEQ ID NO 1428
<211> LENGTH: 5
<212> TYPE: PRT
<213> ORGANISM: Homo sapiens

<400> SEQUENCE: 1428

Gly Arg Pro Gln Gly
1               5

<210> SEQ ID NO 1429
<211> LENGTH: 5
<212> TYPE: PRT
<213> ORGANISM: Homo sapiens

<400> SEQUENCE: 1429

Arg Pro Gln Gly Pro
1               5

<210> SEQ ID NO 1430
<211> LENGTH: 5
<212> TYPE: PRT
<213> ORGANISM: Homo sapiens

<400> SEQUENCE: 1430

Pro Gln Gly Pro Pro
1               5

<210> SEQ ID NO 1431
<211> LENGTH: 5
<212> TYPE: PRT
<213> ORGANISM: Homo sapiens

<400> SEQUENCE: 1431

Gln Gly Pro Pro Gln
1               5

<210> SEQ ID NO 1432
<211> LENGTH: 5
<212> TYPE: PRT
<213> ORGANISM: Homo sapiens

<400> SEQUENCE: 1432

```
Gly Pro Pro Gln Gly
1               5

<210> SEQ ID NO 1433
<211> LENGTH: 5
<212> TYPE: PRT
<213> ORGANISM: Homo sapiens

<400> SEQUENCE: 1433

Pro Pro Gln Gly Gln
1               5

<210> SEQ ID NO 1434
<211> LENGTH: 5
<212> TYPE: PRT
<213> ORGANISM: Homo sapiens

<400> SEQUENCE: 1434

Pro Gln Gly Gln Ser
1               5

<210> SEQ ID NO 1435
<211> LENGTH: 5
<212> TYPE: PRT
<213> ORGANISM: Homo sapiens

<400> SEQUENCE: 1435

Gln Gly Gln Ser Pro
1               5

<210> SEQ ID NO 1436
<211> LENGTH: 5
<212> TYPE: PRT
<213> ORGANISM: Homo sapiens

<400> SEQUENCE: 1436

Gly Gln Ser Pro Gln
1               5

<210> SEQ ID NO 1437
<211> LENGTH: 392
<212> TYPE: PRT
<213> ORGANISM: Homo sapiens

<400> SEQUENCE: 1437

Met Leu Leu Ile Leu Leu Ser Val Ala Leu Leu Ala Leu Ser Ser Ala
1               5                   10                  15

Gln Asn Leu Asn Glu Asp Val Ser Gln Glu Glu Ser Pro Ser Leu Ile
                20                  25                  30

Ala Gly Asn Pro Gln Gly Pro Ser Pro Gln Gly Gly Asn Lys Pro Gln
            35                  40                  45

Gly Pro Pro Pro Pro Gly Lys Pro Gln Gly Pro Pro Gln Gly Gly
        50                  55                  60

Gly Asn Lys Pro Gln Gly Pro Pro Pro Gly Lys Pro Gln Gly Pro
65                  70                  75                  80

Pro Pro Gln Gly Asp Lys Ser Arg Ser Pro Arg Ser Pro Pro Gly Lys
                85                  90                  95
```

```
Pro Gln Gly Pro Pro Pro Gln Gly Gly Asn Gln Pro Gln Gly Pro Pro
                100             105             110
Pro Pro Pro Gly Lys Pro Gln Gly Pro Pro Gln Gly Gly Asn Lys
        115             120             125
Pro Gln Gly Pro Pro Pro Pro Gly Lys Pro Gln Gly Pro Pro Pro Gln
130             135             140
Gly Asp Lys Ser Gln Ser Pro Arg Ser Pro Pro Gly Lys Pro Gln Gly
145             150             155             160
Pro Pro Pro Gln Gly Gly Asn Gln Pro Gln Gly Pro Pro Pro Pro Pro
                165             170             175
Gly Lys Pro Gln Gly Pro Pro Gln Gly Gly Asn Lys Pro Gln Gly
            180             185             190
Pro Pro Pro Pro Gly Lys Pro Gln Gly Pro Pro Pro Gln Gly Asp Lys
        195             200             205
Ser Gln Ser Pro Arg Ser Pro Pro Gly Lys Pro Gln Gly Pro Pro Pro
    210             215             220
Gln Gly Gly Asn Gln Pro Gln Gly Pro Pro Pro Pro Pro Gly Lys Pro
225             230             235             240
Gln Gly Pro Pro Gln Gln Gly Gly Asn Arg Pro Gln Gly Pro Pro Pro
            245             250             255
Pro Gly Lys Pro Gln Gly Pro Pro Pro Gln Gly Asp Lys Ser Arg Ser
            260             265             270
Pro Gln Ser Pro Pro Gly Lys Pro Gln Gly Pro Pro Pro Gln Gly Gly
        275             280             285
Asn Gln Pro Gln Gly Pro Pro Pro Pro Gly Lys Pro Gln Gly Pro
290             295             300
Pro Pro Gln Gly Gly Asn Lys Pro Gln Gly Pro Pro Pro Pro Gly Lys
305             310             315             320
Pro Gln Gly Pro Pro Ala Gln Gly Gly Ser Lys Ser Gln Ser Ala Arg
            325             330             335
Ala Pro Pro Gly Lys Pro Gln Gly Pro Pro Gln Gln Glu Gly Asn Asn
            340             345             350
Pro Gln Gly Pro Pro Pro Ala Gly Gly Asn Pro Gln Gln Pro Gln
        355             360             365
Ala Pro Pro Ala Gly Gln Pro Gln Gly Pro Pro Arg Pro Pro Gln Gly
    370             375             380
Gly Arg Pro Ser Arg Pro Pro Gln
385             390
```

METHODS AND COMPOSITIONS FOR BIOMARKERS OF FATIGUE

STATEMENT OF PRIORITY

This application is a continuation application of, and claims priority to, U.S. application Ser. No. 13/839,332, filed Mar. 15, 2013, which is a continuation-in-part application of, and claims priority to, PCT Application No. PCT/US2012/064798, filed Nov. 13, 2012, which claims the benefit, under 35 U.S.C. §119(e), of U.S. Provisional Application Ser. No. 61/559,632, filed Nov. 14, 2011, the entire contents of each of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9556-4IP_ST25.txt, 187,949 bytes in size, generated on Sep. 30, 2013 and filed electronically via EFS-Web, is provided in lieu of a paper copy. This Sequence Listing is hereby incorporated by reference into the specification for its disclosures.

FIELD OF THE INVENTION

The present invention relates to biomarkers and methods of their use in identifying fatigue, disease states associated with fatigue, recovery from fatigue and/or physical performance capability in a subject.

BACKGROUND OF THE INVENTION

There is great interest in finding methods that can be used to diagnosis, evaluate and/or monitor objectively the disease state referred to as chronic fatigue syndrome (CFS). As one example, an objective, saliva-based measurement tool would be useful in determining whether an individual is experiencing a level of fatigue sufficient to meet a diagnosis of chronic fatigue syndrome. Other applications include monitoring changes in fatigue level, e.g., in a subject diagnosed with CFS.

The present invention provides methods and compositions for diagnosing CFS, identifying subjects having an increased risk or likelihood of having or developing CFS and/or monitoring or evaluating fatigue in a subject by detecting and/or measuring biomarkers in one or more samples from the subject.

SUMMARY OF THE INVENTION

Figure 1:
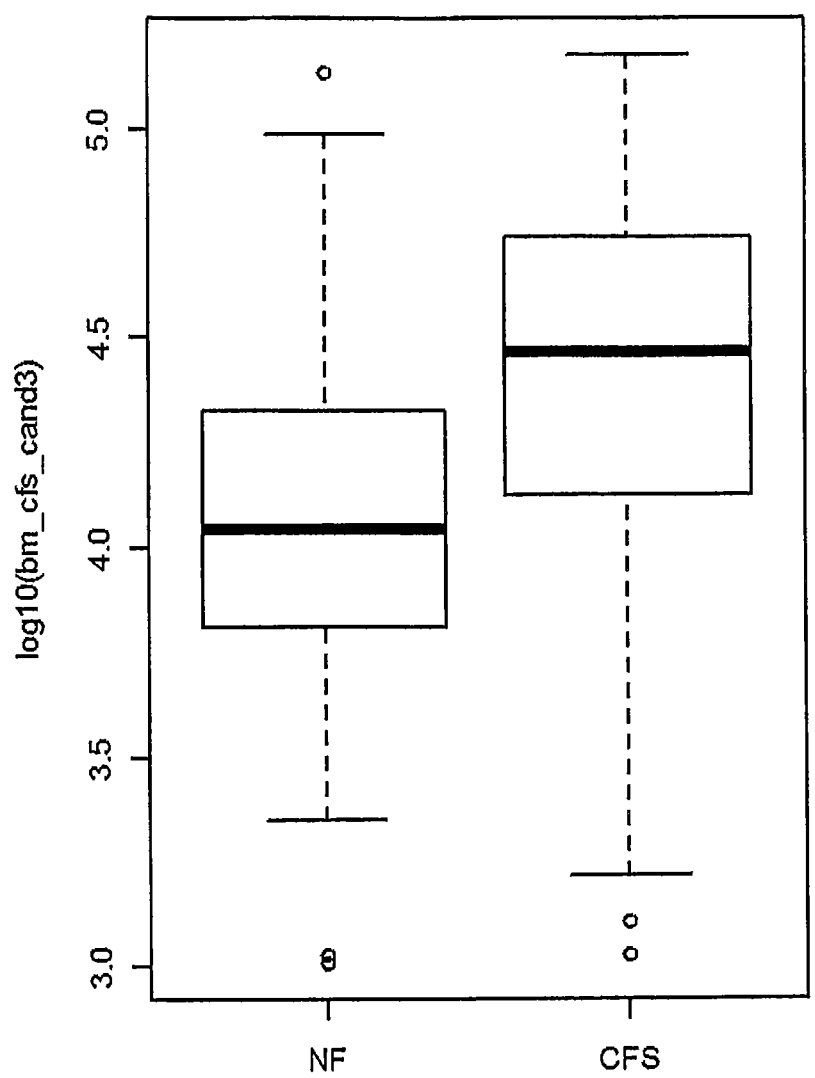
FIG. 1. For the biomarker bm_cfs_cand3, levels are greater in saliva from individuals with chronic fatigue syndrome (CFS) than in saliva from non-fatigued, control individuals (NF). The base 10 logarithm of the ion intensity, as determined by mass spectrometry, is shown as a function of patient type, i.e., CFS vs. NF. Data are shown as boxplots with the solid black line indicating the group median. The hollow box around the solid black line indicates the bounds of the data from the first to the third quartile. The whiskers indicate a distance 1.5× greater than the interquartile range from the nearest edge of the box. A non-parametric test suggested the two samples were unlikely to arise from a common distribution (Wilcoxon rank sum test, $p<0.05$).

In some embodiments, the present invention provides a method of guiding a human subject's sleep schedule, comprising: a) measuring the concentration of a peptide selected from the group consisting of: 1) a peptide comprising the amino acid sequence PPGKPQGPPPQGGNQPQGPPPP-PGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGK-PQGPPPQGGNQPQGPPPPPGKPQ]+[GNPQGPSPQG-GNKPQGPPPPPGKPQ]+[SPPGKPQGPPQQEGNKPQG-PPPPGKPQ])/total protein (µg); c) having the subject initiate or resume a sleep schedule; d) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPP-PPPGKPQ (SEQ ID NO:2), 3) a peptide comprising the amino acid sequence SPPGKPQGPPQQEGNKPQGPPPP-PGKPQ (SEQ ID NO:3), and 4) any combination thereof, in a saliva sample taken from the subject at one or more time points after (c), wherein the peptides of (d) are the same as the peptides of (a); e) calculating the ratio of the concentration of the peptide(s) measured in (d) to the total amount of protein in the sample, according to the equation: ([PPGKPQGPPPQG-GNQPQGPPPPPGKPQ]+[GNPQGPSPQGGNKPQGPPP-PPGKPQ]+[SPPGKPQGPPQQEGNKPQGPPPPGKPQ])/ total protein (µg); and f) guiding the subject's sleep schedule by modifying the duration of subsequent sleep periods using the subject's ratio(s) as calculated in (e), such that an increase in the ratio relative to the previous ratio leads to a subsequent increase in the duration of the subject's sleep period, and a decrease in the ratio or a constant ratio relative to the previous ratio leads to no change in the duration of the subject's sleep period or a subsequent decrease in the duration of the subject's sleep period.

In further embodiments, the present invention provides a method of guiding a human subject's use of a sleep enhancing material and/or sleep enhancing activity, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); c) exposing the subject to the sleep enhancing material and/or sleep enhancing activity; d) measuring the concentration of a peptide selected from the group consisting of: 1) a peptide comprising the amino acid sequence PPGK-PQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPGKPQ])/total protein (µg); and f) guiding the subject's use of the sleep enhancing material and/or sleep enhancing activity using the subject's ratio(s) as calculated in (e), such that an increase in the ratio relative to the previous ratio leads to a subsequent increase in the subject's use of the sleep enhancing material and/or sleep enhancing activity, and a decrease in the ratio or a constant ratio relative to the previous ratio leads to no change or a subsequent decrease in the subject's use of the sleep enhancing material and/or sleep enhancing activity.

The present invention additionally provides a method of guiding a human subject's treatment of a sleep disorder, comprising: a) measuring the concentration of a peptide selected from the group consisting of: 1) a peptide comprising the amino acid sequence PPGKPQGPPPQGGNQPQGPPPP-PGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGK-PQGPPPQGGNQPQGPPPPPGKPQ]+[GNPQGPSPQG-GNKPQGPPPPPGKPQ]+[SPPGKPQGPPQQEGNKPQG-PPPPGKPQ])/total protein (µg); c) treating the subject for the sleep disorder; d) measuring the concentration of a peptide selected from the group consisting of: 1) a peptide comprising the amino acid sequence PPGKPQGPPPQGGNQPQGPPP-PPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGP-PPPPGKPQ]+[GNPQGPSPQGGNKPQGPPPPPGKPQ]+ [SPPGKPQGPPQQEGNKPQGPPPPGKPQ])/total protein (µg); and f) guiding the subject's treatment of the sleep disorder using the subject's ratio(s) as calculated in (e), such that an increase in the ratio relative to the previous ratio leads to a subsequent enhancement of the treatment for the sleep disorder, and a decrease in the ratio or a constant ratio relative to the previous ratio leads to no change or a subsequent reduction of the treatment for the sleep disorder.

Further provided herein is a method of identifying a substance and/or activity that enhances sleep, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); c) exposing the subject to the test substance and/or test activity; d) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNK-PQGPPPPPGKPQ (SEQ ID NO:2), 3) a peptide comprising the amino acid sequence SPPGKPQGPPQQEGNKPQGPP-PPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); and f) determining if the test substance and/or test activity enhances sleep using the subject's ratio(s) as calculated in (e), such that a decrease in the ratio relative to the previous ratio identifies the test substance and/or test activity as a substance and/or an activity that enhances sleep.

In addition, the present invention provides a method of identifying a substance and/or activity that treats a sleep disorder, comprising: a) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); c) exposing the subject to the test substance and/or test activity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); and f) determining if the test substance and/or test activity treats the sleep disorder using the subject's ratio(s) as calculated in (e), such that a decrease in the ratio relative to the previous ratio identifies the test substance and/or test activity as a substance and/or an activity that treats the sleep disorder.

A method is also provided herein of identifying a human subject that is sleep deprived, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from each subject in a population of subjects that are not sleep deprived; b) calculating the ratio of the concentration of the peptide(s) measured in (a) to the total amount of protein in each sample of (a), according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for each of the study subjects in the population of (a); c) establishing a threshold ratio for the population of subjects of (a); d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from a test subject; e) calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the test subject; and f) comparing the ratio of the test subject with the threshold ratio of (c), whereby a ratio of the test subject that is greater than the threshold ratio of (c) identifies the test subject as being sleep deprived.

Also provided herein is a method of identifying a human subject that is sleep deprived, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the subject; and c) comparing the ratio of the subject with a threshold ratio, whereby a ratio of the subject that is greater than the threshold ratio identifies the subject as sleep deprived.

In additional embodiments, the present invention provides a method of guiding a human subject's treatment of fatigue, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); c) treating the subject for fatigue; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); and f) guiding the subject's treatment of fatigue using the subject's ratio(s) as calculated in (e), such that a an increase in the ratio relative to the previous ratio leads to a subsequent enhancement of the treatment for fatigue, and a decrease in the ratio or a constant ratio relative to the previous ratio leads to no change or a subsequent reduction of the treatment for fatigue.

Further provided herein is a method of identifying a substance and/or activity that reduces fatigue, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3)

a peptide comprising the amino acid sequence SPPGKPQG-PPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); c) exposing the subject to the test substance and/or test activity; d) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNK-PQGPPPPPGKPQ (SEQ ID NO:2), 3) a peptide comprising the amino acid sequence SPPGKPQGPPQQEGNKPQGPP-PPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); and f) determining if the test substance and/or test activity reduces fatigue using the subject's ratio(s) as calculated in (e), such that a decrease in the ratio relative to the previous ratio identifies the test substance and/or test activity as a substance and/or an activity that reduces fatigue.

Additionally provided herein is a method of guiding a human subject's treatment of a chronic fatigue syndrome (CFS), comprising: a) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNK-PQGPPPPPGKPQ (SEQ ID NO:2), 3) a peptide comprising the amino acid sequence SPPGKPQGPPQQEGNKPQGPP-PPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPGKPQ])/total protein (µg); c) treating the subject for CFS; d) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPPP-PPGKPQ (SEQ ID NO:2), 3) a peptide comprising the amino acid sequence SPPGKPQGPPQQEGNKPQGPPP-PGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); and f) guiding the subject's treatment of CFS using the subject's ratio(s) as calculated in (e), such that an increase in the ratio relative to the previous ratio leads to a subsequent enhancement of the treatment for CFS, and a decrease in the ratio or a constant ratio relative to the previous ratio leads to no change or a subsequent reduction of the treatment for CFS.

The present invention also provides a method of identifying a substance and/or activity that treats chronic fatigue syndrome (CFS), comprising: a) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPP-PPPGKPQ (SEQ ID NO:2), 3) a peptide comprising the amino acid sequence SPPGKPQGPPQQEGNKPQGPPP-PGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPGKPQ])/total protein (µg); c) exposing the subject to the test substance and/or test activity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from the subject at a time point after step (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPGKPQ])/total protein (µg); and f) determining if the test substance and/or test activity treats CFS using the subject's ratio(s) as calculated in (e), such that a decrease in the ratio relative to the previous ratio identifies the test substance and/or test activity as a substance and/or an activity that treats CFS.

Additionally provided herein is a method of identifying a human subject having an increased likelihood of having or developing chronic fatigue syndrome (CFS), comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from each subject in a population of subjects that do not have a diagnosis of CFS or symptoms of CFS; b) calculating the ratio of the concentration of the peptide(s) measured in (a) to the total amount of protein in each sample of (a), according to the equation: ([PPGKPQGPPPQGGNQPQGPPPPPGKPQ]+ [GNPQGPSPQGGNKPQGPPPPPGKPQ]+[SPPGKPQGP-PQQEGNKPQGPPPPGKPQ])/total protein (µg) to determine a ratio for each of the study subjects in the population of (a); c) establishing a threshold ratio for the population of subjects of (a); d) measuring the concentration of a peptide selected from the group consisting of: 1) a peptide comprising the amino acid sequence PPGKPQGPPPQGGNQPQGPPP-PPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from a test subject; e) calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the test subject; and f) comparing the ratio of the test subject with the threshold ratio of (c), whereby a ratio of the test subject that is greater than the threshold ratio of (c) identifies the subject as having an increased likelihood of having or developing CFS.

In further aspects of this invention, a method is provided of identifying a human subject having an increased likelihood of having or developing chronic fatigue syndrome (CFS), comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the subject; and c) comparing the ratio of the subject with a threshold ratio, whereby a ratio of the subject that is greater than the threshold ratio identifies the subject as having an increased likelihood of having or developing CFS.

Additionally provided herein is a method of guiding a human subject's work load, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); c) having the subject initiate or resume a work load; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject at one or more time points after (c), wherein the peptides of (d) are the same as the peptides of (a); e) calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); and f) guiding the subject's work load by modifying the duration of the subject's work period and/or amount of work the subject does using the subject's ratio(s) as calculated in (e), such that an increase in the ratio relative to the previous ratio leads to a subsequent decrease in the duration of the subject's work period and/or a decrease in the amount of work the subject does, and a decrease in the ratio or a constant ratio relative to the previous ratio leads to no change in the duration of the subject's work period and/or amount of work the subject does or a subsequent increase in the duration of the subject's work period and/or amount of work the subject does.

In further aspects, the present invention provides a method of identifying a human subject sufficiently rested to carry out a work load, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from each subject in a population of subjects that have carried out the work load sufficiently, wherein the sample is taken from each subject at about the time the subject starts the work load; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for each of subject in the population of subjects of (a); c) establishing a threshold ratio for the population of subjects of (a); d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from a test subject; e) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the test subject; and f) comparing the ratio of the test subject with the threshold ratio of (c), whereby a ratio of the test subject that is less than or equal to the threshold ratio of (c) identifies the test subject as being sufficiently rested to carry out the work load and a ratio of the test subject that is greater than the threshold ratio of (c) identifies the test subject as not being sufficiently rested to carry out the workload.

Additionally provided herein is a method of identifying a human subject that is sufficiently rested to carry out a work load, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg) to determine a ratio for the subject; and c) comparing the ratio of the subject with a threshold ratio, whereby a ratio of the subject that is less than or equal to the threshold ratio identifies the subject as being sufficiently rested to carry out the work load and a ratio of the subject that is greater than the threshold ratio identifies the subject as not being sufficiently rested to carry out the work load.

Additionally, the present invention provides a method of identifying a human subject who is fit for duty, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from each subject in a population of subjects that are fit for duty: b) calculating the ratio of the concentration of the peptide(s) measured in (a) to the total amount of protein in the sample, according to the equation: ([PPGKPQGPPPQGGNQPQGP-PPPPGKPQ]+[GNPQGPSPQGGNKPQGPPPPPGKPQ]+ [SPPGKPQGPPQQEGNKPQGPPPPGKPQ])/total protein (µg) to determine a ratio for each subject in the population of subjects of (a); c) establishing a threshold ratio for the population of subjects of (a); d) measuring the concentration of a peptide selected from the group consisting of: 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPP-PPPGKPQ (SEQ ID NO:2), 3) a peptide comprising the amino acid sequence SPPGKPQGPPQQEGNKPQGPPP-PGKPQ (SEQ ID NO:3), and 4) any combination thereof, in a saliva sample taken from a test subject; e) calculating the ratio of the concentration of the peptide(s) measured in (d) to the total amount of protein in the sample, according to the equation: ([PPGKPQGPPPQGGNQPQGPPPPPGKPQ]+ [GNPQGPSPQGGNKPQGPPPPPGKPQ]+[SPPGKPQGP-PQQEGNKPQGPPPPGKPQ])/total protein (µg) to determine a ratio for the test subject; and f) comparing the ratio of the test subject with the threshold ratio of (c), whereby a ratio of the test subject that is greater than the threshold ratio of (c) identifies the test subject as being not fit for duty, and a ratio of the test subject that is the same as or less than the threshold ratio of (c) identifies the test subject as being fit for duty.

Furthermore, the present invention provides a method of identifying a human subject who is fit for duty, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQG-PPQQEGNKPQGPPPPGKPQ (SEQ ID NO:3), and 4) any combination thereof, in a saliva sample taken from the subject; b) calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg) to determine a ratio for the subject; and c) comparing the ratio of the subject with a threshold ratio, whereby a ratio of the subject that is greater than the threshold ratio identifies the subject as being not fit for duty, and a ratio of the subject that is the same as or less than the threshold ratio identifies the subject as being fit for duty.

In a further aspect, the present invention provides a method of identifying a subject as having chronic fatigue syndrome or having an increased likelihood of having or developing chronic fatigue syndrome, comprising: a) measuring the amount of a peptide comprising the amino acid sequence PPGKPQGPPPQGGNQPQGPPPPPGKPQ in a biological sample from each subject in a population of subjects determined not to have chronic fatigue syndrome (non-CFS subjects); b) calculating the amount of the peptide relative to the total amount of protein in each sample of (a) to determine a biomarker index for each subject in the population; c) establishing a threshold biomarker index from the biomarker indices determined in (b); d) measuring the amount of a peptide comprising the amino acid sequence PPGKPQGPPPQGGN-QPQGPPPPPGKPQ in a biological sample from a test subject; and e) calculating the amount of the peptide relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

In an additional aspect, the present invention provides a method of identifying a subject as having chronic fatigue syndrome or having an increased likelihood of having or developing chronic fatigue syndrome, comprising: a) measuring the amount of a peptide comprising the amino acid sequence GNPQGPSPQGGNKPQGPPPPPGKPQ in a biological sample from each subject in a population of subjects determined not to have chronic fatigue syndrome (e.g., non-CFS subjects); b) calculating the amount of the peptide relative to the total amount of protein in each sample of (a) to determine a biomarker index for each subject in the population; c) establishing a threshold biomarker index from the biomarker indices determined in (b); d) measuring the amount of a peptide comprising the amino acid sequence GNPQGPSPQGGNKPQGPPPPPGKPQ in a biological sample from a test subject; and e) calculating the amount of the peptide relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

A further aspect of this invention is a method of identifying a subject as having chronic fatigue syndrome or having an increased likelihood of having or developing chronic fatigue syndrome, comprising: a) measuring the amount of a peptide comprising the amino acid sequence SPPGKPQGPPQQEG-NKPQGPPPPGKPQ in a biological sample from each subject in a population of subjects determined not to have chronic fatigue syndrome (e.g., non-CFS subjects); b) calculating the amount of the peptide relative to the total amount of protein in each sample of (a) to determine a biomarker index for each subject in the population; c) establishing a threshold biomarker index from the biomarker indices determined in (b); d) measuring the amount of a peptide comprising the amino acid sequence SPPGKPQGPPQQEGNKPQGPPPPGKPQ in a biological sample from a test subject; and e) calculating the amount of the peptide relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Further provided herein is a method of identifying a subject as having chronic fatigue syndrome or having an increased likelihood of having or developing chronic fatigue syndrome, comprising: a) measuring the amount of each of 1) a peptide comprising the amino acid sequence PPGKPQGPPPQGGN-QPQGPPPPPGKPQ, 2) a peptide comprising the amino acid sequence GNPQGPSPQGGNKPQGPPPPPGKPQ, and 3) a peptide comprising the amino acid sequence SPPGKPQGP-PQQEGNKPQGPPPPPGKPQ in a biological sample from each subject in a population of subjects determined not to have chronic fatigue syndrome (e.g., non-CFS subjects); b) calculating the amount of the peptides relative to the total amount of protein in each sample of (a) to determine a biomarker index for each subject of the population; c) establishing a threshold biomarker index from the biomarker indices determined in (b); d) measuring the amount of each of 1) a peptide comprising the amino acid sequence PPGKPQGPP-PQGGNQPQGPPPPPGKPQ, 2) a peptide comprising the amino acid sequence GNPQGPSPQGGNKPQGPPPP-PGKPQ, and 3) a peptide comprising the amino acid sequence SPPGKPQGPPQQEGNKPQGPPPPGKPQ in a biological sample from a test subject; and e) calculating the amount of the peptides relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Also provided herein is a method of identifying a subject as having chronic fatigue syndrome or having an increased likelihood of having or developing chronic fatigue syndrome, comprising: a) measuring the amount of two or more peptides selected from the group consisting of: 1) a peptide comprising the amino acid sequence PPGKPQGPPPQGGNQPQGPPP-PPGKPQ, 2) a peptide comprising the amino acid sequence GNPQGPSPQGGNKPQGPPPPPGKPQ, and 3) a peptide comprising the amino acid sequence SPPGKPQGPPQQEG-NKPQGPPPPGKPQ, in a biological sample from each subject in a population of subjects determined not to have chronic fatigue syndrome; b) calculating the amount of the peptides relative to the total amount of protein in each sample of (a) to determine a biomarker index for each subject of the population; c) establishing a threshold biomarker index from the biomarker indices determined in (b); d) measuring the amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEG-NKPQGPPPPGKPQ in a biological sample from a test subject (e.g., wherein the peptides of (d) are the same as peptides as measured in (a)); and e) calculating the amount of the peptides relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

An additional aspect of this invention includes a method of identifying a subject as having chronic fatigue syndrome or having an increased likelihood of having or developing chronic fatigue syndrome, comprising: a) measuring the amount of human basic proline-rich protein 1 (PRB1) in a biological sample from each subject in a population of subjects determined not to have chronic fatigue syndrome (e.g., non-CFS subjects); b) calculating the amount of PRB1 relative to the total amount of protein in each sample of (a) to determine a biomarker index for each subject in the population; c) establishing a threshold biomarker index from the biomarker indices determined in (b); d) measuring the amount of human basic proline-rich protein 1 (PRB1) in a biological sample from a test subject; and e) calculating the amount of PRB1 relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Other aspects of this invention include a method of identifying a subject as having chronic fatigue syndrome or having an increased likelihood of having or developing chronic fatigue syndrome, comprising: a) measuring the amount of human basic proline-rich protein 2 (PRB2) in a biological sample from each subject in a population of subjects determined not to have chronic fatigue syndrome (e.g., non-CFS subjects); b) calculating the amount of PRB2 relative to the total amount of protein in each sample of (a) to determine a biomarker index for each subject in the population; c) establishing a threshold biomarker index from the biomarker indices determined in (b); d) measuring the amount of human basic proline-rich protein 2 (PRB2) in a biological sample from a test subject; and e) calculating the amount of PRB2 relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

The present invention also provides a method of identifying a subject as having chronic fatigue syndrome or having an increased likelihood of having or developing chronic fatigue syndrome, comprising: a) measuring the amount of human basic proline-rich protein 4 (PRB4) in a biological sample from each subject in a population of subjects determined not to have chronic fatigue syndrome (e.g., non-CFS subjects); b) calculating the amount of PRB4 relative to the total amount of protein in each sample of (a) to determine a biomarker index for each subject in the population; c) establishing a threshold biomarker index from the biomarker indices determined in (b); d) measuring the amount of human basic proline-rich protein 4 (PRB4) in a biological sample from a test subject; and e) calculating the amount of PRB4 relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Furthermore, the present invention provides a method of identifying a subject as having chronic fatigue syndrome or having an increased likelihood of having or developing chronic fatigue syndrome, comprising: a) measuring the amount of each of 1) human basic proline-rich protein 1 (PRB1), 2) human basic proline-rich protein 2 (PRB2), and 3) human basic proline-rich protein 4 (PRB4) in a biological sample from each subject in a population of subjects determined not to have chronic fatigue syndrome (e.g., non-CFS subjects); b) calculating the amount of the proteins relative to the total amount of protein in each sample of (a) to determine a biomarker index for each subject in the population; c) establishing a threshold biomarker index from the biomarker indices determined in (b); d) measuring the amount of 1) human basic proline-rich protein 1 (PRB1), 2) human basic proline-rich protein 2 (PRB2), and 3) human basic proline-rich protein 4 (PRB4) in a biological sample from a test subject; and e) calculating the amount of the proteins relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Additionally provided herein is a method of identifying a subject as having chronic fatigue syndrome or having an increased likelihood of having or developing chronic fatigue syndrome, comprising: a) measuring the amount of two or more proteins selected from the group consisting of 1) human basic proline-rich protein 1 (PRB1), 2) human basic proline-rich protein 2 (PRB2), and 3) human basic proline-rich protein 4 (PRB4), in a biological sample from each subject in a population of subjects determined not to have chronic fatigue syndrome; b) calculating the amount of the proteins relative to the total amount of protein in each sample of (a) to determine a biomarker index for each subject in the population; c) establishing a threshold biomarker index from the biomarker indices determined in (b); d) measuring the amount of two or more proteins selected from the group consisting of: 1) human basic proline-rich protein 1 (PRB1), 2) human basic proline-rich protein 2 (PRB2), and 3) human basic proline-rich protein 4 (PRB4), in a biological sample from a test subject, (e.g., wherein the proteins of (d) are the same proteins as measured in (a)); and e) calculating the amount of the proteins relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

In further embodiments, the present invention provides a method of identifying a subject as having chronic fatigue syndrome or having an increased likelihood of having or developing chronic fatigue syndrome, comprising: a) measuring the amount of a peptide comprising the amino acid sequence PPGKPQGPPPQGGNQPQGPPPPPGKPQ in a biological sample from a test subject; and b) calculating the amount of the peptide relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

In addition, the present invention provides a method of identifying a subject as having chronic fatigue syndrome or having an increased likelihood of having or developing chronic fatigue syndrome, comprising: a) measuring the amount of a peptide comprising the amino acid sequence GNPQGPSPQGGNKPQGPPPPPGKPQ in a biological sample from a test subject; and b) calculating the amount of the peptide relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Also provided herein is a method of identifying a subject as having chronic fatigue syndrome or having an increased likelihood of having or developing chronic fatigue syndrome, comprising: a) measuring the amount of a peptide comprising the amino acid sequence SPPGKPQGPPQQEGNKPQGPPPPGKPQ in a biological sample from a test subject; and b) calculating the amount of the peptide relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Furthermore, the present invention provides a method of identifying a subject as having chronic fatigue syndrome or having an increased likelihood of having or developing chronic fatigue syndrome, comprising: a) measuring the amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPGKPQ in a biological sample from a test subject; and b) calculating the amount of the peptides relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

The present invention also provides a method of identifying a subject as having chronic fatigue syndrome or having an increased likelihood of having or developing chronic fatigue syndrome, comprising: a) measuring the amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPPGKPQ, in a biological sample from a test subject; and b) calculating the amount of the peptides relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Additionally, the present invention provides a method of identifying a subject as having chronic fatigue syndrome or having an increased likelihood of having or developing chronic fatigue syndrome, comprising: a) measuring the amount of human basic proline-rich protein 1 (PRB1) in a biological sample from a test subject; and b) calculating the amount of PRB1 relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

In yet further embodiments, the present invention provides a method of identifying a subject as having chronic fatigue syndrome or having an increased likelihood of having or developing chronic fatigue syndrome, comprising: a) measuring the amount of human basic proline-rich protein 2 (PRB2) in a biological sample from a test subject; and b) calculating the amount of PRB2 relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Further provided herein is a method of identifying a subject as having chronic fatigue syndrome or having an increased likelihood of having or developing chronic fatigue syndrome, comprising: a) measuring the amount of human basic proline-rich protein 4 (PRB4) in a biological sample from a test subject; and b) calculating the amount of PRB4 relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

The present invention also provides a method of identifying a subject as having chronic fatigue syndrome or having an increased likelihood of having or developing chronic fatigue syndrome, comprising: a) measuring the amount of 1) human basic proline-rich protein 1 (PRB1), 2) human basic proline-rich protein 2 (PRB2), and 3) human basic proline-rich protein 4 (PRB4) in a biological sample from a test subject; and b) calculating the amount of the proteins relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Furthermore, the present invention provides a method of identifying a subject as having chronic fatigue syndrome or having an increased likelihood of having or developing chronic fatigue syndrome, comprising: a) measuring the amount of two or more proteins selected from the group consisting of: 1) human basic proline-rich protein 1 (PRB1), 2) human basic proline-rich protein 2 (PRB2), and 3) human basic proline-rich protein 4 (PRB4), in a biological sample from a test subject; and b) calculating the amount of the proteins relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Additional aspects of this invention include a method of identifying a decrease over time in fatigue level of a subject, comprising: a) measuring, at a first time point, an amount of a peptide comprising the amino acid sequence PPGKPQGPPPQGGNQPQGPPPPPGKPQ in a first biological sample from the subject; b) calculating the amount of the peptide of (a) relative to the total amount of protein in the first sample to determine a first biomarker index for the subject at the first time point; c) measuring, at a second or subsequent time point(s), an amount of the peptide comprising an amino acid sequence PPGKPQGPPPQGGNQPQGPPPPPGKPQ, in a second or subsequent biological sample(s); and d) calculating the amount of the peptide of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

The present invention further provides a method of identifying a decrease over time in fatigue level of a subject, comprising: a) measuring, at a first time point, an amount of a peptide comprising the amino acid sequence GNPQGPSPQGGNKPQGPPPPPGKPQ, in a first biological sample from the subject; b) calculating the amount of the peptide of (a) relative to the total amount of protein in the first sample to determine a first biomarker index for the subject at the first time point; c) measuring, at a second or subsequent time point(s), an amount of the peptide comprising an amino acid sequence GNPQGPSPQGGNKPQGPPPPPGKPQ in a second or subsequent biological sample(s); and d) calculating the amount of the peptide of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

Also provided herein is a method of identifying a decrease over time in fatigue level of a subject, comprising: a) measuring, at a first time point, an amount of a peptide comprising the amino acid sequence SPPGKPQGPPQQEGNKPQGPPPPPGKPQ in a first biological sample from the subject; b) calculating the amount of the peptide of (a) relative to the total amount of protein in the first sample to determine a first biomarker index for the subject at the first time point; c) measuring, at a second or subsequent time point(s), an amount of the peptide comprising an amino acid sequence SPPGKPQGPPQQEGNKPQGPPPPPGKPQ in a second or subsequent biological sample(s); and d) calculating the amount of the peptide of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

Furthermore, the present invention provides a method of identifying a decrease over time in fatigue level of a subject, comprising: a) measuring, at a first time point, an amount of 1) a peptide comprising the amino acid sequence PPGKPQGPPPQGGNQPQGPPPPPGKPQ, 2) a peptide comprising the amino acid sequence GNPQGPSPQGGNKPQGPPPPGKPQ, and 3) a peptide comprising the amino acid sequence SPPGKPQGPPQQEGNKPQGPPPPPGKPQ in a first biological sample from the subject; b) calculating the amount of the peptides of (a) relative to the total amount of protein in the first sample to determine a first biomarker index for the subject at the first time point; c) measuring, at a second or subsequent time point(s), an amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPPGKPQ in a second or subsequent biological sample(s); and d) calculating the amount of the peptides of (c) relative to the total amount of the protein in the respective sample(s) to determine a second or subsequent biomarker index for the subject at the second or subsequent time point(s), wherein a decrease in the second or subsequent biomarker index relative to the first biomarker index identifies a decrease over time in the fatigue level of the subject.

Furthermore, the present invention provides a method of identifying a decrease over time in fatigue level of a subject, comprising: a) measuring, at a first time point, an amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPPGKPQ in a first biological sample from the subject; b) calculating the amount of the peptides of (a) relative to the total amount of protein in the first sample to determine a first biomarker index for the subject at the first time point; c) measuring, at a second or subsequent time point(s), an amount of 1) a peptide comprising the amino acid sequence PPGKPQGPPPQGGN-QPQGPPPPPGKPQ, 2) a peptide comprising the amino acid sequence GNPQGPSPQGGNKPQGPPPPPGKPQ, and 3) a peptide comprising the amino acid sequence SPPGKPQGP-PQQEGNKPQGPPPPPGKPQ in a second or subsequent biological sample(s) (e.g., wherein the peptides measured in (c) are the same peptides as measured in (a)); and d) calculating the amount of the peptides of (c) relative to the total amount of the protein in the respective sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In an additional aspect, the present invention provides a method of identifying a decrease over time in fatigue level of a subject, comprising: a) measuring, at a first time point, an amount of human basic proline-rich protein 1 (PRB1) in a first biological sample from the subject; b) calculating the amount of the protein of (a) relative to the total amount of protein in the first sample to determine a first biomarker index for the subject at the first time point; c) measuring, at a second or subsequent time point(s), an amount of human basic proline-rich protein 1 (PRB1) in a second or subsequent biological sample(s); and d) calculating the amount of the protein of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In a further aspect, the present invention provides a method of identifying a decrease over time in fatigue level of a subject, comprising: a) measuring, at a first time point, an amount of human basic proline-rich protein 2 (PRB2) in a first biological sample from the subject; b) calculating the amount of the protein of (a) relative to the total amount of protein in the first sample to determine a first biomarker index for the subject at the first time point; c) measuring, at a second or subsequent time point(s), an amount of human basic proline-rich protein 2 (PRB2) in a second or subsequent biological sample(s); and d) calculating the amount of the protein of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

Further provided herein is a method of identifying a decrease over time in fatigue level of a subject, comprising: a) measuring, at a first time point, an amount of human basic proline-rich protein 4 (PRB4) in a first biological sample from the subject; b) calculating the amount of the protein of (a) relative to the total amount of protein in the first sample to determine a first biomarker index for the subject at the first time point; c) measuring, at a second or subsequent time point(s), an amount of human basic proline-rich protein 4 (PRB4) in a second or subsequent biological sample(s); and d) calculating the amount of the protein of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In an additional aspect of this invention, a method is provided, of identifying a decrease over time in fatigue level of a subject, comprising: a) measuring, at a first time point, an amount of 1) human basic proline-rich protein 1 (PRB1), 2) human basic proline-rich protein 2 (PRB2), and 3) human basic proline-rich protein 4 (PRB4) in a first biological sample from the subject; b) calculating the amount of the proteins of (a) relative to the total amount of protein in the first sample to determine a first biomarker index for the subject at the first time point; c) measuring, at a second or subsequent time point(s), an amount of 1) human basic proline-rich protein 1 (PRB1), 2) human basic proline-rich protein 2 (PRB2), and 3) human basic proline-rich protein 4 (PRB4) in a second or subsequent biological sample(s); and d) calculating the amount of the proteins of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In a further aspect of this invention, a method is provided, of identifying a decrease over time in fatigue level of a subject, comprising: a) measuring, at a first time point, an amount of two or more proteins selected from the group consisting of: 1) human basic proline-rich protein 1 (PRB1), 2) human basic proline-rich protein 2 (PRB2), and 3) human basic proline-rich protein 4 (PRB4) in a first biological sample from the subject; b) calculating the amount of the proteins of (a) relative to the total amount of protein in the first sample to determine a first biomarker index for the subject at the first time point; c) measuring, at a second or subsequent time point(s), an amount of two or more proteins selected from the group consisting of: 1) human basic proline-rich protein 1 (PRB1), 2) human basic proline-rich protein 2 (PRB2), and 3) human basic proline-rich protein 4 (PRB4) in a second or subsequent biological sample(s) (e.g., wherein the peptides measured in (c) are the same peptides as measured in (a); and d) calculating the amount of the proteins of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In yet further embodiments, the present invention provides a method of guiding a human subject's treatment for chronic fatigue syndrome (CFS), comprising: a) measuring the concentration of a peptide selected from the group consisting of 1) a peptide comprising the amino acid sequence PPGKPQG-PPPQGGNQPQGPPPPPGKPQ (SEQ ID NO:1), 2) a peptide comprising the amino acid sequence GNPQGPSPQGGNK-PQGPPPPPGKPQ (SEQ ID NO:2), 3) a peptide comprising the amino acid sequence SPPGKPQGPPQQEGNKPQGPP-PPGKPQ, (SEQ ID NO:3), and 4) any combination thereof, in a saliva sample taken from the subject; b) identifying the subject's level of chronic fatigue by calculating the ratio of the concentration of the peptide(s) measured in (a) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPPGKPQ])/total protein (µg); c) having the subject initiate or resume a treatment program for chronic fatigue syndrome; d) measuring the concentration of a peptide selected from the group consisting of 1) a peptide comprising the amino acid sequence PPGKPQGPPPQGGN-QPQGPPPPPGKPQ (SEQ ID NO:1), 2) a peptide comprising the amino acid sequence GNPQGPSPQGGNK-PQGPPPPPGKPQ (SEQ ID NO:2), 3) a peptide comprising the amino acid sequence SPPGKPQGPPQQEGNKPQGPP-PPGKPQ, (SEQ ID NO:3), and 4) any combination thereof, in a saliva sample taken from the subject at one or more time points after (c), wherein the peptides of (d) are the same as the peptides of (a); e) identifying the subject's level of chronic fatigue by calculating the ratio of the concentration of the peptide(s) measured in (d) to the total amount of protein in the sample of (d) according to the equation: ([PPGKPQGPP-PQGGNQPQGPPPPPGKPQ]+[GNPQGPSPQGGNKPQG-PPPPPGKPQ]+[SPPGKPQGPPQQEGNKPQGPPP-PGKPQ])/total protein (µg); and f) guiding the subject's treatment for chronic fatigue syndrome by modifying the intensity of subsequent treatments using the latest of the subject's ratio(s) as calculated in (e), such that an increase in chronic fatigue relative to the previous measurement of chronic fatigue leads to a subsequent increase in the subject's treatment intensity.

Also provided herein is a method of evaluating the effect of a treatment material and/or activity on the chronic fatigue level of a human subject (e.g., a subject diagnosed as having, determined to have or suspected of having chronic fatigue syndrome (CFS), comprising: a) measuring the concentration of a peptide selected from the group consisting of 1) a peptide comprising the amino acid sequence PPGKPQGPPPQGGN-QPQGPPPPPGKPQ (SEQ ID NO:1), 2) a peptide comprising the amino acid sequence GNPQGPSPQGGNKPQGPP-PPPGKPQ (SEQ ID NO:2), a 3) a peptide comprising the amino acid sequence SPPGKPQGPPQQEGNKPQGPPP-PGKPQ (SEQ ID NO:3), and 4) any combination thereof, in a saliva sample taken from a subject at a time point prior to exposing the subject to a treatment material and/or activity; b) identifying the subject's level of chronic fatigue by calculating the ratio of the concentration of the peptide(s) measured in (a) to the total amount of protein in the sample, according to the equation: ([PPGKPQGPPPQGGNQPQGPPPP-PGKPQ]+[GNPQGPSPQGGNKPQGPPPPPGKPQ]+[SP-PGKPQGPPQQEGNKPQGPPPPGKPQ])/total protein (µg); c) exposing the subject to the treatment material and/or performance enhancing activity; d) measuring the concentration of a peptide selected from the group consisting of: 1) a peptide comprising the amino acid sequence PPGKPQGPP-PQGGNQPQGPPPPPGKPQ (SEQ ID NO:1), 2) a peptide comprising the amino acid sequence GNPQGPSPQGGNK-PQGPPPPPGKPQ (SEQ ID NO:2), a 3) a peptide comprising the amino acid sequence SPPGKPQGPPQQEGNKPQGPPP-PPGKPQ (SEQ ID NO:3), and 4) any combination thereof, in a saliva sample taken from the subject at one or more time points after (c), wherein the peptides of (d) are the same as the peptides of (a); e) identifying the subject's level of chronic fatigue by calculating the ratio of the concentration of the peptide(s) measured in (d) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); and f) evaluating the effect of the treatment material and/or activity on the chronic fatigue status of the subject by comparing the ratios of (b) and (e), wherein an increase in the ratio of (e) relative to the ratio of (b) is indicative of increased chronic fatigue of the subject, a decrease in the ratio of (e) relative to the ratio of (b) is indicative of decreased chronic fatigue of the subject, and a constant ratio of (e) relative to the ratio of (b) is indicative of no change in chronic fatigue of the subject.

Additionally provided herein is a method of guiding a human subject's physical training activity, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGK-PQGPPQQEGNKPQGPPPPGKPQ (SEQ ID NO:3), and 4) any combination thereof, in a saliva sample taken from the subject when the subject is in a rested state, wherein the subject is an adult athlete or an amateur athlete; b) identifying the subject's level of physical fatigue by calculating the ratio of the concentration of the peptide(s) measured in (a) to the total amount of protein in the sample, according to the equation: ([PPGKPQGPPPQGGNQPQGPPPPPGKPQ]+[GN-PQGPSPQGGNKPQGPPPPPGKPQ]+[SPPGKPQGP-PQQEGNKPQGPPPPGKPQ])/total protein (µg); c) having the subject initiate or resume a physical training program comprising activities of different intensity; d) measuring the concentration of a peptide selected from the group consisting of: 1) a peptide comprising the amino acid sequence PPGK-PQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGK-PQGPPQQEGNKPQGPPPPGKPQ (SEQ ID NO:3), and 4) any combination thereof, in a saliva sample taken from the subject at one or more time points after (c), wherein the peptides of (d) are the same as the peptides of (a); e) identifying the subject's level of physical fatigue by calculating the ratio of the concentration of the peptide(s) measured in (d) to the total amount of protein in the sample, according to the equation: ([PPGKPQGPPPQGGNQPQGPPPPPGKPQ]+ [GNPQGPSPQGGNKPQGPPPPPGKPQ]+[SPPGKPQGP-PQQEGNKPQGPPPPGKPQ])/total protein (µg); and f) guiding the subject's physical training program by modifying the intensity of subsequent activities using the latest of the subject's ratio(s), as calculated in (e), such that a decrease in the ratio relative to the previous ratio leads to a subsequent increase in the subject's training intensity, an increase in the ratio relative to the previous ratio leads to a subsequent decrease in the subject's training intensity, and a constant ratio relative to the previous ratio leads to a subsequent constant level in the subject's training intensity. In some embodiments, the physical training program can be a military training program.

The present invention also provides a method of evaluating the effect of a performance enhancing material and/or activity on the physical performance capability of a human subject, comprising: a) measuring the concentration of a peptide selected from the group consisting of: 1) a peptide comprising the amino acid sequence PPGKPQGPPPQGGNQPQGPPP-PPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from the subject at a time point prior to exposing the subject to a performance enhancing material or performance enhancing activity, wherein the subject is an adult athlete or amateur athlete; b) identifying the subject's level of physical fatigue by calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPGKPQ])/total protein (µg); c) exposing the subject to the performance enhancing material and/or performance enhancing activity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPPGKPQ (SEQ ID NO:3), and 4) any combination thereof, in a saliva sample taken from the subject at one or more time points after (c), wherein the peptides of (d) are the same as the peptides of (a); e) identifying the subject's level of physical fatigue by calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPPGKPQ])/total protein (μg); and f) evaluating the effect of the performance enhancing material and/or activity on the physical performance capability of the subject by comparing the ratios of (b) and (e), wherein an increase in the ratio of (e) relative to the ratio of (b) is indicative of reduced physical performance capability of the subject, a decrease in the ratio of (e) relative to the ratio of (b) is indicative of improved physical performance capability of the subject, and a constant ratio of (e) relative to the ratio of (b) is indicative of no change in physical performance capability of the subject.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and/or all possible combinations of one or more of the associated listed items, as well as the lack of and and/or combinations when interpreted in the alternative ("or").

Furthermore, the term "about" as used herein when referring to a measurable value such as an amount of a compound or agent of this invention, dose, time, temperature, and the like, is meant to encompass variations of ±20%, ±10%, ±5%, ±1%, ±0.5%, or even±0.1% of the specified amount.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery of a modulation of biomarkers (e.g., modulation of peptide and/or protein levels) as measured in a biological sample from a subject that correlate with the subject's status with regard to having chronic fatigue syndrome, having an increased risk or likelihood of having or developing chronic fatigue syndrome and/or having an altered (e.g., increased or decreased) level of fatigue over time.

Thus, in one embodiment, the present invention provides a method of identifying a subject as having chronic fatigue syndrome or having an increased likelihood of having or developing chronic fatigue syndrome, comprising: a) measuring the amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and/or 3) a peptide comprising the amino acid sequence SPPGKPQGPPQQEGNKPQGPPPPPGKPQ, in any combination, in a biological sample from each subject in a population of subjects determined not to have chronic fatigue syndrome (e.g., non-CFS subjects); b) calculating the amount of the peptide(s) relative to the total amount of protein in each sample of (a) to determine a biomarker index for each subject of the population; c) establishing a threshold biomarker index from the biomarker indices determined in (b); d) measuring the amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and/or 3) a peptide comprising the amino acid sequence SPPGKPQGPPQQEGNKPQGPPPPPGKPQ, in any combination, in a biological sample from a test subject; and e) calculating the amount of the peptide(s) relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

In a further embodiment, the present invention provides a method of identifying a subject as having chronic fatigue syndrome or having an increased likelihood of having or developing chronic fatigue syndrome, comprising: a) measuring the amount of 1) human basic proline-rich protein 1 (PRB1), 2) human basic proline-rich protein 2 (PRB2), and/or 3) human basic proline-rich protein 4 (PRB4), in any combination, in a biological sample from each subject in a population of subjects determined not to have chronic fatigue syndrome (e.g., non-CFS subjects); b) calculating the amount of the protein(s) relative to the total amount of protein in each sample of (a) to determine a biomarker index for each subject in the population; c) establishing a threshold biomarker index from the biomarker indices determined in (b); d) measuring the amount of 1) human basic proline-rich protein 1 (PRB1), 2) human basic proline-rich protein 2 (PRB2), and/or 3) human basic proline-rich protein 4 (PRB4), in any combination, in a biological sample from a test subject; and e) calculating the amount of the protein(s) relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

In an additional embodiment, the present invention provides a method of identifying a decrease over time in fatigue level of a subject, comprising: a) measuring, at a first time point, an amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and/or 3) a peptide comprising the amino acid sequence SPPGKPQGPPQQEGNKPQGPPPPPGKPQ, in any combination, in a first biological sample from the subject; b) calculating the amount of the peptide(s) of (a) relative to the total amount of protein in the first sample to determine a first biomarker index for the subject at the first time point; c) measuring, at a second or subsequent time point(s), an amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and/or 3) a peptide comprising the amino acid sequence SPPGKPQGPPQQEG-NKPQGPPPPGKPQ, in any combination, in a second or subsequent biological sample(s); and d) calculating the amount of the peptide(s) of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

Furthermore, the present invention provides a method of identifying a subject as having chronic fatigue syndrome or having an increased likelihood of having or developing chronic fatigue syndrome, comprising: a) measuring an amount of 1) a peptide comprising the amino acid sequence PPGKPQGPPPQGGNQPQGPPPPPGKPQ, 2) a peptide comprising the amino acid sequence GNPQGPSPQGGNK-PQGPPPPPGKPQ, and 3) a peptide comprising the amino acid sequence SPPGKPQGPPQQEGNKPQGPPPPGKPQ, in any combination, in a biological sample from a test subject; and b) calculating the amount of the peptide(s) relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

The present invention also provides a method of identifying a subject as having chronic fatigue syndrome or having an increased likelihood of having or developing chronic fatigue syndrome, comprising: a) measuring an amount of 1) human basic proline-rich protein 1 (PRB1), 2) human basic proline-rich protein 2 (PRB2), and 3) human basic proline-rich protein 4 (PRB4), in any combination, in a biological sample from a test subject; and b) calculating the amount of the protein(s) relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

In an additional embodiment of this invention, a method is provided, of identifying a decrease over time in fatigue level of a subject, comprising: a) measuring, at a first time point, an amount of 1) human basic proline-rich protein 1 (PRB1), 2) human basic proline-rich protein 2 (PRB2), and/or 3) human basic proline-rich protein 4 (PRB4), in any combination, in a first biological sample from the subject; b) calculating the amount of the protein(s) of (a) relative to the total amount of protein in the first sample to determine a first biomarker index for the subject at the first time point; c) measuring, at a second or subsequent time point(s), an amount of 1) human basic proline-rich protein 1 (PRB1), 2) human basic proline-rich protein 2 (PRB2), and/or 3) human basic proline-rich protein 4 (PRB4) in a second or subsequent biological sample(s); and d) calculating the amount of the protein(s) of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In addition, the present invention provides a method of identifying an increase over time in fatigue level of a subject, comprising: a) measuring, at a first time point, an amount of 1) a peptide comprising the amino acid sequence PPGKPQG-PPPQGGNQPQGPPPPPGKPQ, 2) a peptide comprising the amino acid sequence GNPQGPSPQGGNKPQGPPPP-PGKPQ, and/or 3) a peptide comprising the amino acid sequence SPPGKPQGPPQQEGNKPQGPPPPGKPQ, in any combination, in a first biological sample from the subject; b) calculating the amount of the peptide(s) of (a) relative to the total amount of protein in the first sample to determine a first biomarker index for the subject at the first time point; c) measuring, at a second or subsequent time point(s), an amount of 1) a peptide comprising the amino acid sequence PPGKPQGPPPQGGNQPQGPPPPPGKPQ, 2) a peptide comprising the amino acid sequence GNPQGPSPQGGNK-PQGPPPPPGKPQ, and/or 3) a peptide comprising the amino acid sequence SPPGKPQGPPQQEGNKPQGPPPPGKPQ, in any combination, in a second or subsequent biological sample(s); and d) calculating the amount of the peptide(s) of (c) relative to the total amount of the protein in the second or subsequent sample(s) to determine a second or subsequent biomarker index for the subject at the second or subsequent time point(s), wherein an increase in the second or subsequent biomarker index relative to the first biomarker index identifies an increase over time in the fatigue level of the subject.

In an additional embodiment of this invention, a method is provided, of identifying an increase over time in fatigue level of a subject, comprising: a) measuring, at a first time point, an amount of 1) human basic proline-rich protein 1 (PRB1), 2) human basic proline-rich protein 2 (PRB2), and/or 3) human basic proline-rich protein 4 (PRB4), in any combination, in a first biological sample from the subject; b) calculating the amount of the protein(s) of (a) relative to the total amount of protein in the first sample to determine a first biomarker index for the subject at the first time point; c) measuring, at a second or subsequent time point(s), an amount of 1) human basic proline-rich protein 1 (PRB1), 2) human basic proline-rich protein 2 (PRB2), and/or 3) human basic proline-rich protein 4 (PRB4) in a second or subsequent biological sample(s); and d) calculating the amount of the protein(s) of (c) relative to the total amount of the protein in the second or subsequent sample(s) to determine a second or subsequent biomarker index for the subject at the second or subsequent time point(s), wherein an increase in the second or subsequent biomarker index relative to the first biomarker index identifies an increase over time in the fatigue level of the subject.

Also provided herein is a method of identifying a subject as having chronic fatigue syndrome or having an increased likelihood of having or developing chronic fatigue syndrome, comprising: a) measuring the amount of two or more peptides selected from the group consisting of: 1) a peptide comprising the amino acid sequence PPGKPQGPPPQGGNQPQGPPP-PPGKPQ, 2) a peptide comprising the amino acid sequence GNPQGPSPQGGNKPQGPPPPPGKPQ, and 3) a peptide comprising the amino acid sequence SPPGKPQGPPQQEG-NKPQGPPPPGKPQ, in a biological sample from each subject in a population of subjects determined not to have chronic fatigue syndrome; b) calculating the amount of the peptides relative to the total amount of protein in each sample of (a) to determine a biomarker index for each subject of the population; c) establishing a threshold biomarker index from the biomarker indices determined in (b); d) measuring the amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEG-NKPQGPPPPGKPQ in a biological sample from a test subject (e.g., wherein the peptides of (d) are the same as peptides as measured in (a)); and e) calculating the amount of the peptides relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

Additionally provided herein is a method of identifying a subject as having chronic fatigue syndrome or having an increased likelihood of having or developing chronic fatigue syndrome, comprising: a) measuring the amount of two or more proteins selected from the group consisting of 1) human basic proline-rich protein 1 (PRB1), 2) human basic proline-rich protein 2 (PRB2), and 3) human basic proline-rich protein 4 (PRB4), in a biological sample from each subject in a population of subjects determined not to have chronic fatigue syndrome; b) calculating the amount of the proteins relative to the total amount of protein in each sample of (a) to determine a biomarker index for each subject in the population; c) establishing a threshold biomarker index from the biomarker indices determined in (b); d) measuring the amount of two or more proteins selected from the group consisting of: 1) human basic proline-rich protein 1 (PRB1), 2) human basic proline-rich protein 2 (PRB2), and 3) human basic proline-rich protein 4 (PRB4), in a biological sample from a test subject, (e.g., wherein the proteins of (d) are the same proteins as measured in (a)); and e) calculating the amount of the proteins relative to the total amount of protein in the sample of (d) to determine a biomarker index for the test subject, wherein a biomarker index of the test subject that is higher than the threshold biomarker index of (c) identifies the subject as having chronic fatigue syndrome or having an increased likelihood of having or developing chronic fatigue syndrome.

The present invention also provides a method of identifying a subject as having chronic fatigue syndrome or having an increased likelihood of having or developing chronic fatigue syndrome, comprising: a) measuring the amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPGKPQ, in a biological sample from a test subject; and b) calculating the amount of the peptides relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Furthermore, the present invention provides a method of identifying a subject as having chronic fatigue syndrome or having an increased likelihood of having or developing chronic fatigue syndrome, comprising: a) measuring the amount of two or more proteins selected from the group consisting of: 1) human basic proline-rich protein 1 (PRB1), 2) human basic proline-rich protein 2 (PRB2), and 3) human basic proline-rich protein 4 (PRB4), in a biological sample from a test subject; and b) calculating the amount of the proteins relative to the total amount of protein in the sample of (a) to determine a biomarker index for the test subject, wherein a biomarker index of the test subject that is higher than a threshold biomarker index identifies the subject as having chronic fatigue syndrome or having an increased likelihood of having or developing chronic fatigue syndrome.

Furthermore, the present invention provides a method of identifying a decrease over time in fatigue level of a subject, comprising: a) measuring, at a first time point, an amount of two or more peptides selected from the group consisting of: 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPGKPQ in a first biological sample from the subject; b) calculating the amount of the peptides of (a) relative to the total amount of protein in the first sample to determine a first biomarker index for the subject at the first time point; c) measuring, at a second or subsequent time point(s), an amount of 1) a peptide comprising the amino acid sequence PPGKPQGPPPQGGNQPQGPPPPPGKPQ, 2) a peptide comprising the amino acid sequence GNPQGPSPQGGNKPQGPPPPPGKPQ, and 3) a peptide comprising the amino acid sequence SPPGKPQGPPQQEGNKPQGPPPPGKPQ in a second or subsequent biological sample(s) (e.g., wherein the peptides measured in (c) are the same peptides as measured in (a)); and d) calculating the amount of the peptides of (c) relative to the total amount of the protein in the respective sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In a further aspect of this invention, a method is provided, of identifying a decrease over time in fatigue level of a subject, comprising: a) measuring, at a first time point, an amount of two or more proteins selected from the group consisting of: 1) human basic proline-rich protein 1 (PRB1), 2) human basic proline-rich protein 2 (PRB2), and 3) human basic proline-rich protein 4 (PRB4) in a first biological sample from the subject; b) calculating the amount of the proteins of (a) relative to the total amount of protein in the first sample to determine a first biomarker index for the subject at the first time point; c) measuring, at a second or subsequent time point(s), an amount of two or more proteins selected from the group consisting of: 1) human basic proline-rich protein 1 (PRB1), 2) human basic proline-rich protein 2 (PRB2), and 3) human basic proline-rich protein 4 (PRB4) in a second or subsequent biological sample(s) (e.g., wherein the peptides measured in (c) are the same peptides as measured in (a); and d) calculating the amount of the proteins of (c) relative to the total amount of the protein in the second or subsequent sample(s) to determine a second or subsequent biomarker index for the subject at the second or subsequent time point(s), wherein a decrease in the second or subsequent biomarker index relative to the first biomarker index identifies a decrease over time in the fatigue level of the subject.

In yet further embodiments, the present invention provides a method of guiding a human subject's treatment for chronic fatigue syndrome (CFS), comprising: a) measuring the concentration of a peptide selected from the group consisting of 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ, (SEQ ID NO:3), and 4) any combination thereof, in a saliva sample taken from the subject; b) identifying the subject's level of chronic fatigue by calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (µg); c) having the subject initiate or resume a treatment program for chronic fatigue syndrome; d) measuring the concentration of a peptide selected from the group consisting of 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), 3) a peptide comprising the amino acid sequence SPPGKPQGPPQQEGNKPQGPPPPGKPQ, (SEQ ID NO:3), and 4) any combination thereof, in a saliva sample taken from the subject at one or more time points after (c), wherein the peptides of (d) are the same as the peptides of (a); e) identifying the subject's level of chronic fatigue by calculating the ratio of the concentration of the peptide(s) measured in (d) to the total amount of protein in the sample of (d) according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (μg); and f) guiding the subject's treatment for chronic fatigue syndrome by modifying the intensity of subsequent treatments using the latest of the subject's ratio(s) as calculated in (e), such that an increase in chronic fatigue relative to the previous measurement of chronic fatigue leads to a subsequent increase in the subject's treatment intensity.

Also provided herein is a method of evaluating the effect of a treatment material and/or activity on the chronic fatigue level of a human subject (e.g., a subject diagnosed as having, determined to have or suspected of having chronic fatigue syndrome (CFS), comprising: a) measuring the concentration of a peptide selected from the group consisting of 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from a subject at a time point prior to exposing the subject to a treatment material and/or activity; b) identifying the subject's level of chronic fatigue by calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (μg); c) exposing the subject to the treatment material and/or performance enhancing activity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from the subject at one or more time points after (c), wherein the peptides of (d) are the same as the peptides of (a); e) identifying the subject's level of chronic fatigue by calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (μg); and f) evaluating the effect of the treatment material and/or activity on the chronic fatigue status of the subject by comparing the ratios of (b) and (e), wherein an increase in the ratio of (e) relative to the ratio of (b) is indicative of increased chronic fatigue of the subject, a decrease in the ratio of (e) relative to the ratio of (b) is indicative of decreased chronic fatigue of the subject, and a constant ratio of (e) relative to the ratio of (b) is indicative of no change in chronic fatigue of the subject.

Additionally provided herein is a method of guiding a human subject's physical training activity, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from the subject when the subject is in a rested state, wherein the subject is an adult athlete or an amateur athlete; b) identifying the subject's level of physical fatigue by calculating the ratio of the concentration of the peptide(s) measured in (a) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (μg); c) having the subject initiate or resume a physical training program comprising activities of different intensity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from the subject at one or more time points after (c), wherein the peptides of (d) are the same as the peptides of (a); e) identifying the subject's level of physical fatigue by calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGPPQQEGNKPQGPPPPGKPQ])/total protein (μg); and f) guiding the subject's physical training program by modifying the intensity of subsequent activities using the latest of the subject's ratio(s), as calculated in (e), such that a decrease in the ratio relative to the previous ratio leads to a subsequent increase in the subject's training intensity, an increase in the ratio relative to the previous ratio leads to a subsequent decrease in the subject's training intensity, and a constant ratio relative to the previous ratio leads to a subsequent constant level in the subject's training intensity. In some embodiments, the physical training program can be a military training program.

The present invention also provides a method of evaluating the effect of a performance enhancing material and/or activity on the physical performance capability of a human subject, comprising: a) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGKPQGPPQQEGNKPQGPPPPGKPQ (SEQ ID NO:3), and 4) any combination thereof, in a saliva sample taken from the subject at a time point prior to exposing the subject to a performance enhancing material or performance enhancing activity, wherein the subject is an adult athlete or amateur athlete; b) identifying the subject's level of physical fatigue by calculating the ratio of the concentration of the peptide(s) measured in (a) to the total amount of protein in the sample, according to the equation: ([PPGKPQGPPPQGGN-QPQGPPPPPGKPQ]+[GNPQGPSPQGGNKPQGPPPP-PGKPQ]+[SPPGKPQGPPQQEGNKPQGPPPPPGKPQ])/total protein (μg); c) exposing the subject to the performance enhancing material and/or performance enhancing activity; d) measuring the concentration of a peptide selected from the group consisting of: 1) a peptide comprising the amino acid sequence PPGKPQGPPPQGGNQPQGPPPPPGKPQ (SEQ ID NO:1), 2) a peptide comprising the amino acid sequence GNPQGPSPQGGNKPQGPPPPPGKPQ (SEQ ID NO:2), a 3) a peptide comprising the amino acid sequence SPPGK-PQGPPQQEGNKPQGPPPPGKPQ (SEQ ID NO:3), and 4) any combination thereof, in a saliva sample taken from the subject at one or more time points after (c), wherein the peptides of (d) are the same as the peptides of (a); e) identifying the subject's level of physical fatigue by calculating the ratio of the concentration of the peptide(s) measured in (d) to the total amount of protein in the sample, according to the equation: ([PPGKPQGPPPQGGNQPQGPPPPPGKPQ]+[GNPQGPSPQGGNKPQGPPPPPGKPQ]+[SPPGKPQGP-PQQEGNKPQGPPPPGKPQ])/total protein (μg); and f) evaluating the effect of the performance enhancing material and/or activity on the physical performance capability of the subject by comparing the ratios of (b) and (e), wherein an increase in the ratio of (e) relative to the ratio of (b) is indicative of reduced physical performance capability of the subject, a decrease in the ratio of (e) relative to the ratio of (b) is indicative of improved physical performance capability of the subject, and a constant ratio of (e) relative to the ratio of (b) is indicative of no change in physical performance capability of the subject.

In methods wherein the level of more than one peptide or protein is measured for a subject, the biomarker index for the subject could be determined by any combination of the peptide or protein data. For example, the biomarker index might be a simple sum of the different peptide or protein levels, e.g., simple addition of the peptide or protein levels and division of the sum by the total amount of protein in the sample. More complex combinations of peptide or protein data might also be used. For example, the biomarker index could be calculated as a weighted sum of the various peptides or proteins, whereby the measured peptide or protein levels are multiplied by independent weighting factors before the values are summed; it is possible that one of the weighting factors could be zero. Higher-order mathematical combinations of peptide or protein levels might also be considered. For example, an equation for calculating the biomarker index might include a squared, cubed, or other higher-order term for one or more of the various peptides or proteins.

As used herein, "biomarker" can mean any chemical or biological entity that is produced by cells and/or by commensal flora, or substances that are produced by cells or commensal flora that might be then chemically modified by extracellular enzymes, free radicals produced by cells of the body and/or other naturally occurring processes and that is found, for example, in the saliva, urine, blood, vaginal secretion, tears, feces, sputum, hair, nails, skin, wound fluid, nasal swab, lymph, perspiration, oral mucosa, vaginal mucosa, or the anus, or in serum or plasma obtained from blood. Thus, in the methods of this invention, the sample can be any biological fluid or tissue that can be used in an assay of this invention, including but not limited to, serum, plasma, blood, saliva, semen, lymph, cerebrospinal fluid, prostatic fluid, urine, sputum, oral mucosa, nasal mucosa, duodenal fluid, gastric fluid, skin, endothelium, biopsy material from a salivary gland, biopsy material of a parotid gland, biopsy material of other glands of the mouth, secretions of the salivary gland, secretions of the parotid gland, secretions of other glands of the mouth, joint fluid, body cavity fluid, tear fluid, anal secretions; vaginal secretions, perspiration, whole cells, cell extracts, tissue, biopsy material, aspirates, exudates, slide preparations, fixed cells, tissue sections, etc.

In various embodiments of this invention, the biological sample can be prepared according to methods well known in the art and as described in the Examples section herein, to be a small molecular weight (SMW) sample. In particular embodiments of this invention, the biological sample is saliva.

In some embodiments, a biomarker of this invention can be, but is not limited to, a peptide or polypeptide comprising, consisting essentially of and/or consisting of the amino acid sequence PPGKPQGPPPQGGNQPQGPPPPPGKPQ, the amino acid sequence GNPQGPSPQGGNKPQGPPPP-PGKPQ, and/or the amino acid sequence SPPGKPQGP-PQQEGNKPQGPPPPGKPQ, singly or in any combination. In some embodiments, the biomarker of this invention can be, but is not limited to human basic proline-rich protein 1 (PRB1), human basic proline-rich protein 2 (PRB2), and/or 3) human basic proline-rich protein 4 (PRB4), the amino acid sequence and nucleotide sequence of each of which is known in the art, as exemplified in Table 2.

In further embodiments, a biomarker of this invention can be a peptide comprising, consisting essentially of or consisting of any fragment of human basic proline-rich protein 1 (PRB1), human basic proline-rich protein 2 (PRB2), and/or 3) human basic proline-rich protein 4 (PRB4). For example, the biomarker of this invention can be a peptide comprising, consisting essentially of or consisting of one or more 5 mers, 6 mers, 7 mers, 8 mers, 9 mers or 10 mers of the amino acid sequence of any of human basic proline-rich protein 1 (PRB1), human basic proline-rich protein 2 (PRB2), and/or 3) human basic proline-rich protein 4 (PRB4).

As a nonlimiting example, a biomarker of this invention can be a peptide comprising, consisting essentially of or consisting of at least about five amino acids (e.g., 5, 6, 7, 8, 9, 10, 11, 12, 13, 14) to at least about 15, 20, 25, 30, 35, 40, 45, 50, 50, 70, 80, 90, 100, 125, 150, 175 or 200 amino acids (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 1120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, etc.), wherein the peptide comprises one or more (e.g., 2, 3, 4, 5, 6, 7, 8, 9, 10, 11, 12, 13, 14, 15, 16, 17, 18, 19 or 20) of the 5 mer peptides listed in Table 1. As a nonlimiting example, a biomarker peptide of this invention can be 20 amino acids in length and can comprise two of the 5 mer peptides of Table 1, which can be contiguous as provided in the protein sequence from which the 5 mer peptides were derived. The remaining 10 amino acids can be on either side of each 5 mer, between each 5 mer or both. Furthermore, the remaining amino acids can be amino acids that are contiguous with the 5 mer peptides and/or noncontiguous with the 5 mer peptides (e.g., amino acids that are not present in the order provided in the protein sequence from which the 5 mer peptides were derived). The 5 mers of the PRB proteins provided in Table 1 are exemplary, as the present invention also encompasses 6 mers, 7 mers, 8 mers, 9 mers, etc., of these PRB proteins as noted above, the amino acid sequence of any of which would be readily determined by one of skill in the art.

In further embodiments, a biomarker of this invention can comprise, consist essentially of or consist of any peptide or protein listed in Table 1, singly or in any combination. The biomarker of this invention can also comprise, consist essentially of or consist of any fragment of any peptide or protein listed in Table 1.

Thus, in certain embodiments, the present invention is directed to a biomarker, which is a peptide or polypeptide (i.e., protein) as described herein and the present invention can employ or involve one or more of the peptides and proteins set forth herein in any method and/or kit of this invention, singly and/or in any combination. In certain other embodiments, the present invention provides a nucleic acid encoding a biomarker of this invention and the methods of this invention can employ or involve one or more of the nucleic acids of this invention in any method/and or kit of this invention.

A biomarker of this invention can be detected and/or quantified in a sample by a variety of methods well known in the art for detecting and/or quantifying substances in biological samples. For example, for detecting and/or quantifying a biomarker that is a peptide or polypeptide, standard methods for detecting and/or quantifying peptides and/or polypeptides in sample can be employed. Nonlimiting examples of such methods include direct protein measurement, absorbance at 280 nm, absorbance at 205 nm, extinction coefficient assay, Lowry assay, biuret assay, Bradford assay, bicinchoninic acid assay (BCA), amido black assay, colloidal gold assay, immunoassay or other specific binding assay employing an antibody or ligand that specifically binds a peptide or polypeptide, protein separation assays such as electrophoresis, gas chromatography (GC), high performance liquid chromatography (HPLC), mass spectrometry (MS), etc., as are well known in the art.

Other methods of detection can include bioassays using mammalian or bacterial cells wherein an output is proportional to the concentration of peptide in the sample solution, and solid phase methods wherein binding to a surface coated with a peptide recognizing molecule triggers an output electrical signal or change in optical property.

In some embodiments of this invention, peptides and/or proteins in a sample of this invention can be measured by BCA.

For detection and/or quantification of a nucleic acid encoding a biomarker of this invention, standard methods for detection and/or quantification of nucleic acids in a sample can be employed. Non-limiting examples include hybridization assays, amplification assays, sequencing protocols, etc., as are well known in the art.

The term "biomarker index" as used herein means the ratio of the amount of biomarker peptide or protein to the total amount of protein in the biological sample. For example, the biomarker index can be a value determined by calculating the relative amount of peptide in nmoles per µg of total protein (e.g., as determined by BCA) in the biological sample. The term "threshold biomarker index" as used herein means the biomarker index calculated from the biomarker indices from a population of subjects that defines the threshold value for identifying a subject as having chronic fatigue syndrome or having an increased likelihood or risk of having or developing chronic fatigue syndrome. The threshold biomarker index is calculated from the biomarker index of each subject in a population of subjects determined not to have chronic fatigue syndrome (e.g., non-CFS subjects). In some embodiments, a predetermined or previously established threshold biomarker index can be used in the methods described herein to identify a subject as having chronic fatigue syndrome or having an increased likelihood of having or developing chronic fatigue syndrome. Such a predetermined or previously established threshold biomarker index can be determined according to the teachings set forth herein (see, e.g., Example 3) as well as art-known teachings.

A subject of this invention is any animal in which identification of chronic fatigue syndrome, identification of increased likelihood or risk of having or developing chronic fatigue syndrome and/or identification of changes in fatigue level over time is needed or desired. In some embodiments, the subject is mammal and in particular embodiments the subject is a human. In other embodiments, the subject can be a horse, a dog or any other mammal about which the information obtained from the methods of this invention is needed or desired. In some embodiments, the subject can be diagnosed with chronic fatigue syndrome and/or have symptoms of chronic fatigue syndrome or other fatigue-related disorder and in some embodiments the subject can have no diagnosis or symptom(s) of chronic fatigue syndrome or any other fatigue-related disorder. A subject of this invention that has an "increased likelihood" or "increased risk" of having or developing chronic fatigue syndrome can be a subject having symptoms and/or signs of chronic fatigue syndrome or other fatigue associated disorder or such a subject can be a subject who is not having symptoms and/or signs of chronic fatigue syndrome or other fatigue-associated disorder. A subject of this invention can have an increased risk or increased likelihood of having or developing chronic fatigue syndrome due to environmental and/or genetic factors as would be known to one of skill in the art. By "increased likelihood" or "increased risk" of having or developing chronic fatigue syndrome it is meant that the increase is relative to a control (e.g., a subject whose biomarker index is at or below the threshold biomarker index).

In the methods of this invention employing measurements over time, the time intervals can be minutes, hours, days, weeks, months and/or years in any order and in any combination.

In the methods of this invention that recite a first time point and a second or subsequent time points or later time points, in some embodiments, the first time point can be prior to performance of an activity (e.g., physical, athletic, mental, training, normal activity of daily living, etc.) and the second or subsequent time points can be during and/or after performance of the activity. In some embodiments, the first time point can be during and/or after the performance of activity and the second or subsequent points can be at a later time following completion of the activity.

Physical activity and/or athletic activity as described herein can be but is not limited to ultra-endurance exercise, a military operation, military training, running, walking, bicycling, weight lifting, swimming, a standardized physical test course including, for example, those used by the military, a triathlon, a biathlon, shooting of a rifle, shooting of a handgun, the aiming of computerized target equipment, staying awake, hiking, hiking while carrying a large burden on the back, physical activities of daily living and any combination thereof.

As used herein, the term "ultra-endurance exercise" means a single continuous session of physical activity and/or athletic activity during which the subject performs said activity for a minimum of four hours with an average exertion equal to or greater than 70% of ventalitory threshold, as described in Harger-Domitrovich et al., 2007, Medicine & Science in Sports & Exercise. For example, ten hours of continuous repetition of a one-hour exercise regimen consisting of 9 min. of upper-body ergometry, 19 min. of cycling, and 20 min. of treadmill walking with 1-min transition between modes, followed by a 10-min. rest and feeding period.

Military training is defined as the process of preparing military individuals and units to perform their assigned functions and missions, particularly to prepare for combat and wartime functions. "Covering every aspect of military activity, training is the principal occupation of military forces when not actually engaged in combat." (*Brassey's Encyclopedia of Land Forces and Warfare*, By Franklin D. Margiotta). Training may include for example physical tasks such as swimming, hiking when equipped with full military gear, running, moving stealthily, climbing, performing the aforementioned tasks under extreme environmental conditions such as high and low temperatures, high altitude or under conditions where flora and fauna pose significant hazard.

Military operations are defined for the purposes of this instant invention as the activities engaged in by soldiers, sailors and airmen during performance of duties during periods of war and peace. Military operations may include tasks related to engagement of enemy combatants. These tasks may include, but are not limited to the following examples, pursuing the enemy on foot, flying unmanned drone aircraft, operating electronic equipment, manning guns in flight on an airplane, performing law enforcement duties and providing intelligence.

Normal activities of daily living, as defined by the National Cancer Institute, include eating, dressing, getting into or out of a bed or chair, taking a bath or shower, and using the toilet. Instrumental activities of daily living are activities related to independent living and include preparing meals, managing money, shopping, doing housework, and using a telephone.

The terms "fatigue" and "fatigued state" as used herein mean weariness or exhaustion from labor, exertion, exercise, or stress, including loss of physical strength and bodily and mental capabilities.

The term "chronic fatigue" as used herein describes fatigue lasting about six or more consecutive months, which is not due or identified to be due to ongoing exertion or other medical conditions associated with fatigue.

"Chronic fatigue syndrome" or "CFS" as used herein describes the condition or status of a subject (e.g., a patient) who meets at least one of the criteria set forth for example, in 1) the CDC definition (1994) and also called the Fukuda definition, 2) The Oxford criteria (1991), which includes CFS of unknown etiology and a subtype called post-infectious fatigue syndrome (PIFS), 3) The 2003 Canadian Clinical working definition, which states that "[a] patient with ME/CFS will meet the criteria for fatigue, post-exertional malaise and/or fatigue, sleep dysfunction, and pain; have two or more neurological/cognitive manifestations and one or more symptoms from two of the categories of autonomic, neuroendocrine, and immune manifestations; and the illness will persist for at least 6 months," 4) CFS/ME guideline for the National Health Service in England and Wales, produced in 2007 by the National Institute for Health and Clinical Excellence (NICE), and 5) other criteria including gene expression markers, genetic profiles and/or biomarkers as are known in the art. See, e.g., "Chronic Fatigue Syndrome/Myalgic Encephalomyelitis, A Primer for Clinical Practitioners" by the International Association for Chronic Fatigue Syndrome/Myalgic Encephalomyelitis (IACFS/ME), 2012 Edition, the entire contents of which are incorporated by reference herein. See also the following websites: www.iacfsme.org and www.cdc.gov/cfs/general/index.html, the entire contents of each of which are incorporated by reference herein.

A "treatment program for chronic fatigue syndrome" describes a physician-directed program including one or more of the treatments for Chronic Fatigue Syndrome recommended by the Centers for Disease Control and Prevention, International Association for Chronic Fatigue Syndrome/Myalgic Encephalomyelitis, and/or other recognized organizations with expertise in Chronic Fatigue Syndrome As used herein, "increasing the intensity of a treatment program" means changing a subject's treatment program such that the supervising physician believes that the level or intensity of future treatment is greater than the previous level or intensity of treatment.

Nonlimiting examples of treatments for chronic fatigue syndrome (CFS) include 1) cognitive behavioral therapy, 2) graded exercise therapy as a form of physical therapy, 3) pacing or energy management therapy, 4) pharmacotherapy including, e.g., Amitriptyline, Doxepin, Nortriptyline, Cyclobenzaprine, Trazodone, Gabapentin, Pregabalin, Promethazine, Diphenhydramine, Clonazepam, Orphenadrine, Ropinirole, pramipexole, Melatonin, Zolpidem, Zopiclone, Mirtazapine, Acetaminophen, Aspirin, Diclofenac, Gabapentin, Duloxetine, Codeine phosphate, oxycodone, hydrocodone, morphine, Tramadol, Modafinil, Armnodafanil, Methylphenindate, Dexamphetamine, Caffeine, Amphetamine salts Isoprinosine, anti-viral medications, rintatolimod, rituximab, antibiotics, anti-parasitics, dietary supplementation, vitamin D, vitamin B-12, B-complex vitamins, essential fatty acids, zinc and herbal remedies, light and radiation therapy, and any combination of these agents and therapies.

Also as used herein, the term "rested" or "rested state" or "non-fatigued state" means having sufficient rest from bodily and/or mental exertion, either before physical exercise and/or after recovery from fatigue.

"Perceived level of fatigue" as used herein means an individual's personal estimate or assessment of their fatigue and their ability to carry out tasks requiring a certain level of physical and/or cognitive performance In addition, as used herein, "physical performance capability" means the capacity to accomplish a task which requires expenditure of a particular amount of energy. These tasks include, but are not limited to lifting objects, carrying objects, maintaining a certain pace of walking, running and/or cycling and maintaining a particular heart rate for a specified period. Capability represents a subject's potential for energy expenditure over a particular period of time.

The term "fitness" as used herein means good health or physical condition, especially as the result of exercise and proper nutrition.

In some embodiments of this invention, a subject of this invention is any animal in which identification of chronic fatigue syndrome, identification of increased likelihood or risk of having or developing chronic fatigue syndrome and/or identification of changes in fatigue level over time is needed or desired. In some embodiments, the subject is mammal and in particular embodiments the subject is a human. In other embodiments, the subject can be a horse, a dog or any other mammal about which the information obtained from the methods of this invention is needed or desired.

In some embodiments, the subject can be diagnosed with chronic fatigue syndrome and/or have symptoms of chronic fatigue syndrome or other fatigue-related disorder and in some embodiments the subject can have no diagnosis or symptom(s) of chronic fatigue syndrome or any other fatigue-related disorder. A subject of this invention that has an "increased likelihood" or "increased risk" of having or developing chronic fatigue syndrome can be a subject having symptoms and/or signs of chronic fatigue syndrome or other fatigue associated disorder or such a subject can be a subject who is not having symptoms and/or signs of chronic fatigue syndrome or other fatigue-associated disorder. A subject of this invention can have an increased risk or increased likelihood of having or developing chronic fatigue syndrome due to environmental and/or genetic factors as would be known to one of skill in the art. By "increased likelihood" or "increased risk" of having or developing chronic fatigue syndrome it is meant that the increase is relative to a control (e.g., a subject whose biomarker index is at or below the threshold biomarker index).

In some embodiments, a population of study subjects of this invention includes healthy male and/or female volunteers less than the age of 42 that are in good physical condition and not suffering from known diseases and/or healthy young (less than 25 years old) military members being screened for selection to Special Forces in the United States Military.

In some embodiments of this invention, a subject of this invention can be military personnel, a shift worker, a laborer, a truck driver, airline personnel, assembly line worker, a patient at a sleep clinic, an amateur athlete, a professional athlete, a worker in the oil and/or gas industry, a train driver, an astronaut, a space traveler, a coal miner, an air traffic controller and any combination thereof. A subject of this invention can also be any subject engaged in training and/or engaged in athletics, other employment or other activities outside of defined military duties. A subject of this invention may also be engaged in any work occupation as listed in the Standard Occupational Classification (SOC) System Manual, Version 2010, published by the US Department of Commerce and/or *Brassey's Encyclopedia of Land Forces and Warfare*, By Franklin D. Margiotta (1996) and/or The International Classification of Sleep Disorders Revised (2001) (ISBN-10: 157488087X) and/or "Sleep Disorders and Sleep Deprivation: An Unmet Public Health Problem" Harvey R. Colten and Bruce M. Altevogt, Editors, Committee on Sleep Medicine and Research, ISBN: 0-309-65727-X, 424 pages, (2006), the entire contents of each of which are incorporated by reference herein.

As used herein, a "sleep schedule" refers to periods of time allocated to sleep and taken at a specific time over some defined and recurring period. This can mean, as a non-limiting example, allocating a sleep period of 8 hours starting at 10 PM where the recurring period is 24 hours long where each recurring period starts at 6 AM. In another example one sleep period is 2 hours and starts at 4 PM and a second period starts at 1AM and is 4 hours long where the recurring period is 24 hours long where each recurring period starts at 6 AM.

Guiding a subject's sleep schedule can be done by modifying the duration of the sleep periods, the number of sleep periods per day, and/or the time at which sleep periods are started. The recurring period may be determined, for example, by the subject's work schedule and/or any convenient recurring time pattern for example per day, week, month, etc.

Also as used herein, a "sleep enhancing material" refers to foods that are ingested, drugs that are administered by the oral route, intravenous route, transdermal route, intranasal route, via inhalation, by intra-ocular route, by vaginal route, and/or by rectal delivery route or other means, or complex mixtures that are delivered through a combination of routes in the form of a bath or immersion. Nonlimiting examples of a sleep enhancing material include an herbal tea, warm milk, turkey, a large meal, an alcoholic beverage, a dietary supplement, a mud bath, a salt bath, an FDA-approved drug agent with a specific indication for treatment of a sleep disorder including, e.g., insomnia, narcolepsy, sleep apnea, depression, anxiety, and sleep disorder associated with shift work.

Furthermore, a "sleep enhancing activity" refers to actions taken by the subject to promote sleepiness and thereby sleep, and/or actions taken by others directed towards the subject to promote sleepiness and thereby sleep, and/or actions taken by an automated system directed towards the subject to promote sleepiness and thereby sleep. Nonlimiting examples of a sleep enhancing activity include reading while lying down, reading poetry, watching television, listening to music, exposure to electromagnetic fields, having sex, soaking in warm water, massage, counting sheep and/or other redundant mental activity.

As used herein, "treatment of a sleep disorder" includes actions taken by a medical doctor or other medical practitioner on the subject to reduce symptoms associated with a sleep disorder or actions taken by a non-medical therapist or counselor on the subject to treat a sleep disorder or action taken by the spouse or friend or acquaintance of the subject to treat a sleep disorder or action taken by the subject to treat a sleep disorder. Nonlimiting examples of a treatment of a sleep disorder include taking an FDA approved agent and/or using a device for treatment of sleep disorder as prescribed by the subject's physician, psychological therapy delivered by a therapist to the subject to reduce anxiety and thereby mitigate sleep disorder, cognitive engagement by a spouse to improve marital relationship thereby reducing sleep disorder, a commitment and/or action on the part of the subject to work less thereby reducing sleep disorder. Enhancement of a treatment of a sleep disorder means increased intensity and/or frequency and/or dose and/or adding a new or additional treatment to an existing treatment regimen Reduction of a treatment of a sleep disorder means reduced intensity or frequency and/or dose and/or removing a treatment from an existing treatment regimen.

"Treatment of fatigue" as used herein means medical interventions and/or other physical and/or mental actions and/or changes in behavior to reduce fatigue. Nonlimiting examples of a treatment of fatigue include the use of medical interventions that may include drugs, surgery, and/or use of a approved medical device and/or approved medical therapy intended to reduce fatigue, the use of cognitive therapy and/or counseling to promote or elicit behaviors that reduce fatigue by reducing exposure to fatiguing activities and/or promoting activities that reduce fatigue. Specific non-limiting examples include taking a prescribed drug to promote restful sleep, thereby reducing fatigue, and/or engaging in fatigue mitigation counseling that leads, for example, to scheduling of more time for sleep.

As used herein, the term "work load" refers to cognitive and/or physical tasks that are required and/or desired for living. This includes tasks that are performed at home and outside the home. This includes, for example tasks related to activities of daily living and/or tasks accomplished or performed at a subject's workplace.

As also used herein, "fitness for duty" means having the ability to perform cognitive and/or physical tasks associated with daily living and/or work and having the ability to perform these tasks within reasonable periods of time and at a certain level of quality.

A "threshold ratio" describes a level of the ratio that is associated with a high likelihood of being able to perform a specific physical and/or cognitive task and/or to be fit for duty or to be in a non-fatigued state.

To perform a physical activity and/or athletic activity at a sufficient level means the ability to perform a task at a level that is required for professional advancement, required to pass a test, and/or required to complete a study. This also may include but is not limited to meeting individual personal physical and performance goals, satisfying job eligibility requirements, and/or meeting criteria required to continue working at a task, for example determining whether a person is too fatigued to drive a truck.

In some embodiments, to be "sufficiently rested to carry out a work load" includes having the ability to perform a task at a level that is required for professional advancement, required to pass a test and/or meet a predetermined threshold of performance and/or required to complete a study.

In some embodiments, a population of study subjects of this invention includes healthy male and/or female volunteers less than the age of 42 that are in good physical condition and not suffering from known diseases (e.g., determined not to have chronic fatigue syndrome) and/or healthy young (less than 25 years old) military members being screened for selection to Special Forces in the United States Military.

To perform a physical activity and/or athletic activity at a sufficient level means the ability to perform a task at a level that is required for professional advancement, required to pass a test, and/or required to complete a study. This also may include but is not limited to meeting individual personal physical and performance goals, satisfying job eligibility requirements, and/or meeting criteria required to continue working at a task, for example determining whether a person is too fatigued to drive a truck.

In some embodiments, to be "sufficiently rested to carry out a work load" includes having the ability to perform a task at a level that is required for professional advancement, required to pass a test and/or meet a predetermined threshold of performance and/or required to complete a study.

The term "chronic fatigue syndrome" as used herein describes an art-known syndrome, the signs and symptoms of which are described in the literature (see, e.g., Reeves et al. "Prevalence of chronic fatigue syndrome in metropolitan, urban, and rural Georgia" *Population Health Metrics* 5:5 (2007), the entire contents of which are incorporated by reference herein). Common symptoms and signs of chronic fatigue syndrome include fatigue, loss of memory or concentration, sore throat, enlarged lymph nodes in the neck and/or armpits, unexplained muscle pain, pain that moves from one joint to another without swelling or redness, headache of a new type, pattern or severity, unrefreshing sleep, and extreme exhaustion lasting more than 24 hours after physical or mental exercise. To meet the diagnostic criteria of chronic fatigue syndrome, a subject typically must have unexplained, persistent fatigue for six months or more, along with at least four of the following signs and symptoms: loss of memory or concentration, sore throat, enlarged lymph nodes in the neck or armpits, unexplained muscle pain, pain that moves from one joint to another without swelling or redness, headache of a new type, pattern or severity, unrefreshing sleep, and extreme exhaustion lasting more than 24 hours after physical or mental exercise.

The biomarkers and biomarker indices of this invention are correlated with chronic fatigue syndrome, fatigue, a fatigued state, an increase or decrease in fatigue, an increase or decrease in physical performance, a subject's perceived level of fatigue, recovery from a fatigued state, and/or an increased or decreased likelihood of performing an activity at a sufficient level as described herein according to methods well known in the art and as disclosed in the Examples provided herein. In general, identifying such correlation involves conducting analyses that establish a statistically significant association and/or a statistically significant correlation between the presence of a biomarker or biomarker index or a combination of biomarkers or biomarker indices and a change in the subject (e.g., from rested to fatigued state, during and/or after performance of physical activity or other defined or standardized activity) as detected according to standard methods. An analysis that identifies a statistical association (e.g., a significant association) between the biomarker or biomarker index or between the combination of biomarkers or biomarker indices and the change in the subject establishes a correlation between the increase or decrease of the biomarker or biomarker index or combination of biomarkers or biomarker indices in a subject and the change being analyzed.

It would be well understood by one of skill in the art that the methods of the present invention can be carried out on multiple subjects and the data compiled to produce mean and median values that indicate fatigue, a fatigued state, an increase or decrease in fatigue, an increase or decrease in physical performance, a subject's perceived level of fatigue, recovery from a fatigued state, and/or an increased or decreased likelihood of performing a physical activity at a sufficient level according to this invention. It would also be understood that the statistical limits described by the data obtained from groups of subjects can be applied to individual subjects' response. Thus, it would be understood that in some embodiments of this invention, the methods of this invention can be carried out using a computer, wherein, for example, the data from multiple subjects are stored in a computer database and analyzed according to art-known methods of statistical and mathematical analysis to identify means, medians, trends, statistically significant changes, variances, etc.

Thus, in some embodiments, the methods of this invention can be carried out using a computer. Thus the present invention provides a computer-assisted method of identifying fatigue, a fatigued state, an increase or decrease in fatigue, an increase or decrease in physical performance, a subject's perceived level of fatigue, recovery from a fatigued state, and/or an increased or decreased likelihood of performing a physical activity at a sufficient level. The method involves the steps of (a) storing a database of biological data for a plurality of subjects, the biological data that is being stored including for each of said plurality of subjects: (i) a description of the status of the subject and/or physical/athletic activity performed by the subject, (ii) a description of any performance enhancing material and/or activity administered to, contacted with and/or implemented by the subject; (iii) a description of measurements according to art-known methods detecting a change in the status or performance in the subject; and (iv) a description of measurements of biomarkers or biomarker indices in the subject; and then (b) querying the database to determine the relationship between a change in the measurement of biomarkers or biomarker indices in the subject and change in performance or status of the subject. Such querying can be carried out prospectively or retrospectively on the database by any suitable means, but is generally done by statistical analysis in accordance with known techniques, as described herein.

Compositions of the Invention

Further aspects of the present invention include an isolated peptide comprising, consisting essentially of, or consisting of the amino acid sequence of PPGKPQGPPPQGGNQPQGP-PPPPGKPQ (SEQ ID NO:1), an isolated peptide comprising, consisting essentially of, or consisting of the amino acid sequence of GNPQGPSPQGGNKPQGPPPPPGKPQ (SEQ ID NO:2), and/or an isolated peptide comprising, consisting essentially of or consisting of the amino acid sequence of SPPGKPQGPPQQEGNKPQGPPPPGKPQ (SEQ ID NO:3) and a composition comprising any of these isolated peptides, singly or in any combination in a pharmaceutically acceptable carrier.

Also provided herein is an isolated peptide comprising, consisting essentially of or consisting of about five amino acids to about 15, 20, 25, 30, 35, 40, 45, 50, 50, 70, 80, 90 or 100 amino acids (including any value between 5 and 100 not explicitly recited herein), wherein the peptide comprises one or more (e.g., 2, 3, 4, 5, 6, 7, 8, 9, 10, 11, 12, 13, 14, 15, 16, 17, 18, 19 or 20) of the 5 mer peptides listed in Table 1, as well as a composition comprising any of these isolated peptides, singly or in any combination in a pharmaceutically acceptable carrier.

"Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

In some embodiments of this invention, a biomarker peptide and/or protein of this invention can be used, in any combination, as an antiviral, an antimicrobial, and/or an antifungal agent. Thus, the biomarker peptides and/or proteins of this invention can be used in methods of treating and/or preventing disorders such as disorders associated with fatigue (e.g., chronic fatigue syndrome), viral infection, disease associated with viral infection, microbial infection, disease associated with microbial infection, fungal infection, disease associated with fungal infection, and any combination thereof. Dosages, modes and regimens of administration for peptides and proteins as described herein would be determined by one of skill in the art according to art-known protocols (see, e.g., *Remington's Pharmaceutical Science*; latest edition).

In some embodiments, the present invention provides a biomarker protein or peptide of this invention, a nucleic acid comprising a nucleotide sequence encoding a biomarker protein or peptide of this invention, a vector comprising said nucleic acid and a cell containing said vector. The biomarker, the nucleic acid, the vector and/or the cell can be present singly and/or in any combination in a composition comprising a pharmaceutically acceptable carrier.

In other embodiments of this invention, a nucleic acid having the nucleotide sequence or a substantially similar nucleotide sequence of the gene encoding a biomarker protein or peptide of this invention can be used as a probe in a nucleic acid hybridization assay for the detection of nucleic acid encoding a biomarker protein or peptide in various tissues and/or body fluids of a subject of this invention. The probe can be used in any type of nucleic acid hybridization assay including Southern blots (Southern, 1975, *J Mol. Biol.* 98:508), Northern blots (Thomas et al., 1980, *Proc. Natl Acad. Sci.* U.S.A. 77:5201-05), colony blots (Grunstein et al., 1975, *Proc. Natl Acad. Sci.* U.S.A. 72:3961-65), slot blots, dot blots, etc. Stringency of hybridization can be varied depending on the requirements of the assay according to methods well known in the art. Assays for detecting nucleic acid encoding a protein in a cell, or the amount thereof, typically involve first contacting the cells or extracts of the cells containing nucleic acids therefrom with an oligonucleotide probe that specifically binds to nucleic acid encoding a protein or peptide as described herein (typically under conditions that permit access of the oligonucleotide to intracellular material), and then detecting the presence or absence of binding of the oligonucleotide probe thereto. Any suitable assay format can be employed (see, e.g., U.S. Pat. No. 4,358, 535; U.S. Pat. Nos. 4,302,204; 4,994,373; 4,486,539; 4,563, 419; and 4,868,104, the disclosures of each of which are incorporated herein by reference in their entireties).

As used herein, the terms peptide and polypeptide are used to describe a chain of amino acids, which correspond to those encoded by a nucleic acid. A peptide usually describes a chain of amino acids of from two to about 50 amino acids and polypeptide usually describes a chain of amino acids having more than about 50 amino acids. The term polypeptide can refer to a linear chain of amino acids or it can refer to a chain of amino acids, which have been processed and folded into a functional protein. It is understood, however, that 50 is an arbitrary number with regard to distinguishing peptides and polypeptides and the terms may be used interchangeably for a chain of amino acids around 50. The peptides and polypeptides of the present invention can be obtained by isolation and purification of the peptides and polypeptides from cells or body fluids or tissues where they are found naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes can be made in the nucleic acid sequence of the underlying gene(s) and/or amino acid sequence of the peptides and polypeptides of the present invention and still obtain a peptide or polypeptide having like or otherwise desirable characteristics. Such changes can occur in natural isolates or can be synthetically introduced using site-specific mutagenesis, the procedures for which, such as mismatch polymerase chain reaction (PCR), are well known in the art. One of skill in the art will also understand that polypeptides and nucleic acids that contain modified and/or synthetic amino acids and nucleotides, respectively (e.g., to increase the half-life and/or the therapeutic efficacy of the molecule), as are well known in the art, can be used in the methods of the invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to a sequence that is naturally occurring or may include alternative codons that encode the same amino acid as that which is found in the naturally occurring sequence. Furthermore, nucleic acids may include codons that represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The present invention further provides a kit for detection and/or quantification of the biomarkers of this invention. In some embodiments, such a kit can comprise one or more antibodies, ligands and/or aptamers, along with suitable buffers, wash solutions, dilution buffers, secondary antibodies, detection reagents, etc., for the detection of antigen/antibody complex formation, ligand/target complex formation and/or aptamer/target complex formation under various conditions. In another embodiment, a kit of this invention can comprise a nucleic acid probe or primer that is complementary to a nucleotide sequence encoding a biomarker of this invention, along with suitable buffers, wash solutions, dilution buffers, detection reagents, etc. for the amplification of target nucleic acid and/or detection of nucleic acid hybridization under various conditions.

Thus, in some embodiments, the present invention provides a kit comprising an antibody that specifically reacts with a biomarker of this invention and reagents for detecting antigen/antibody complex formation.

Further provided is a kit comprising an aptamer that specifically reacts with a biomarker of this invention and reagents for detecting aptamer/target molecule complex formation.

In addition, a kit is provided herein, comprising a nucleic acid that hybridizes under high stringency conditions with a nucleic acid encoding a biomarker of this invention and reagents for detecting nucleic acid hybridization complex formation.

Screening Methods

In addition, the present invention provides a method of identifying a substance that binds a peptide or protein of this invention, comprising contacting the peptide or protein with a test compound under conditions whereby binding between the peptide or protein and the test compound can be detected; and detecting binding between the peptide or protein and the test compound.

Further provided is a method of identifying a substance having the ability to inhibit or enhance the binding activity of a peptide or protein of this invention, comprising contacting the substance with the peptide or protein under conditions whereby binding can occur and detecting a decrease or increase in the amount of binding in the presence of the substance as compared to a control amount of binding in the absence of the substance, thereby identifying a substance having the ability to inhibit or enhance the binding activity of the peptide or protein.

For the methods of this invention that employ the detection of binding, such assays are well known in the art and can employ, for example, an antibody, ligand and/or aptamer that binds a peptide of this invention either directly or indirectly.

Also provided herein is a method of identifying a compound that modulates the activity of a peptide or protein of this invention, comprising contacting the peptide or protein with a test compound under conditions whereby modulation of the activity of the peptide or protein can be detected. Because there is an association between fatigue and a change in the levels of the peptides and proteins of this invention, the peptides and proteins may serve a role in, for example, communicating a state of high energy demand to target organs, altering function of organs involved in mobilization of energy, modulating the activity of organs involved with the mobilization of energy stores including adipose tissue, the liver and muscle, modulating the activity of gastrointestinal mucosal leading to increased absorption of sugars, converting amino acids to sugars, or modifying the metabolic and enzymatic activity of commensal bacteria residing in the gastrointestinal tract leading to increased availability of sugars and free fatty acids that can be used to accomplish physical work by voluntary muscle, modulating the activity of the liver, pancreas, duodenum and other organs that secrete enzymes, emulsifiers and other substances that affect the processing of food, altering the distribution and targeting of sugars, lipids and proteins in the blood. These activities can be measured using in vitro cell-based assays with various output functions that can be used to determine activity, cell-free assays that measure association with specific receptors or important regulatory molecules, gene expression assays, and methods that involve measurement of functional outputs or alterations of metabolic production, fat mobilization and other phenomenon associated with fatigue or the ability to perform physical and cognitive tasks.

Additionally, the present invention provides a method of identifying immunomodulating activity in a peptide or protein of this invention, specifically by employing the peptide or protein in an assay for immunomodulating activity and detecting immunomodulating activity in the presence of the peptide or protein as compared to a control, thereby identifying immunomodulating activity in the peptide or protein. In this method, the assay for immunomodulating activity can be, but is not limited to, antibody production (or other assay to detect humoral immune response, T cell activation (or other assay to detect cellular immune response), nitric oxide production, interleukin 2 (IL-2) secretion and any combination thereof.

Furthermore, a method is provided herein of identifying antiviral, antimicrobial and/or antifungal activity in a peptide or protein of this invention, comprising employing the peptide or protein in an assay for antiviral antimicrobial and/or antifungal activity and detecting antiviral, antimicrobial and/or antifungal activity in the presence of the peptide or protein as compared to a control, thereby identifying antiviral, antimicrobial and/or antifungal activity in the peptide or protein. Protocols for identifying antiviral, antimicrobial and/or antifungal activity in a substance are well known in the art.

The term "antibody" as used herein, includes, but is not limited to a polypeptide encoded by an immunoglobulin gene or immunoglobulin genes, or a fragment thereof "Antibody" also includes, but is not limited to, a polypeptide encoded by an immunoglobulin gene or immunoglobulin genes, or a fragment thereof, which specifically binds to and recognizes the biomarkers of this invention.

The term "epitope" means an antigenic determinant that is specifically bound by an antibody. Epitopes usually consist of surface groupings of molecules such as amino acids and/or sugar side chains and usually have specific three-dimensional structural characteristics, as well as specific charge characteristics.

The terms "specifically binds to" and "specifically reactive with" refer to a binding reaction that is determinative of the presence of the antigen and antibody or aptamer and target in the presence of a heterogeneous population of proteins, nucleic acids and/or other biologics. Thus, under designated assay conditions, the specified antibodies and antigens and/or aptamers and targets bind to one another and do not bind in a significant amount to other components present in a sample.

In some embodiments employing antibodies, a variety of immunoassay formats can be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

An "immunologically reactive fragment" of a protein refers to a portion of the protein or peptide that is immunologically reactive with a binding partner, e.g., an antibody, which is immunologically reactive with the protein itself.

Antibodies to biomarkers of this invention can be generated using methods that are well known in the art. Such antibodies can include, but are not limited to, polyclonal, monoclonal, chimeric, humanized, fully human, single chain, Fab fragments, and/or fragments produced by an expression library, including e.g., phage display. (See, e.g., Paul, FUNDAMENTAL IMMUNOLOGY, 3rd Ed., 1993, Raven Press, New York, for antibody structure and terminology.)

Antibody fragments that contain specific binding sites for a biomarker of this invention can also be generated. For example, such fragments include, but are not limited to, the $F(ab')_2$ fragments that can be produced by pepsin digestion of the antibody molecule, and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254, 1275-1281 (1989)).

For the production of antibodies, various hosts including goats, rabbits, rats, mice, humans, and others, may be immunized by injection with a protein or any fragment or oligopeptide or conjugate thereof that has immunogenic properties. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and *Corynebacterium parvum*.

Monoclonal antibodies can be prepared using any technique that provides for the production of antibody molecules by continuous cell lines in culture. These include, but are not limited to, the hybridoma technique, the human B-cell hybridoma technique, and the EBV-hybridoma technique (Kohler et al. (1975) *Nature* 256:495-497; Kozbor et al. (1985) *J. Immunol. Methods* 81:31-42; Cote et al. (1983) *Proc. Natl. Acad. Sci.* 80:2026-2030; Cole et al. (1984) *Mol. Cell Biol.* 62:109-120). Briefly, the procedure can be as follows: an animal is immunized with a protein or immunogenic fragment or oligopeptide or conjugate thereof. Lymphoid cells (e.g., splenic lymphocytes) are then obtained from the immunized animal and fused with immortalizing cells (e.g., myeloma or heteromyeloma) to produce hybrid cells. The hybrid cells are screened to identify those that produce the desired antibody.

Human hybridomas that secrete human antibody can be produced by the Kohler and Milstein technique and according to art-known protocols. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi et al. *Bio Techniques* 4(4):214-221 (1986); Sun et al. *Hybridoma* 5 (1986).

The monoclonal antibodies of this invention specific for biomarker epitopes of this invention can also be used to produce anti-idiotypic (paratope-specific) antibodies. (See e.g., McNamara et al., *Science* 220, 1325-26 (1984); Kennedy et al., *Science* 232:220 (1986).) These antibodies resemble the biomarker epitope and thus can be used as an antigen to stimulate an immune response against the biomarker.

In addition, techniques developed for the production of "chimeric antibodies," the splicing of mouse antibody genes to human antibody genes to obtain a molecule with appropriate antigen specificity and biological activity can be used (Morrison et al. *Proc. Natl. Acad. Sci.* 81:6851-6855 (1984); Neuberger et al., *Nature* 312:604-608 (1984); Takeda et al., *Nature* 314:452-454 (1985)). Alternatively, techniques described for the production of single chain antibodies can be adapted, using methods known in the art, to produce biomarker protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi et al., *Proc. Natl. Acad. Sci.* 86:3833-3837 (1989)); Winter et al., *Nature* 349:293-299 (1991)).

Various immunoassays can be used to identify biomarkers of this invention. Such immunoassays typically involve the measurement of antigen/antibody complex formation between a biomarker protein or peptide and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J. Immunol.*, 135: 2589-2542 (1985).)

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 20030073147, the entire contents of each of which are incorporated by reference herein.

In some embodiments, the biomarker of this invention can be detected and/or quantified in an assay employing an aptamer, a molecule that binds tightly to the biomarker in a manner similar to an antibody, a ligand or a small molecule. As used herein, the term "aptamer" includes any nucleic acid molecule or small peptide that specifically recognizes and binds a target molecule (e.g., a target peptide such as a biomarker of this invention). An "oligonucleotide-based aptamer" is defined as an aptamer made primarily, although not exclusively, from DNA and/or RNA bases. A "peptide-based aptamer" is defined as an aptamer made primarily, although not exclusively, from amino acids.

In some embodiments, an aptamer can be a small, usually stabilized, nucleic acid molecule that includes a binding domain for a target molecule (e.g., a biomarker of this invention). Oligonucleotide-based aptamers of this invention are oligonucleotides, or short (typically <100 bp) polymers of either DNA or RNA that have been selected from random pools based on their ability to bind nucleic acid, proteins, small organic compounds, and even entire organisms, usually with high affinity.

Oligonucleotide-based aptamers are typically developed to bind particular ligands using a previously described selection technique referred to as SELEX (Systematic Evolution of Ligands by Exponential Enrichment). This technique allows for selection of aptamers both in vivo and in vitro. Methods of making aptamers are described in several publications, for example, Ellington and Szostak, *Nature* 346:818 (1990), Tuerk and Gold, *Science* 249:505 (1990), U.S. Pat. No. 5,582, 981, PCT Publication No. WO 00/20040, U.S. Pat. No. 5,270, 163, Lorsch and Szostak, *Biochemistry*, 33:973 (1994), Mannironi et al., *Biochemistry* 36:9726 (1997), Blind, *Proc. Nat'l. Acad. Sci. USA* 96:3606-3610 (1999), Huizenga and Szostak, *Biochemistry*, 34:656-665 (1995), PCT Publication Nos. WO 99/54506, WO 99/27133, WO 97/42317 and U.S. Pat. No. 5,756,291.

Generally, in their most basic form, in vitro selection techniques for identifying oligonucleotide-based aptamers involve first preparing a large pool of oligonucleotides of the desired length that contain at least some central region that is randomized or mutagenized. For instance, a common oligonucleotide pool for aptamer selection might contain a region of 20-100 randomized nucleotides flanked on both ends by a relatively short (15-25 bp) region of nucleotides with defined sequence useful for the binding of PCR primers. The oligonucleotide pool is amplified using standard PCR techniques.

The original oligonucleotide pool is typically made of DNA bases. However, before the selection step, it can be converted to RNA bases using in vitro transcription methods well known in the art. During the selection step, the oligonucleotide library is allowed to interact with the target molecule, which is either free in solution or adhered to a physical surface such as a bead. In either case, the chemical environment of the interaction is typically controlled to simulate conditions anticipated for the final application of the invention, for example temperature, pH and osmolality matched to physiological conditions. When selection occurs in solution, capillary electrophoresis is used to separate bound from unbound oligonucleotides. For selection methods that use solid surfaces, bound and unbound oligonucleotide are separated by several rounds of washing of the surface. Bound oligonucleotide is isolated and amplified using standard PCR techniques. If the library was converted from DNA to RNA before selection, then reverse transcription must be used prior to PCR amplification. The amplified oligonucleotide sequences are then put through another round of the same type of selection. Typically, the selection process requires a total of three to ten iterative rounds to produce a high-affinity aptamer. In the final step, the amplified DNA is cloned and sequenced using standard procedures to identify the sequence of the oligonucleotides that are capable of acting as aptamers for the target molecule. Once a sequence has been identified for a tightly binding oligonucleotide-based aptamer, the nucleotide-based aptamer may be further refined and optimized for binding affinity by performing additional rounds of selection starting from a pool of oligonucleotides containing controlled levels of randomized mutations of the original oligonucleotide sequence.

In further embodiments, an oligonucleotide-based aptamer can include at least one modified nucleotide base. The term "modified nucleotide base" encompasses nucleotides with a covalently modified base and/or sugar. For example, modified nucleotides include nucleotides having sugars that are covalently attached to low molecular weight organic groups other than a hydroxyl group at the 3' position and other than a phosphate group at the 5' position. Such modified nucleotides can also include 2' substituted sugars such as 2'-O-methyl; 2'-O-alkyl; 2'-O-allyl; 2'-S-alkyl; 2'-S-allyl; 2'-fluoro; 2'-halo; or 2'-azido-ribose, carbocyclic sugar analogues, a-anomeric sugars; epimeric sugars such as arabinose, xyloses or lyxoses, pyranose sugars, furanose sugars, and sedoheptulose.

Modified nucleotides of this invention can include but are not limited to, alkylated purines and/or pyrimidines; acylated purines and/or pyrimidines; and other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psuedouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6-diaminopurine; methylpseudouracil; 1-methylguanine; and 1-methylcytosine.

Oligonucleotide-based aptamers of this invention can be synthesized from conventional phosphodiester linked nucleotides using standard solid or solution phase synthesis techniques that are known in the art. Linkages between nucleotides can use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments, the present invention can employ monoclonal or polyclonal nucleotide-based aptamers. A "monoclonal nucleotide-based aptamer" as used herein includes a single aptamer with a known nucleotide sequence. A "polyclonal nucleotide-based aptamer" as used herein includes a population of aptamers with the same or different nucleotide sequences that all have an affinity for the same target molecule.

In other embodiments, an aptamer of this invention can be a recombinant protein or peptide that has been selected for specific binding to a target molecule according to methods known in the art (see, e.g., Hoppe-Seyler, Crnkovic-Mertens et al. 2004). The peptide-based aptamer can be a short peptide domain inserted into a supporting protein scaffold that enhances both specificity and affinity by conformationally constraining the peptide sequence (Colas, Cohen et al. 1996; Cohen, Colas et al. 1998; Buerger, Nagel-Wolfrum et al. 2003). In some embodiments of the present invention employing a peptide-based aptamer, the term "peptide-based aptamer" can be used to designate the peptide in the scaffold protein while the term "peptide" can refer to the inserted sequence.

In the methods of the present invention employing peptide-based aptamers, assays similar to the immunoassays described herein can be carried out to detect and/or quantify a biomarker of this invention, whereby a peptide-based aptamer is used in place of an antibody and an aptamer/target molecule complex, rather than an antibody/antigen complex is detected. The immunoassays described herein can also be adapted to employ an oligonucleotide-based aptamer in place of an antibody, for the detection of a nucleic acid/target molecule complex. In some embodiments, the immunoassays of this invention can also be modified to employ both aptamers and antibodies to detect and/or quantify a biomarker of this invention. Modification of any known immunoassay to accommodate the detection of binding of a nucleotide- or peptide-based aptamer to a target molecule would be well known to one of ordinary skill in the art.

As used herein, the term "signaling aptamer" includes aptamers with reporter molecules, such as a fluorescence dye, attached to the aptamer in such a way that upon conformational changes resulting from the interaction of the aptamer with a target molecule, the reporter molecule yields a differential signal, such as, for example, a change in fluorescence intensity. Alternatively, the amount of target molecule present may be quantified by the direct binding and retention of a fluorescently tagged aptamer on a solid surface or by the binding of a fluorescently tagged aptamer that recognizes the aptamer or antibody that binds specifically to the target molecule, i.e., secondary fluorescence assay. Examples of signaling aptamers can be found, for example, in U.S. Pat. No. 6,706,481, the entire contents of which are incorporated by reference herein for the disclosure of aptamers, methods of making aptamers and/or methods of using aptamers.

The present invention is more particularly described in the Examples set forth below, which are not intended to be limiting of the embodiments of this invention.

EXAMPLES

Example 1

Discovery of Salivary Biomarkers for Chronic Fatigue Syndrome Sample Collection and Liquid Chromatography-Mass Spectrometry (LC-MS) Analysis Sample Collection Saliva samples were collected using a cotton swab-based collection system (Salivette, Sarstedt, Newton, N.C.). Samples were stored at −80° C., shipped on dry ice and processed according to the manufacturer's instructions.

Protein Content

The level of protein in each saliva sample was quantified using the colorimetric bicinchoninic assay (BCA). Absorbance measurements (562 nm) and standard solutions were used to construct a calibration curve and linear regression was used to determine the final protein concentration for the unknown sample.

Size-Based Centrifugal Filtration

The supernatant was spun through a 50 kDa molecular-weight cutoff (MWCO) filter (regenerated cellulose, Millipore, Billerica, Mass.) at 3,000 g for approximately 1 h at 22° C. The resulting filtrate was loaded into a 10 kDa MWCO filter (regenerated cellulose, Millipore) and spun for 1 h at 3,000 g at 22° C. The concentration of peptide and protein in the resulting filtrate was then determined using a commercially available kit for the BCA assay calibrated using bovine serum albumin standards. To remove salts and increase the concentration of peptides, ~100 μg of protein was passed through a commercially available peptide trap (Michrom, Auburn, Calif.). The peptide concentration was again quantified using the BCA assay. The sample volume was then reduced using a heated centrifugal concentrator (Centrivap, Labconco, Kansas City, Mo.). Concentrated samples were labeled with a mass-specific variant of acetic anhydride, i.e., acetic anhydride with either methyl protons or methyl deuterons (Yu et al., 2004). The labeling mixture consisted of a 1:250 dilution of mass-specific acetic anhydride prepared in ethanol with 50 mM triethylammonium bicarbonate. Samples were incubated for 1 h at 37° C. and then concentrated as described above. Finally, two aliquots (~2.5 μg each) from the same sample, labeled separately with light and heavy forms of acetic anhydride, were combined and injected onto the LC-MS system.

Ion-Trap Mass Spectrometry Detection

The various components of the processed saliva were separated using an ultra-high-pressure liquid chromatography (UPLC) system (Acquity, Waters, Milford, Mass.) with the outlet flowing directly into an ion-trap mass spectrometer (Bruker, Esquire 3000+, Billerica, Mass.). The UPLC was configured with a reversed-phase column (BEH300 C18, 1.7 μm particle, 2.1×100 mm, Waters) and the components were eluted from the column by varying the concentration of methanol in the running buffer linearly over a range from 10 to 35% at a flow rate of 0.3 ml/min. MS scans were collected at 2-5 Hz.

Analysis of LC-MS Data

A custom analysis program was written in LabVIEW (National Instruments, Austin, Tex.) to allow for the objective and automated identification of peak pairs within the data set separated by the expected mass-to-charge (m/z) differences appropriate for labeling with acetic anhydride, e.g., delta m/z of 3 for a singly charged ion that has been labeled with one acetate group, delta m/z of 6 for a singly charged ion that has been labeled with two acetate groups, etc. Because the overall number of ions identified in the CFS samples was lower than typical saliva samples examined previously, this analysis also included comparison of single ions, i.e., delta m/z of 0. Cluster analysis was used to identify peak pairs common to the group at the beginning and end of the study.

High-Resolution MS Sequencing of Salivary Peptides

To determine the amino acid sequence of ions of interest, fractions (~1 min wide) of eluent near the elution time of the target ion were collected from LC injections of labeled saliva. Five fractions were pooled for high-resolution mass spectrometric analysis (12T LTQ-FT Ultra, ProSight PC).

Statistical Analysis

Statistical analysis was conducted using R (version 2.11.1) (Team 2010). For box plots, the horizontal line represents the median value while the boundaries of the rectangle indicate the range of the middle two quartiles. The whiskers indicate a distance 1.5× greater than the interquartile range from the nearest edge of the box. Open circles indicate points beyond the whiskers.

Results

Saliva samples were collected and analyzed as described above. The resulting LC-MS runs were analyzed with custom-written software, which enabled searches for clusters of mass-peak pairs within each group, i.e., searches for ions that were present in the LC-MS data for the majority of members of a particular group. Each LC-MS run was evaluated using the custom application and a list of detected mass pairs was written to a text file. In a typical LC-MS run, hundreds of thousands to millions of peaks were detected, of which several thousand were separated by one of the expected mass differences. The locations of these ion clusters were plotted with retention time serving as the x-coordinate and m/z serving as the y-coordinate.

Figure 2:
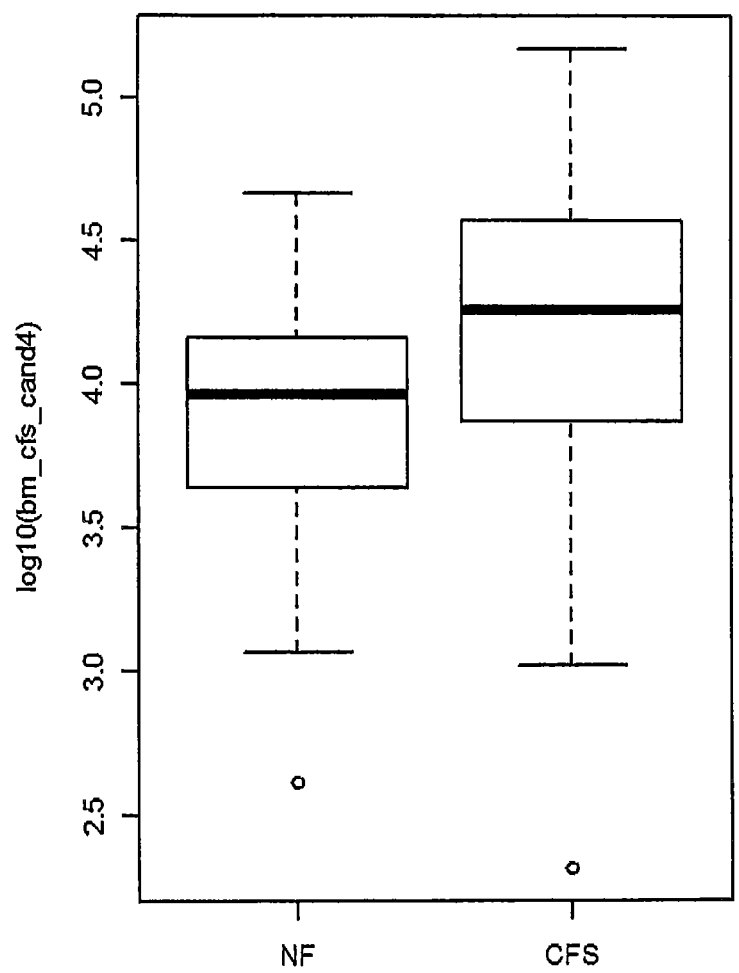
FIG. 2. For the biomarker bm_cfs_cand4, levels are greater in saliva from individuals with chronic fatigue syndrome (CFS) than in saliva from non-fatigued, control individuals (NF). The base 10 logarithm of the ion intensity, as determined by mass spectrometry, is shown as a function of patient type, i.e., CFS vs. NF. Data are shown as boxplots with the solid black line indicating the group median. The hollow box around the solid black line indicates the bounds of the data from the first to the third quartile. The whiskers indicate a distance 1.5× greater than the interquartile range from the nearest edge of the box. A non-parametric test suggested the two samples were unlikely to arise from a common distribution (Wilcoxon rank sum test, $p<0.05$).
Figure 3:
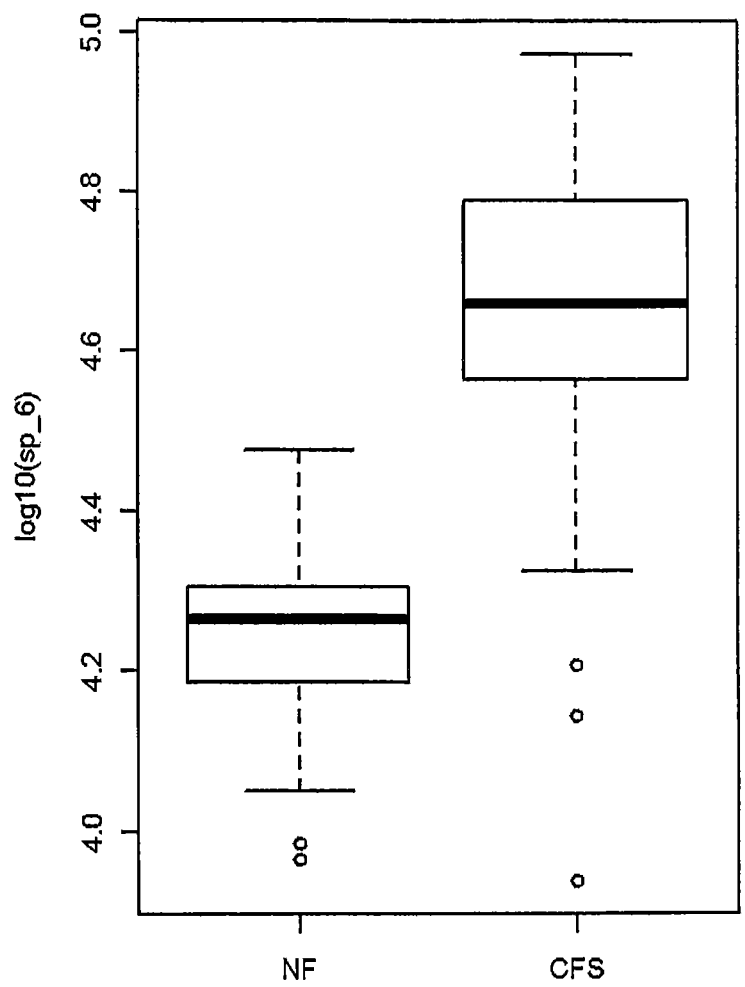
FIG. 3. For the biomarker sp_6, levels are greater in saliva from individuals with chronic fatigue syndrome (CFS) than in saliva from non-fatigued, control individuals (NF). The base 10 logarithm of the ion intensity, as determined by mass spectrometry, is shown as a function of patient type, i.e., CFS vs. NF. Data are shown as boxplots with the solid black line indicating the group median. The hollow box around the solid black line indicates the bounds of the data from the first to the third quartile. The whiskers indicate a distance 1.5× greater than the interquartile range from the nearest edge of the box. A non-parametric test suggested the two samples were unlikely to arise from a common distribution (Wilcoxon rank sum test, $p<0.05$).

From this plot of clusters, sites of potential biomarkers were identified, i.e., those sites for which a cluster appeared in one group, but not in the other. The coordinates of these sites were recorded and used to quantify the ion intensity at that location for each individual in the study. Data for three CFS-biomarker candidates are shown in FIGS. 1-3.

Quantifying Data Collected in an Ion Trap Mass Spectrometer

For the purposes of the study, the following approach for identifying biomarkers has been used. After the small-molecular-weight components of saliva were separated, the total protein concentration of the sample was estimated using a standard BCA assay. Using the estimated protein concentration, a total of 4 μg of protein was injected for each sample in an attempt to normalize the amount of material injected.

High-Resolution Mass Spectrometry Data

Amino acid sequence data for three peptides were obtained using high-resolution mass spectrometry. The high-resolution analysis returned the following sequences for the three peptides using the single-letter amino acid notation: (1) GNPQGPSPQGGNKPQGPPPPPGKPQ [bm_cfs_cand3], (2) PPGKPQGPPPQGGNQPQGPPPPPGKPQ [bm_cfs_cand4], and (3) SPPGKPQGPPQQEGNKPQGPPPPPGKPQ [sp_6]. The genes containing the sequences (1-3) are described below.

Genetic Information for Proteins Containing the Amino Acid Sequence of the Peptides The Proline-rich Salivary Proteins (PRPs) constitute up to 70% of the soluble protein found in human saliva, and homologous proteins have been reported in non-human primates as well as in other animals, including rats, mice and hamsters. In humans, PRPs are the products of two gene families located on chromosome 12: (i) the HaeIII family, comprising two almost identical genes, PRH1 and PRH2, which code for acidic PRPs, and (ii) the BstN1 family, which includes four genes (PRB1, PRB2, PRB3 and PRB4) and codes for basic PRPs. With post-transcriptional and post-translational processing, these six genes are responsible for at least thirteen different human protein products. In addition, a number of allelic forms, representing minor changes in amino acid composition, have also been identified for each of these genes. A variety of functions have been suggested for PRPs in saliva including protection against bacterial pathogens, regulation of calcium phosphate deposition, and most recently as a protective mechanism against dietary tannins and other phenolic compounds.

The biomarker with the amino acid sequence GNPQGPSPQGGNKPQGPPPPPGKPQ is derived from one of the PRB genes, PRB1, as a primary translation product containing 392 amino acids. These two PRB genes code for primary translation products of 392 amino acids (PRB1) and 416 amino acids (PRB2). Removal of the signal peptide produces Basic Salivary Proline-rich Protein 1 and Basic Salivary Proline-rich Protein 2, and further modifications yield several smaller products from each protein. Two of the final products of the PRB1 gene (Basic Salivary Proline-rich Protein 1 and Proline-rich Peptide II-2) contain amino acid sequence (1) [bm_cfs_cand3]. The method of release of the peptide into saliva is unclear. A detailed search of well-characterized proteases did not reveal any with enzymatic specificities that would generate this peptide fragment from the larger proteins.

The biomarker peptide with the amino acid sequence PPGKPQGPPPQGGNQPQGPPPPPGKPQ derives from one, or perhaps both, of a pair of the basic proline-rich protein genes, PRB1 and PRB2, which are closely linked to the PRH genes. These two genes code for primary translation products of 392 amino acids (PRB1) and 416 amino acids (PRB2). Removal of the signal peptide produces Basic Salivary Proline-rich Protein 1 and Basic Salivary Proline-rich Protein 2, and further modifications yield several smaller products from each protein. Three of the final products of the PRB1 gene (Basic Salivary Proline-rich Protein 1, Proline-rich Peptide II-2 and Basic Peptide IB-6) and three from the PRB2 gene (Basic Salivary Proline-rich Protein 2, Basic Proline-rich Peptide IB-7 and Basic Proline-rich Peptide IB-8c) contain amino acid sequence (2) [bm_cfs_cand4]. As with sequence (1), it is as yet unclear whether only one or both of the PRB1 and PRB2 genes is the source of amino acid sequence (2).

The biomarker peptide with the amino acid sequence SPPGKPQGPPQQEGNKPQGPPPPPGKPQ derives from one of the basic proline-rich protein genes, PRB4. The gene codes for a primary translation products of 247 amino acids. Removal of the signal peptide produces Basic Salivary Proline-rich Protein 4, and further modifications yield several smaller products from each protein. Only one of the final products of the PRB4 gene (Basic Salivary Proline-rich Protein 4) contains amino acid sequence (3) [sp_6].

Example 2

Measurement of Biomarker(s)

1. Collect a sample of saliva from the test subject.
   a. Collect saliva by having the subject spit directly into a collection vial or tube.
   b. Collect saliva using a matrix-mediated approach, such as the commercially available Salivette system developed by Salimetrics.
2. Prepare sample for injection into liquid chromatography-mass spectrometry (LC-MS) system.
   a. For saliva collected as in (1a):
      i. Spin saliva at 4 k g for 45 min at 4° C.
      ii. Determine protein concentration using bicinchoninic acid (BCA) assay with bovine serum albumin (BSA) as standard.
      iii. Process saliva through molecular-weight-cutoff filters using 50 kDa and 10 kDa filters, sequentially.
      iv. Pass final supernatant through peptide trap (Michrom, C8).
      v. Determine protein concentration using BCA assay with BSA as standard.
      vi. Dry the sample in a heated chamber with reduced pressure (Centrivap).
      vii. Reconstitute the sample in water with 0.1% acetic acid at a concentration of 0.1 µg of protein/µl.
      viii. Inject a sample containing 4 µg of protein, as determined by BCA assay, into LC-MS system.
   b. For saliva collected as in (1b):
      i. Extract raw saliva from matrix according to manufacturer's instructions.
      ii. Follow steps (2. a.ii-vii)
3. Run LC-MS analysis using a linear gradient of acidified (0.1%) water and methanol (95% to 65% water) to elute compounds from a reversed-phase column.
4. Measure the height of the peak for peptides of interest, as described herein.
5. Inject into the LC-MS system standard peptide solutions in at least three different concentrations using concentration values falling within the normal range of each peptide for 4 µg human saliva.
6. Create a calibration curve for the peptide standards by plotting peak height vs. concentration.
7. For each peptide of interest, use the standard curve results in (6) and divide by 4 µg to determine the relative amount of peptide per µg of total salivary protein, i.e., the biomarker index for each peptide.

Example 3

Determining a Threshold Ratio

1. Using the measurement method described in Example 2, measure the level of peptide in each sample collected from a group of subjects (e.g., a population) determined not to have chronic fatigue syndrome (non-CFS subjects). Such a determination can be made for example as set forth in Reeves et al. ("Prevalence of chronic fatigue syndrome in metropolitan, urban, and rural Georgia" *Population Health Metrics* 5:5 (2007), the entire contents of which are incorporated by reference herein).
2. Determine the median value of the peptide for the population of non-CFS subjects.
3. Determine the standard deviation of the peptide for the population of non-CFS subjects.
4. Set the threshold ratio for identifying a subject as having chronic fatigue syndrome or having an increased likelihood of having or developing chronic fatigue syndrome equal to the following: Two times the standard deviation as determined in (3) plus the median as determined in (2).

Example 4

Novel Salivary Biomarker Associated with Chronic Fatigue Syndrome

Background.

At present, diagnosis of chronic fatigue syndrome (CFS) requires a lengthy and expensive period of clinical examination to rule out all other causes of fatigue. Thus, many patients do not receive timely treatment or are misdiagnosed. Definitive rapid diagnosis is needed to improve the clinical outcomes for patients suffering from CFS.

Methodology/Principal Findings.

Saliva samples were obtained during a survey of the population of the state of Georgia (United States). The goal of this study was to determine incidence of undiagnosed CFS in the general population. Samples of saliva were maintained as a frozen archive until time of analysis. From the archive, samples from 46 subjects with CFS and 45 samples from normal controls were selected for further analysis. The ionizable components below 5 kDa were identified using liquid chromatography-mass spectrometry (LC-MS). Patterns of ion intensity as functions of retention time and mass-to-charge ratio were compared to identify significant differences between the CFS and control groups. A single biomarker candidate for CFS was identified. This biomarker candidate was approximately three times more abundant in saliva from CFS subjects than in saliva from control subjects (p<0.001, Wilcoxon's signed rank). The sensitivity and specificity of the biomarker candidate with respect to correctly identifying CFS are 88 and 91%, respectively. The Receiver Operating Characteristic (ROC) Area-Under-the-Curve (AUC) is 0.935 (95% CI 0.864 to 0.976). De novo sequencing by high-resolution MS revealed that the biomarker candidate was a peptide of molecular weight 2,633 Da. The amino acid sequence of the identified peptide is found within the sequence of the saliva-specific 42 kDa basic Proline-Rich-Protein, PRB4.

Conclusions/Significance.

A salivary peptide identified as a candidate biomarker for CFS may facilitate rapid diagnosis of CFS.

Chronic fatigue syndrome is an orphan disease wrapped in mystery. The etiology of the disease is not clear nor is its diagnosis and prognosis. Even the Fukuda definition, so frequently cited, describes CFS as unexplained fatigue [1]. The absence of clear etiological contributions is highlighted by the variety of labels for the condition including immune dysfunction syndrome, neuroendocrine immune dysfunction syndrome, allergic encephalomyelitis, post viral syndrome and neurasthenia, among others. The self-reported symptoms consistent with CFS include intense fatigue with a duration greater than six months, which is not relieved by rest and causes tiredness that impairs performance of daily activities. CFS is associated with a wide spectrum of symptoms including pain, headaches, cognitive disorders, sleep disorders, anxiety, depression and fatigue exacerbated by exercise. The search for effective treatments has been hampered by the lack of comprehension of the molecular and cellular basis for the development and progression of CFS.

The intense fatigue in CFS has been a cause of confusion with several other chronic conditions such as fibromyalgia, irritable bowel syndrome, and temporomandibular joint syndrome. A lengthy clinical evaluation, including a complete and detailed medical history, should be conducted to rule out other causes of fatigue and to characterize fatigue's form, time of onset, durations, triggering factors, relationship with rest and physical activities. The lack of objective criteria, specific signs and/or tests for the diagnosis of disease has led to an underestimation of CFS prevalence [2]. Although some have estimated that more than 800,000 people suffer from CFS in the US [3], causing a loss of $9 billion annually just in earnings and productivity [4], CDC has projected that only 9-16% of individuals with CFS had been diagnosed [5]. Even when detected, the average time from the beginning of the symptoms to the diagnosis of the syndrome is around 5 years [6]. Because the fatigue associated with CFS is so severe, patients with CFS are 4 times more likely to forgo needed healthcare than non-fatigued subjects [7], worsening the overall health outlook beyond the immediate impact of the disease itself.

Specific salivary peptides can be used to determine the physical fatigue status of athletes and adults during exercise [10]. Specifically the ratio of two endogenous peptides declined by approximately 1,000 fold from a rested state to a physically fatigued state over a period of several hours. Following rest, the peptide levels recovered. Both peptides are derived from a family of saliva specific proteins call Proline Rich Proteins (PRPs). These proteins and their associated peptides are only found in the saliva. In a separate study, the ratio of these peptides, termed the Fatigue Biomarker Index or FBI, was used to investigate physical fatigue levels of candidates for US military Special Forces [11]. These studies showed that a single measurement of the FBI made prior to the start of a rigorous selection process lasting 12 weeks was one of only four variables needed to predict who would ultimately pass and who would fail. In general, those candidates who failed, for reasons related to poor physical performance, had lower FBI levels, and thus higher levels of baseline fatigue than those individuals that passed. This suggests that levels of the FBI may indicate a physiological state of fatigue that is persistent and ultimately affects performance capability over a relatively long period of time. Taken together these findings suggested that saliva may provide an objective means of evaluating chronic fatigue.

In the current study, a comparative proteomic analysis directed at the low molecular weight, <5 kD, fraction of saliva was conducted. The goal of the study was to identify differences between CFS and control subjects. The results demonstrate that there is at least one peptide, derived from the family PRPs, which is significantly elevated in CFS patients relative to controls. This peptide offers promise as an objective diagnostic laboratory test for CFS.

Study Subjects

Figure 4:
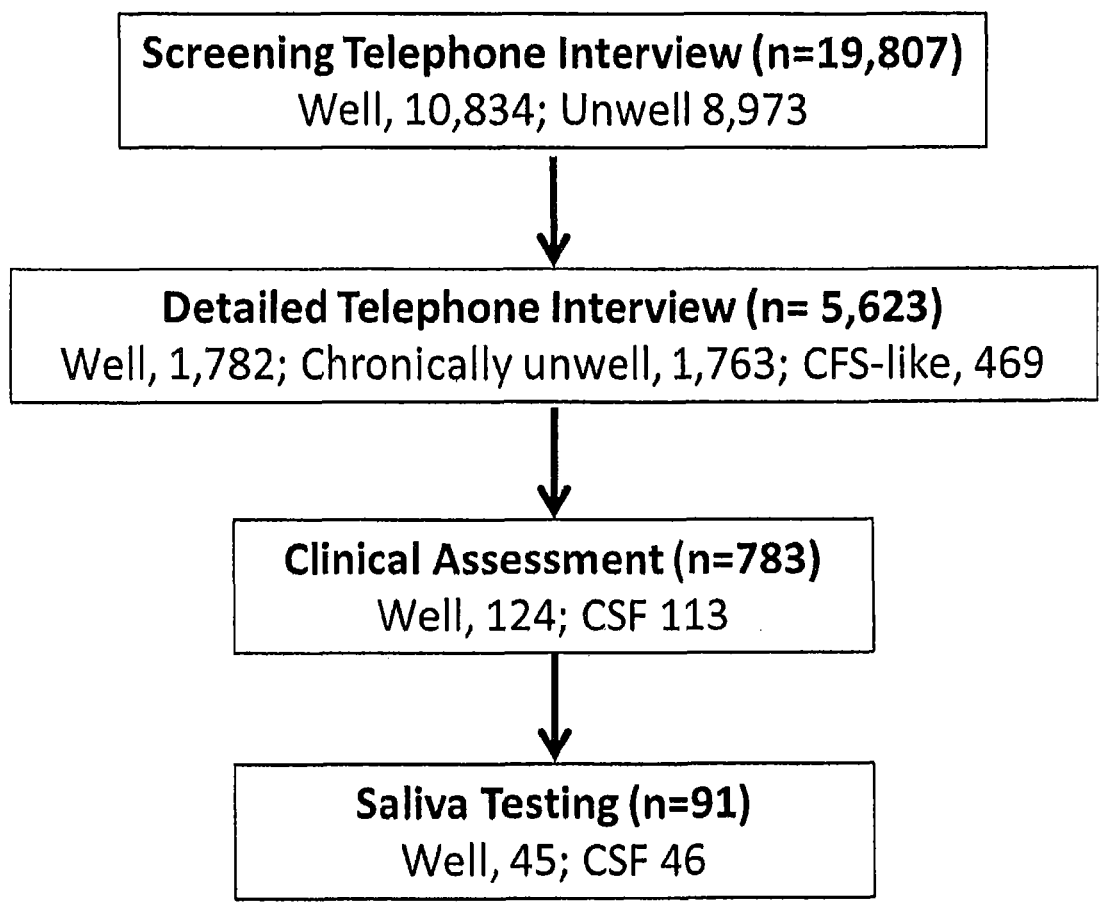
FIG. 4. A flow chart regarding the inclusion/exclusion of patients, showing procedure for obtaining 46 and 45 CFS and control saliva samples, respectively, from 21,165 subjects.

Study saliva samples were obtained from a large cross-sectional population based study of CFS and chronic un-wellness in Georgia, investigating the prevalence of CFS between September 2004 and July 2005 conducted by the Centers for Disease Control and Prevention[7]. Briefly, 10,837 households with 21,165 members were contacted initially by telephone interview. At the end of screening and selection a total of 112 participants met established clinical criteria for CFS using the criteria established by the 1994 international research case definition [1] using validated test instruments as specified by the International CFS Study Group [12] and CDC standards [13]. A total of 147 subjects identified as non-fatigued were identified during the Georgia study. The control subjects were clinically evaluated and saliva samples were obtained. Saliva samples were collected from these subjects and controls for the purpose of determining salivary cortisol levels [14]. In all cases, the sample obtained at 8 AM was used for the purpose of biomarker discovery. A total of 46 and 45 CFS and control saliva samples, respectively, were obtained for the purpose of biomarker discovery (FIG. 4). Samples were stored at −80° C. and shipped on dry ice until thawed for processing.

Processing of Saliva

Saliva samples were thawed at room temperature and spun for 10 minutes to remove particulates. The resulting supernatant was filtered sequentially through 50 kDa and 10 kDa molecular-weight cutoff filters (regenerated cellulose, Millipore, Billerica, Mass.) to produce a low molecular weight fraction of saliva. Approximately 100 ug of peptide, as determined by BCA, was desalted using a C-8 column designed for this purpose (Michrom, Auburn, Calif.).

Ion-Trap Mass Spectrometry to Identify Putative Biomarkers of CFS

Ion-trap mass spectrometers are capable of detecting components between a m/z of 150 to 2,000 with a precision of 0.1 m/z. The processed low-molecular weight saliva fraction was introduced onto an ultra-high-pressure liquid chromatography (UPLC) system (Acquity, Waters, Milford, Mass.) with the outlet flowing directly into an ion-trap mass spectrometer (Bruker, Esquire 3000+, Billerica, Mass.). The UPLC was configured with a reversed-phase column (BEH300 C18, 1.7 µm particle, 2.1×100 mm, Waters) and the components were eluted from the column by varying the concentration of methanol in the running buffer linearly over a range from 10 to 35% at a flow rate of 0.3 ml/min. MS scans were collected at 2-5 Hz. An analysis program (PeakQuest, Hyperion Biotechnology, San Antonio, Tex.) was used to identify putative biomarkers. PeakQuest enables identification of changes in the relative abundance of peptides. In this case, PeakQuest identifies component peptides that vary significantly in relative abundance compared to normal controls.

Definitive Chemical Identification of CFS Biomarkers

All putative biomarkers were found in a normal healthy pool of standard saliva (Hyperion Biotechnology Inc., San Antonio, Tex.). Portions of normal pool saliva were processed in the manner described and fractions 1 minute wide corresponding to the elution time were collected. Fractions were combined and concentrated and evaluated using high-resolution mass spectrometry (HRMS) (12T LTQ-FT Ultra, Pro Sight PC). HRMS provides a very precise estimation of peptides and peptide fragment mass, e.g., m/z±0.00001. During HRMS, peptide ions are fragmented by electron bombardment leading to specific disruption of peptide bonds. The disruption leads to the production of smaller peptides and individual amino acids obtained from the parent peptide. The mass of these resulting fragments is determined with great precision. The estimated masses acquired in this manner are then compared to theoretical masses that are found on extensive tables. The theoretical composition of the fragments enables a reconstruction of the parent peptide. This process is known as de novo sequencing. The de novo sequence determined in this manner can be confirmed by synthesizing the peptide called for from the de novo sequence. If the synthesized peptide demonstrates similar retention time and m/z on the system used for discovery (ion-trap instrument), the identity of the biomarker is confirmed. The de novo sequence data was used to direct synthesis of biomarker peptides. Milligram quantities of biomarkers were synthesized (Anaspec, Fremont, Calif.). The elution times and MS/MS fragmentation patterns of the synthesized peptides were observed and compared to similar data obtained from processed saliva.

Statistical Analysis

Statistical analysis was conducted using SYSTAT (SPSS Inc., Chicago, Ill.). The receiver operator characteristic (ROC) curve was calculated and analyzed using MedCalc ver. 12.2.1, (MedCalc Software, Mariakerke, Belgium). The standard error associated with ROC associated Area Under the Curve (AUC) was calculated using the method of DeLong [15]. Comparison between control and CFS was made by t-tests. Comparisons of distribution of subjects to control and CFS groups according to lifestyle, health factors and demographic factors were made using the Chi-square statistic.

Figure 5:
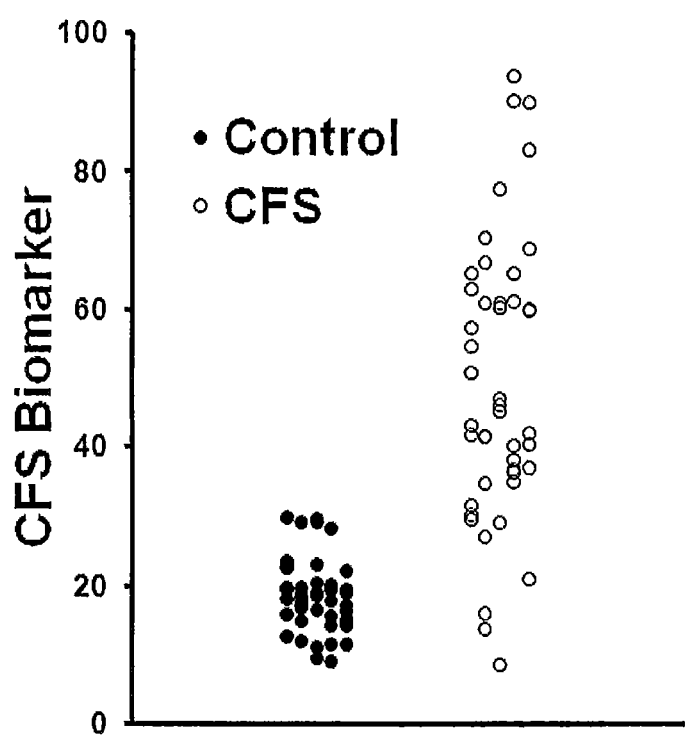
FIG. 5. CFS biomarker levels in CFS and normal subjects. Y-axis shows thousands of intensity units corresponding to concentration of CFS biomarker peptide in saliva normalized to total protein. Each circle represents a single sample.

A biomarker candidate for CFS was identified. Specifically, levels of the biomarker candidate were higher in CFS subjects than control as shown in FIG. 5. Setting a threshold value to 28,840 intensity units leads to a test with sensitivity of 91% and specificity of 88%. With regard to CFS, it is desirable to provide the highest possible confidence with regard to diagnosis. To increase confidence in positive diagnosis, a measured value above 35,000 provides 100% confidence of a diagnosis of CFS. However, at this level, 8 of 46 patients that are identified as having CFS based on clinical signs are incorrectly determined to be normal.

Subsequently, de novo sequencing of the putative biomarker using a high-resolution mass spectrometer led to chemical identification of the biomarker candidate, a peptide with the amino acid sequence SPPGKPQGPPQQEGNKPQGPPPPGKPQ. The observed mass of the whole peptide was 2725.3907, which is in good agreement with the theoretical mass of 2725.3900 (p=6.88 E-73). A peptide of the same sequence was synthesized and tested on the original LC-MS system used for discovery studies. The retention time, m/z and fragmentation pattern of the synthesized peptide on the LC-MS system used for discovery were virtually identical to those observed for the ion of interest originally identified in saliva.

The amino acid sequence of the candidate CFS biomarker is found within the amino acid sequence of the human salivary protein, Basic Proline Rich Protein 4 (PRB4_HUMAN, P10163). This sequence is not found within any other known animal, bacterial or plant proteins. In humans, PBR4 is known to be expressed only in the parotid and other saliva glands.

Analysis was performed to determine if levels of the biomarker candidate were dependent on various demographic factors. Table 3 shows the distribution of subjects according to use of medication, gender, race, smoking, regularity of menstruation, menopause status, and obesity. Table 3 indicates that the CFS subjects are more likely to be taking medication, be smokers and have irregular menstruation than the normal subjects group. Table 3 shows that age and BMI are not statistically different between CFS and normal subjects.

Because the distribution of demographic factors is quite different between CFS and normal subjects, it may be argued that the CFS biomarker candidate identified in this study is instead a measure of factors related specifically to sampling differences. In other words, the biomarker candidate may be associated with medication usage, smoking or other demographic factors. To examine this possibility, CFS subjects were compared statistically using t-test. These results are shown in Table 4. Medication status, gender, race, smoking status, quality of menstruation, menopause status, and obesity were not associated with CFS biomarker level. Similarly, relationship of age and BMI to biomarker level was also examined. In this case no association was observed between these factors and level of the biomarker in CFS subjects. Taken together these observations suggest that the CFS biomarker is associated only with CFS and not with other factors examined here.

Figure 6:
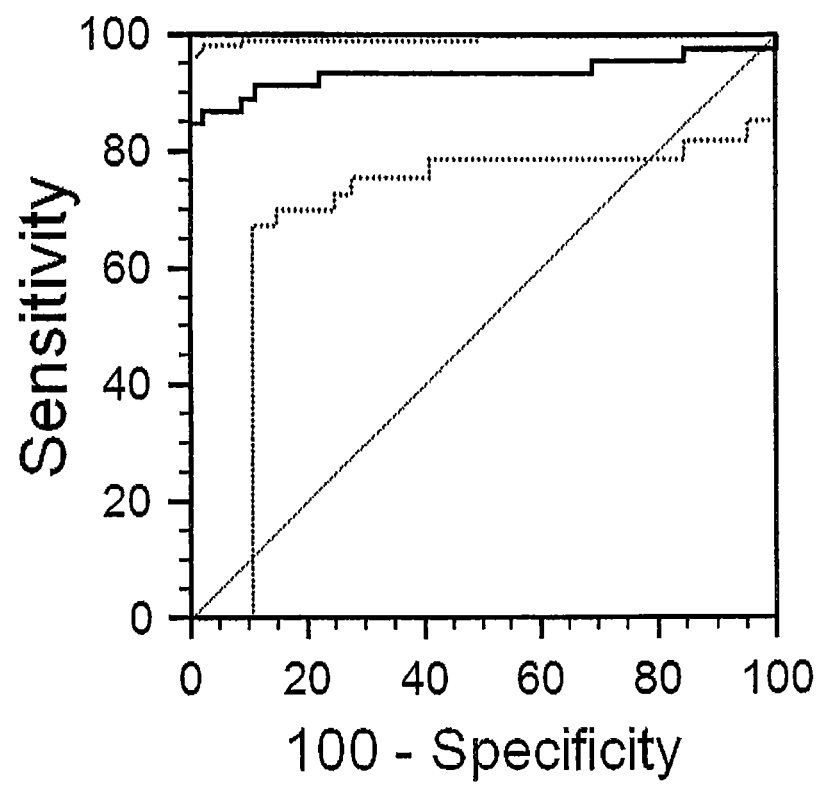
FIG. 6. ROC curve for CFS salivary biomarker. Heavy solid line indicates sensitivity as a function of specificity (100-sensitivity). Dotted lines indicate 95% confidence interval. Light diagonal line indicates relationship between sensitivity and specificity if both CFS and control populations are the same. P-value associated with a comparison between the observed ROC AUC and ROC AUC=0.5 (no discrimination between diseased and normal) is <0.0001.

The diagnostic utility was evaluated through construction of a Receiver Operating Characteristic (ROC) curve. The ROC curve is shown in FIG. 6. The calculated Area-Under-the-Curve (AUC) of this ROC curve is 0.935 with a standard error of 0.0319 and with a 95% confidence interval using the binomial exact method of 0.864 to 0.976. A diagnostic test that has ROC AUC of 1.0 indicates a test that is able to perfectly discriminate between subjects with the disease and those that do not have the disease. A ROC AUC of 0.5 indicates a test that does no better than random assignment of individuals to groups.

The present study confirms that saliva can be used for detection and evaluation of disease-associated biomarkers and that CFS modulates the expression of a very specific set of molecules. A battery of biochemical and bioinformatic tools was employed to identify a 2.7 kDa peptide present in the salivary samples from CFS patients, at levels much higher than that of normal subjects. By identifying the amino acid sequence of this peptide and performing a search against the non-redundant GenBank® database, it was determined that the 2.7 kDa peptide is a fragment of human salivary proline-rich protein 4 (PRB4).

PRB4 belongs to the family of human salivary proline-rich proteins (PRPs), which include six closely linked genes on chromosome 12p13.2. All of the PRP genes are similar in structure, with complex electrophoretic patterns. Each PRP gene is approximately 4.0 kb in length and contains four exons, the third of which is entirely composed of 63-bp tandem repeats and encodes the proline-rich portion of the protein products. Exon 3 contains different numbers of tandem repeats in the different PRP genes. Variation in the numbers of these repeats is also responsible for length variations in different alleles of the PRB genes.

Currently, there are no specific biological or morphological biomarkers to establish per se the diagnosis of CFS. Its diagnosis is indefinite, and established through the exclusion of other diseases causing fatigue. Several studies have been conducted toward discovery of CFS biomarker(s), but the outcomes have been uncertain.

In conclusion, in the present study, a specific salivary biomarker was detected in subjects with CFS. Further studies are being designed to evaluate if the identified salivary 2.7 kDa peptide is not only a diagnostic biomarker but also a prognostic tool as well. In addition, other roles for this peptide, e.g., as a potential mediator of disease development and its progression, are currently being assessed.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

REFERENCES

1. Fukuda, K., et al., *The chronic fatigue syndrome: a comprehensive approach to its definition and study. International Chronic Fatigue Syndrome Study Group*. Ann Intern Med, 1994. 121(12): p. 953-9.
2. Fernandez, A. A., A. P. Martin, and M. I. Martinez, [*Chronic fatigue syndrome. Consensus document*]. Aten Primaria, 2009. 41(10): p. 529-31.
3. Jason, L. A., et al., *Chronic fatigue syndrome: the need for subtypes*. Neuropsychol Rev, 2005. 15(1): p. 29-58.
4. Reynolds, K. J., et al., *The economic impact of chronic fatigue syndrome*. Cost Eff Resour Alloc, 2004. 2(1): p. 4.
5. Albright, F., et al., *Evidence for a heritable predisposition to Chronic Fatigue Syndrome*. BMC Neurol, 2011. 11: p. 62.
6. Cairns, R. and M. Hotopf, *A systematic review describing the prognosis of chronic fatigue syndrome*. Occup Med (Lond), 2005. 55(1): p. 20-31.
7. Lin, J. M., et al., *Barriers to healthcare utilization in fatiguing illness: a population-based study in Georgia*. BMC Health Serv Res, 2009. 9: p. 13.
8. Hardt, M., et al., *Toward defining the human parotid gland salivary proteome and peptidome: identification and characterization using 2D SDS-PAGE, ultrafiltration, HPLC, and mass spectrometry*. Biochemistry, 2005. 44(8): p. 2885-99.
9. Denny, P. C., et al., *A novel saliva test for caries risk assessment*. J Calif Dent Assoc, 2006. 34(4): p. 287-90, 292-4.
10. Michael, D. J., et al., *Fatigue biomarker index: an objective salivary measure of fatigue level*. Accid Anal Prev, 2012. 45 Suppl: p. 68-73.
11. Kalns, J., et al., *Predicting success in the tactical air combat party training pipeline*. Mil Med, 2011. 176(4): p. 431-7.
12. Reeves, W. C., et al., *Identification of ambiguities in the 1994 chronic fatigue syndrome research case definition and recommendations for resolution*. BMC Health Serv Res, 2003. 3(1): p. 25.
13. Reeves, W. C., et al., *Prevalence of chronic fatigue syndrome in metropolitan, urban, and rural Georgia*. Popul Health Metr, 2007. 5: p. 5.
14. Nater, U. M., et al., *Attenuated morning salivary cortisol concentrations in a population-based study of persons with chronic fatigue syndrome and well controls*. J Clin Endocrinol Metab, 2008. 93(3): p. 703-9.
15. DeLong, G. R. and J. T. Dwyer, *Correlation of family history with specific autistic subgroups: Asperger's syndrome and bipolar affective disease*. J Autism Dev Disord, 1988. 18(4): p. 593-600.
16. Minaguchi, K., G. Madapallimattam, and A. Bennick, *The presence and origin of phosphopeptides in human saliva*. Biochem J, 1988. 250(1): p. 171-7.
17. Cai, K. and A. Bennick, *Processing of acidic proline-rich proprotein by human salivary gland convertase*. Arch Oral Biol, 2004. 49(11): p. 871-9.
18. Zoukhri, D., et al., *Discovery of putative salivary biomarkers for Sjogren's syndrome using high resolution mass spectrometry and bioinformatics*. J Oral Sci, 2012. 54(1): p. 61-70.
19. Raison, C. L., J. M. Lin, and W. C. Reeves, *Association of peripheral inflammatory markers with chronic fatigue in a population-based sample*. Brain Behav Immun, 2009. 23(3): p. 327-37.
20. Aslakson, E., et al., *Replication of an empirical approach to delineate the heterogeneity of chronic unexplained fatigue*. Popul Health Metr, 2009. 7: p. 17.
21. Hu, S., et al., *Differentially expressed protein markers in human submandibular and sublingual secretions*. Int J Oncol, 2004. 25(5): p. 1423-30.
22. Jerjes, W. K., et al., *Diurnal patterns of salivary cortisol and cortisone output in chronic fatigue syndrome*. J Affect Disord, 2005. 87(2-3): p. 299-304.
23. Gaab, J., et al., *Hypothalamic-pituitary-adrenal axis reactivity in chronic fatigue syndrome and health under psychological, physiological, and pharmacological stimulation*. Psychosom Med, 2002. 64(6): p. 951-62.
24. Dodds, M. W., D. A. Johnson, and C. K. Yeh, *Health benefits of saliva: a review*. J Dent, 2005. 33(3): p. 223-33.
25. Cannon, J. G., et al., *Acute phase responses and cytokine secretion in chronic fatigue syndrome*. J Clin Immunol, 1999. 19(6): p. 414-21.
26. Skowera, A., et al., *High levels of type 2 cytokine producing cells in chronic fatigue syndrome*. Clin Exp Immunol, 2004. 135(2): p. 294-302.
27. Caligiuri, M., et al., *Phenotypic and functional deficiency of natural killer cells in patients with chronic fatigue syndrome*. J Immunol, 1987. 139(10): p. 3306-13.
28. ter Wolbeek, M., et al., *Glucocorticoid sensitivity of immune cells in severely fatigued adolescent girls: a longitudinal study*. Psychoneuroendocrinology, 2008. 33(3): p. 375-85.

Azen E A. "Genetics of Salivary Protein Polymorphisms" *Critical Reviews in Oral Biology and Medicine* 4:479-484 (1993)

Minaguchi K and Bennick A. "Genetics of Human Salivary Proteins" *Journal of Dental Research* 68:2-15 (1989)

Kim H and Maeda N. "Structures of Two HaeIII-type Genes in the Human Salivary Proline-rich Protein Multigene Family" *Journal of Biological Chemistry* 261:6712-6718 (1985)

Carlson D M. "Salivary Proline-rich Proteins: Biochemistry, Molecular Biology and Regulation of Expression" *Critical Reviews in Oral Biology and Medicine* 4:495-502 (1993)

Messana et al. "Trafficking and Postsecretory Events Responsible for the Formation of Secreted Human Salivary Peptides" *Molecular and Cellular Proteomics* 7:911-926 (2008)

```
Basic Proline-rich Protein 2 (PRB2; UniProt:
P02812)
MLLILLSVALLALSSAQNLNEDVSQEESPSLIAGNPQGAPPQGGNKPQGP
PSPPGKPQGPPPQGGNQPQGPPPPGKPQGPPPQGGNKPQGPPPPGKPQG
PPPQGDKSRSPRSPPGKPQGPPPQGGNQPQGPPPPGKPQGPPPQGGNKP
QGPPPPGKPQGPPPQGDNKSRSSRSPPGKPQGPPPQGGNQPQGPPPPGK
PQGPPPQGGNKPQGPPPPGKPQGPPPQGDNKSQSARSPPGKPQGPPPQGG
NQPQGPPPPGKPQGPPPQGGNKSQGPPPPGKPQGPPPQGGSKSRSSRSP
PGKPQGPPPQGGNQPQGPPPPGKPQGPPPQGGNKPQGPPPPGKPQGPPP
QGGSKSRSARSPPGKPQGPPQQEGNNPQGPPPPAGGNPQQPQAPPAGQPQ
GPPRPPQGGRPSRPPQ 5-mer peptides of P02812
MLLIL    SPPGK    PQGDK    PPPGK    PQGGG    PPPPP
LLILL    PPGKP    QGDKS    PPGKP    PQGGN    PPPPG
LILLS    PGKPQ    GDKSR    PGKPQ    QGGNK    PPPGK
ILLSV    GKPQG    DKSRS    GKPQG    GGNKP    PPGKP
LLSVA    KPQGP    KSRSP    KPQGP    GNKPQ    PGKPQ
LSVAL    PQGPP    SRSPR    PQGPP    NKPQG    GKPQG
SVALL    QGPPP    RSPRS    QGPPP    KPQGP    KPQGP
VALLA    GPPPQ    SPRSP    GPPPQ    PQGPP    PQGPP
ALLAL    PPPQG    PRSPP    PPPQG    QGPPP    QGPPP
LLALS    PPQGG    RSPPG    PPQGD    GPPPP    GPPPQ
LALSS    PQGGN    SPPGK    PQGDN    PPPPG    PPPQG
ALSSA    QGGNQ    PPGKP    QGDNK    PPPGK    PPQGG
LSSAQ    GGNQP    PGKPQ    GDNKS    PPGKP    PQGGN
SSAQN    GNQPQ    GKPQG    DNKSR    PGKPQ    QGGNK
SAQNL    NQPQG    KPQGP    NKSRS    GKPQG    GGNKS
AQNLN    QPQGP    PQGPP    KSRSS    KPQGP    GNKSQ
QNLNE    PQGPP    QGPPP    SRSSR    PQGPP    NKSQG
NLNED    QGPPP    GPPPQ    RSSRS    QGPPP    KSQGP
LNEDV    GPPPP    PPPQG    SSRSP    GPPPQ    SQGPP
NEDVS    PPPPP    PPQGG    SRSPP    PPPQG    QGPPP
EDVSQ    PPPPG    PQGGN    RSPPG    PPQGD    GPPPP
DVSQE    PPPGK    QGGNQ    SPPGK    PQGDN    PPPPG
VSQEE    PPGKP    GGNQP    PPGKP    QGDNK    PPPGK
SQEES    PGKPQ    GNQPQ    PGKPQ    GDNKS    PPGKP
QEESP    GKPQG    NQPQG    GKPQG    DNKSQ    PGKPQ
EESPS    KPQGP    QPQGP    KPQGP    NKSQS    GKPQG
ESPSL    PQGPP    PQGPP    PQGPP    KSQSA    KPQGP
SPSLI    QGPPP    QGPPP    QGPPP    SQSAR    PQGPP
PSLIA    GPPPQ    GPPPP    GPPPQ    QSARS    QGPPP
SLIAG    PPPQG    PPPPG    PPPQG    SARSP    GPPPQ
LIAGN    PPQGG    PPPGK    PPQGG    ARSPP    PPPQG
IAGNP    PQGGN    PPGKP    PQGGN    RSPPG    PPQGG
AGNPQ    QGGNK    PPGKP    QGGNQ    SPPGK    PQGGS
GNPQG    GGNKP    PGKPQ    GGNQP    PPGKP    QGGSK
NPQGA    GNKPQ    GKPQG    GNQPQ    PGKPQ    GGSKS
PQGAP    NKPQG    KPQGP    NQPQG    GKPQG    GSKSR
QGAPP    KPQGP    PQGPP    QPQGP    KPQGP    SKSRS
GAPPQ    PQGPP    QGPPP    PQGPP    PQGPP    KSRSS
APPQG    QGPPP    GPPPQ    QGPPP    QGPPP    SRSSR
PPQGG    GPPPP    PPPQG    GPPPP    GPPPQ    RSSRS
PQGGN    PPPPG    PPQGG    PPPPG    PPPQG    SSRSP
QGGNK    PPPGK    PQGGN    PPPPG    PPQGG    SRSPP
GGNKP    PPGKP    QGGNK    PPGKP    PQGGN    RSPPG
GNKPQ    PGKPQ    GGNKP    PGKPQ    QGGNQ    SPPGK
NKPQG    GKPQG    GNKPQ    GKPQG    GGNQP    PPGKP
KPQGP    KPQGP    NKPQG    KPQGP    GNQPQ    PGKPQ
PQGPP    KPQGP    KPQGP    PQGPP    NQPQG    GKPQG
QGPPS    QGPPP    PQGPP    QGPPP    QPQGP    KPQGP
GPPSP    GPPPQ    QGPPP    PQGPP    PQGPP    PQGPP
PPSPP    PPPQG    GPPPP    GPPPQ    QGPPP    QGPPP
PSPPG    PPQGD    PPPPG    PPPQG    GPPPP    GPPPQ
PPPQG    SARSP    GRPSR
```

```
PPQGG    ARSPP    RPSRP
PQGGN    RSPPG    PSRPP
QGGNQ    SPPGK    SRPPQ
GGNQP    PPGKP
GNQPQ    PGKPQ
NQPQG    GKPQG
QPQGP    KPQGP
PQGPP    PQGPP
QGPPP    QGPPQ
GPPPP    GPPQQ
PPPPP    PPQQE
PPPPG    PQQEG
PPPGK    QQEGN
PPGKP    QEGNN
PGKPQ    EGNNP
GKPQG    GNNPQ
KPQGP    NNPQG
PQGPP    NPQGP
QGPPP    PQGPP
GPPPQ    QGPPP
PPPQG    GPPPP
PPQGG    PPPPA
PQGGN    PPPAG
QGGNK    PPAGG
GGNKP    PAGGN
GNKPQ    AGGNP
NKPQG    GGNPQ
KPQGP    GNPQQ
PQGPP    NPQQP
QGPPP    PQQPA
GPPPP    QQPAP
PPPPG    QPQAP
PPPGK    PQAPP
PPGKP    QAPPA
PGKPQ    APPAG
GKPQG    PPAGQ
KPQGP    PAGQP
PQGPP    AGQPQ
QGPPP    GQPQG
GPPPQ    QPQGP
PPPQG    PQGPP
PPQGG    QGPPR
PQGGS    GPPRP
QGGSK    PPRPP
GGSKS    PRPPQ
GSKSR    RPPQG
SKSRS    PPQGG
KSRSA    PQGGR
SRSAR    QGGRP
RSARS    GGRPS
```

```
Basic Proline-rich Protein 3 (PRB3; UniProt:
Q04118)
MLLILLSVALLALSSAQSLNEDVSQEESPSVISGKPEGRRPQGGNQPQRT
PPPPGKPEGRPPQGGNQSQGPPPRPGKPEGPPPQGGNQSQGPPPRPGKPE
GQPPQGGNQSQGPPPRPGKPEGPPPQGGNQSQGPPPRPGKPEGPPPQGGN
QSQGPPPHPGKPEGPPPQGGNQSQGPPPRPGKPEGPPPQGGNQSQGPPPR
PGKPEGPPPQGGNQSQGPPPRPGKPEGSPSQGGNKPQGPPPHPGKPQGPP
PQEGNKPQRPPPPGRPQGPPPPGGNPQQPLPPPAGKPQGPPPPPQGGRPH
RPPQGPPPQ 5-mer peptides of Q04118
MLLIL    PPPGK    PPQGG    GPPPH    EGPPP    KPQRP
LLILL    PPGKP    PQGGN    PPPHP    GPPPQ    PQRPP
LILLS    PGKPE    QGGNQ    PPHPG    PPPQG    QRPPP
ILLSV    GKPEG    GGNQS    PHPGK    PPQGG    RPPPP
LLSVA    KPEGR    GNQSQ    HPGKP    PQGGN    PPPPG
LSVAL    PEGRP    NQSQG    PGKPE    QGGNQ    PPPGR
SVALL    EGRPP    QSQGP    GKPEG    GGNQS    PPGRP
VALLA    GRPPQ    SQGPP    KPEGP    GNQSQ    PGRPQ
ALLAL    RPPQG    QGPPP    PEGPP    NQSQG    GRPQG
LLALS    PPQGG    GPPPR    EGPPP    QSQGP    RPQGP
LALSS    PQGGN    PPPRP    GPPPQ    SQGPP    PQGPP
ALSSA    QGGNQ    PPRPG    PPPQG    QGPPP    QGPPP
LSSAQ    GGNQS    PRPGK    PPQGG    GPPPR    GPPPP
SSAQS    GNQSQ    RPGKP    PQGGN    PPPRP    PPPPG
SAQSL    NQSQG    PGKPE    QGGNQ    PPRPG    PPPGG
AQSLN    QSQGP    GKPEG    GGNQS    PRPGK    PPGGN
QSLNE    SQGPP    KPEGP    GNQSQ    RPGKP    PGGNP
SLNED    QGPPP    PEGPP    NQSQG    PGKPE    GGNPQ
LNEDV    GPPPR    EGPPP    QSQGP    GKPEG    GNPQQ
```

```
NEDVS    PPPRP    GPPPQ    SQGPP    KPEGS    NPQQP
EDVSQ    PPRPG    PPPQG    QGPPP    PEGSP    PQQPL
DVSQE    PRPGK    PPQGG    GPPPR    EGSPS    QQPLP
VSQEE    RPGKP    PQGGN    PPPRP    GSPSQ    QPLPP
SQEES    PGKPE    QGGNQ    PPRPG    SPSQG    PLPPP
QEESP    GKPEG    GGNQS    PRPGK    PSQGG    LPPPA
EESPS    KPEGP    GNQSQ    RPGKP    SQGGN    PPPAG
ESPSV    PEGPP    NQSQG    PGKPE    QGGNK    PPAGK
SPSVI    EGPPP    QSQGP    GKPEG    GGNKP    PAGKP
PSVIS    GPPPQ    SQGPP    KPEGP    GNKPQ    AGKPQ
SVISG    PPPQG    QGPPP    PEGPP    NKPQG    GKPQG
VISGK    PPQGG    GPPPR    EGPPP    KPQGP    KPQGP
ISGKP    PQGGN    PPPRP    GPPPQ    PQGPP    PQGPP
SGKPE    QGGNQ    PPRPG    PPPQG    QGPPP    QGPPP
GKPEG    GGNQS    PRPGK    PPQGG    GPPPH    GPPPP
KPEGR    GNQSQ    RPGKP    PQGGN    PPPHP    PPPPP
PEGRR    NQSQG    PGKPE    QGGNQ    PPHPG    PPPPQ
EGRRP    QSQGP    GKPEG    GGNQS    PHPGK    PPPQG
GRRPQ    SQGPP    KPEGP    GNQSQ    HPGKP    PPQGG
RRPQG    QGPPP    PEGPP    NQSQG    PGKPQ    PQGGR
RPQGG    GPPPR    EGPPP    QSQGP    GKPQG    QGGRP
PQGGN    PPPRP    GPPPQ    SQGPP    KPQGP    GGRPH
QGGNQ    PPRPG    PPPQG    QGPPP    PQGPP    GRPHR
GGNQP    PRPGK    PPQGG    GPPPR    QGPPP    RPHRP
GNQPQ    RPGKP    PQGGN    PPPRP    GPPPQ    PHRPP
NQPQR    PGKPE    QGGNQ    PPRPG    PPPQG    HRPPQ
QPQRT    GKPEG    GGNQS    PRPGK    PPQEG    RPPQG
PQRTP    KPEGQ    GNQSQ    RPGKP    PQEGN    PPQGQ
QRTPP    PEGQP    NQSQG    PGKPE    QEGNK    PQGQP
RTPPP    EGQPP    QSQGP    GKPEG    EGNKP    QGQPP
TPPPP    GQPPQ    SQGPP    KPEGP    GNKPQ    GQPPQ
PPPPG    QPPQG    QGPPP    PEGPP    NKPQR

Basic Proline-rich Protein 4 (PRB4; UniProt:
E9PAL0)
MLLILLSVALLALSSAESSSEDVSQEESLFLISGKPEGRRPQGGNQPQRP
PPPPGKPQGPPPQGGNQSQGPPPPGKPEGRPPQGGNQSQGPPPHPGKPE
RPPPQGGNQSQGTPPPPGKPERPPPQGGNQSHRPPPPPGKPERPPPQGGN
QSQGPPPHPGKPEGPPPQEGNKSRSARSPPGKPQGPPQQEGNKPQGPPPP
GKPQGPPPAGGNPQQPAPPAGKPQGPPPPPQGGRPPRPAQGQQPPQ 5-mer peptides of E9PAL0
MLLIL    PPPGK    GPPPH    GPPPA
LLILL    PPGKP    PQGGN    PPPHP    PPPAG
LILLS    PGKPQ    QGGNQ    PPHPG    PPAGG
ILLSV    GKPQG    GGNQS    PHPGK    PAGGN
LLSVA    KPQGP    GNQSQ    HPGKP    AGGNP
LSVAL    PQGPP    NQSQG    PGKPE    GGNPQ
SVALL    QGPPP    QSQGT    GKPEG    GNPQQ
VALLA    GPPPQ    SQGTP    KPEGP    NPQQP
ALLAL    PPPQG    QGTPP    PEGPP    PQQPA
LLALS    PPQGG    GTPPP    EGPPP    QQPQA
LALSS    PQGGN    TPPPP    GPPPQ    QPQAP
ALSSA    QGGNQ    PPPPG    PPPQE    PQAPP
LSSAE    GGNQS    PPPGK    PPQEG    QAPPA
SSAES    GNQSQ    PPGKP    PQEGN    APPAG
SAESS    NQSQG    PGKPE    QEGNK    PPAGK
AESSS    QSQGP    GKPER    EGNKS    PAGKP
ESSSE    SQGPP    KPERP    GNKSR    AGKPQ
SSSED    QGPPP    PERPP    NKSRS    GKPQG
SSEDV    GPPPP    ERPPP    KSRSA    KPQGP
SEDVS    PPPPP    RPPPQ    SRSAR    PQGPP
EDVSQ    PPPPG    PPPQG    RSARS    QGPPP
DVSQE    PPPGK    PPQGG    SARSP    GPPPP
VSQEE    PPGKP    PQGGN    ARSPP    PPPPP
SQEES    PGKPE    QGGNQ    RSPPG    PPPPQ
QEESL    GKPEG    GGNQS    SPPGK    PPPQG
EESLF    KPEGR    GNQSS    PPGKP    PPQGG
ESLFL    PEGRP    NQSSG    PGKPQ    PQGGR
SLFLI    EGRPP    QSHRP    GKPQG    QGGRP
LFLIS    GRPPQ    SHRPP    KPQGP    GGRPP
FLISG    RPPQS    HRPPP    PQGPP    GRPPR
LISGK    PPQGG    RPPPQ    QGPPP    RPPRP
ISGKP    PQGGN    PPPPG    GPPPQ    PPRPA
SGKPE    QGGNQ    PPPPG    PPPQE    PRPAQ
GKPEG    GGNQS    PPPGK    PPQEG    RPAQG
KPEGR    GNQSQ    PGKPQ    QQEGN    PAQGQ
PEGRR    NQSQG    PGKPE    QEGNK    AQGQQ
EGRRP    QSQGP    GKPER    EGNKP    QGQQP
GRRPQ    SQGPP    KPERP    GNKPQ    GQQPP
RRPQG    QGPPP    PERPP    NKPQG    QQPPQ
```

...

```
RPQGG    GPPPH    ERPPP    KPQGP
PQGGN    PPPHP    RPPPQ    PQGPP
QGGNQ    PPHPG    PPPQG    QGPPP
GGNQP    PHPGK    PPQGG    GPPPP
GNQPQ    HPGKP    PQGGN    PPPPG
NQPQR    PGKPE    QGGNQ    PPPGK
QPQRP    GKPER    GGNQS    PPGKP
PQRPP    KPERP    GNQSQ    PGKPQ
QRPPP    PERPP    NQSQG    GKPQG
RPPPP    ERPPP    QSQGP    KPQGP
PPPPP    RPPPQ    SQGPP    PQGPP
PPPPG    PPPQG    QGPPP    QGPPP

Basic Proline-rich Protein 4 (PRB4; UniProt:
P10163)
MLLILLSVALLALSSAESSSEDVSQEESLFLISGKPEGRRPQGGNQPQRP
PPPPGKPQGPPPPQGGNQSQGPPPPGKPEGRPPQGGNQSQGPPPHPGKPE
RPPPQGGNQSQGPPPTPGKPEGPPPQGGNQSQGTPPPPGKPEGRPPQGGN
QSQGPPPHPGKPERPPPQGGNQSHRPPPPPGKPERPPPQGGNQSQGPPPHPGKPEGPPPQEGNKSRSARSPPGKPQGPP
QQEGNKPQGPPPPGKPQGPPPPGGNPQQPAPPAGKPQGPPPPPQGGRPPRPAQGQQPPQ 5-mer peptides of P10163
MLLIL    PPPGK    PPQGG    GTPPP    ERPPP    KPQGP
LLILL    PPGKP    PQGGN    TPPPP    RPPPQ    PQGPP
LILLS    PGKPQ    QGGNQ    PPPPG    PPPQG    QGPPP
ILLSV    GKPQG    GGNQS    PPPGK    PPQGG    GPPPP
LLSVA    KPQGP    GNQSQ    PPGKP    PQGGN    PPPPG
LSVAL    PQGPP    NQSQG    PGKPE    QGGNQ    PPPGK
SVALL    QGPPP    QSQGP    GKPEG    GGNQS    PPGKP
VALLA    GPPPP    SQGPP    KPEGR    GNQSQ    PGKPQ
ALLAL    PPPPQ    QGPPP    PEGRP    NQSQG    GKPQG
LLALS    PPPQG    GPPPH    EGRPP    QSQGP    KPQGP
LALSS    PPQGG    PPPHP    GRPPQ    SQGPP    PQGPP
ALSSA    PQGGN    PPHPG    RPPQG    QGPPP    QGPPP
LSSAE    QGGNQ    PHPGK    PPQGG    GPPPH    GPPPP
SSAES    GGNQS    HPGKP    PQGGN    PPPHP    PPPPG
SAESS    GNQSQ    PGKPE    QGGNQ    PPHPG    PPPGG
AESSS    QSQGP    GKPES    GGNQS    PHPGK    PPGGN
ESSSE    SQGPP    KPESR    GNQSQ    HPGKP    PGGNP
SSSED    QGPPP    PESRP    NQSQG    PGKPE    GGNPQ
SSEDV    GPPPP    ESRPP    QSQGP    GKPEG    GNPQQ
SEDVS    PPPPP    SRPPQ    SQGPP    KPEGP    NPQQP
EDVSQ    PPPPG    RPPQG    QGPPP    PEGPP    PQQPQ
DVSQE    PPPGK    PPQGG    GPPPH    EGPPP    QQPQA
VSQEE    PPGKP    PQGGH    PPPHP    GPPPQ    QPQAP
SQEES    PGKPE    QGGHQ    PPHPG    PPPQE    PQAPP
QEESL    GKPEG    GGHQS    PHPGK    PPQEG    QAPPA
EESLF    KPEGR    GHQSQ    HPGKP    PQEGN    APPAG
ESLFL    PEGRP    HQSQG    PGKPE    QEGNK    PPAGK
SLFLI    EGRPP    QSQGP    GKPER    EGNKS    PAGKP
LFLIS    GRPPQ    SQGPP    KPERP    GNKSR    AGKPQ
FLISG    RPPQG    QGPPP    PERPP    NKSRS    GKPQG
LISGK    PPQGG    GPPPT    ERPPP    KSRSA    KPQGP
ISGKP    PQGGN    PPPTP    RPPPQ    SRSAR    PQGPP
SGKPE    QGGNQ    PPTPG    PPPQG    RSARS    QGPPP
GKPEG    GGNQS    PTPGK    PPQGG    SARSP    GPPPP
KPEGR    GNQSQ    TPGKP    PQGGN    ARSPP    PPPPQ
PEGRR    NQSQG    PGKPE    QGGNQ    RSPPG    PPPPQ
EGRRP    QSQGP    GKPEG    GGNQS    SPPGK    PPPQG
GRRPQ    SQGPP    KPEGP    GNQSH    PPGKP    PPQGG
RRPQG    QGPPP    PEGPP    NQSHR    PGKPQ    PQGGR
RPQGG    GPPPP    EGPPP    QSHRP    GKPQG    QGGRP
PQGGN    PPPHP    GPPPQ    SHRPP    KPQGP    GGRPP
QGGNQ    PPHPG    PPPQE    HRPPP    PQGPP    GRPPR
GGNQP    PHPGK    PPQEG    RPPPP    QGPPP    RPPRP
GNQPQ    HPGKP    PQEGN    PPPPP    GPPPP    PPRPA
NQPQR    PGKPE    QEGNK    PPPPG    PPPPQ    PRPAQ
QPQRP    GKPER    EGNKP    PPGKP    PPPQE    RPAQG
PQRPP    KPERP    GNKPQ    PGKPQ    PPQEG    PAQGQ
QRPPP    PERPP    NKPQG    GKPQ     QQEGN    AQGQQ
RPPPP    ERPPP    QSQGT    KPER     EGNKP    QGQQP
PPPPP    RPPPQ    SQGTP    KPERP    GNKPQ    GQQPP
PPPPG    PPPQG    QGTPP    PERPP    NKPQG    QQPPQ
```

Salivary acidic proline-rich phosphoprotein 1/2
(PRH1/PRH2; UniProt: P02810)
MLLILLSVALLAFSSAQDLDEDVSQEDVPLVISDGGDSEQFIDEERQGPP
LGGQQSQPSAGDGNQDDGPQQGPPQQGGQQQQGPPPPQGKPQGPPQGGH
PPPPQGRPQGPPQQGGHPRPPRGRPQGPPQQGGHQQGPPPPPGKPQGPP
PQGGRPQGPPQGQSPQ 5-mer peptides of P02810

| | | | |
|---|---|---|---|
| MLLIL | GGQQS | PPQGR | GRPQG |
| LLILL | GQQSQ | PQGRP | RPQGP |
| LILLS | QQSQP | QGRPQ | PQGPP |
| ILLSV | QSQPS | GRPQG | QGPPQ |
| LLSVA | SQPSA | RPQGP | GPPQG |
| LSVAL | QPSAG | PQGPP | PPQGQ |
| SVALL | PSAGD | QGPPQ | PQGQS |
| VALLA | SAGDG | GPPQQ | QGQSP |
| ALLAF | AGDGN | PPQQG | GQSPQ |
| LLAFS | GDGNQ | PQQGG | |
| LAFSS | DGNQD | QQGGH | |
| AFSSA | GNQDD | QGGHP | |
| FSSAQ | NQDDG | GGHPR | |
| SSAQD | QDDGP | GHPRP | |
| SAQDL | DDGPQ | HPRPP | |
| AQDLD | DGPQQ | PRPPR | |
| QDLDE | GPQQG | RPPRG | |
| DLDED | PQQGP | PPRGR | |
| LDEDV | QQGPP | PRGRP | |
| DEDVS | QGPPQ | RGRPQ | |
| EDVSQ | GPPQQ | GRPQG | |
| DVSQE | PPQQG | RPQGP | |
| VSQED | PQQGG | PQGPP | |
| SQEDV | QQGGQ | QGPPQ | |
| QEDVP | QGGQQ | GPPQQ | |
| EDVPL | GGQQQ | PPQQG | |
| DVPLV | GQQQQ | PQQGG | |
| VPLVI | QQQQG | QQGGH | |
| PLVIS | QQQGP | QGGHQ | |
| LVISD | QQGPP | GGHQQ | |
| VISDG | QGPPP | GHQQG | |
| ISDGG | GPPPP | HQQGP | |
| SDGGD | PPPPQ | QQGPP | |
| DGGDS | PPPQG | QGPPP | |
| GGDSE | PPQGK | GPPPP | |
| GDSEQ | PQGKP | PPPPP | |
| DSEQF | QGKPQ | PPPPG | |
| SEQFI | GKPQG | PPPPG | |
| EQFID | KPQGP | PPPGK | |
| QFIDE | PQGPP | PPGKP | |
| FIDEE | QGPPQ | PGKPQ | |
| IDEER | GPPQQ | GKPQG | |
| DEERQ | PPQQG | KPQGP | |
| EERQG | PQQGG | PQGPP | |
| ERQGP | QQGGH | QGPPP | |
| RQGPP | QGGHP | GPPPQ | |
| QGPPL | GGHPP | PPPQG | |
| GPPLG | GHPPP | PPQGG | |
| PPLGG | HPPPP | PQGGR | |
| PLGGQ | PPPPQ | QGGRP | |
| LGGQQ | PPPQG | GGRPQ | |

TABLE 2

Basic Proline-rich Protein 1 (PRB1; UniProt: P04280)

MLLILLSVALLALSSAQNLNEDVSQEESPSLIAGNPQGPSPQGGNKPQGP

PPPPGKPQGPPPQGGNKPQGPPPPGKPQGPPPQGDKSRSPRSPPGKPQGP

PPQGGNQPQGPPPPGKPQGPPPQGGNKPQGPPPPGKPQGPPPQGDKSQS

PRSPPGKPQGPPPQGGNQPQGPPPPPGKPQGPPPQGGNKPQGPPPPGKPQ

GPPPQGDKSQSPRSPPGKPQGPPPQGGNQPQGPPPPGKPQGPPQQGGNR

TABLE 2-continued

Basic Proline-rich Protein 1 (PRB1; UniProt: P04280)

PQGPPPPGKPQGPPPQGDKSRSPQSPPGKPQGPPPQGGNQPQGPPPPPGK

PQGPPPQGGNKPQGPPPPGKPQGPPAQGGSKSQSARAPPGKPQGPPQQEG

NNPQGPPPPAGGNPQQPQAPPAGQPQGPPRPPQGGRPSRPPQ

TABLE 3

Distribution of CFS and normal subjects with regard to demographic and other factors. Expressed as percentage where CFS n = 46 and normal subject n = 45. Chi-square statistic. Body weight is defined as normal, BMI between 18.5 to 24.9, overweight 25.0 to 29.9, and obese greater than 30 (www.cdc.gov/obesity/adult/defining.html). A smoker is defined as anyone who answered yes to the question "Have you ever smoked cigarettes regularly?"

| | CFS | Normal | p-value |
|---|---|---|---|
| Medication | | | 0.001 |
| Not Medicated | 43.5 | 97.8 | |
| Medicated | 56.5 | 2.2 | |
| Gender | | | 0.059 |
| Female | 78.3 | 69.2 | |
| Male | 21.7 | 30.8 | |
| Race | | | 0.385 |
| American Indian | 4.3 | 0.0 | |
| Black | 15.2 | 15.6 | |
| Other | 2.2 | 0.0 | |
| White | 78.3 | 84.4 | |
| Smoking | | | 0.005 |
| Smoker | 67.4 | 37.8 | |
| Non-Smoker | 32.6 | 62.2 | |
| Menstruation | | | 0.016 |
| Normal | 16.7 | 44.4 | |
| Irregular | 83.3 | 55.6 | |
| Menopause | | | 0.109 |
| Yes | 61.1 | 40.7 | |
| No | 38.9 | 59.3 | |
| Obesity | | | 0.127 |
| Normal | 17.4 | 33.3 | |
| Overweight | 39.1 | 40.0 | |
| Obese | 43.5 | 26.7 | |
| Age | 50.4 | 48.0 | 0.218 |
| BMI | 28.6 | 27.1 | 0.100 |

TABLE 4

Comparison of CFS subjects CFS biomarker level within group

| CFS Subjects compared | Mean | SD | p-value |
|---|---|---|---|
| Medication | | | |
| Not Medicated (n = 20) | 52160 | 19727 | 0.465 |
| Medicated (n = 26) | 47736 | 20737 | |
| Gender | | | |
| Female (n = 36) | 50684 | 21557 | 0.43 |
| Male (n = 10) | 45969 | 14632 | |
| Race | | | |
| White (n = 36) | 49889 | 21060 | 0.875 |
| Other (n = 10) | 48833 | 17743 | |
| Smoking | | | |
| Smoker (n = 31) | 47053 | 18888 | 0.25 |
| Non-Smoker (n = 15) | 55047 | 22387 | |
| Menstruation (female only) | | | |
| Irregular (n = 30) | 55830 | 20599 | 0.525 |
| Normal (n = 6) | 49655 | 21935 | |

TABLE 4-continued

Comparison of CFS subjects CFS biomarker level within group

| CFS Subjects compared | Mean | SD | p-value |
|---|---|---|---|
| Menopause (female only) | | | |
| Yes (n = 22) | 48307 | 23014 | 0.397 |
| No (n = 14) | 54420 | 19262 | |

TABLE 4-continued

Comparison of CFS subjects CFS biomarker level within group

| CFS Subjects compared | Mean | SD | p-value |
|---|---|---|---|
| Obesity | | | |
| Normal (n = 8) | 52905 | 20554 | 0.633 |
| Overweight or Obese (n = 38) | 48976 | 20339 | |

What is claimed is:

1. A method of guiding a human subject's sleep schedule, comprising:

a) measuring the concentration of a peptide selected from the group consisting of: 1) a peptide comprising the amino acid sequence PPGKPQGPPPQGGNQPQGPP-PPPGKPQ (SEQ ID NO:1), 2) a peptide comprising the amino acid sequence GNPQGPSPQGGNKPQGPPPP-PGKPQ (SEQ ID NO:2), 3) a peptide comprising the amino acid sequence SPPGKPQGPPQQEGNKPQGP-PPPGKPQ (SEQ ID NO:3), and 4) any combination thereof, in a saliva sample taken from the subject;

b) calculating the ratio of the concentration of the peptide(s) measured in (a) to the total amount of protein in the sample, according to the equation: ([PPGKPQG-PPPQGGNQPQGPPPPPGKPQ SEQ ID NO:1]+[GN-PQGPSPQGGNKPQGPPPPPGKPQ SEQ ID NO: 2]+[SPPGKPQGPPQQEGNKPQGPPPPGKPQ SEQ ID NO;3])/total protein (µg);

c) having the subject initiate or resume a sleep schedule;

d) measuring the concentration of a peptide selected from the group consisting of: 1) a peptide comprising the amino acid sequence PPGKPQGPPPQGGNQPQGPP-PPPGKPQ (SEQ ID NO:1), 2) a peptide comprising the amino acid sequence GNPQGPSPQGGNKPQGPPPP-PGKPQ (SEQ ID NO:2), 3) a peptide comprising the amino acid sequence SPPGKPQGPPQQEGNKPQGP-PPPGKPQ (SEQ ID NO:3), and 4) any combination thereof, in a saliva sample taken from the subject at one or more time points after (c), wherein the peptides of (d) are the same as the peptides of (a);

e) calculating the ratio of the concentration of the peptide(s) measured in (d) to the total amount of protein in the sample, according to the equation: ([PPGKPQG-PPPQGGNQPQGPPPPPGKPQ SEQ ID NO:1]+[GN-PQGPSPQGGNKPQGPPPPPGKPQ SEQ ID NO: 2]+[SPPGKPQGPPQQEGNKPQGPPPPGKPQ SEQ ID NO;3])/total protein (μg); and f) guiding the subject's sleep schedule by modifying the duration of subsequent sleep periods using the subject's ratio(s) as calculated in (e), such that an increase in the ratio relative to the previous ratio leads to a subsequent increase in the duration of the subject's sleep period, and a decrease in the ratio or a constant ratio relative to the previous ratio leads to no change in the duration of the subject's sleep period or a subsequent decrease in the duration of the subject's sleep period.

\* \* \* \* \*